United States Patent
Winter-Holt et al.

(10) Patent No.: US 11,136,338 B2
(45) Date of Patent: Oct. 5, 2021

(54) FUSED THIAZOLOPYRIMIDINE DERIVATIVES AS MNKS INHIBITORS

(71) Applicant: LIFEARC, London (GB)

(72) Inventors: Jon James Winter-Holt, London (GB); Edward Giles Mciver, London (GB); Martin Ambler, London (GB); Stephen Lewis, London (GB); Joanne Osborne, London (GB); Kayleigh Webb-Smith, London (GB)

(73) Assignee: LIFEARC, London (GB)

( * ) Notice: Subject to any disclaimer, the term of this patent is extended or adjusted under 35 U.S.C. 154(b) by 0 days.

(21) Appl. No.: 16/855,701

(22) Filed: Apr. 22, 2020

(65) Prior Publication Data

US 2020/0247822 A1    Aug. 6, 2020

Related U.S. Application Data

(63) Continuation of application No. 15/776,536, filed as application No. PCT/GB2016/053580 on Nov. 16, 2016, now Pat. No. 10,669,284.

(30) Foreign Application Priority Data

Nov. 20, 2015    (GB) .................................. 1520500

(51) Int. Cl.
| | |
|---|---|
| C07D 513/04 | (2006.01) |
| C07D 519/00 | (2006.01) |
| A61K 31/519 | (2006.01) |
| A61K 31/429 | (2006.01) |
| A61P 35/04 | (2006.01) |

(52) U.S. Cl.
CPC .......... *C07D 513/04* (2013.01); *A61K 31/429* (2013.01); *A61K 31/519* (2013.01); *A61P 35/04* (2018.01); *C07D 519/00* (2013.01)

(58) Field of Classification Search
CPC .................................................... C07D 513/04
See application file for complete search history.

(56) References Cited

U.S. PATENT DOCUMENTS

| | | | |
|---|---|---|---|
| 8,754,079 B2 | 6/2014 | Lehmann-Lintz et al. | |
| 8,853,193 B2 | 10/2014 | Heckel et al. | |
| 2005/0153989 A1 | 7/2005 | Grotzfield et al. | |
| 2010/0247517 A1* | 9/2010 | Austen .................... | A61P 25/16 424/130.1 |
| 2012/0128686 A1* | 5/2012 | Austen .................... | A61P 29/00 424/158.1 |

FOREIGN PATENT DOCUMENTS

| | | | |
|---|---|---|---|
| EP | 1724268 A1 | 11/2006 | |
| EP | 1731523 A1 | 12/2006 | |
| WO | 2005067546 A2 | 7/2005 | |
| WO | 2006014325 A2 | 2/2006 | |
| WO | 2008057402 A2 | 5/2008 | |
| WO | WO-2008057402 A2 * | 5/2008 | ........... A61K 31/519 |
| WO | 2014118226 A1 | 1/2014 | |
| WO | 2014135480 A1 | 9/2014 | |
| WO | WO-2014135480 A1 * | 9/2014 | ........... A61K 31/497 |
| WO | 2015004024 A1 | 1/2015 | |

OTHER PUBLICATIONS

Patani et al. Chem. Rev. 1996, 96, 3147-3176 (Year: 1996).*
Sheridan, R.P. J. Chem. Inf. Comput. Sci. 2002, 42, 103-108 (Year: 2002).*
International Search Report of PCT/GB2016/053580 dated Jan. 2, 2017, 4 pp.
Berge et al. (1977) "Pharmaceutical Salts," Journal of Pharmaceutical Sciences, 66(1):21 pages.
Buxade et al. (2005) "The Mnks Are Novel Components in the Control of TNFalpha Biosynthesis and Phosphorylate and Regulate hmRNP A1 ," Immunity, 23:177-189.
Buxade et al. (2008) "The Mnks: MAP kinase-interacting kinasess (MAP kinase signal-integrating kinases)," Frontiers in Bioscience, 5359-5374.
Cherla et al. (2006) "Shiga toxin 1-induced cytokine production is mediated by MAP kinase pathways and translation initiation factor eIF4E in the macrophage-like THP-1 cell line," Journal of Leukocyte Biology, 79:397-407.

(Continued)

*Primary Examiner* — Matthew P Coughlin
(74) *Attorney, Agent, or Firm* — Lathrop GPM LLP; Brian C. Trinque

(57) ABSTRACT

The present invention relates to compounds of formulae I and II, or pharmaceutically acceptable salts or esters thereof. Further aspects of the invention relate to pharmaceutical compositions and therapeutic uses of said compounds in the treatment of diseases of uncontrolled cell growth, proliferation and/or survival, inappropriate cellular immune responses, inappropriate cellular inflammatory responses, or neurodegenerative disorders, preferably tauopathies, even more preferably. Alzheimer's disease.

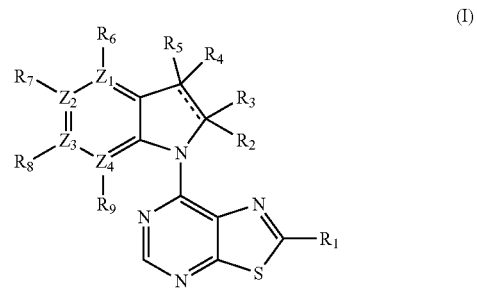

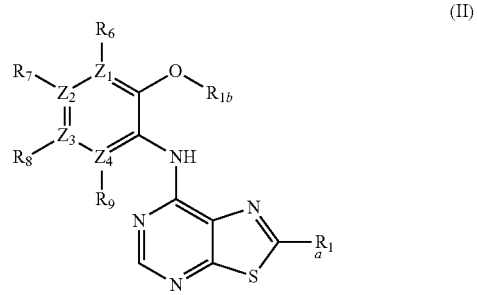

16 Claims, No Drawings

(56) References Cited

OTHER PUBLICATIONS

Chrestensen et al. (2007) "Loss of MNK function sensitizes fibroblasts to serum-withdrawal induced apoptosis," Genes to Cells, 12:1133-1140.
Fingl et al. (1975) Introduction, Generak Principles, The Pharmacological Basis of Therapeutics, Chapter 1, 46 pages.
Gennaro, Alfonso R., (1985) Remington's Pharmaceutical Sciences, 17th Edition, 9 pages.
Jauch et al., (2006) "Mitogen-activated protein kinases interacting kinases are autoinhibited by a reprogrammed activation segment," The EMBO Journal, 25:4020-4032.
Kjellerup et al. (2008) "Pro-inflammatory cytokine release in keratinocytes is mediated through the MAPK signal-intergrating kinases," Experimental Dermatology, 17:498-504.
Konicek et al. (2008) "Targeting the elF4F translation initiation complex for cancer therapy," Cell Cycle, 7(16):2466-2471.
Konicek et al. (2011) "Therapeutic Inhibition of MAP Kinase Interacting Kinase Blocks Eukaryotic Initiation Factor 4E Phosphorylation and Suppresses Outgrowth of Experimental Lung Metastases," Cancer Res., 71(5):1849-1857.
March, Jerry (1985) Advanced Organic Chemistry, Third Edition, 5 pages.
Nikolcheva et al., "A translational rheostat for RFLAT-1 regulates RANTES expression inT lymphocytes," J. Clin. Invest., 110:119-126.
Noubade et al. (2011) "Activation of p38 in CD4 T cells controls IL-17 production and autoimmune encephalomyelitis," Blood, 118(12):3290-3300.
Rowlett et al. (2008) "MNK kinases regulate multiple TLR pathways and innate proinflammatory cytokines in macrophages," Am. J. Physiol. Gastrointest. Liver Physiol., 294:G452-G459.
Teo et al., (2015) "Pharmacologic Inhibition of MNKs in Acute Myeloid Leukemia," Molecular Pharmacology, 88:380-389.
Teo et al., (2015) "Pharmacologic co-inhibition of MNKs and mTORC1 synergistically suppresses proliferation and perturbs cell cycle progression in blast crisis-chronic myeloid leukemia cells," Cancer Letters, 357:612-623.
Ueda et al., (2010) "Combined deficiency for MAP kinase-interacting kinase 1 and 2 (Mnk1 and Mnk2) delays tumor development," PNAS, 107(32):13984-13990.
Wade et al. (1994) Handbook of Pharmaceutical Excipients, Second Edition.
Wendel et al. (2007) "Dissecting elF4E action in tumorigenesis," Genes and Development, 21:3232-3237.

\* cited by examiner

FUSED THIAZOLOPYRIMIDINE DERIVATIVES AS MNKS INHIBITORS

The present invention relates to fused thiazolopyrimidine compounds that are capable of inhibiting one or more kinases, more particularly, MAP kinase-interacting serine/threonine-protein kinases (MNKs). The compounds have potential therapeutic applications in the treatment of a variety of disorders, including proliferative disorders, and neurodegenerative diseases such as Alzheimer's disease.

BACKGROUND TO THE INVENTION

The present invention relates to chemical compounds that inhibit the enzymatic activity of MAP kinase-interacting serine/threonine-protein kinases (MNKs). MNK proteins are encoded by the two genes MKNK1 and MKNK2 which give rise to MNK1 and 2. Both proteins come in two isoforms generated by alternative splicing. The shorter isoform, referred to as MNK1b/2b, lacks the MAP kinase binding domain which results in low basal activity (Buxade et al. Front Biosci 2008, 5359-5373). Mnk1a is activated through ERK and p38 but not JNK binding, whereas MNK2a appears to be only activated by ERK.

The catalytic domains of MNK1 and 2 are very similar. The domains are, however, very distinct from other kinases as they display a DFD motif in the ATP binding site instead of the typical DFG motif, which suggests an altered activation loop confirmation (Jauch et al. EMBO J 2006, 4020-4032). MNK1/2 are ubiquitously expressed with phosphorylate eukaryotic initiation factor 4E (eIF4E), cytoplasmic phospholipase A2 (cPLA2) heterogeneous nuclear RNA-binding protein A1 (hnRNP A1), polypyrimidine-tract binding protein-associated splicing factors (PSF) and Sprouty 2 (hSPRY2) (Buxade et al. Front Biosci 2008, 5359-5373).

MNKs have been linked to cancer through the phosphorylation of eIF4E. eIF4E is an oncogene which is amplified in cancer and is solely phosphorylated by MNKs (Konicek et al. Cell Cycle 2008, 2466-2471). eIF4E overexpression induces tumour formation in animals models. Increased phosphorylation of eIF4E has been observed in many solid tumours and lymph node metastasis where it correlates with poor prognosis. eIF4E is the rate limiting factor in cap-dependent translation where it directs ribosomes to the cap structure of mRNA-freely or as part of the eIF4F pre-initiation complex. Almost all proteins require eIF4E for translation. Phosphorylation of eIF4E leads to preferred translation of mRNA involved in cell survival, angiogenesis and cancer metastasis, such as mRNA for cyclin D1, Myc, Mcl-1, Bcl-2 and VEGF. These mRNAs are usually less efficiently translated due to long and complex 5'UTRs. Phosphorylation of eIF4 does not affect the overall translation rate but has been suggested to aid polysome formation, which facilitates more efficient translation.

A number of MNK1/MNK2 Inhibitors are known in the art. For example, U.S. Pat. Nos. 8,754,079 and 8,853,193 (both in the name of Boehringer Ingelheim international GMBH) disclose thienopyrimidine compounds that are capable of inhibiting MNK1 and/or MNK2. Likewise, WO 2014/135480 (Bayer Pharma Aktiengesellschaft) discloses thiazolopyrimidines substituted by an indazolyl or 2-oxo-2, 3,dihydro-1,3-benzothiazolyl group. WO 2014/118226 (Bayer Pharma Aktiengesellschaft) discloses substituted pyrazolylopyrimidinylamino-indazoles that are capable of inhibiting MNK1 and/or MNK2.

The present invention seeks to provide alternative compounds that are capable of interfering with the activity of MNK and its pathways. Such compounds have potential therapeutic applications in the treatment of a variety of disorders, including proliferative disorders and neurodegenerative disorders.

STATEMENT OF INVENTION

A first aspect of the invention relates to a compound of formula (I), or a pharmaceutically acceptable salt or ester thereof,

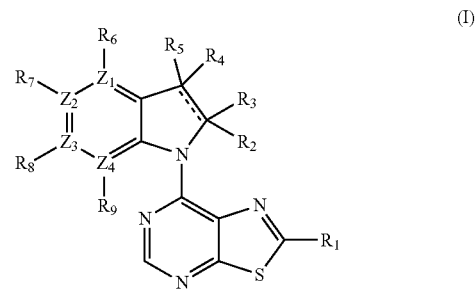

(I)

wherein:

$R_1$ is selected from:
  CO—$NR_{12}R_{13}$, wherein $R_{12}$ and $R_{13}$ are each independently selected from H, alkyl, cycloalkyl and heterocycloalkyl, wherein said alkyl group is optionally substituted by one or more $R_{14}$ groups, and said heterocycloalkyl is optionally substituted by one or more $R_{10}$ groups; or $R_{12}$ and $R_{13}$ are linked, together with the nitrogen to which they are attached, to form a heterocycloalkyl group optionally containing one or more additional heteroatoms, and optionally substituted by one or more $R_{10}$ groups;
  hydroxyalkyl;
  H;
  $NH_2$;
  NH-alkyl, wherein said alkyl group is optionally substituted with one or more $R_{14}$ groups;
  NH—CO-heterocycloalkyl;
  heterocycloalkyl optionally substituted by one or more $R_{10}$ groups; and
  alkoxy optionally substituted with one or more $R_{14}$ groups;

$R_2$, $R_3$, $R_4$ and $R_5$ are each independently selected from H, alkyl, hydroxyalkyl and $(CH_2)_n$—$R_{12}$;
or $R_2$ and $R_5$ are linked to form a cycloalkyl or heterocycloalkyl group each of which may be optionally further substituted with one or more $R_{10}$ groups;
or $R_4$ and $R_5$ are linked to form a cycloalkyl or heterocycloalkyl group each of which may be optionally further substituted with one or more $R_{10}$ groups;
or one of $R_2$ and $R_3$ is absent, one of $R_4$ and $R_5$ is absent, and the dashed line is a double bond;
$Z_1$, $Z_2$, $Z_4$ and $Z_4$ are all C;
$R_6$, $R_7$, $R_8$ and $R_9$ are each independently selected from H, CN, $NO_2$, OH, alkoxy, NHCO-alkyl, halo and haloalkyl; or
$Z_1$, $Z_3$ and $Z_4$ are all C, $Z_2$ is N, $R_7$ is absent and $R_6$, $R_8$ and $R_9$ are as defined above; or
$Z_2$, $Z_3$ and $Z_4$ are all C, $Z_1$ is N, $R_6$ is absent and $R_7$, $R_8$ and $R_8$ are as defined above;
n is an integer from 1 to 10;
each $R_{12'}$ is independently selected from $NH_2$, $NHR_{10}$, $NR_{10}R_{11}$ and heterocycloalkyl, wherein said heterocycloalkyl is optionally further substituted by one or more $R_{10}$ groups; each $R_{10}$ and $R_{11}$ is independently alkyl; and each $R_{14}$ is independently selected from OH, alkoxy, haloalkyl, $NH_2$, $NHR_{10}$, $NR_{10}R_{11}$, heteroaryl and heterocycloalkyl, wherein said heterocycloalkyl is optionally further substituted by one or more $R_{10}$ groups.

A second aspect of the invention relates to a compound of formula (II), or a pharmaceutically acceptable salt or ester thereof,

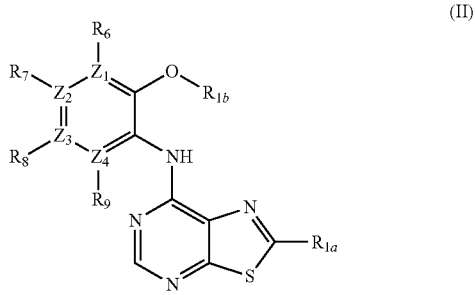

(II)

wherein:
$R_b$ is selected from alkyl, cycloalkyl and heterocycloalkyl, each of which may be optionally substituted by one or more groups selected from halo and alkoxy; $R_{1a}$ is selected from:
  CO—$NR_{12a}R_{13a}$, wherein $R_{12a}$ and $R_{13a}$ are each independently selected from H, alkyl, cycloalkyl and mono or bicyclic heterocycloalkyl, wherein said alkyl group is optionally substituted by one or more $(CH_2)_m R_{14a}$ groups, and said heterocycloalkyl is optionally substituted by one or more groups selected from $R_{10}$ and $(CH_2)_m R_{14a}$; or $R_{12a}$ and $R_{13a}$ are linked, together with the nitrogen to which they are attached, to form a heterocycloalkyl group optionally containing one or more additional heteroatoms, and optionally substituted by one or more groups selected from $R_{10}$ and $(CH_2)_m R_{14a}$;
  hydroxyalkyl;
  COOH; and
  H;
$Z_1$, $Z_2$, $Z_3$ and $Z_4$ are all C;
$R_6$, $R_7$, $R_8$ and $R_9$ are each independently selected from H, CN, $NO_2$, OH, alkoxy, NHCO-alkyl, halo and haloalkyl; or $Z_1$, $Z_3$ and $Z_4$ are all C, $Z_2$ is N, $R_7$ is absent and $R_6$, $R_8$ and $R_9$ are as defined above; or
$Z_2$, $Z_3$ and $Z_4$ are all C, $Z_1$ is N, $R_6$ is absent and $R_7$, $R_8$ and $R_9$ are as defined above; m is an integer from 1 to 10;
each $R_{10}$ and $R_{11}$ is independently alkyl;
each $R_{14a}$ is independently selected from $CO_2R_{10}$, COOH, OH, alkoxy, haloalkyl, $NH_2$, $NHR_{10}$, $NR_{10}R_{11}$, heteroaryl and heterocycloalkyl, wherein said heterocycloalkyl is optionally further substituted by one or more $R_{10}$ groups.

Advantageously, the presently claimed compounds are capable of inhibiting MNK1 and/or MNK2. Moreover, in one embodiment, the presently claimed compounds advantageously exhibit improved selectivity for MNK1 and/or MNK2 over other kinases compared to compounds known in the art.

A third aspect of the invention relates to a pharmaceutical composition comprising at least one compound as described above and a pharmaceutically acceptable carrier, diluent or excipient.

A fourth aspect of the invention relates to a compound as described above for use in medicine.

A fifth aspect of the invention relates to a compound as described above for use in treating a proliferative disorder.

A sixth aspect of the invention relates to a compound as described above for use in treating a neurodegenerative disease such as Alzheimer's Disease.

A seventh aspect of the invention relates to the use of a compound as described above in the preparation of a medicament for treating or preventing a proliferative disorder, or a neurodegenerative disease.

An eighth aspect of the invention relates to the use of a compound as described above in the preparation of a medicament for the prevention or treatment of a disorder caused by, associated with or accompanied by any abnormal kinase activity, wherein the kinase is preferably MNK.

A ninth aspect of the invention relates to a method of treating a mammal having a disease state alleviated by inhibition of a kinase (preferably MNK), wherein the method comprises administering to a mammal a therapeutically effective amount of a compound as described above.

A tenth aspect of the invention relates to the use of a compound as described above in an assay for identifying further candidate compounds capable of inhibiting a kinase, preferably MNK.

DETAILED DESCRIPTION

The present invention relates to fused thiazolopyrimidine compounds that are capable of inhibiting one or more kinases, more particularly MNK.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tort-butyl, pentyl, hexyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

"Heterocycloalkyl" refers to a monocyclic or bicyclic aliphatic group containing one or more heteroatoms selected from nitrogen, oxygen and sulphur, which is optionally interrupted by one or more —(CO)— groups in the ring and/or which optionally contains one or more double bonds in the ring. Where the heteroatom is sulphur, it can be in oxidised or reduced form, i.e. S, SO or $SO_2$. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Compounds of Formula (I)

One aspect of the invention relates to compounds of formula (I) as described above.

In one aspect, the invention relates to a compound of formula (I), or a pharmaceutically acceptable salt or ester thereof,

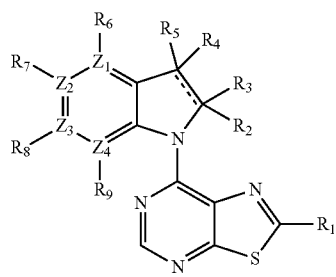

(I)

wherein:
$R_1$ is selected from:
  CO—$NR_{12}R_{13}$, wherein $R_{12}$ and $R_{13}$ are each independently selected from H, alkyl, cycloalkyl and heterocycloalkyl, wherein said alkyl group is optionally substituted by one or more $R_{14}$ groups, and said heterocycloalkyl is optionally substituted by one or more $R_{10}$ groups; or $R_{12}$ and $R_{13}$ are linked, together with the nitrogen to which they are attached, to form a heterocycloalkyl group optionally containing one or more additional heteroatoms, and optionally substituted by one or more $R_{10}$ groups;
  hydroxyalkyl;
  H;
  $NH_2$;
  NH-alkyl, wherein said alkyl group is optionally substituted with one or more $R_{14}$ groups;
  NH—CO-heterocycloalkyl;
  heterocycloalkyl optionally substituted by one or more $R_{10}$ groups; and
  alkoxy optionally substituted with one or more $R_{14}$ groups;
$R_2$, $R_3$, $R_4$ and $R_5$ are each independently selected from H, alkyl, hydroxyalkyl and $(CH_2)_n$—$R_{12}$;
or $R_2$ and $R_3$ are linked to form a cycloalkyl or heterocycloalkyl group each of which may be optionally further substituted with one or more $R_{10}$ groups;
or $R_4$ and $R_5$ are linked to form a cycloalkyl or heterocycloalkyl group each of which may be optionally further substituted with one or more $R_{10}$ groups;
or one of $R_2$ and $R_3$ is absent, one of $R_4$ and $R_5$ is absent, and the dashed line is a double bond;
$Z_1$, $Z_2$, $Z_3$ and $Z_4$ are all C;
$R_6$, $R_7$, $R_8$ and $R_9$ are each independently selected from H, CN, $NO_2$, OH, alkoxy, NHCO-alkyl, halo and haloalkyl; or $Z_1$, $Z_3$ and $Z_4$ are all C, $Z_2$ is N, $R_7$ is absent and $R_6$, $R_8$ and $R_9$ are as defined above; or
$Z_2$, $Z_3$ and $Z_4$ are all C, $Z_1$ is N, $R_6$ is absent and $R_7$, $R_8$ and $R_9$ are as defined above;
n is an integer from 1 to 10;
each $R_{12}$ is independently selected from $NH_2$, $NHR_{10}$, $NR_{10}R_{11}$ and heterocycloalkyl, wherein said heterocycloalkyl is optionally further substituted by one or more $R_{10}$ groups; each $R_{10}$ and $R_{11}$ is independently alkyl; and
each $R_{14}$ is independently selected from OH, alkoxy, haloalkyl, $NH_2$, $NHR_{10}$, $NR_{10}R_{11}$, heteroaryl and heterocycloalkyl, wherein said heterocycloalkyl is optionally further substituted by one or more $R_{10}$ groups.

Preferably, $R_1$, $R_2$, $R_3$ and $R_4$ are all present, i.e. there is a single bond between the carbon bearing $R_1/R_2$ and the carbon bearing $R_3/R_4$.

In one preferred embodiment, $Z_1$, $Z_2$, $Z_3$ and $Z_4$ are all C.

In one preferred embodiment, $R_2$, $R_3$, $R_4$ and $R_5$ are each independently selected from H, alkyl, and $(CH_2)_n$—$R_{12}$.

In one preferred embodiment;
$R_2$, $R_3$, $R_4$ and $R_5$ are all H; or
$R_2$ and $R_3$ are both H, and $R_4$ and $R_5$ are both Me; or
$R_2$ and $R_3$ are both H, and $R_4$ and $R_4$ are linked to form a cycloalkyl or heterocycloalkyl group.

In one preferred embodiment, $R_6$, $R_7$, $R_8$ and $R_9$ are each independently selected from H and halo.

In one preferred embodiment:
$Z_1$, $Z_2$, $Z_3$ and $Z_4$ are all C;
$R_6$, $R_7$, $R_8$ and $R_9$ are all H; or
$R_8$, $R_9$ and $R_{10}$ are all H and $R_7$ is selected from fluoro, chloro, bromo, methyl and $CF_3$; and
$R_2$, $R_3$, $R_4$ and $R_5$ are each independently selected from H, alkyl, and $(CH_2)_n$—$R_{12}$.

In one preferred embodiment:
$R_2$, $R_3$, $R_4$ and $R_5$ are each independently selected from H, hydroxyalkyl, alkyl, and $(CH_2)_n$—$R_{12}$, where n is 1 or 2 and $R_{12}$ is selected from $NH_2$, OH, NMe, $NMe_2$, pyrrolidin-1-yl, piperidin-1-yl and 4-methylpiperazin-1-yl.

In one preferred embodiment, $R_1$ is CO—$NR_{12}R_{13}$.

In one preferred embodiment, $R_1$ is CO—$NR_{12}R_{13}$ wherein:
one of $R_{12}$ and $R_{13}$ is H and the other is selected from:
  tetrahydropyran-4-yl;
  piperdin-4-yl;
  cyclopropyl;
  tetrahydrofuran-4-yl;
  N-methylpiperidin-4-yl;
  alkyl optionally substituted by one or more groups selected from NHMe, $NH_2$, $NMe_2$, piperidin-4-yl, N-methylpiperidin-4-yl, tetrahydrofuranyl, OH, $CF_3$, OMe and pyrrolidin-1-yl; or
$R_{12}$ and $R_{13}$ are linked, together with the nitrogen to which they are attached, to form a piperazinyl or morpholinyl group optionally substituted by one or more $R_{10}$ groups.

Compounds of Formula (II)

One aspect of the invention relates to compounds of formula (II) as described above.

In one preferred embodiment:
$Z_1$, $Z_2$, $Z_3$ and $Z_4$ are all C;
$R_6$, $R_7$, $R_8$ and $R_9$ are all H; or
$R_7$, $R_8$ and $R_9$ are all H and $R_7$ is halo.

In one preferred embodiment, $Z_1$, $Z_2$, 7- and $Z_4$ are all C, $R_6$, $R_8$ and $R_9$ are all H, and $R_7$ is fluoro.

In one preferred embodiment, $R_b$ is alkyl, more preferably, isopropyl.

In another embodiment, $R_b$ can be linked to the nitrogen of the NH linker group (the hydrogen of the NH group being absent) to form a heterocycloalkyl group, preferably a 5- or 6-membered heterocycloalkyl group, more preferably, a 6-membered heterocycloalkyl group.

In another embodiment, $R_b$ can be linked to $R_5$ (where $Z_1$ is carbon) to form a heterocycloalkyl group, preferably a 5- or 6-membered heterocycloalkyl group.

In one preferred embodiment, $R_{1a}$ is $CO-NR_{12a}R_{13a}$ wherein:
one of $R_{12a}$ and $R_{13a}$ is H and the other is selected from:
  alkyl optionally substituted by one or more groups selected from $NR_{10}R_{11}$, COOH, OH and heterocycloalkyl; and
  mono or bicyclic heterocycloalkyl optionally substituted by one or more groups selected from $R_{10}$ and $CO_2R_{10}$; or
$R_{12a}$ and $R_{13a}$ are linked, together with the nitrogen to which they are attached, to form a piperidinyl group optionally substituted by one or more groups selected from $R_{10}$ and $(CH_2)_m R_{14a}$.

In one preferred embodiment, $R_{1a}$ is alkyl optionally substituted by one or more groups selected from $NR_{10}R_{11}$ and a heterocycloalkyl group selected from piperidinyl, morpholinyl, piperazinyl, pyrrolidinyl, tetrahydropyranyl, wherein said heterocycloalkyl group is optionally substituted by one or more $R_{10}$ groups.

In one preferred embodiment, $R_{1a}$ is a heterocycloalkyl group selected from, piperidinyl, quinuclidinyl, azetidinyl, morpholinyl, piperazinyl, pyrrolidinyl and tetrahydropyranyl, each of which is optionally substituted by one or more $R_{10}$ groups.

In one embodiment, the compound of the invention is selected from the following:

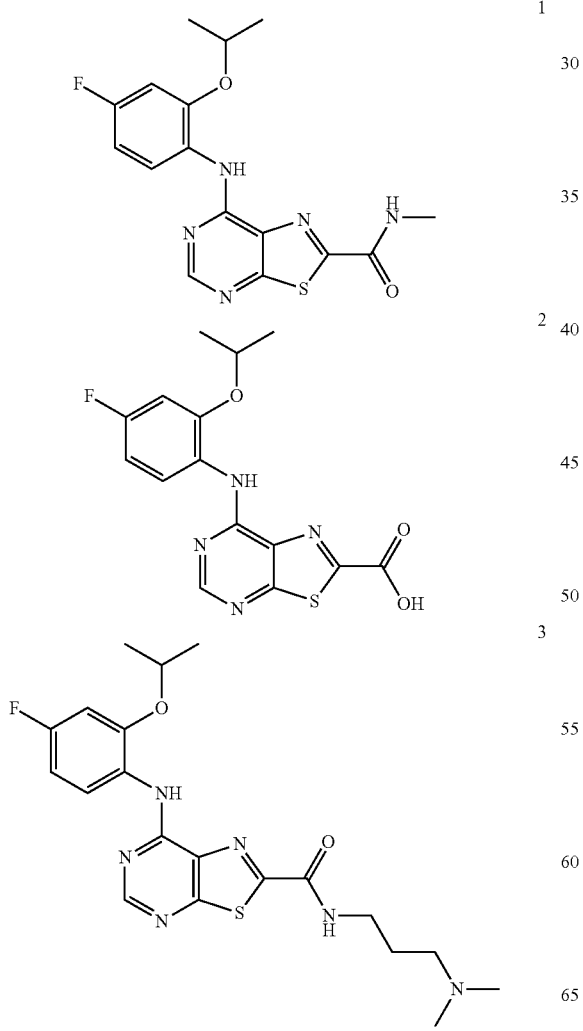

-continued

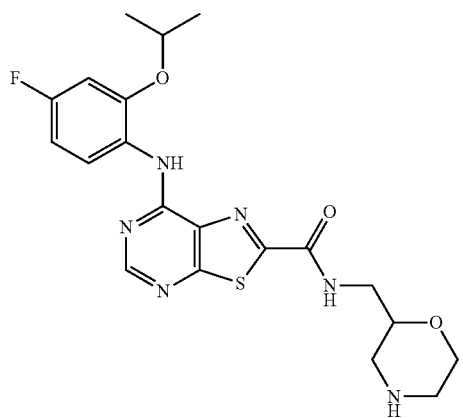

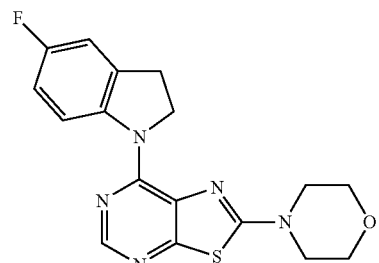

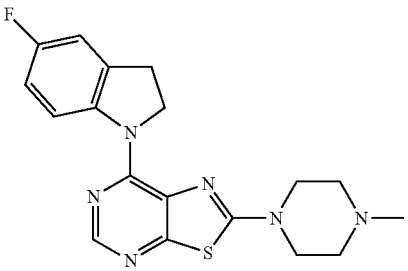

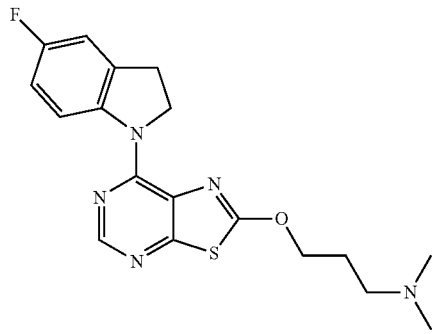

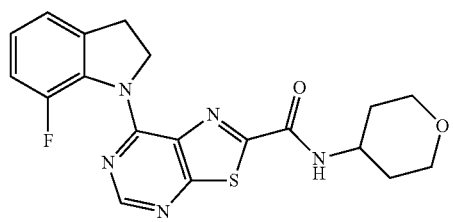

5 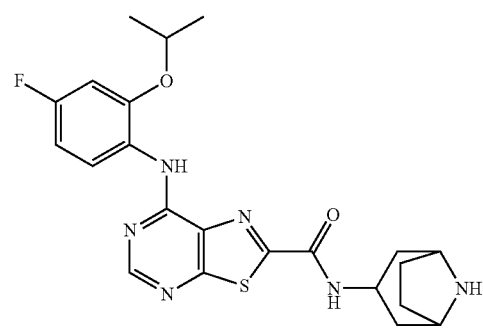
6 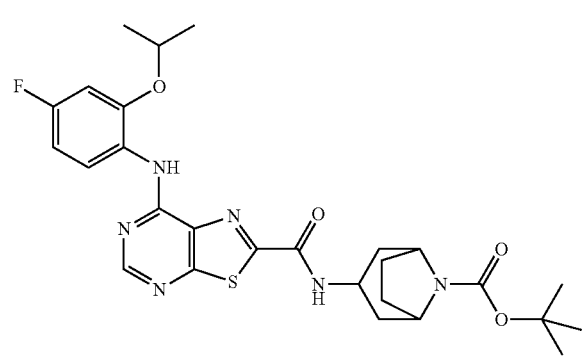
7 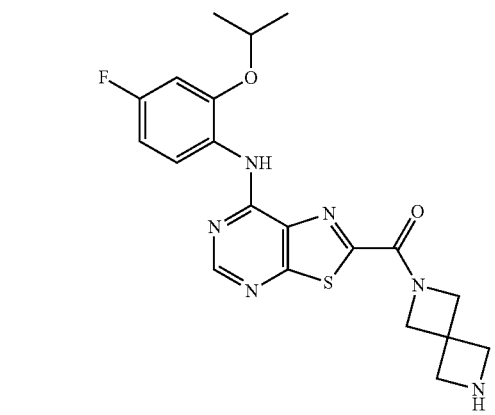
8 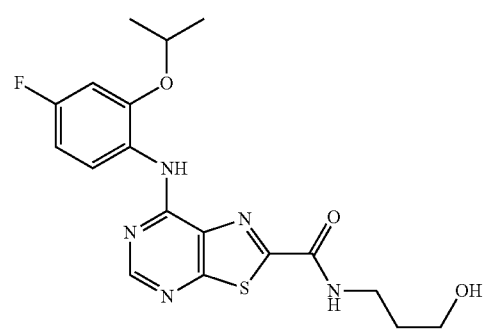
9 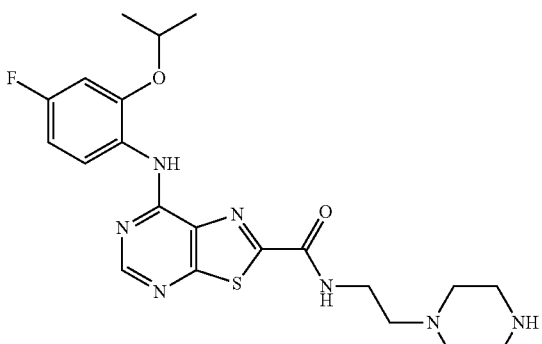
91 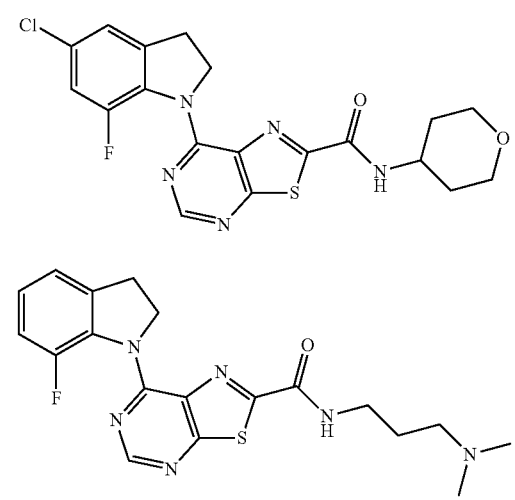
92, 93 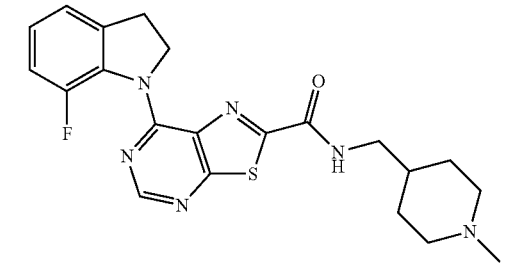
94 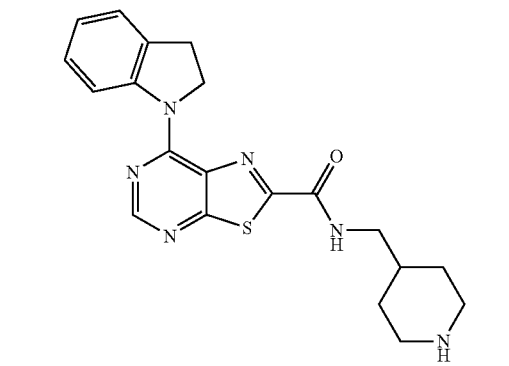

-continued
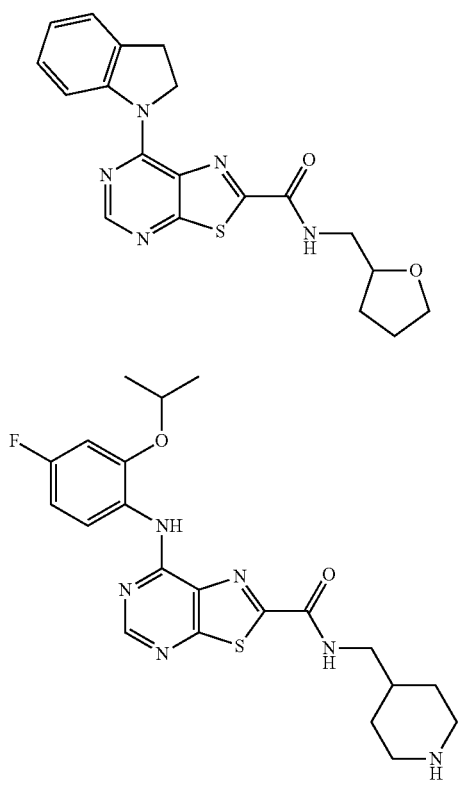
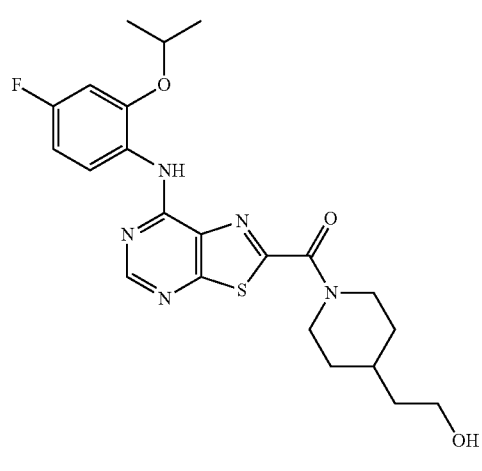
-continued
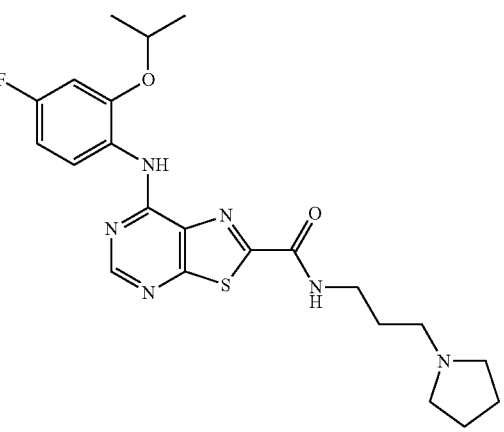
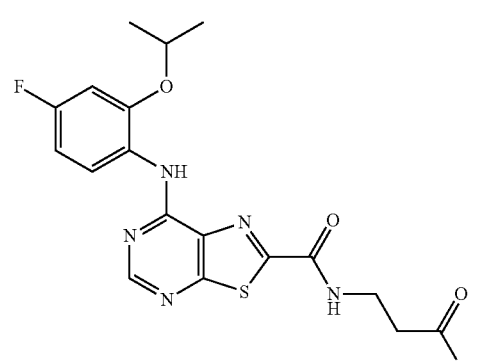
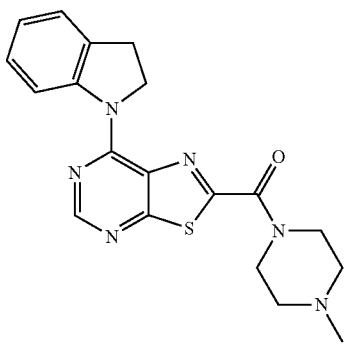
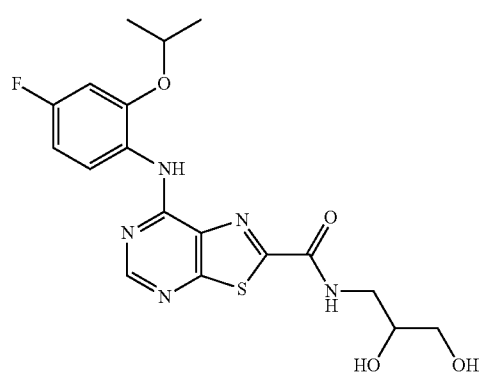
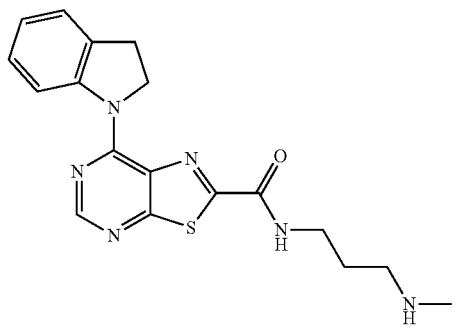

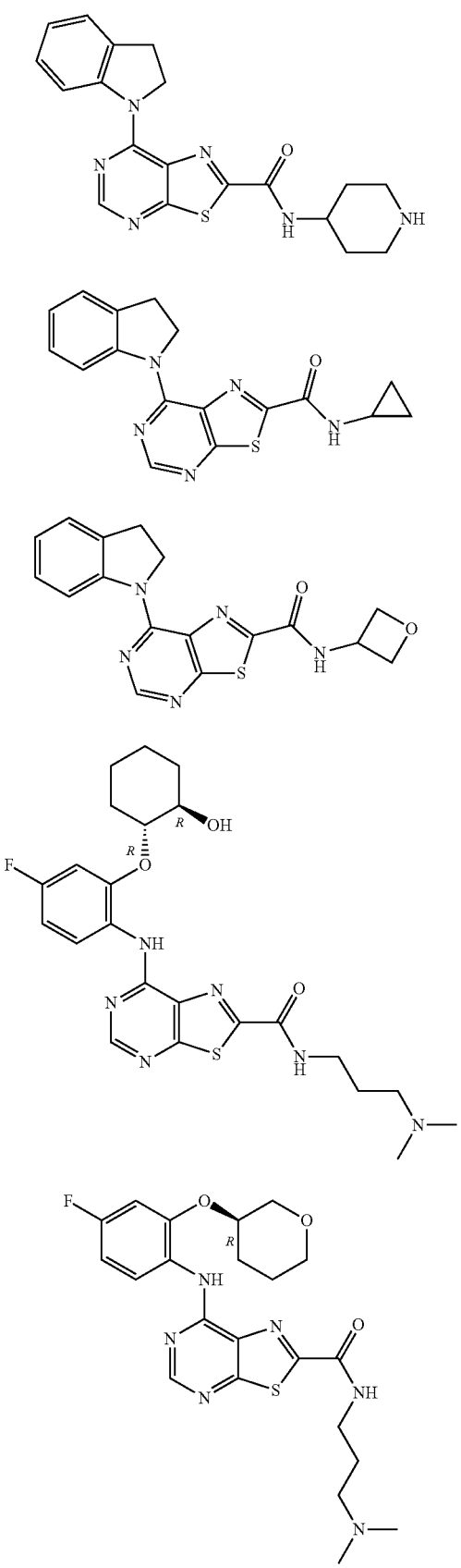
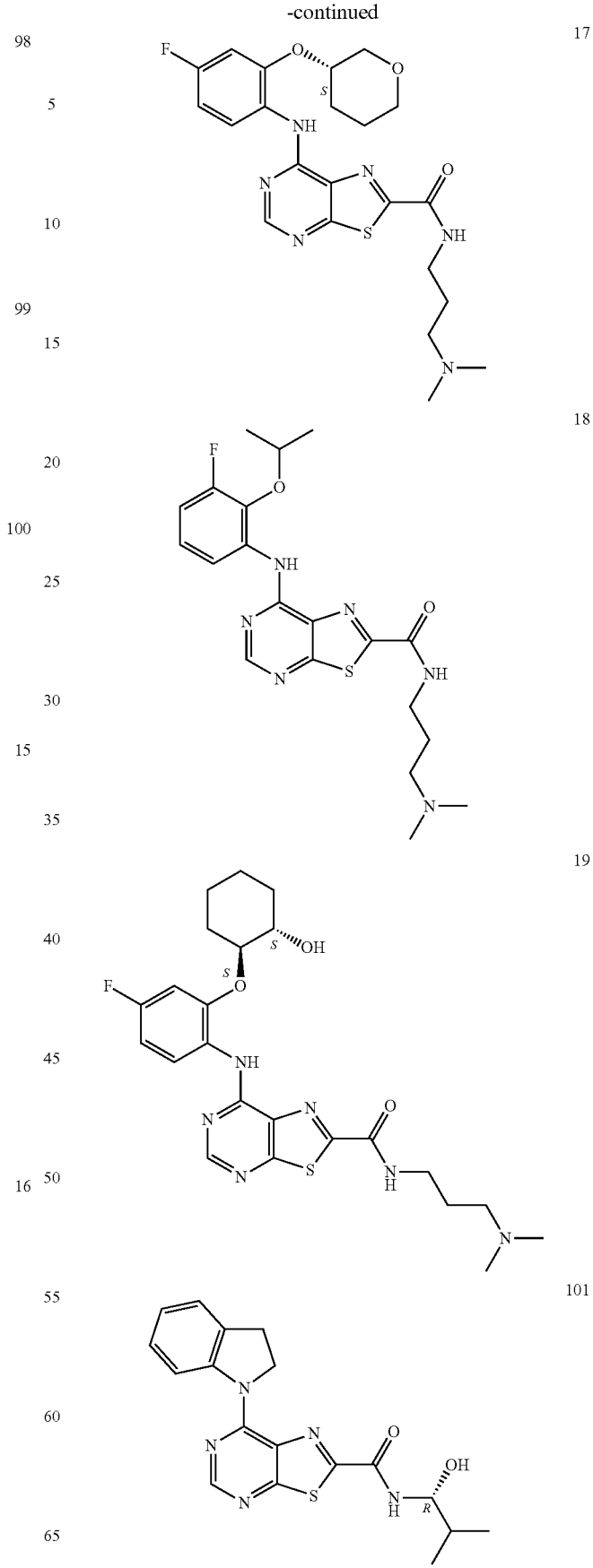

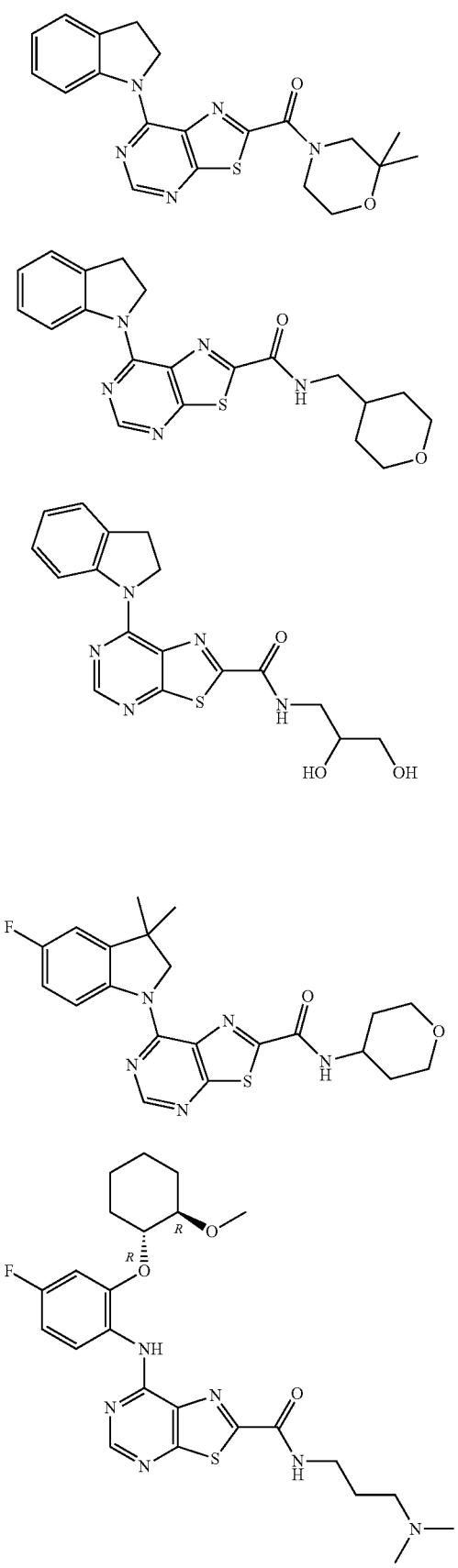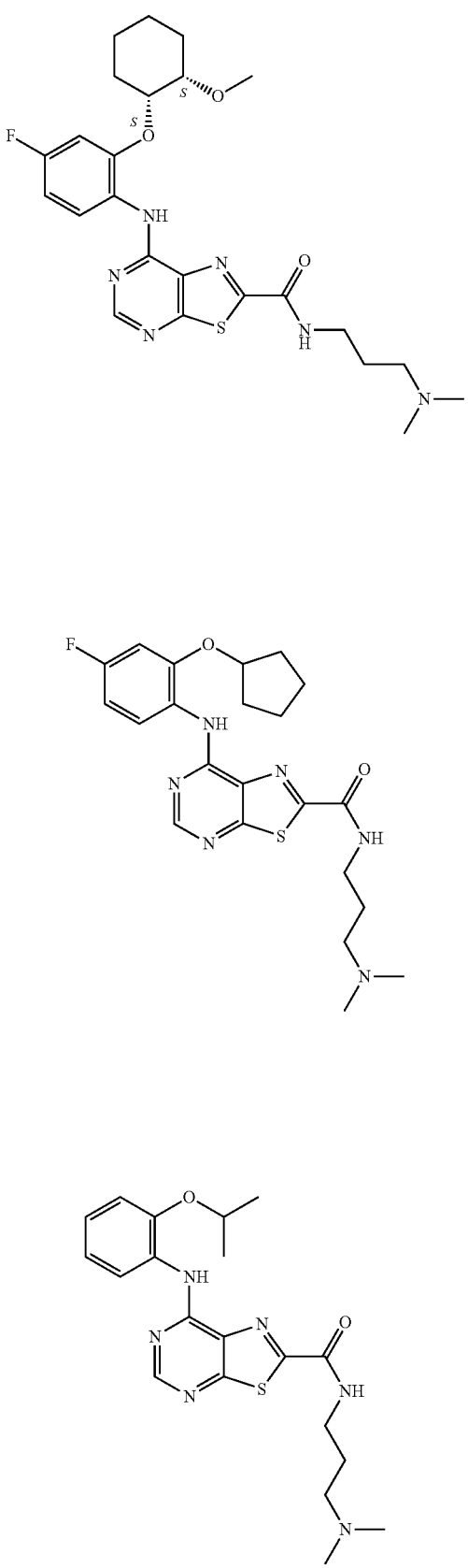

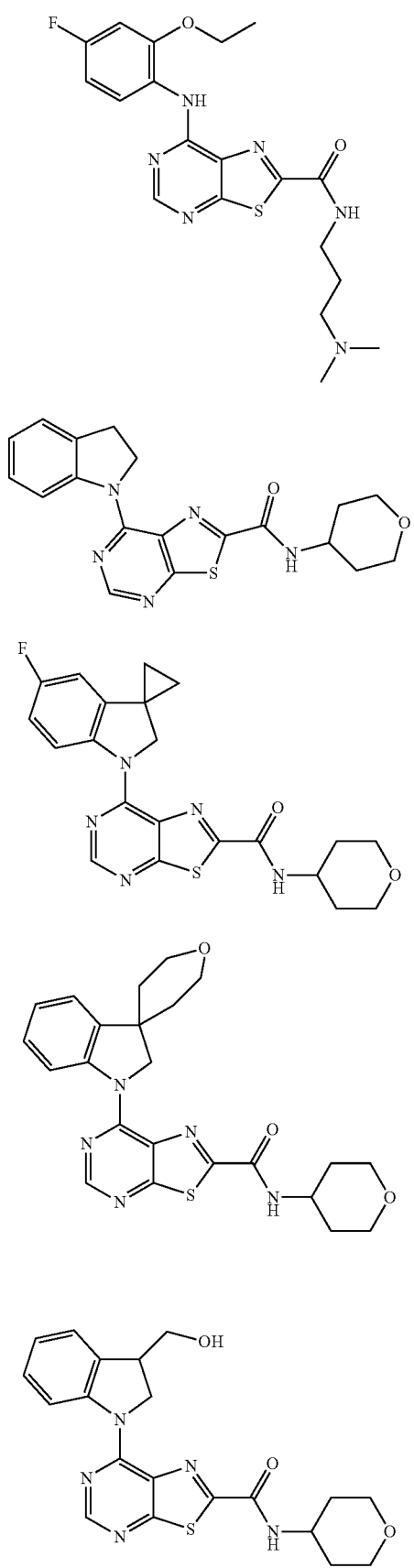
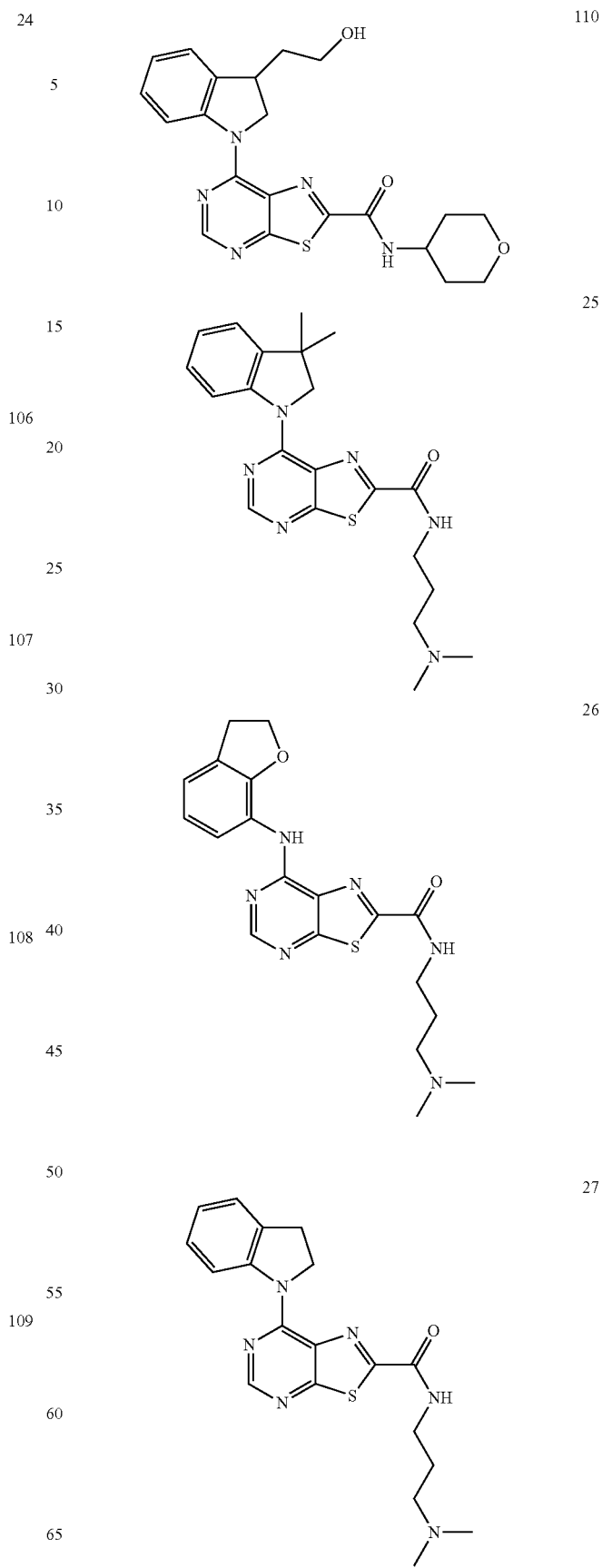

-continued
28
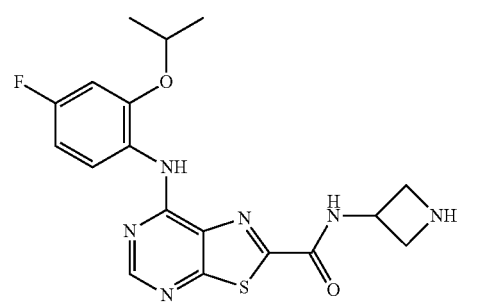
29
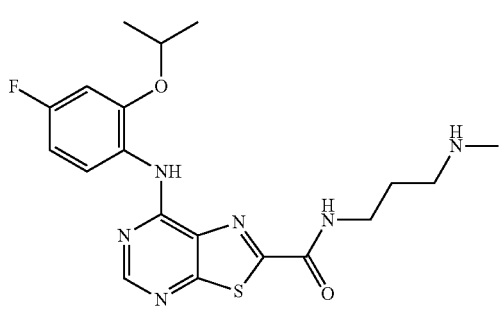
111
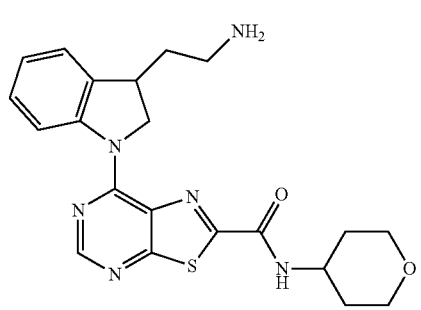
112
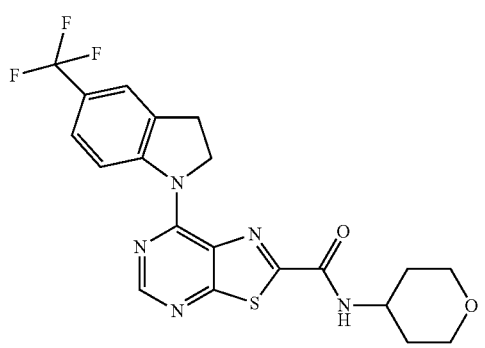
113
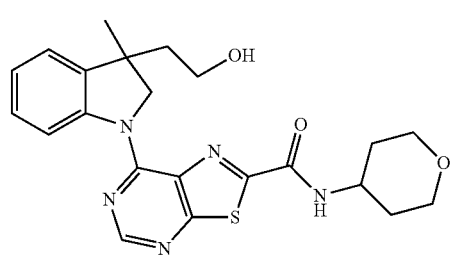
-continued
114
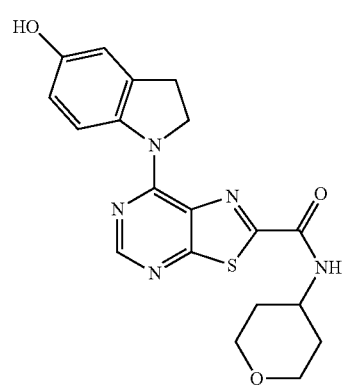
115
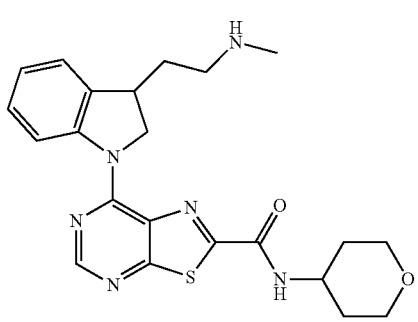
30
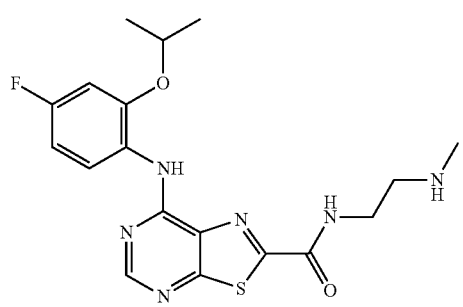
31
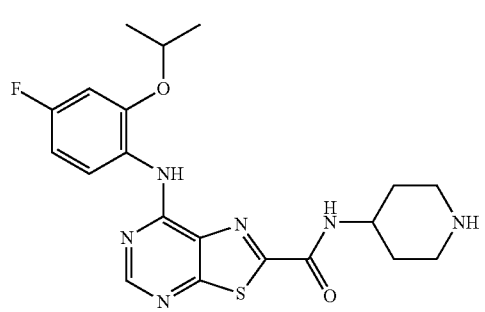
32
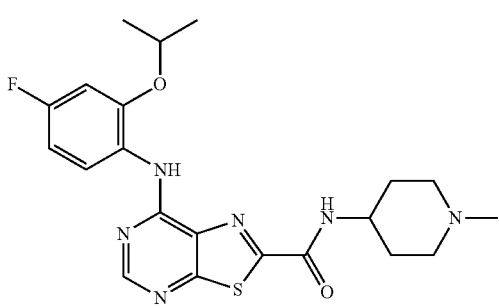

33
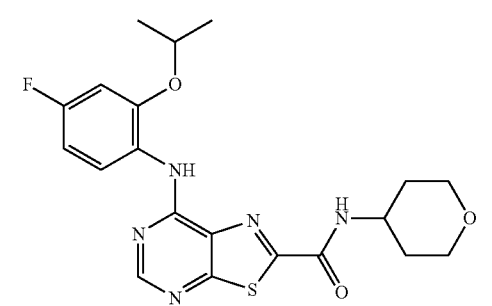
34
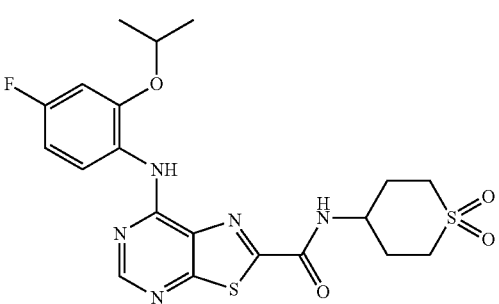
116
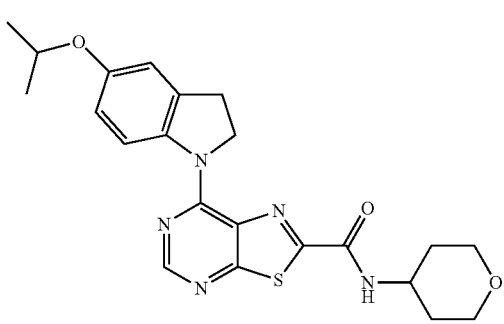
117
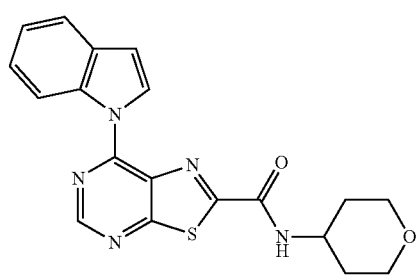
118
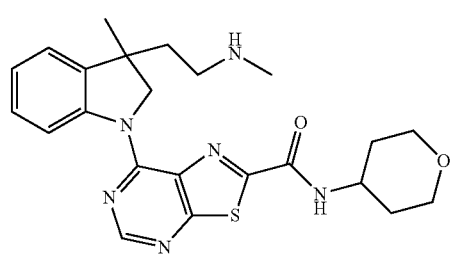
119
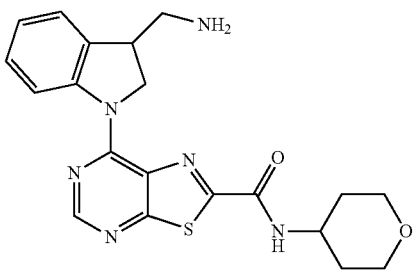
120
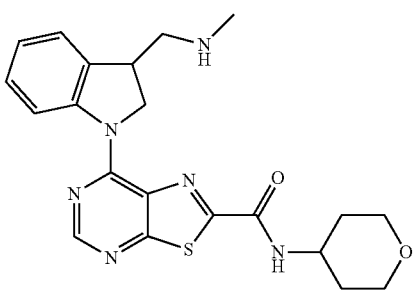
35
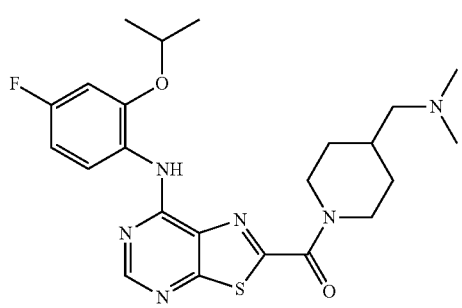
36
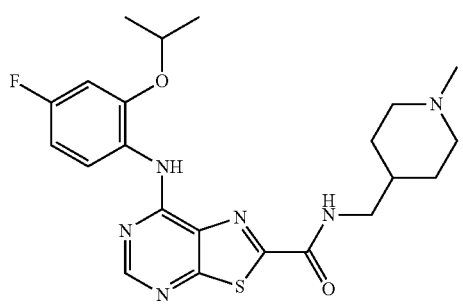
37
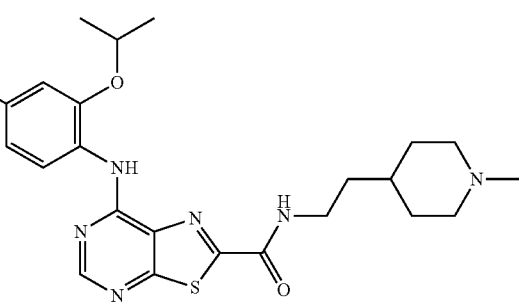

38
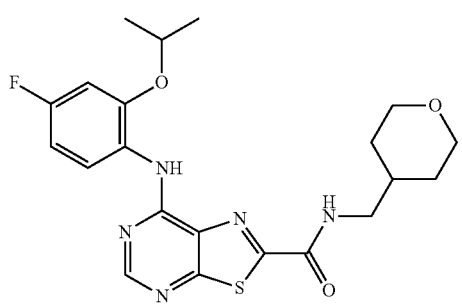
39
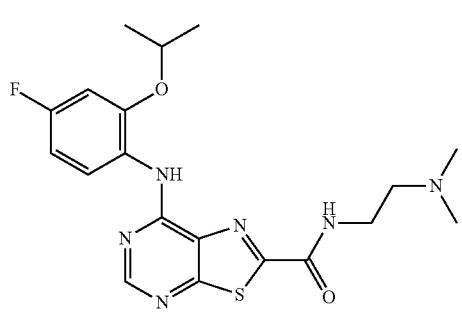
121
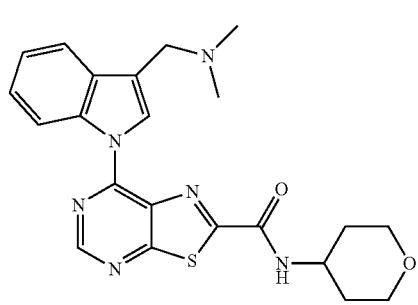
122
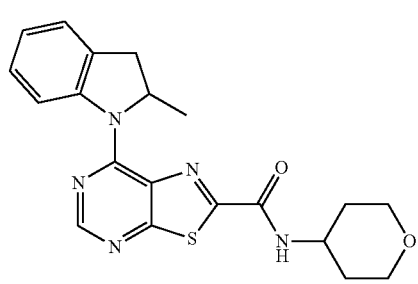
123
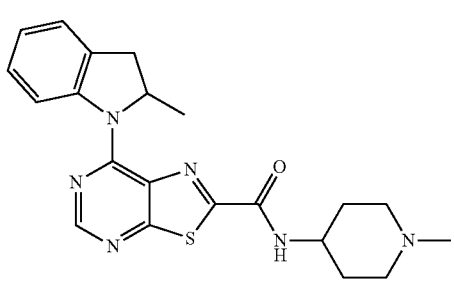
125
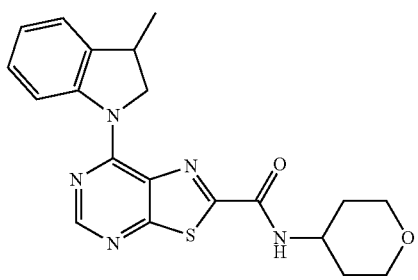
124
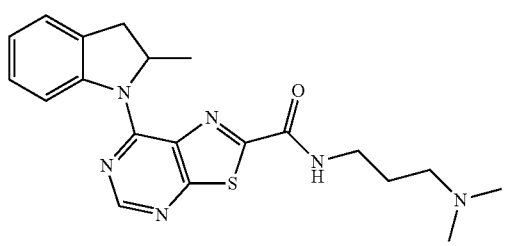
40
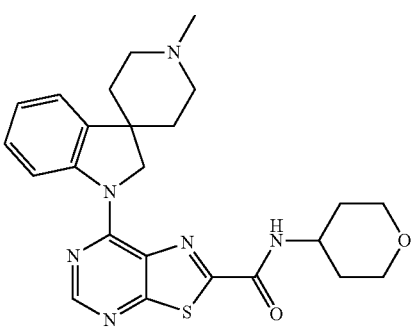
41
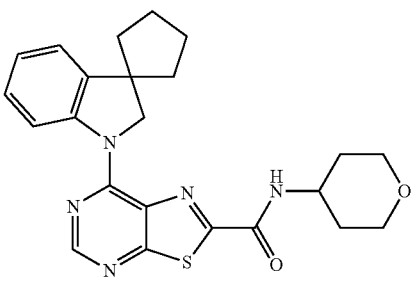
42
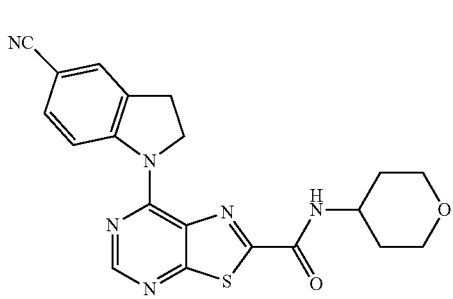

43
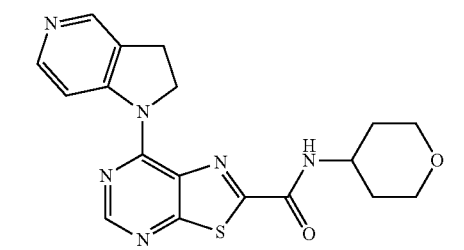
44
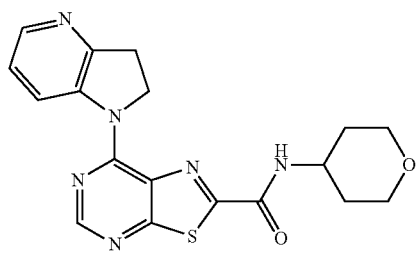
126
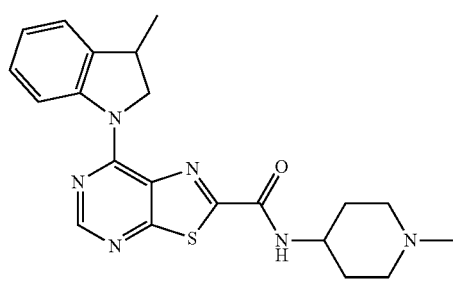
127
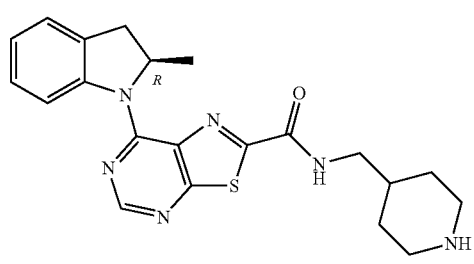
128
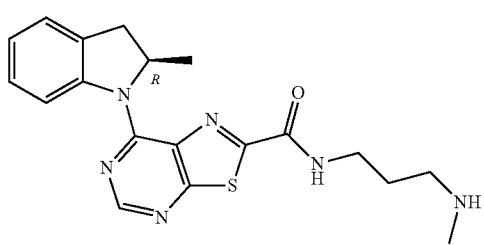
129
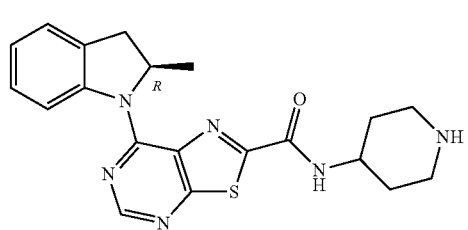
130
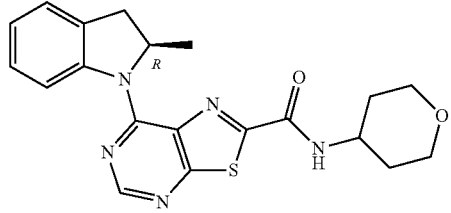
45
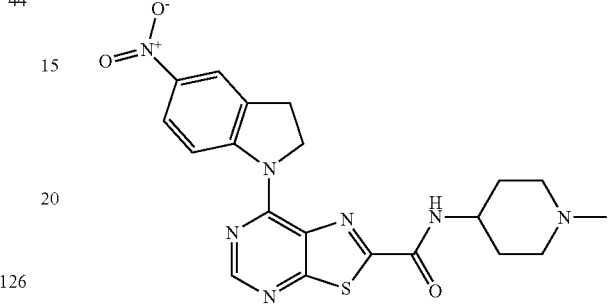
46
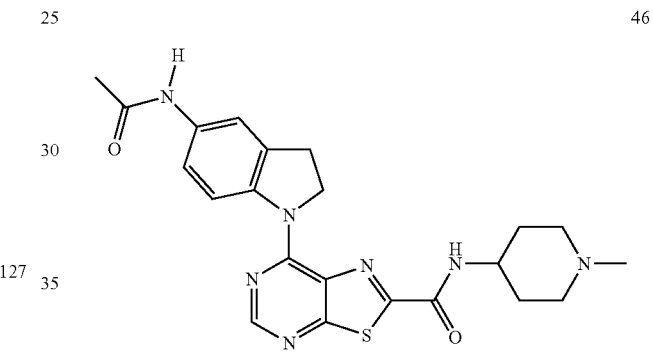
47
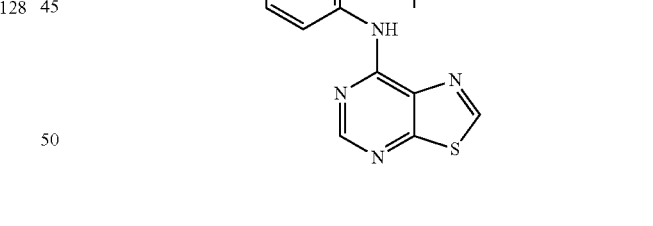
48
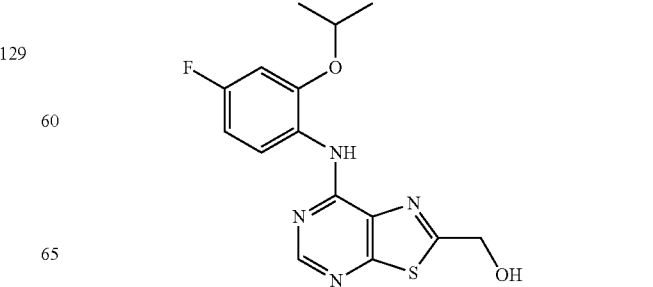

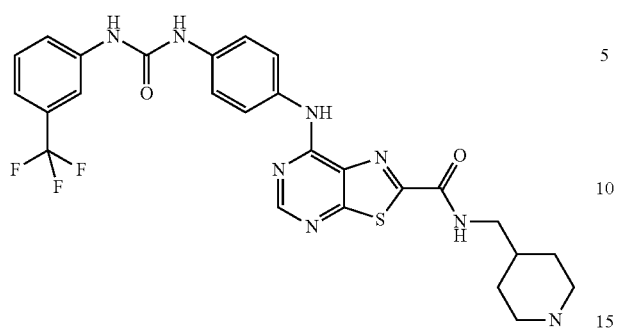
49
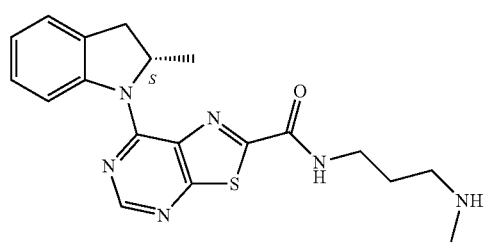
131
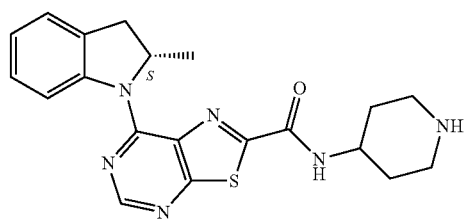
132
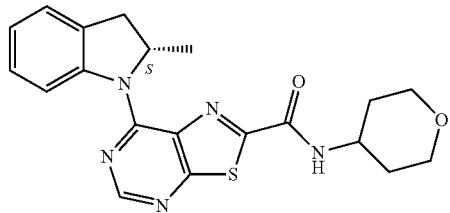
133
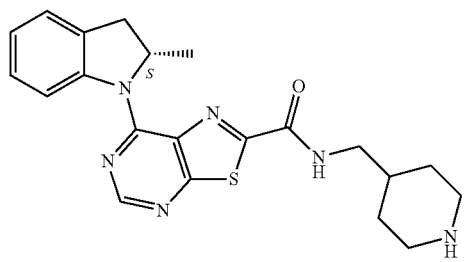
134
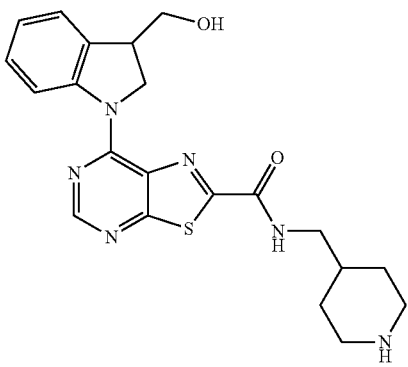
135
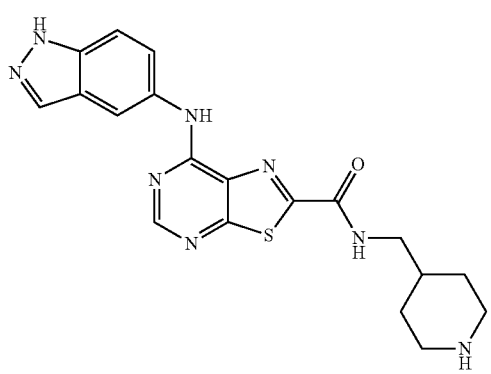
50
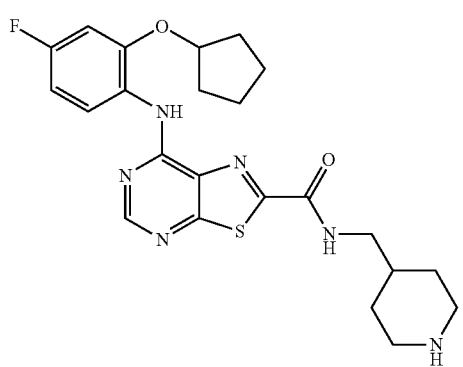
51
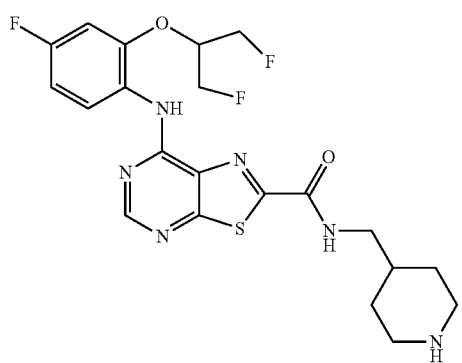
52

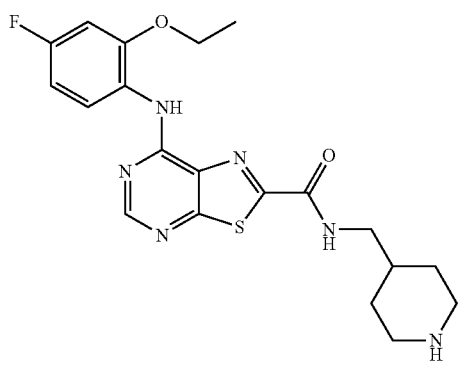
53
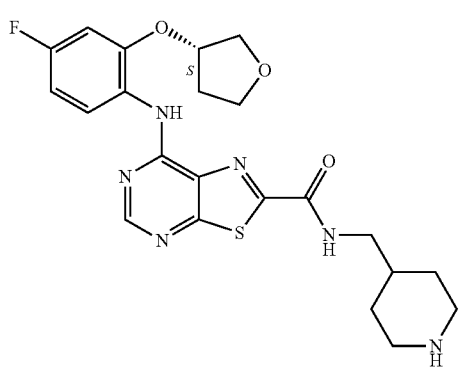
54
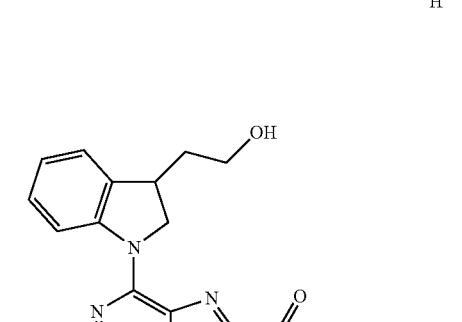
136
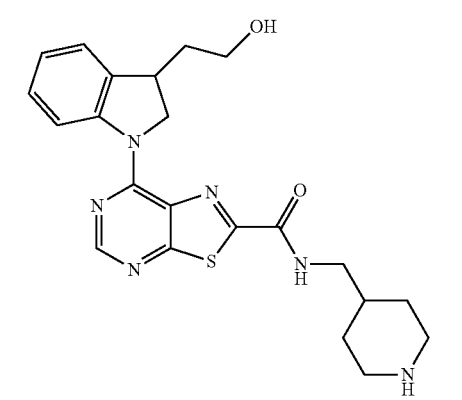
137
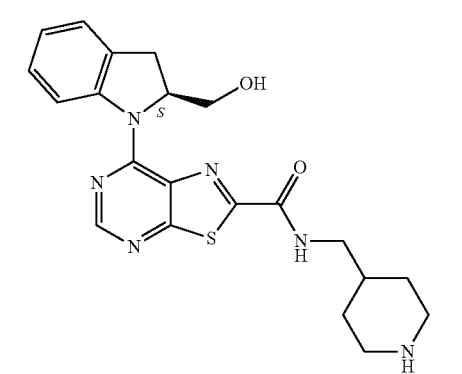
138
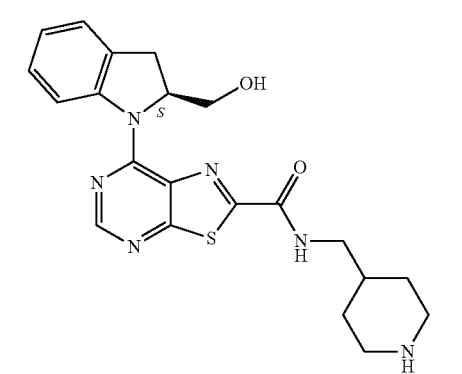
139
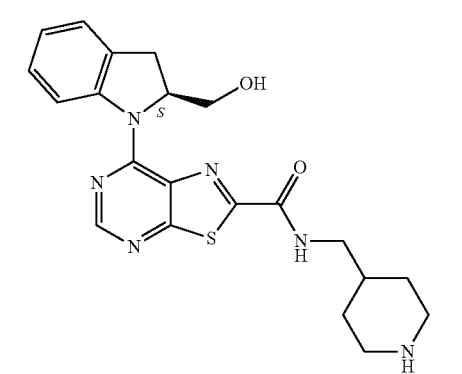
140
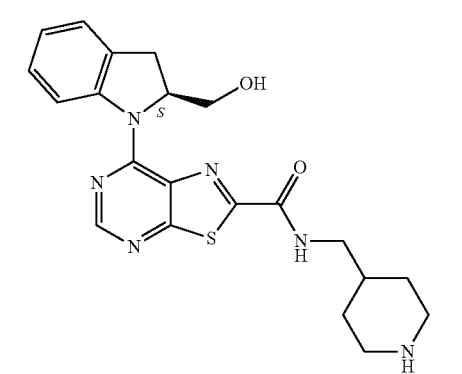
55

-continued
56
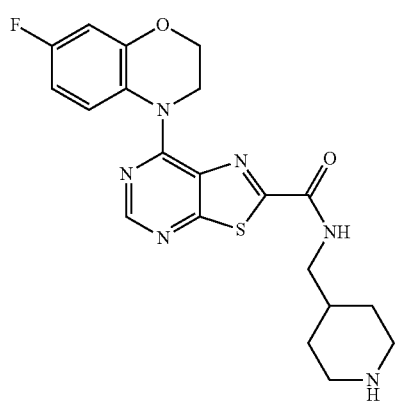
57
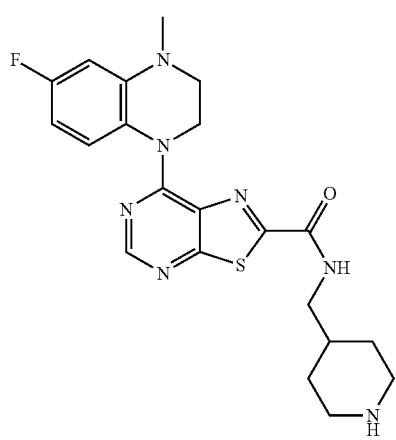
58
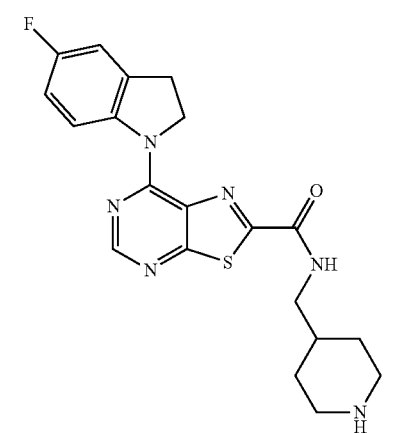
-continued
59
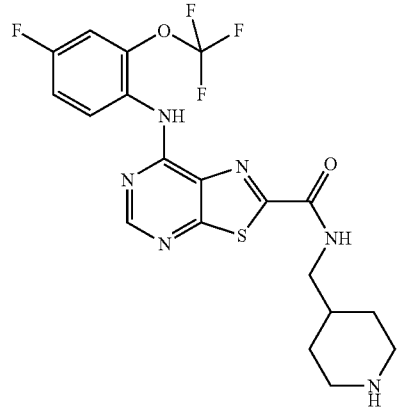
141
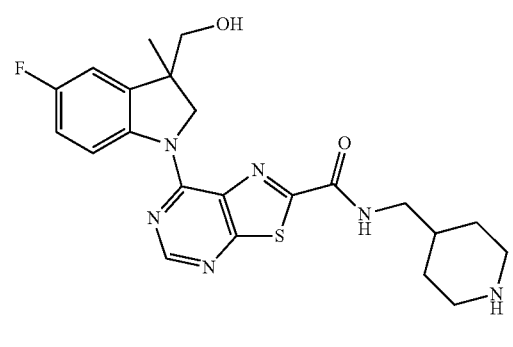
142
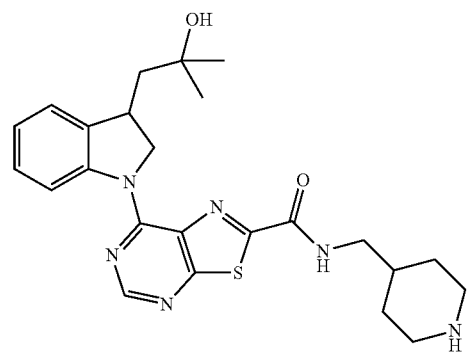
143
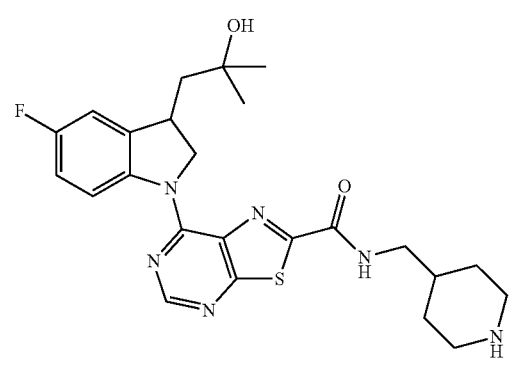

144
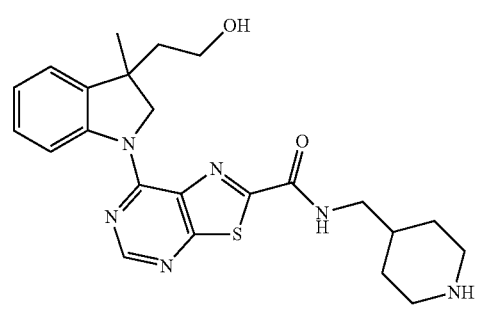
145
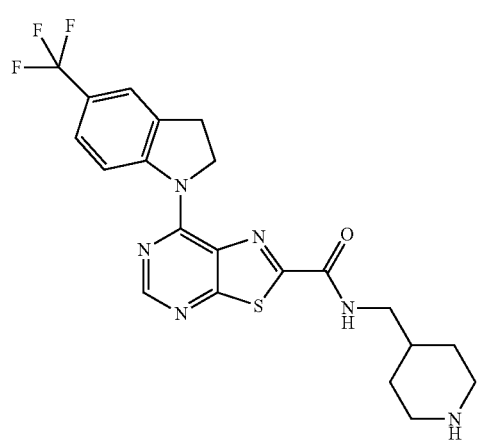
60
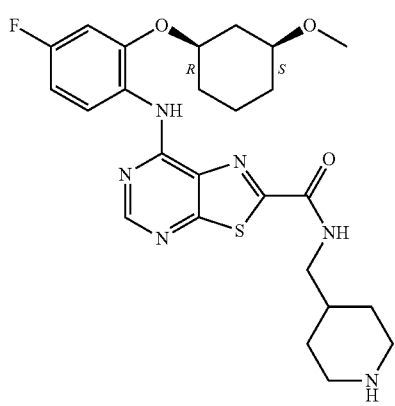
61
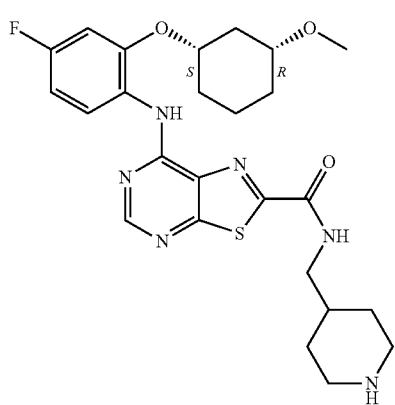
62
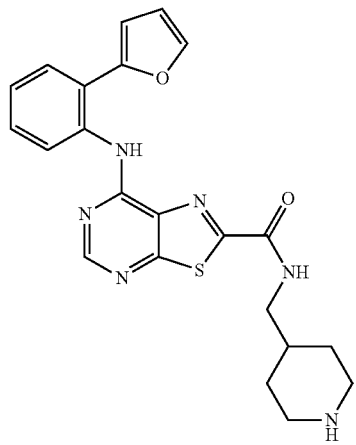
63
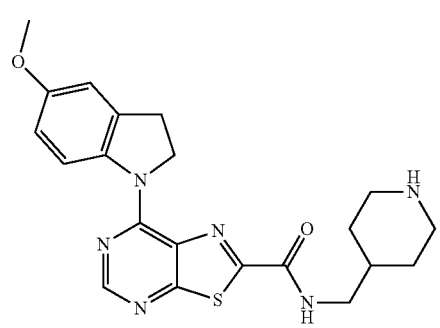
64
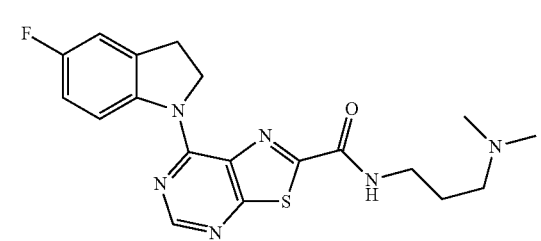
146
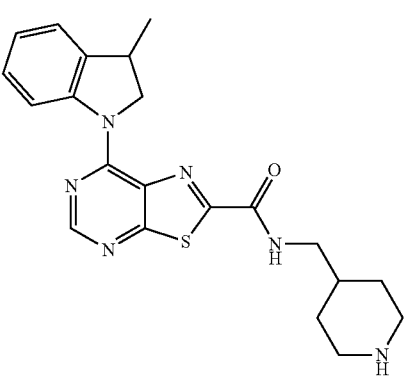

147 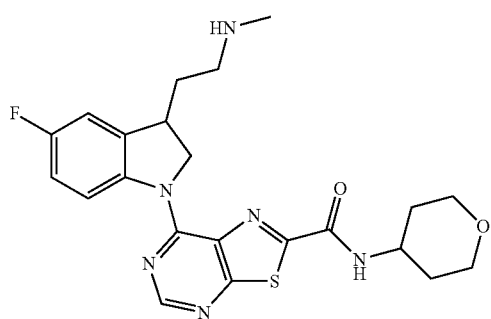
148 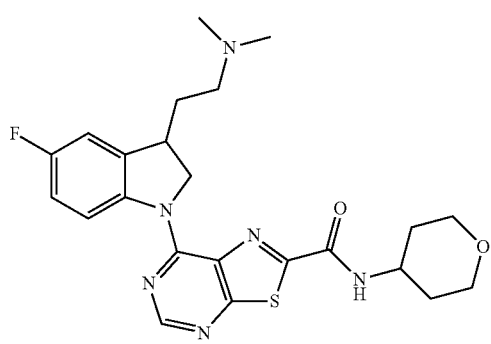
149 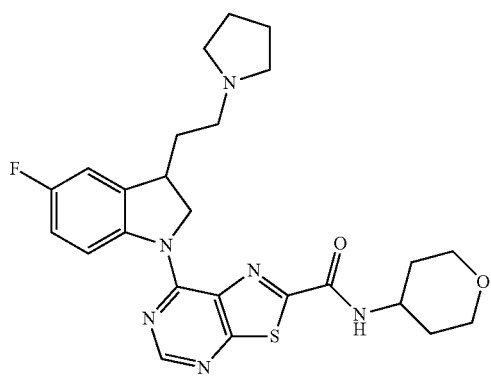
150 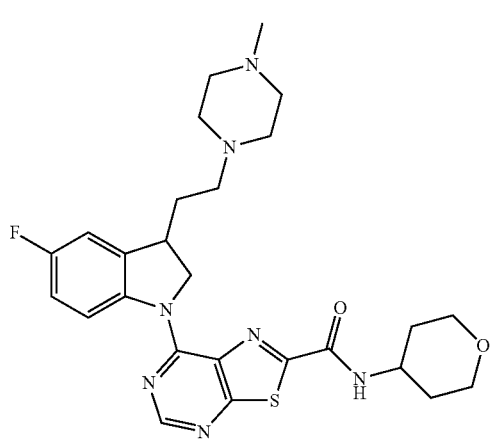
65 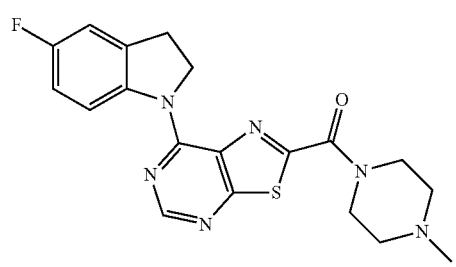
66 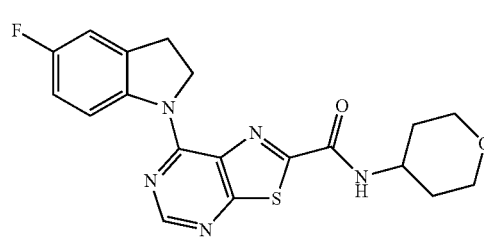
67 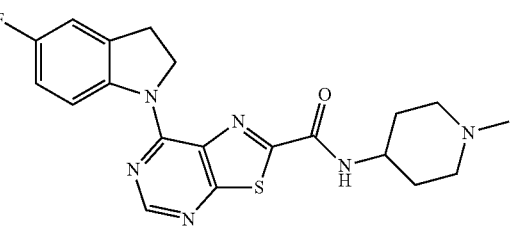
68 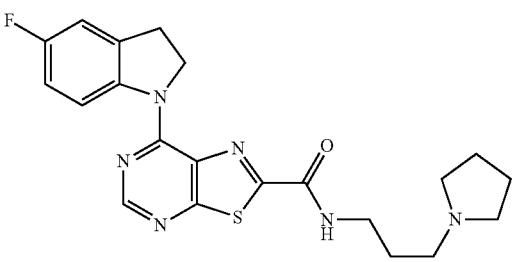
69 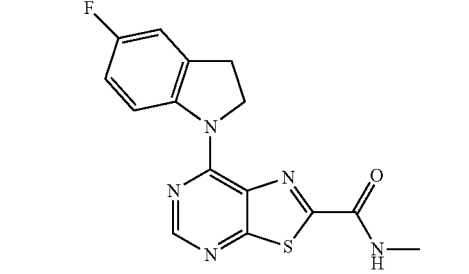

151 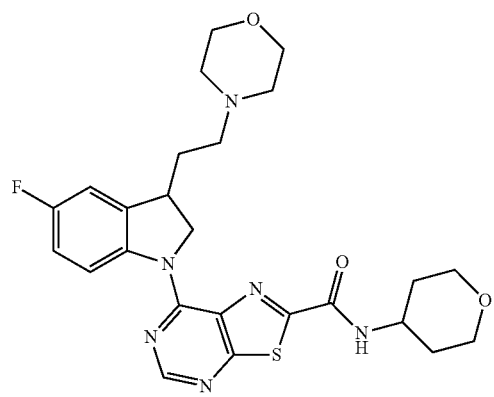
155 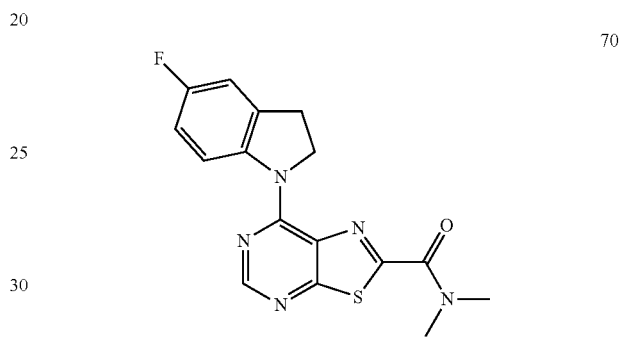
152 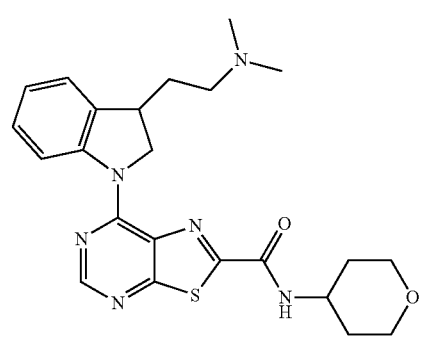
70 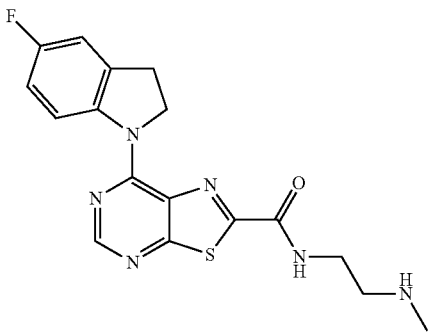
153 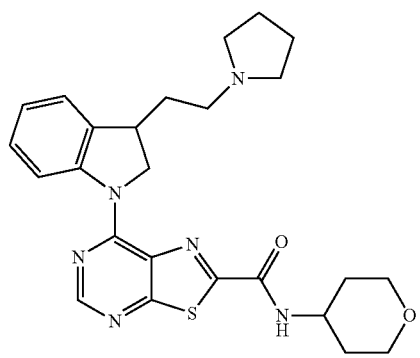
71
154 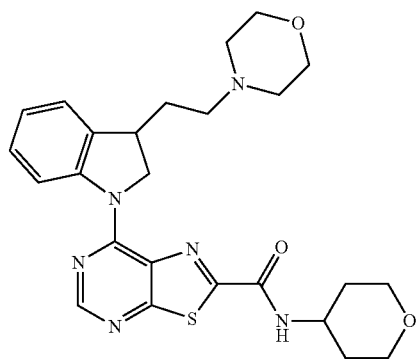
72 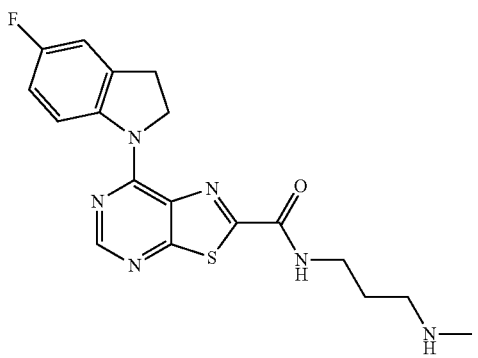

73
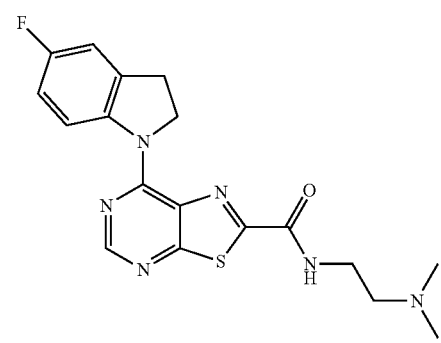
74
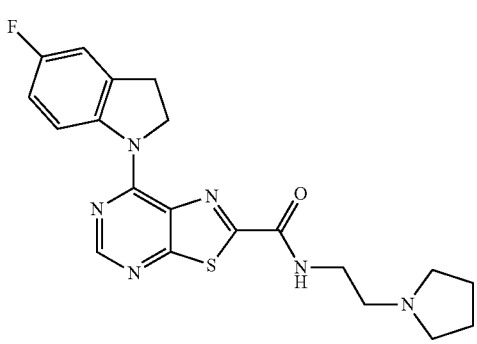
156
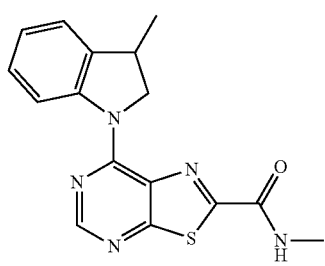
157
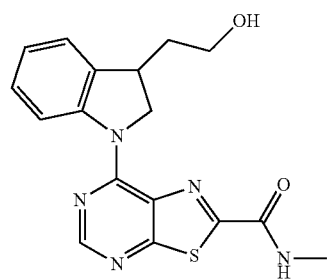
158
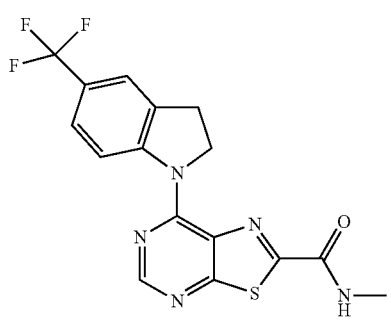
159
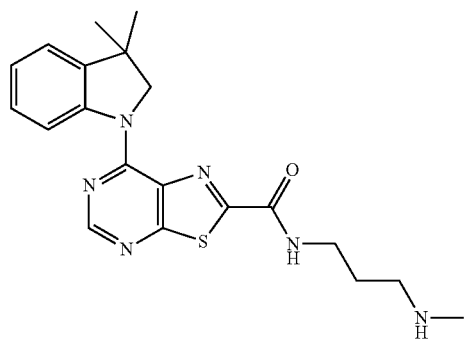
160
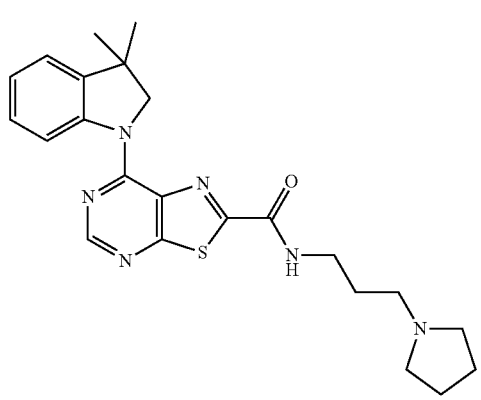
75
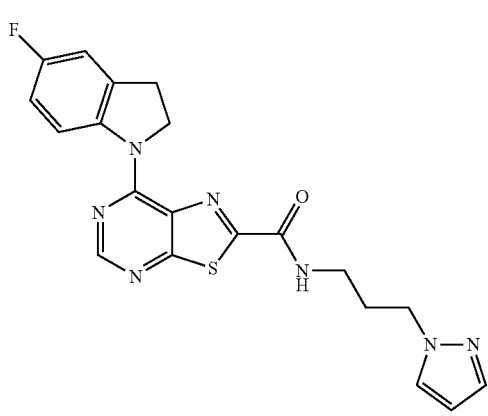
76
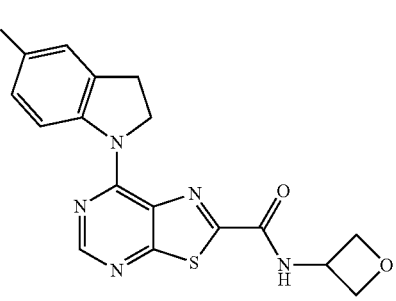

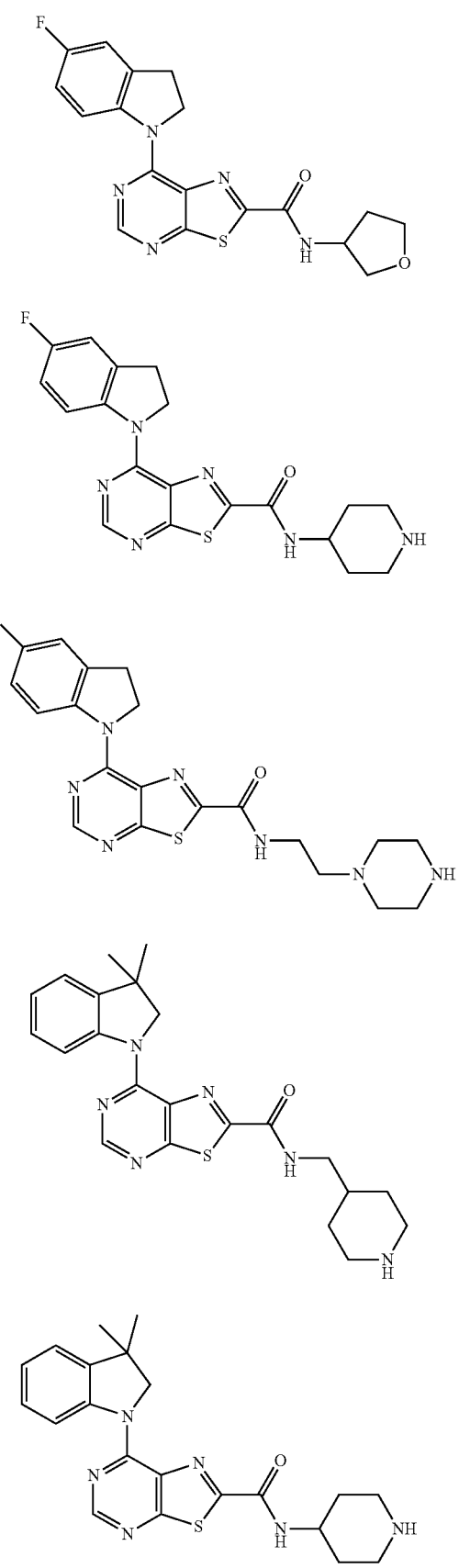
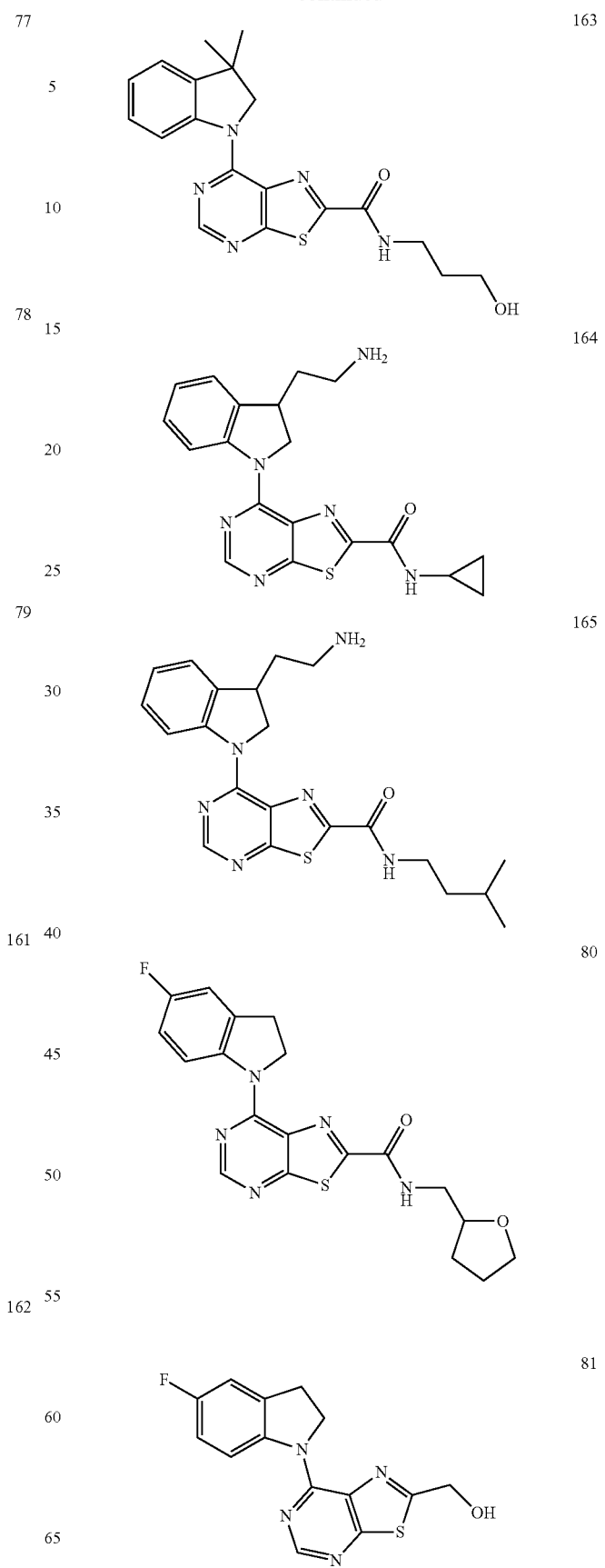

82 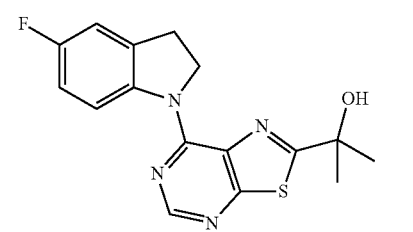
83 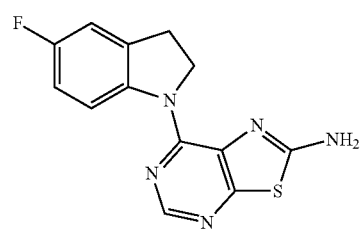
166 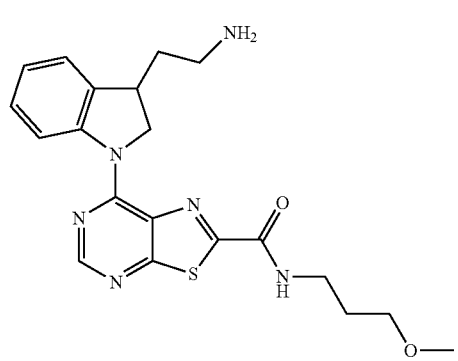
167 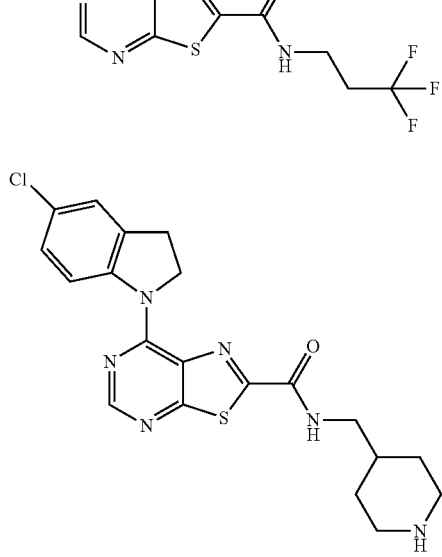
168 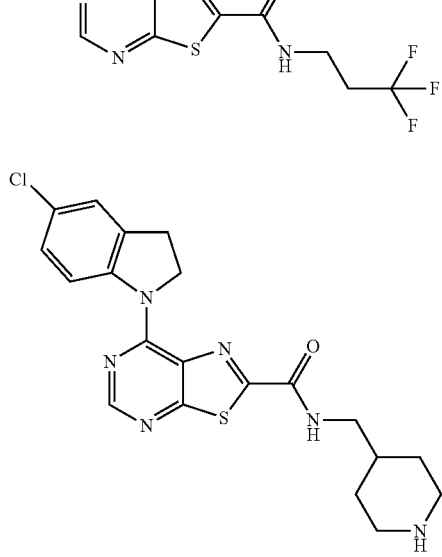
169 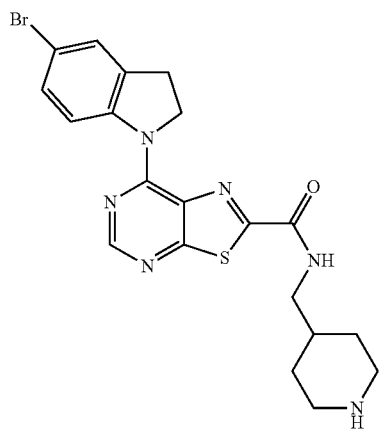
84 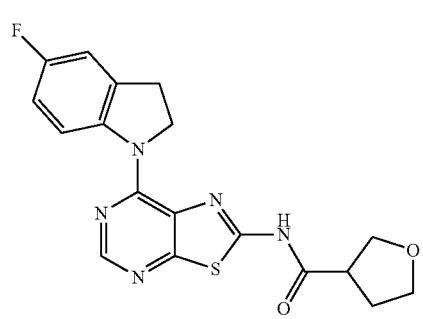
85 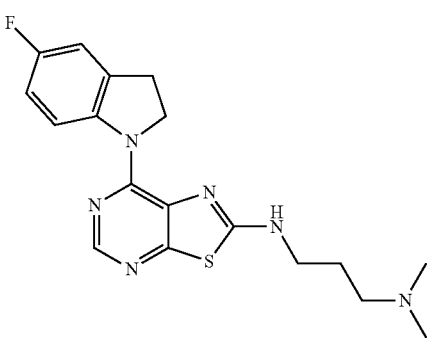
86 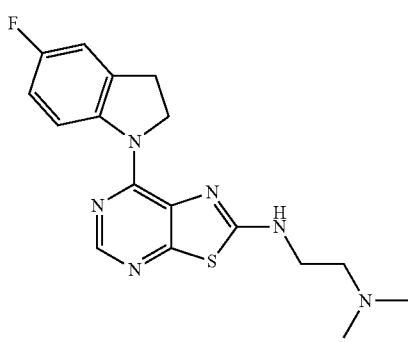

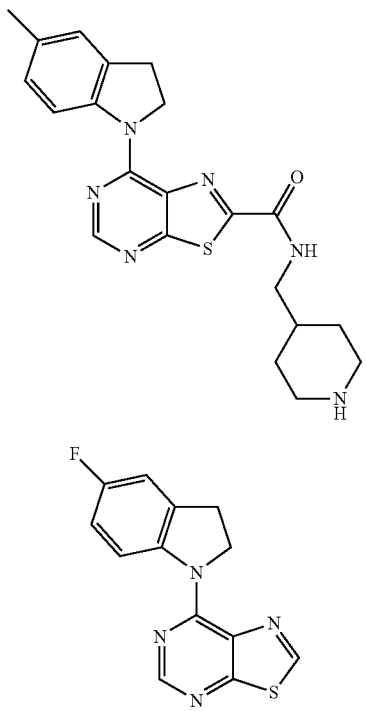

and pharmaceutically acceptable salts thereof.

Therapeutic Applications

A further aspect of the invention relates to a compound as described above for use in medicine.

Another aspect of the invention relates to a compound as described above for use in treating a proliferative disorder.

In one preferred aspect, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is mediated by the MKNK-1 pathway.

In one preferred embodiment, the disease of uncontrolled cell growth, proliferation and/or survival, inappropriate cellular immune response, or inappropriate cellular inflammatory response is a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

As MNKs are the only kinases known to phosphorylate eIF4E, inhibition of eIF4E phosphorylation through inhibition of MNKs is expected to negatively affect these pathways and hence interfere with progression of cancer and metastases. Surprisingly, MNK1/2 double KO mice show no overt phenotype, which is unexpected given the central role of eIF4E. Still, MNK phosphorylation of eIF4E on Serin 209 is believed to be important for eIF4E's oncogenic activity as overexpression of constitutively active MNK1 but not kinase-inactive MNK1 was shown to accelerate tumour formation in mouse embryonic fibroblasts (Chrestensen et al. Genes Cells 2007, 1133-1140). Constitutively active MNK1 but not kinase dead was also shown to promote tumour growth in an Eμ-Myc transgenic model in hematopoletic stem cells. Vice versa, deficiency of MNKs (double KO) was found to delay the development of tumours in a lymphoma model induced by the loss of PTEN (Ueda et al. Proc Natl Acad Sci USA 2010, 13984-13990). This is in line with results obtained using mutated forms of eIF4E. eIF4E S209D mimics the phosphorylated version eIF4E and eIF4E S209A cannot be phosphorylated. Mice reconstituted with cells expressing the S209A mutant were defective at promoting tumorigenesis. By contrast, mice reconstituted with cells expressing the phosphomimetic S209D mutant displayed accelerated tumor onset (Wendel et al. Genes Dev 2007, 3232-3237).

Pharmacological inhibition of MNK using anti-fungal agent cercosporamide was shown to effectively block eIF4E phosphorylation within 30 minutes after oral administration in normal mouse tissues and xenografted tumors, reducing tumor growth in HCT116 xenograft models, and suppressing the outgrowth of B16 melanoma lung metastases. Collectively, these data substantiate the notion that blocking Mnk function, and eIF4E phosphorylation, may be an attractive anticancer strategy (Konicek at al. Cancer Res 2011, 1849-1857). This notion has been further supported by the use of more specific MNK inhibitory compounds in cellular models of leukemia, where MNK inhibitors were shown to have an anti-proliferative effect (Teo et al. Mol Pharmacol 2015, 380-389, Too et al. Cancer Lett 2015, 612-623).

In addition to cancer MNKs are promising targets for anti-inflammatory therapy. MNKs were shown to be involved in regulating TNF-production on a post transcriptional level. TNF expression is controlled via AU-rich elements in the 3'UTR of its mRNA. MNK inhibition or knockdown of MNK1 was shown to inhibit TNF production in Jurkat cells, whereas overexpression of the 3'UTR of TNF enhanced the expression of a reporter construct (Buxade at al. Immunity 2005, 177-189). In the macrophage cell line RAW264.7 stimulation with different TLR agonists, LPS or CpG DNA in presence of MNK inhibitor reduced TNF production, correlating with an increase in TNF mRNA decay (Rowlett et al. Am J Physiol Gastrointest Liver Physiol 2008, G452-459). In BMDMs isolated from a spontaneous mouse model of Crohn's disease-like ileitis, treatment with MNK inhibitor inhibited production of TNF and IL-6. A study in the monocytic cell line THP-1 showed that the release of IL-11 and IL-8 induced by Shiga toxin could be blocked by MNK inhibitor CGP57380 by 73-96% (Cherla et al. J Leukoc Biol 2006, 397-407). In neutrophils, it was shown that MNK plays a role in the activation of neutrophils in response to LPS and TNF stimulation. MNK inhibition not only affected cytokine production by neutrophils but also inhibited the anti-apoptotic effect of TNF and LPS on neutrophils.

Another study shows reduced TNF-production in keratinocytes in the presence of MNK inhibitor CGP57380 along with decreased expression of IL-1 β and IL-6, thereby implicating MNK in regulation of pro-inflammatory cytokine expression in inflammatory skin diseases (Kjellerup et al. Exp Dermatol 2008, 498-504). Interleukin 17 is proinflammatory cytokine that acts synergistically with TNF and IL-1β. In murine CD4 T cells which were activated under Th17 conditions in the presence of MNK inhibitor, blockage of eIF-4E phosphorylation was detected, resulting in reduced IL-17 production without affecting IL-17 mRNA (Noubade et al. Blood 2011, 3290-3300). RANTES, which is a chemokine involved in the terminal differentiation of T cells was found to be indirectly regulated by MNK via its major transcriptional regulator RFLAT1. Inhibition of MNK was shown to reduce RFLAT1 production (Nikolcheva et al. J Clin Invest 2002, 119-126).

Another aspect of the invention relates to a compound as described above for use in treating a neurodegenerative disorder, more preferably a tauopathy.

Tauopathies are a class of neurodegenerative diseases associated with the pathological aggregation of tau protein-in the human brain. The best-known of these illnesses is Alzheimer's disease (AD), wherein tau protein is deposited within neurons in the form of neurofibrillary tangles (NFTs). Tangles are formed by hyperphosphorylation of a microtubule-associated protein known as tau, causing it to aggregate in an insoluble form. These aggregations of hyperphosphorylated tau protein are also referred to as PHF, or "paired helical filaments".

In one preferred embodiment of the invention, the tauopathy is Alzheimer's disease.

Another aspect relates to the use of a compound as described above in the preparation of a medicament for treating or preventing a neurodegenerative disorder. Preferably, the neurodegenerative disorder is Alzheimer's Disease.

Another aspect relates to the use of a compound as described above in the preparation of a medicament for treating or preventing a proliferative disorder, preferably cancer or leukemia.

Preferably, the compound is administered in an amount sufficient to inhibit one or more kinases, preferably MNK 1 and/or MNK2.

In one preferred embodiment, the compound is administered in an amount to inihibit MNK1.

In one preferred embodiment, the compound is administered in an amount to inihibit MNK2.

Yet another aspect relates to the use of a compound of the invention in the preparation of a medicament for the prevention or treatment of a disorder caused by, associated with or accompanied by any abnormal activity against a biological target, wherein the target is a kinase, more preferably MNK.

Another aspect of the invention relates to a method of treating a protein kinase related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of a protein kinase, wherein the method comprises administering to a mammal a therapeutically effective amount of a compound according to the invention.

Preferably, the disease state is alleviated by the inhibition of the protein kinase MNK.

Preferably, the mammal is a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a protein kinase together in such a manner that the compound can affect the enzyme activity of the protein kinase either directly; i.e., by interacting with the protein kinase itself or indirectly; i.e., by interacting with another molecule on which the catalytic activity of the protein kinase is dependent. As used herein, administration can be accomplished either in vitro, i.e. In a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{60}$ and the $ED_{60}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{60}$ with little or no toxicity. The dosage may vary within this range depending upon the dosage form employed and the route of administration utilized. The exact formulation, route of administration and dosage can be chosen by the individual physician in view of the patient's condition. (see, e.g., Fingi et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "kinase related disease or disorder" refers to a disease or disorder characterized by inappropriate kinase activity or over-activity of a kinase as defined herein. Inappropriate activity refers to either; (I) kinase expression in cells which normally do not express said kinase; (ii) increased kinase expression leading to unwanted cell proliferation, differentiation and/or growth; or, (iii) decreased kinase expression leading to unwanted reductions in cell proliferation, differentiation and/or growth. Over-activity of kinase refers to either amplification of the gene encoding a particular kinase or production of a level of kinase activity, which can correlate with a cell proliferation, differentiation and/or growth disorder (that is, as the level of the kinase increases, the severity of one or more of the symptoms of the cellular disorder increases). Over activity can also be the result of ligand independent or constitutive activation as a result of mutations such as deletions of a fragment of a kinase responsible for ligand binding.

Preferred diseases or disorders that the compounds described herein may be useful in preventing, include neurodegenerative disorders such as Alzheimer's Disease, and proliferative disorders, such as cancer.

Thus, the present invention further provides use of compounds as defined herein for the manufacture of medicaments for the treatment of diseases where it is desirable to inhibit MNK. Such diseases include proliferative disorders and neurodegenerative disorders such as Alzheimer's Disease, as described above.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and PJ Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or on-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicroblals, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or (II) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylproplonate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydrolodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) or (II) where any hydrogen atom has been replaced by a deuterium atom, isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I)/(II) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an Individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of the invention may be administered to inhibit the kinase implicated with a particular condition or disease. Of course, this dosage amount will further be modified according to the type of administration of the compound. For example, to achieve an "effective amount" for acute therapy, parenteral administration of a compound of general formula (I) or (II) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e.

before, simultaneously, or after delivery. Such scheduling may be a feature of all the active agents identified herein.

In one preferred embodiment, the additional active agent is selected from an antidiabetic agent, a lipid lowering agent, a cardiovascular agent, an antihypertensive agent, a diuretic agent, a thrombocyte aggregation inhibitor, an antineoplastic agent and an anti-obesity agent.

In one preferred embodiment, the additional active agent is selected from a histamine antagonist, a bradikinin antagonist, serotonin antagonist, leukotriene, an anti-astinnatic, an NSAID, an antipyretic, a corticosteroid, an antibiotic, an analgetic, a uricosuric agent chemotherapeutic agent, an anti gout agent, a bronchodilator, a cyclooxygenase-2 inhibitor, a steroid, a 5-lipoxygenase inhibitor, an innmmosuppressive agent, a leukotriene antagonist, a cytostatic agent, an antineoplastic agent, am Tor inhibitor, a Tyrosine kinase inhibitor, antibodies or fragments thereof against cytokines and soluble parts (fragments) of cytokine receptors.

Assay

A further aspect of the invention relates to the use of a compound as described above in an assay for identifying further candidate compounds capable of inhibiting one or more kinases, more preferably MNK.

Preferably, the assay is a competitive binding assay.

More preferably, the competitive binding assay comprises contacting a compound of the invention with a kinase, preferably MNK, and a candidate compound and detecting any change in the interaction between the compound according to the invention and the kinase.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to a kinase, said method comprising the steps of:
(i) contacting a ligand with a kinase in the presence of a known substrate of said kinase;
(ii) detecting any change in the interaction between said kinase and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove. Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders as described above.

The above methods may be used to screen for a ligand useful as an inhibitor of one or more kinases.

Compounds of the invention are useful both as laboratory tools and as therapeutic agents. In the laboratory certain compounds of the invention are useful in establishing whether a known or newly discovered kinase contributes a critical or at least significant biochemical function during the establishment or progression of a disease state, a process commonly referred to as 'target validation'.

The present invention is further described by way of the following non-limiting examples.

EXAMPLES

General Procedures for Synthesis of Compounds

Chromatography

Preparative high pressure liquid chromatography was carried out using apparatus made by Agilent. The apparatus is constructed such that the chromatography is monitored by a multi-wavelength UV detector (G1365B manufactured by Agilent) and an MM-ES+APCl mass spectrometer (G-1956A, manufactured by Agilent) connected in series, and if the appropriate criteria are met the sample is collected by an automated fraction collector (G1364B manufactured by Agilent). Collection can be triggered by any combination of UV or mass spectrometry or can be based on time. Typical conditions for the separation process are as follows: Chromatography column was an Xbridge C-18 (19×100 mm); the gradient was run over a 7 minute period at a flow rate of 40 ml/min (gradient at start: 10% methanol and 90% water, gradient at finish: 100% methanol and 0% water; as buffer: either 0.1% formic acid, 0.1% ammonium hydroxide or 0.1% trifluoroacetic acid was added to the water). It will be appreciated by those skilled in the art that it may be necessary or desirable to modify the conditions for each specific compound, for example by changing the solvent composition at the start or at the end, modifying the solvents or buffers, changing the run time, changing the flow rate and/or the chromatography column. Flash chromatography refers to silica gel chromatography and carried out using an SP4 or an isolara 4 MPLC system (manufactured by Biotage); pre-packed silica gel cartridges (supplied by Biotage); or using conventional glass column chromatography.

Analytical Methods

¹H Nuclear magnetic resonance (NMR) spectroscopy was carried out using an ECX400 spectrometer (manufactured by JEOL) In the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; br, broad.

Analytical LCMS was typically carried out using an Agilent HPLC instrument with C-18 Xbridge column (3.5 μm, 4.6×30 mm, gradient at start: 10% organic phase and 90% water, gradient at finish: organic and 0% water; as buffer either 0.1% ammonium hydroxide or 0.1% trifluoroacetic acid was added to the water). The organic solvent was either acetonitrile or methanol. A flow rate of 3 mL/min was used with UV detection at 254 and 210 nm.

Mass spectra were recorded using a MM-ES+APCl mass spectrometer (G-1956A, manufactured by Agilent). Where thin layer chromatography (TLC) has been used it refers to silica gel TLC using silica gel MK6F 60 Å plates, $R_f$ is the distance travelled by the compound divided by the distance travelled by the solvent on a TLC plate.

Compound Preparation

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

Where reactions are carried out using microwave irradiation, the microwave used is an initiator 60 supplied by Biotage. The actual power supplied varies during the course of the reaction in order to maintain a constant temperature.

Some hydrogenations were carried out using an H-Cube® Continuous-flow Hydrogenation Reactor manufactured by ThalesNano. The catalysts are supplied by ThalesNano as cartridges "CatCarts" The pressure, flow rate, temperature and cartridge are indicated in the experimental section. The equipment was used in accordance with the manufacturer operating procedure. The person skilled in the art will appreciate that it may be necessary or desirable to run repeat cycles of the reaction mixture and in some instances, replace the cartridge between cycles to improve the yield of the reaction.

ABBREVIATIONS

A list of some common abbreviations are shown below— where other abbreviations are used which are not listed, these will be understood by the person skilled in the art.

DCM=Dichloromethane
DMF=N,N-Dimethylformamide
THF=Tetrahydrofuran
MeOH=Methanol
TFA=Trifluoroacetic acid
Xantphos=4,5-Bis(diphenylphosphino)-9,9-dimethylxanthene
HATU=N, N,N',N'-Tetramethyl-O-(7-azabenzotriazol-1-yl) uronium-hexafluorophosphate
EDCI=1,3-Propanediamine, N3-(ethylcarbonimidoyl)-N1, N1-dimethyl-, hydrochloride
DCC=1,3-Dicyclohexylcarbodiimide
$Pd_2(dba)_3$.tris(dibenzylideneacetone)dipalladium(0)
TEA=Triethylamine
rm=Reaction mixture
rt=Room temperature
AcOH=Acetic acid
IPA=isopropanol DIPEA=N,N-diisopropylethylamine
TBSMSCI=Tertiarybutyldimethylsilyl chloride
MeCN=Acetonitrile
$NH_3$=Ammonia
EtOH=Ethanol
EtOAc=Ethyl Acetate
LCMS=Mass spectrometry directed high pressure liquid chromatography
UV=Ultraviolet
SCX=Strong cation exchange
TPAP=Tetrapropylammonium perruthenate
DMSO=Dimethylsulphoxide
BINAP=2,2'-bis(diphenylphosphino)-1,1'-binaphthyl
TPAP=Tetrapropylammonium perruthenate
DIAD=Diisopropyl azodicarboxylate
NMO=N-Methylmorpholine N-oxide Intermediate 1

Ethyl 7-(4-fluoro-2-isopropoxy-anilino)thiazolo[5,4-d]pyrimidine-2-carboxylate

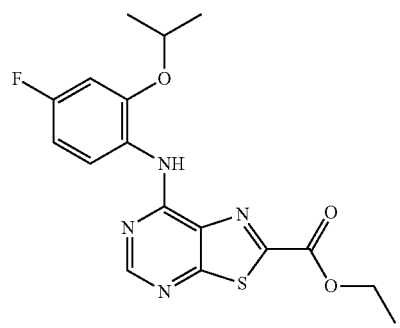 [SMILES: CCOC(=O)c1nc2c(Nc3ccc(F)cc3OC(C)C)ncnc2s1]

To a solution of ethyl 7-methylsulfanylthiazolo[5,4-d]pyrimidine-2-carboxylate (0.5 g, 1.9 mmol) in DCM (20 ml) was added m-CPBA (675 mg, 3.9 mmol) and stirred for 2 hours at room temperature. 4-Fluoro-2-isopropxyaniline (331 mg, 1.9 mmol) in dioxane (20 ml) was then added and stirred for 1.5 hours. The mixture was diluted with DCM and water, the organic layer separated, dried and concentrated onto silica. The compound was purified via column chromatography (20-80% EtOAc in Pet. Ether) to give an orange solid (706 mg, 95%); ¹H NMR (400 MHz, CHLOROFORM-d) δ ppm 1.45 (d, J=5.95 Hz, 6H), 1.50 (t, J=6.90 Hz, 3H), 4.52-4.58 (m, 2H), 4.58-4.67 (m, 1H), 6.69-6.81 (m, 2H), 8.55 (dd, J=8.93, 6.18 Hz, 1H), 8.68 (s, 1H), 8.69-8.73 (m, 1H); LC-MS (ESI): (MH+) 377.1

Intermediate 2

7-Methylsulfanylthiazolo[5,4-d]pyrimidine-2-carboxylic acid

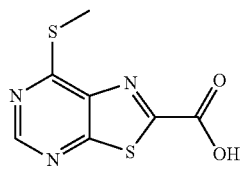

To a solution of ethyl 7-methylsulfanylthiazolo[5,4-d]pyrimidine-2-carboxylate (5 g, 19.6 mmol) in THF (100 ml) was added 15% NaOH$_{(aq)}$ (40 ml, 98 mmol) and stirred for 2 hours. The mixture was acidified with 2M HCl$_{(aq)}$ and the resulting pale yellow solid collected and dried via vacuum filtration to give 7-methylsulfanylthiazolo[5,4-d]pyrimidine-2-carboxylic acid (4.45 g, 100%); $^1$H NMR (400 MHz, DMSO-d$_6$) δ ppm 2.70 (s, 3H), 8.94-9.10 (m, 1H)

Intermediate 3

Tert-butyl 4-[[(7-methylsulfanylthiazolo[5,4-d]pyrimidine-2-carbonyl)amino]methyl]piperidine-1-carboxylato

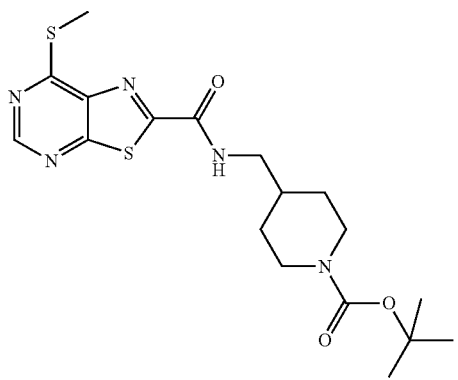 [SMILES: CSc1ncnc2sc(C(=O)NCC3CCN(C(=O)OC(C)(C)C)CC3)nc12]

Thionyl chloride (30 ml) was added to intermediate 2 (4.45 g, 19.6 mmol) and the mixture heated at reflux for 2.5 hours, until an orange solution was formed. The mixture was cooled and concentrated to give a yellow solid, which was taken up in DCM (30 ml) and cooled to 0° C. Triethylamine (8.48 ml, 58.8 mmol) was added to the mixture, followed by dropwise addition of tert-butyl 4-(aminomethyl)piperidine-1-carboxylate (4.61 g, 21.6 mmol) and stirring was continued overnight. The mixture was diluted with DCM and water, the organic phase separated, dried and concentrated onto silica. Purification by flash column chromatography (gradient elution from 10-50% EtOAc in Pet. Ether) gave a peach solid (5.49 g, 68%); $^1$H NMR (400 MHz, CHLOROFORM-d) δ ppm 1.19-1.28 (m, 2H), 1.46 (s, 9H), 1.73-1.80 (m, 2H), 1.82-1.91 (m, 1H), 2.73 (m, 5H), 3.42 (m, 2H), 4.10-4.21 (m, 2H), 7.49 (br. t, J=6.4 Hz, 1H), 8.89 (s, 1H); LC-MS (ESI): (MH+—BOC) 324.0

Intermediate 4

N-[3-(dimethylamino)propyl]-7-methylsulfanylthiazolo[5,4-d]pyrimidine-2-carboxamide

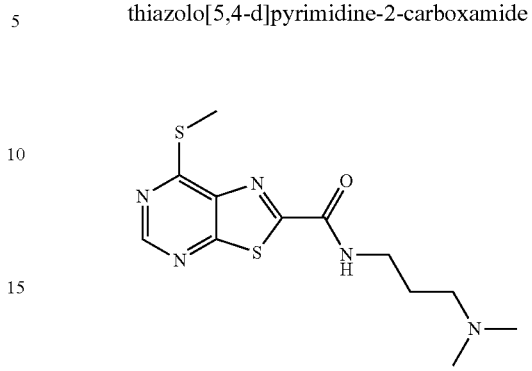

Intermediate 2 (2 g, 8.81 mmol) was refluxed in thionyl chloride (20 ml) for 4 h and the mixture was concentrated under reduced pressure. The residue was dissolved in DCM (50 ml), cooled to 0° C. and triethylamine (3.67 ml, 26.3 mmol) followed by N',N'-dimethylpropane-1,3-diamine (1.67 ml, 10.6 mmol) was added, and the resulting mixture was stirred at room temperature for 18 h. The mixture was diluted with DCM and quenched with water. The layers were separated, the aqueous phase was extracted with DCM, the combined organic phases were washed (brine), dried (MgSO$_4$) and concentrated under reduced pressure. Purification by flash chromatography (gradient elution from 0-10% (2M ammonia in methanol) in dichloromethane) gave a pale yellow solid (1.75 g, 64%). $^1$H NMR (400 MHz, DMSO-d$_6$) δ ppm 1.72 (quin, J=6.87 Hz, 2H), 2.22 (s, 6H), 2.37 (t, J=6.64 Hz, 2H), 2.71 (s, 3H), 3.34-3.41 (m, 2H), 9.01 (s, 1H), 9.53 (t, J=5.72 Hz, 1H); LC-MS (ESI): (MH+) 312.

Intermediate 5

1-(4-Nitrophenyl)-3-[3-(trifluoromethyl)phenyl]urea

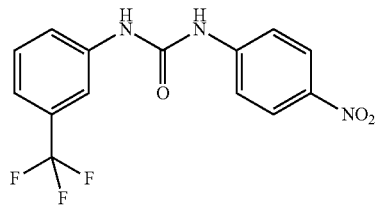

To a solution of 4-nitroaniline (1 g, 7.25 mmol and triethylamine (3.14 ml, 21.7 mmol) in THF (20 ml) was added 3-(trifluoromethyl)phenyl isothiocyante (1.5 g, 7.97 mmol) and stirred overnight. The mixture was diluted with EtOAc and water, the organic layer separated, dried and concentrated onto silica. The compound was purified via column chromatography (gradient elution from 20-100% EtOAc in Pet. Ether) to give a yellow solid (1.047 g, 45%); $^1$H NMR (400 MHz, DMSO-d$_6$) δ ppm 7.25-7.36 (m, 2H), 7.49 (m, 2H), 7.54-7.60 (m, 1H), 7.65-7.71 (m, 1H), 7.98 (a, 1H), 8.13-8.21 (m, 1H), 9.10-9.30 (m, 1H), 9.51-9.67 (m, 1H).

Intermediate 6

1-(4-Aminophenyl)-3-[3-(trifluoromethyl)phenyl]urea

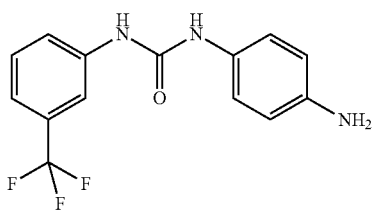 [SMILES: Nc1ccc(NC(=O)Nc2cccc(C(F)(F)F)c2)cc1]

A solution of intermediate 5 (100 mg, 0.31 mmol) in MeOH (5 ml) and EtOAc (5 ml) was hydrogenated using the H-Cube flow reactor (Cartridge: 10% Pd/C; flow rate: 1 ml/min$^{-1}$; temperature: 35° C.; H$_2$ pressure: Full H$_2$ Pressure. The final solution was concentrated to give 1-(4-aminophenyl)-3-[3-(trifluoromethyl)phenyl]urea (71 mg, 79%), a white solid; $^1$H NMR (400 MHz, DMSO-d$_6$) δ ppm 4.74 (br. s, 2H), 6.47 (m, 2H), 7.03 (m, 2H), 7.18-7.25 (m, 1H), 7.40-7.50 (m, 2H), 7.96 (s, 1H), 8.20 (s, 1H), 8.82 (s, 1H); LC-MS (ESI): (MH$^+$) 296.1

Intermediate 7

Ethyl 7-(5-fluoroindolin-1-yl)thiazolo[5,4-d]pyrimidine-2-carboxylate

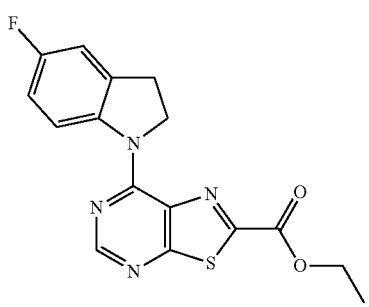 [SMILES: CCOC(=O)c1nc2c(N3CCc4cc(F)ccc43)ncnc2s1]

To a solution of ethyl 7-methylsulfanylthiazolo[5,4-d]pyrimidine-2-carboxylate (8.25 g, 32 mmol) in DCM (50 ml) was added m-CPBA (11.05 g, 64 mmol) and the resulting mixture stirred for 2 hours, prior to addition of 5-fluoroindoline (4.43 g, 32 mmol) in 1,4-dioxane (20 ml) was added and stirring was continued overnight. A yellow precipitate formed, which was collected and dried via vacuum filtration to afford ethyl 7-(5-fluoroindolin-1-yl)thiazolo[5,4-d]pyrimidine-2-carboxylate, a yellow solid (8.8 g, 80%); $^1$H NMR (400 MHz, DMSO-d$_6$) δ ppm 1.34 (t, J=7.3 Hz, 3H), 3.33 (t, 2H), 4.43 (q, J=6.9 Hz, 2H), 4.81 (t, J=7.8 Hz, 2H), 7.04-7.12 (m, 1H), 7.18-7.25 (m, 1H), 8.59-8.70 (m, 2H); LC-MS (ESI): (MH$^+$) 345.0

Intermediate 8

7-(5-Fluoroindolin-1-yl)thiazolo[5,4-d]pyrimidine-2-carboxylic acid

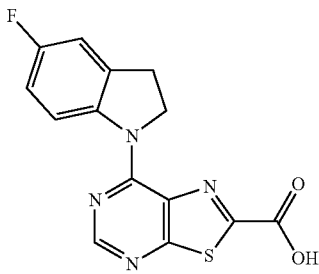 [SMILES: O=C(O)c1nc2c(N3CCc4cc(F)ccc43)ncnc2s1]

To a solution of intermediate 7 (5.46 g, 16 mmol) in THF (70 ml) was added 2M NaOH$_{(aq)}$ (24 ml, 48 mmol) and the mixture stirred for 2 hours. The mixture was acidified with 2M HCl$_{(aq)}$ at which point a yellow precipitate was formed. The precipitate was collected and dried via vacuum filtration to give a yellow solid (3.2 g, 82%); $^1$H NMR (400 MHz, DMSO-d$_6$) δ ppm 3.20-3.28 (m, 2H), 4.82 (t, J=8.7 Hz, 2H), 7.02 (td, J=9.2, 2.8 Hz, 1H), 7.16 (dd, J=8.2, 2.3 Hz, 1H), 8.52 (s, 1H), 8.56 (dd, J=9.2, 5.0 Hz, 1H); LC-MS (ESI): (MH$^+$) 273.0

Intermediate 9

N-(7-Chlorothiazolo[5,4-d]pyrimidin-2-yl)benzamide

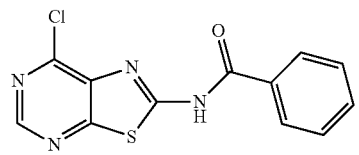 [SMILES: O=C(Nc1nc2c(Cl)ncnc2s1)c1ccccc1]

To a solution of 4,6-dichloropyrimidin-5-amine (250 mg, 1.5 mmol) in acetone (15 ml) was added benzyl isothiocynate (300 mg, 1.8 mmol) and the mixture heated at 60° C. for 4 hours. The mixture was cooled and concentrated by approximately half, at which point a yellow solid precipitated. The solid was collected and dried under vacuum filtration to give yellow solid (248 mg, 56%); $^1$H NMR (400 MHz, DMSO-d$_6$) δ ppm 7.54-7.63 (m, 2H), 7.67-7.75 (m, 1H), 8.12-8.23 (m, 2H), 8.90 (s, 1H)

Intermediate 10

N-[7-(5-Fluoroindolin-1-yl)thiazolo[5,4-d]pyrimidin-2-yl]benzamide

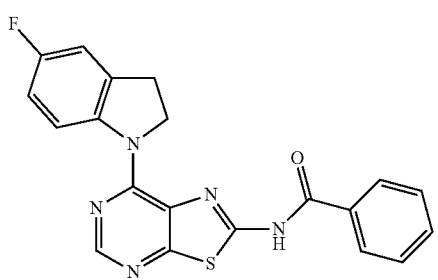 [SMILES: O=C(Nc1nc2c(N3CCc4cc(F)ccc43)ncnc2s1)c1ccccc1]

Intermediate 9 (100 mg, 0.34 mmol), 5-fluoroindoline (81 mg, 0.34 mmol), 4M HCl in dioxane (0.1 ml) and propan-2-ol (2 ml) were combined, sealed in a microwave vial and heated at 140° C. under microwave irradiation for 20 minutes. The mixture was cooled and the solid collected by vacuum filtration to give N-[7-(5-fluoroindolin-1-yl)thiazolo[5,4-d]pyrimidin-2-yl]benzamide, a yellow solid (135 mg, 80%); $^1$H NMR (400 MHz, DMSO-d) δ ppm 3.29 (t, J=8.70 Hz, 2H), 4.90 (t, J=8.47 Hz, 2H), 7.06 (td, J=9.04, 2.98 Hz, 1H), 7.19 (dd, J=8.47, 2.98 Hz, 1H), 7.55-7.62 (m, 2H), 7.66-7.74 (m, 1H), 8.10-8.17 (m, 2H), 8.52-8.59 (m, 2H); LC-MS (ESI): (MH$^+$) 392.0

Intermediate 11

2-Bromo-7-(5-fluoroindolin-1-yl)thiazolo[5,4-d]pyrimidine

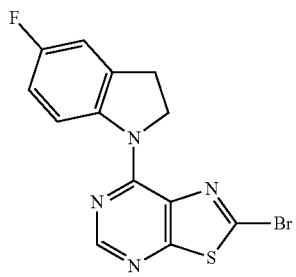 [SMILES: Fc1ccc2c(c1)CCN2c1ncnc2sc(Br)nc12]

Tert-butyl nitrite (72 mg, 0.697 mmol) was added to a solution of 7-(5-fluoroindolin-1-yl)thiazolo[5,4-d]pyrimidin-2-amine (100 mg, 30.35 mmol) and copper (II) bromide (181 mg, 0.523 mmol) in acetonitrile (4 mL) to give a brown suspension. The mixture was heated at 80° C. for 24 hours to give a green precipitate. The precipitate was collected by vacuum filtration, washed with diethyl ether (2×5 mL) and dried under vacuum to give a green solid (10 mg, 82%); $^1$H NMR (400 MHz, DMSO-d$_6$) δ ppm 8.75 (br. s, 1H), 8.52 (dd, J=8.70, 5.04 Hz, 1H), 7.17 (dd, J=9.16, 2.75 Hz, 1H), 7.04 (dd, J=9.16, 2.75 Hz, 1H), 4.68 (s, 2H), 3.24 (t, J=8.24 Hz, 2H); LC-MS (ESI): (MH$^+$) 350.9/352.9

Intermediate 12

7-Fluoroindoline

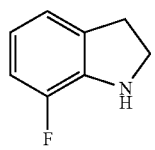

To a solution of 7-fluoroindole (1 g, 7.4 mmol) in DCM (20 ml) was added TFA (5 ml) and cooled to 0° C. Sodium borohydride (562 mg, 14.8 mmol) was added portion wise and stirred overnight. The mixture was basified with sat. Na$_2$CO$_{3(aq)}$ the organic layer separated, dried and concentrated to give 7-fluoroindoline, as a brown oil (986 mg, 97%); $^1$H NMR (400 MHz, CHLOROFORM-d) δ ppm 3.07 (t, J=8.50 Hz, 2H), 3.61 (t, J=8.50 Hz, 2H), 6.59-6.67 (m, 1H), 6.89 (dd, J=7.33, 0.92 Hz, 2H)

Intermediate 13

Ethyl 7-(7-fluoroindolin-1-yl)thiazolo[5,4-d]pyrimidine-2-carboxylate

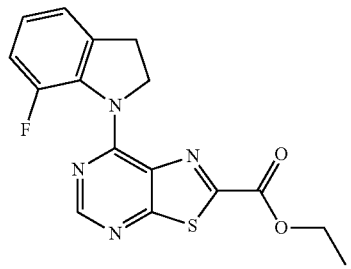 [SMILES: CCOC(=O)c1nc2c(N3CCc4cccc(F)c43)ncnc2s1]

To a solution of ethyl 7-methylsulfanylthiazolo[5,4-d]pyrimidine-2-carboxylate (750 mg, 2.9 mmol) in DCM (30 ml) was added m-CPBA (1.38 g, 6.2 mmol) at 0° C. and the mixture was stirred for 2 hours. Intermediate 12 (443 mg, 3.2 mmol) in dioxane (20 ml) was then added and stirring was continued overnight. The mixture was diluted with DCM and water, the organic layer separated, dried and concentrated onto silica. The compound was purified via column chromatography (2-20% EtOAc in Pet. Ether) to give a yellow gum (260 mg, 25%); $^1$H NMR (400 MHz, CHLOROFORM-d) δ ppm 1.46 (t, J=7.10 Hz, 3H), 3.26 (t, J=7.90 Hz, 2H), 4.51 (q, J=7.40 Hz, 2H), 4.77 (t, J=7.90 Hz, 2H), 6.97-7.11 (m, 3H), 8.67 (s, 1H); LC-MS (ESI): (MH$^+$) 345.0

Intermediate 14

7-(7-Fluoroindolin-1-yl)thiazolo[5,4-d]pyrimidine-2-carboxylic acid

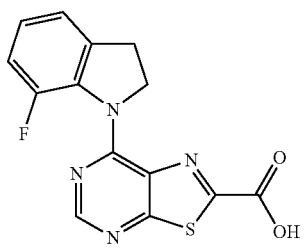 [SMILES: O=C(O)c1nc2c(N3CCc4cccc(F)c43)ncnc2s1]

To a solution of intermediate 13 (260 mg, 0.76 mmol) In THF (2 ml) was added 15% NaOH$_{(aq)}$ (2 ml) and stirred for 3 hours. The mixture was acidified with 2M HCl$_{(aq)}$ and the resulting precipitate collected and dried via vacuum filtration to give 7-(7-fluoroindolin-1-yl)thiazolo[5,4-d]pyrimidine-2-carboxylic acid (210 mg, 88%); $^1$H NMR (400 MHz, DMSO-d$_6$) δ ppm 3.25 (t, J=7.80 Hz, 2H), 4.67 (t, J=7.80 Hz, 2H), 7.03-7.28 (m, 3H), 8.67 (s, 1H); LC-MS (ESI): (MH$^+$) 317.0

Intermediate 15

Ethyl 7-(indolin-1-yl)thiazolo[5,4-d]pyrimidine-2-carboxylate

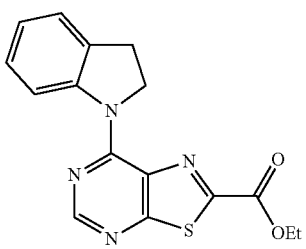 [SMILES: CCOC(=O)c1nc2c(N3CCc4ccccc43)ncnc2s1]

To a stirred solution of ethyl 7-(methylthio)thiazolo[5,4-d]pyrimidine-2-carboxylate (2.50 g, 9.80 mmol) in DCM (20 mL) at 0° C. was added m-CPBA (3.37 g, 19.6 mmol). The resultant mixture was stirred at 0° C. and allowed to warm up to room temperature over 2 hours. Indoline (1.17 g, 9.80 mmol) in dioxane (5 mL) was added and the solution was stirred at room temperature overnight. The mixture was quenched by addition of DCM and water, the organic layer separated and washed with water (2×10 mL). The organic layer was separated, dried and concentrate onto silica. The crude solid was purified by column chromatography (10% EtOAc in Pet. Ether) to give a yellow solid (1.94 g, 61%); $^1$H NMR (400 MHz, DMSO-d) δ ppm 8.63 (m, 2H), 7.32 (d, J=7.33 Hz, 1H), 7.24 (t, J=7.33 Hz, 1H), 7.07 (d, J=7.79 Hz, 1H), 4.78 (m, 2H), 4.44 (d, J=6.87 Hz, 2H), 3.30 (t, J=6.87 Hz, 2H), 1.34 (t, J=7.10 Hz, 3H); LC-MS (ESI): (MH$^+$) 327.0

Intermediate 16

7-(Indolin-1-yl)thiazolo[5,4-d]pyrimidine-2-carboxylic acid

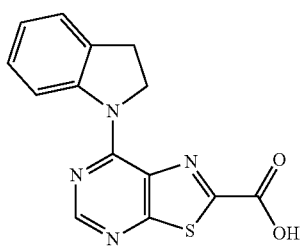 [SMILES: O=C(O)c1nc2c(N3CCc4ccccc43)ncnc2s1]

Intermediate 15 (1.94 g, 5.95 mmol) was suspended in THF (25 mL) and 2M NaOH$_{(aq)}$ (12 mL) added at 0° C. The mixture was acidified to pH1 and the yellow solid collected via vacuum filtration. The solid was washed with ether (2×10 mL) and dried to give 7-(indolin-1-yl)thiazolo[5,4-d]pyrimidine-2-carboxylic acid (1.70 g, 96%); $^1$H NMR (400 MHz, DMSO-d$_6$) δ ppm 8.66 (s, 1H), 8.62 (d, J=7.80 Hz, 1H), 7.32 (d, J=7.33 Hz, 1H), 7.23 (t, J=8.70 Hz, 1H), 7.06 (t, J=7.30 Hz, 1H), 4.78 (t, J=8.20 Hz, 2H), 3.28 (t, J=8.70 Hz, 2H); LC-MS (ESI): (MH$^+$—COOH), 255.0

Intermediate 17

7-Methylsulfanyl-N-tetrahydropyran-4-yl-thiazolo[5,4-d]pyrimidine-2-carboxamide

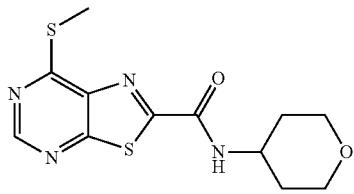 [SMILES: CSc1ncnc2sc(C(=O)NC3CCOCC3)nc12]

Intermediate 2 (1.38 g, 6.1 mmol) was to added thionyl chloride (12 ml) and the mixture heated at reflux for 4 hours, until an orange solution was formed. The mixture was cooled and concentrated to give a yellow solid, which was taken up in DCM (30 ml). Triethylamine (2.5 ml, 18 mmol) added at 0° C., followed by dropwise addition of 4-amino-tetrahydropyran (920 mg, 9.1 mmol), and the mixture was stirred overnight. The mixture was diluted with DCM and water, the organic phase separated, dried and concentrated onto silica. The compound was purified via column chromatography (gradient elution from 0-60% EtOAc in Pet. Ether) to give a white solid (1.28 g, 68%); $^1$H NMR (400 MHz, DMSO-d) δ ppm 1.66-1.86 (m, 4H), 2.70 (s, 3H), 3.35-3.43 (m, 2H), 3.84-3.93 (m, 2H), 3.99-4.11 (m, 1H), 9.00 (s, 1H), 9.16 (d, J=8.24 Hz, 1H); LC-MS (ESI): (MH$^+$) 311.0

Intermediate 18

7-Chloro-N-tetrahydropyran-4-yl-thiazolo[5,4-d]pyrimidine-2-carboxamide

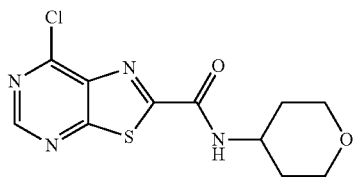

Sulfuryl chloride (1.95 ml, 24 mmol) In DCM (20 ml) was added slowly to a suspension of intermediate 17 (1.49 g, 4.8 mmol) in acetonitrile (40 mL) at 0'C and the resulting mixture stirred for 1.5 hours. The mixture was basified with sat. NaHCO$_3$ $_{(aq)}$ the organic phase separated, dried and concentrated to give an off white solid (1.2 g, 83%); $^1$H NMR (400 MHz, DMSO-d$_6$) δ ppm 1.67-1.86 (m, 4H), 3.34-3.44 (m, 2H), 3.85-3.94 (m, 2H), 4.01-4.13 (m, 1H), 9.12 (s, 1H), 9.36 (d, J=8.20 Hz, 1H);

Intermediate 19

1-Acetyl-5-fluoro-indolin-2-one

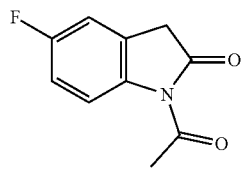

5-fluoroindolin-2-one (250 mg, 1.6 mmol) was added to acetic anhydride (1 ml, 8.3 mmol) and heated at reflux for 2 hours. The mixture was cooled, poured onto iced water and which point a precipitate formed. The solid was filtered, washed with water and dried by vacuum filtration to give 1-acetyl-5-fluoro-indolin-2-one (279 mg, 87%); ¹H NMR (400 MHz, DMSO-d₆) δ ppm 2.54 (s, 3H), 3.84 (s, 2H), 7.09-7.18 (m, 1H), 7.20-7.30 (m, 1H), 8.08 (dd, J=8.93, 4.81 Hz, 1H).

Intermediate 20

1-Acetyl-5-fluoro-3,3-dimethyl-indolin-2-one

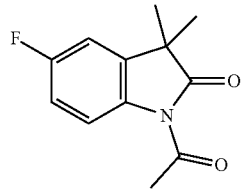 [SMILES: CC(=O)N1C(=O)C(C)(C)c2cc(F)ccc21]

To a solution of intermediate 19 (279 mg, 1.4 mmol) in DMF (5 ml) was added a 60% dispersion of NaH in mineral oil (127 mg, 3.2 mmol) and the mixture was stirred for 30 minutes prior to addition of methyl iodide (0.23 ml, 3.6 mmol) and stirring was continued overnight. The mixture was concentrated and water added, and the resulting precipitate was collected and dried by vacuum filtration to give a dark red solid (271 mg, 85%); ¹H NMR (400 MHz, DMSO-d₆) δ ppm 1.38 (s, 6H), 2.56 (8, 3H), 7.12-7.19 (m, 1H), 7.41-7.46 (m, 1H), 8.09-8.15 (m, 1H).

Intermediate 21

5-Fluoro-3,3-dimethyl-indolin-2-one

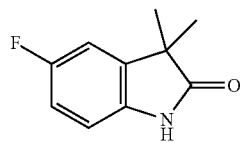

To a solution of intermediate 20 (270 mg, 1.2 mmol) in propan-2-ol (5 ml) was added water (1 mL) and 12M HCl (1 ml) and the mixture heated at reflux for 1.5 hours. The mixture was cooled, concentrated, water added and the resulting solid collected via vacuum filtration to give a yellow solid (200 mg, 91%); ¹H NMR (400 MHz, DMSO-d₆) δ ppm 1.24 (s, 6H), 6.81 (dd, J=8.70, 4.58 Hz, 1H), 6.94-7.02 (m, 1H), 7.25 (dd, J=8.24, 2.75 Hz, 1H), 10.35 (br. s, 1H).

Intermediate 22

5-Fluoro-3,3-dimethyl-indoline

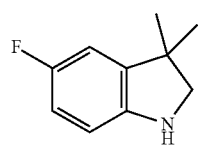

To a solution of Intermediate 21 (200 mg, 1.1 mmol) in THF (5 ml) was added a 1.6M solution of lithium aluminium hydride in diethyl ether (1.34 ml, 1.34 mmol) drop wise and the mixture heated at reflux for 1 hour. The mixture was cooled, water added (2 ml) carefully and the solid filtered. The filtrate was concentrated to give 5-fluoro-3,3-dimethyl-indoline, as dark red oil (120 mg, 65%); ¹H NMR (400 MHz, DMSO-d₆) δ ppm 1.21 (s, 6H), 3.17 (d, J=2.29 Hz, 2H), 5.35 (br. s, 1H), 6.43 (dd, J=8.24, 4.58 Hz, 1H), 6.71 (ddd, J=9.62, 8.70, 2.75 Hz, 1H), 6.83-6.87 (m, 1H); LC-MS (ESI): (MH⁺) 166.1

Intermediate 23

1'-Acetyl-5'-fluoro-spiro[cyclopropane-1,3-indoline]-2'-one

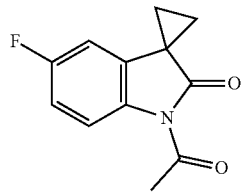

To a solution of Intermediate 19 (250 mg, 1.3 mmol) In DMF (5 ml) was added a 60% dispersion of NaH in mineral oil (110 mg, 2.8 mmol) and left to stir for 30 minutes. 1,2-dibromoethane (258 mg, 1.4 mmol) was added and the mixture stirred overnight. EtOAc and water were added to the mixture, the organic layer separated, washed with water (×3) and brine. The organic phase was dried, concentrated onto silica and purified via column chromatography (gradient elution from 10-100% EtOAc in Pet. Ether) to give an off white solid (120 mg, 42%); ¹H NMR (400 MHz, CHLOROFORM-d) δ ppm 1.58-1.64 (m, 2H) 1.85-1.91 (m, 2H) 2.70 (s, 3H) 6.56 (dd, J=7.79, 2.75 Hz, 1H) 6.96-7.01 (m, 1H) 8.25-8.31 (m, 1H)

Intermediate 24

5'-Fluorospiro[cyclopropane-1,3-indoline]

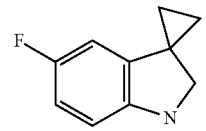 [SMILES: Fc1ccc2c(c1)C1(CC1)CN2]

Intermediate 24 was made in an analogous manner to Intermediate 22, from Intermediate 23 to give 1'-acetyl-5'-fluoro-spiro[cyclopropane-1,3'-indoline]-2'-one; LC-MS (ESI): (MH⁺) 164.1

Intermediate 25

Spiro[indoline-3,4'-tetrahydropyran]

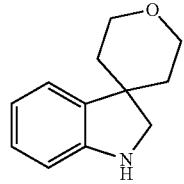 [SMILES: c1ccc2c(c1)NCC21CCOCC1]

To a solution of phenyl hydrazine (500 mg, 4.6 mmol) in acetic acid (15 ml) was added tetrahydropyran-4-carbaldehyde (528 mg 4.6 mmol) and heated at 80° C. for 3 hours. The mixture was cooled, DCE (15 ml) and sodium triacetoxyborohydride (1.28 g, 6.0 mmol) added and stirred for 1 hour. Another 0.5 equivalents of sodium triacetoxyborohydride were added and stirred for a further hour. The mixture was concentrated, taken up in EtOAc, washed with 2M $Na_2CO_{3\ (aq)}$ and the organic phase separated, dried and concentrated onto silica. The compound was purified via column chromatography (gradient elution from 5-15% EtOAc in Pet. Ether) to give a yellow solid (151 mg, 17%); $^1$H NMR (400 MHz, CHLOROFORM-d) δ ppm 1.64-1.71 (m, 2H), 2.00 (ddd, J=13.62, 12.02, 4.58 Hz, 2H), 3.55 (s, 2H), 3.57-3.62 (m, 2H), 3.94-4.02 (m, 2H), 6.67 (dt, J=7.80, 0.90 Hz, 1H), 6.78 (td, J=7.30, 0.90 Hz, 1H), 7.07 (td, J=7.80, 1.20 Hz, 1H), 7.11 (d, J=7.33 Hz, 1H); LC-MS (ESI): (MH$^+$) 190.1

Intermediate 26

O1-tert-butyl O3-methyl indole-1,3-dicarboxylate

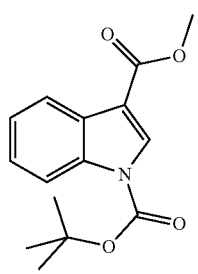 [SMILES: COC(=O)c1cn(C(=O)OC(C)(C)C)c2ccccc12]

To a solution of methyl-3-indolecarboxylate (2 g, 11.4 mmol) in THF (40 ml) was added a 60% dispersion of sodium hydride in mineral oil (594 mg, 14.8 mmol) and the mixture was stirred for 20 min. BOC anhydride (3.22 g, 14.8 mmol) was added and stirred overnight. The mixture was diluted with EtOAc and water, the organic layer separated, dried and concentrated onto silica. The compound was purified by column chromatography (gradient elution from 2-5% EtOAc in Pet. Ether) to give a white solid (2.3 g, 74%); $^1$H NMR (400 MHz, CHLOROFORM-d) δ ppm 1.70 (s, 9H), 3.96 (s, 3H), 7.32-7.42 (m, 2H), 8.14-8.22 (m, 2H), 8.28 (s, 1H).

Intermediate 27

O1-tert-butyl O3-methyl indoline-1,3-dicarboxylate

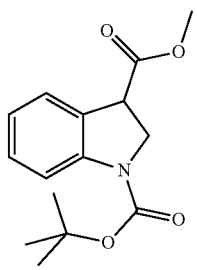 [SMILES: COC(=O)C1CN(C(=O)OC(C)(C)C)c2ccccc21]

To a solution of Intermediate 26 (1 g, 3.6 mmol) in MeOH (100 ml) and DCM (30 ml), at 0° C., was added magnesium powder (438 mg, 18.2 mmol) and the mixture was stirred for 3 hours. More magnesium powder (250 mg, 10.4 mmol) was added and stirring was continued overnight. The mixture was decanted into sat $NH_4Cl_{(aq)}$ and acidified to approximately pH4. DCM was added, the organic phase was separated, dried and concentrated to give a light yellow oil (953 mg, 95%); $^1$H NMR (400 MHz, CHLOROFORM-d) δ ppm 1.57 (br. s., 9H), 3.80 (s, 3H), 4.06-4.16 (m, 1H), 4.18-4.26 (m, 1H), 4.34-4.48 (m, 1H), 6.93-7.00 (m, 1H), 7.24 (t, J=8.01 Hz, 1H), 7.34-7.39 (m, 1H), 7.70-7.96 (m, 1H).

Intermediate 28

Methyl indoline-3-carboxylate

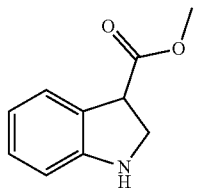

To a solution of Intermediate 27 (953 mg, 3.45 mmol) in DCM (10 ml) was added TFA (3 ml) and the mixture was stirred for 1 hour. The mixture was neutralised with sat. $NaHCO_{(aq)}$ and extracted with DCM. The organic phase was separated, dried and concentrated to give a brown oil (455 mg, 75%); $^1$H NMR (400 MHz, CHLOROFORM-d) δ ppm 3.73-3.78 (m, 1H), 3.78 (s, 3H), 3.94-3.98 (m, 1H), 4.17-4.25 (m, 1H), 6.68 (d, J=7.79 Hz, 1H), 6.72-6.80 (m, 1H), 7.07-7.13 (m, 1H), 7.29-7.33 (m, 1H); LC-MS (ESI): (MH$^+$) 178.0

Intermediate 29

Indolin-3-ylmethanol

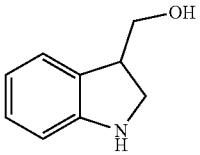 [SMILES: OCC1CNc2ccccc21]

To a solution of Intermediate 28 (100 mg, 0.57 mmol) in THF (5 ml) was added a 1M solution of lithium aluminium hydride in THF (1.1 ml, 1.1 mmol) dropwise and the mixture heated at reflux for 45 minutes. The mixture was cooled, 1 ml of water added and the solids removed via filtration. The filtrate was concentrated to give indolin-3-ylmethanol, a brown oil (65 mg, 76%); $^1$H NMR (400 MHz, CHLOROFORM-d) δ ppm 3.45-3.54 (m, 2H), 3.66-3.72 (m, 1H), 3.79-3.83 (m, 2H), 6.67 (d, J=7.79 Hz, 1H), 6.75 (td, J=7.30, 0.90 Hz, 1H), 7.08 (td, J=7.79, 0.92 Hz, 1H), 7.16 (d, J=6.87 Hz, 1H); LC-MS (ESI): (MH$^+$) 150.2

Intermediate 30

2-(1H-indol-3-yl)ethanol

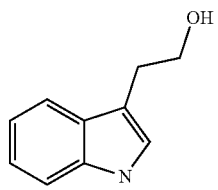 [SMILES: OCCc1c[nH]c2ccccc12]

To a solution of 3-indoleacetic acid (1 g, 5.7 mmol) in THF (30 ml) was added a 1M solution of lithium aluminium hydride in THF (11.4 ml, 11.4 mmol) and the mixture refluxed for 3 hours. The mixture was cooled, 0.43 ml of water carefully added, followed by 0.43 ml of 15% NaOH$_{(aq)}$ and finally 1.5 ml of water. The solids were filtered from the mixture, washed with EtOAc and the filtrate concentrated to give 2-(1H-Indol-3-yl)ethanol (919 mg, 100%); $^1$H NMR (400 MHz, CHLOROFORM-d) δ ppm 3.06 (t, J=6.40 Hz, 2H), 3.93 (t, J=6.40 Hz, 2H), 7.10 (d, J=2.29 Hz, 1H), 7.12-7.18 (m, 1H), 7.20-7.26 (m, 1H), 7.36-7.41 (m, 1H), 7.64 (dd, J=8.01, 1.14 Hz, 1H), 8.10 (br. s., 1H).

Intermediate 31

2-Indolin-3-ylethanol

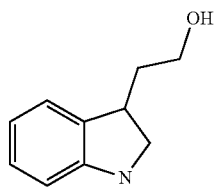

To a solution of Intermediate 30 (919 mg, 5.7 mmol) In DCM (20 ml) was added TFA (5 ml) followed by sodium borohydride (434 mg, 11.4 mmol) and stirred overnight. The mixture was diluted with DCM and neutralised with sat. Na$_2$CO$_3$. The organic phase was separated, dried and concentrated onto silica. The compound was purified via column chromatography (10-100% EtOAc in Pet. Ether) to give 2-indolin-3-ylethanol, as an orange oil (157 mg, 17%); $^1$H NMR (400 MHz, CHLOROFORM-d) δ ppm 1.82 (m, 1H), 2.11 (m, 1H), 3.33 (dd, J=8.70, 5.95 Hz, 1H), 3.43-3.52 (m, 1H), 3.56-3.64 (m, 1H), 3.67-3.76 (m, 2H), 6.70 (d, J=7.79 Hz, 1H), 6.75-6.81 (m, 1H), 7.03-7.10 (m, 1H), 7.12 (d, J=7.60 Hz, 1H); LC-MS (ESI): (MH$^+$) 164.1

Intermediate 32

Tert-butyl N-(2-indolin-3-ylethyl)carbamate

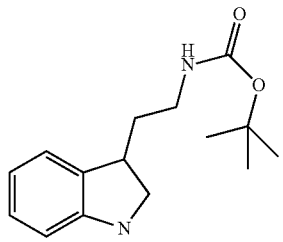 [SMILES: CC(C)(C)OC(=O)NCCC1CNc2ccccc21]

To a solution of tryptamine (1 g, 6.25 mmol) in DCM (10 ml) was added TFA (2 ml) followed by sodium borohydride (475 mg, 12.5 mmol) and stirred overnight. The mixture was diluted with DCM and neutralised with sat. Na$_2$CO$_{3(aq)}$. The organic phase was separated, dried and concentrated to give 2-indolin-3-ylethanamine, a yellow oil. This was taken up in DCM (30 ml), triethylamine (0.90 ml, 6.2 mmol) added followed by BOC anhydride (1.35 g, 6.2 mmol) and stirred overnight. The mixture was diluted with DCM and water. The organic layer separated, dried and concentrated onto silica. The compound was purified via column chromatography (gradient elution from 5-25% EtOAc in Pet. Ether) to give a yellow oil (684 mg, 42%); $^1$H NMR (400 MHz, CHLOROFORM-d) δ ppm 1.46 (s, 9H), 1.72 (m, 1H), 1.90-2.04 (m, 1H), 3.15-3.28 (m, 2H), 3.28-3.41 (m, 1H), 3.58-3.77 (m, 1H), 4.06-4.11 (m, 1H), 4.57 (m, 1H), 6.90-6.99 (m, 1H), 7.08-7.22 (m, 2H), 7.37-8.06 (m, 1H); LC-MS (ESI): (MH$^+$) 263.2

Intermediate 33

5-(Trifluoromethyl)indoline

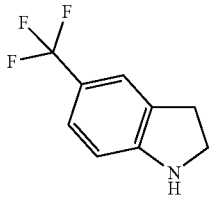 [SMILES: FC(F)(F)c1ccc2c(c1)CCN2]

To a solution of 5-(trifluoromethyl)indole (100 mg, 0.55 mmol) and TFA (0.5 mL) in DCM (10 mL) was added NaBH$_4$ (42 mg, 1.10 mmol) and the mixture stirred overnight. The reaction mixture was diluted with DCM (10 mL) and quenched with sat. NaHCO$_3$ (5 mL). The organic layer was washed with water (2×10 mL), dried and concentrated in vacuo to give an orange gum (126 mg, 122% mass recovery); $^1$H NMR (400 MHz, CHLOROFORM-d) δ ppm 7.66 (m, 1H), 7.61 (m, 1H), 7.44 (m, 1H), 3.95 (t, J=7.79 Hz, 2H), 3.39 (t, J=8.24 Hz, 2H); LC-MS (ESI): (MH$^+$) 188.2. Used without further purification.

Intermediate 34

Ethyl 7-(2-methylindolin-1-yl)thiazolo[5,4-d]pyrimidine-2-carboxylate

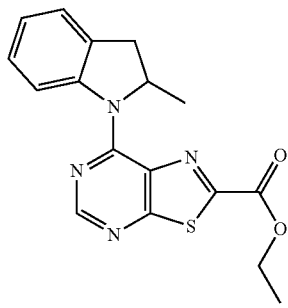 [SMILES: CCOC(=O)c1nc2c(N3c4ccccc4CC3C)ncnc2s1]

Intermediate 34 was made analogously to Intermediate 15 from ethyl 7-(methylthio)thiazolo[5,4-d]pyrimidine-2-carboxylate and 2-methylindoline. $^1$H NMR (400 MHz, CHLOROFORM-d) δ ppm 1.40 (d, J=6.41 Hz, 3H), 1.47 (t, J=6.90 Hz, 3H), 2.83 (d, J=15.60 Hz, 1H), 3.52 (dd, J=15.60, 8.70 Hz, 1H), 4.44-4.57 (m, 2H), 5.92-6.07 (m, 1H), 7.08-7.14 (m, 1H), 7.28-7.33 (m, 2H), 8.65-8.71 (m, 2H); LC-MS (ESI): (MH$^+$) 341.1

Intermediate 35

Ethyl 7-(3-methylindolin-1-yl)thiazolo[5,4-d]pyrimidine-2-carboxylate

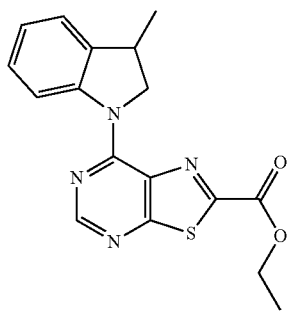 [SMILES: CCOC(=O)c1nc2c(N3CC(C)c4ccccc43)ncnc2s1]

Intermediate 35 was made analogously to Intermediate 14 from 3-methyl indoline and ethyl 7-(methylthio)thiazolo[5,4-d]pyrimidine-2-carboxylate LC-MS (ESI): (MH$^+$) 341.1.

Intermediate 36

7-(2-Methylindolin-1-yl)thiazolo[5,4-d]pyrimidine-2-carboxylic acid

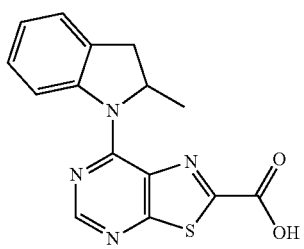 [SMILES: CC1Cc2ccccc2N1c1ncnc2sc(C(=O)O)nc12]

To a solution of Intermediate 34 (943 mg, 2.8 mmol) in THF (10 ml) was added 15% NaOH$_{(aq)}$ (5 ml) and stirred for 1 hour. The mixture was acidified to pH1 with 2M HCl and the resulting precipitate was filtered and dried to give a brown solid (852 mg, 98%); $^1$H NMR (400 MHz, DMSO-d$_6$) δ ppm 1.28 (d, J=5.95 Hz, 3H), 2.83 (d, J=16.03 Hz, 1H), 3.50 (dd, J=15.80, 8.93 Hz, 1H), 5.84-5.98 (m, 1H), 7.06-7.15 (m, 1H), 7.28 (t, J=8.01 Hz, 1H), 7.37 (d, J=7.33 Hz, 1H), 8.62 (d, J=8.24 Hz, 1H), 8.67 (s, 1H);

Intermediate 37

(S)-indolin-2-ylmethanol

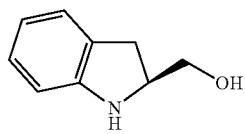 [SMILES: OC[C@@H]1Cc2ccccc2N1]

Borane (38 ml, 1.0M in THF, 38 mmol) was added drop wise to a suspension of (S)-indoline-2-carboxylic acid (2.50 g, 15.2 mmol) at 0° C. and the resultant solution stirred at RT for 48 hours. To this was added DCM and water and the organic phase washed with water (2×20 ml). The organic phase was separated, dried and concentrated to give an orange oil (856 mg, 38%); $^1$H NMR (400 MHz, CHLOROFORM-d) δ ppm 7.08 (d, J=7.33 Hz, 1H), 7.02 (d, J=1.37 Hz, 1H), 6.72 (td, J=7.44, 1.14 Hz, 1H), 6.64 (d, J=7.79 Hz, 1H), 4.02 (m, 1H), 3.70 (dd, J=10.76, 3.89 Hz, 1H), 3.56 (dd, J=10.76, 6.64 Hz, 1H), 3.08 (d, J=9.16 Hz, 1H), 2.83 (d, J=7.78 Hz, 1H); LC-MS (ESI): (MH$^+$) 150.

Intermediate 38

(S)-tert-butyl 2-(hydroxymethyl)indoline-1-carboxylate

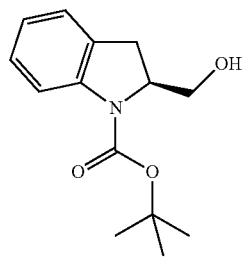 [SMILES: CC(C)(C)OC(=O)N1c2ccccc2C[C@H]1CO]

To a solution of Intermediate 37 (856 mg, 5.74 mmol) in DCM (5 mL) was added BOC$_2$O (1.38 g, 6.32 mmol) and the solution stirred at room temp for 48 hours. To the resultant yellow solution was added DCM (5 mL) and sat. NaHCO$_3$ $_{(aq)}$ (5 mL). The organic layer was washed with sat. NaHCO$_3$ (q (2×5 mL), separated and concentrated to give a yellow oil (1.40 g, 89%)$^1$H NMR (400 MHz, CHLOROFORM-d) δ ppm 7.51 (br. s, 1H), 7.14 (m, 2H), 6.94 (t, J=7.33 Hz, 1H), 4.59 (br. s, 1H), 3.69 (s, 2H), 3.33 (m, 1H), 2.79 (br. s, 1H), 1.58 (s, 9H); LC-MS (ESI): (MH$^+$—BOC) 150.1.

Intermediate 39

(S)-tert-butyl 2-((tosyloxy)methyl)indoline-1-carboxylate

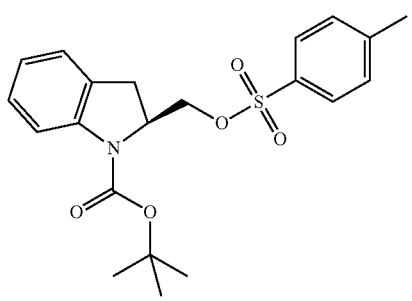 [SMILES: Cc1ccc(S(=O)(=O)OC[C@@H]2Cc3ccccc3N2C(=O)OC(C)(C)C)cc1]

Tosyl chloride (2.13 g, 11.20 mmol) and pyridine (12 mL) were added to a solution of Intermediate 38 in DCM (6 mL) and the resulting mixture was stirred at room temp for 16 hours. The mixture was quenched by addition of DCM and water and the organic layer separated and washed with water (2×10 mL). The organic layer was separated, dried and concentrated to give a pink oil (1.46 g, 64%); $^1$H NMR (400 MHz, CHLOROFORM-d) δ ppm 7.68 (d, J=8.70 Hz, 2H), 7.29 (d, J=8.23 Hz, 2H), 7.11 (m, 2H), 6.93 (t, J=7.33 Hz, 1H), 4.59 (m, 1H), 4.18 (m, 1H), 3.97 (br. s., 1H), 3.27 (m, 1H), 2.93 (dd, J=16.49, 1.83 Hz, 1H), 2.42 (s, 3H), 1.47 (br. s., 9H); LC-MS (ESI): (MH$^+$) 400.0

Intermediate 40

(R)-tert-butyl 2-methylindoline-1-carboxylate

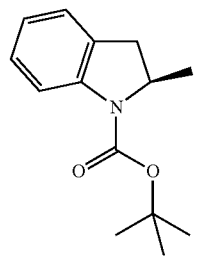 [SMILES: C[C@@H]1Cc2ccccc2N1C(=O)OC(C)(C)C]

Sodium borohydride (335 mg, 9.06 mmol) was added to a solution of Intermediate 39 (1.46 g, 3.62 mmol) in DMSO (20 mL) and the reaction mixture stirred at 100° C. for 18 hours. To the resultant yellow solution was added DCM and water, the organic layer separated and washed with water (2×10 mL). The organic layer was separated, dried and concentrated to give a yellow oil (547 mg, 65%). $^1$H NMR (400 MHz, CHLOROFORM-d) δ ppm 1.27 (d, J=6.41 Hz, 3H) 1.56 (s, 9H) 2.57-2.61 (m, 2H) 3.33 (dd, J=16.03, 9.62 Hz, 1H) 4.42-4.57 (m, 1H) 6.89-6.95 (m, 1H) 7.10-7.19 (m, 2H)

Intermediate 41

(R)-2-Methylindoline

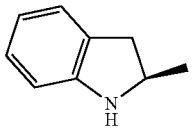

To a solution of Intermediate 40 (547 mg, 235 mmol) in DCM (5 mL) was added TFA (2 mL) and the reaction mixture was stirred at room temp for 1 hour. The solution was concentrated and the resultant orange oil taken up in methanol and passed through an SCX cartridge. The product was eluted with 2M ammonia in methanol and the eluent concentrated to give an orange oil (547 mg, 65%); $^1$H NMR (400 MHz, CHLOROFORM-d) δ ppm 7.10 (d, J=7.33 Hz, 1H), 7.03 (t, J=7.80 Hz, 1H), 6.70 (t, J=8.70 Hz, 1H), 6.63 (d, J=7.79 Hz, 1H), 4.01 (m, 1H), 3.16 (dd, J=15.11, 8.70 Hz, 1H), 2.66 (dd, J=15.11, 7.79 Hz, 1H), 1.31 (d, J=5.95 Hz, 3H).

Intermediate 42

(R)-Ethyl 7-(2-methylindolin-1-yl)thiazolo[5,4-d]pyrimidine-2-carboxylate

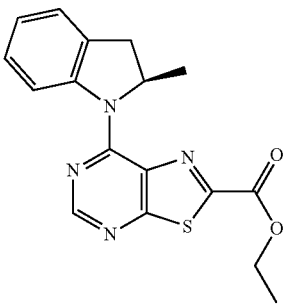 [SMILES: CCOC(=O)c1nc2c(N3c4ccccc4C[C@H]3C)ncnc2s1]

m-CPBA (639 mg, 3.70 mmol) was added to a stirring solution of ethyl 7-(methylthio)thiazolo[5,4-d]pyrimidine-2-carboxylate (472 mg, 1.85 mmol) In DCM (10 mL) at 0° C. The resultant mixture was stirred at 0° C. and allowed to warm up to room temperature over 2 hours after which Intermediate 41 (264 mg, 1.85 mmol) and dioxane (5 mL) was added to yield a dark green solution. The solution was left to stir at room temperature for 16 hours. To this was added DCM and water, the organic layer separated and washed with water (2×10 mL). The organic layer was separated, dried and concentrated to give a yellow solid. This was taken up in methanol and passed through an SCX cartridge. The product was eluted with 2M ammonia in methanol and the eluent concentrated to give a yellow solid (350 mg, 65%). $^1$H NMR (400 MHz, CHLOROFORM-d) δ ppm 1.38-1.41 (d, 3H) 1.47 (t, 3H) 2.83 (d, J=15.57 Hz, 1H) 3.52 (dd, J=15.57, 9.16 Hz, 1H) 4.48-4.55 (q, 2H) 5.95-6.03 (m, 1H) 7.11 (td, J=7.33, 0.92 Hz, 1H) 7.31 (dt, J=7.67, 3.72 Hz, 2H) 8.65-8.67 (m, 1H) 8.67-8.71 (m, 1H); LC-MS (ESI): (MH$^+$) 341.0

Intermediate 43

(R)-7-(2-methylindolin-1-yl)thiazolo[5,4-d]pyrimidine-2-carboxylic acid

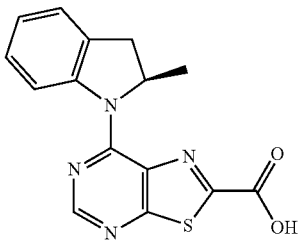 [SMILES: C[C@@H]1Cc2ccccc2N1c1ncnc2sc(C(=O)O)nc12]

Intermediate 42 (5.46 g, 16.2 mmol) was suspended in THF (70 mL) and 2M NaOH$_{(aq)}$ (24 mL) added at 0° C. and stirred for 30 mins. The mixture was acidified to pH1 and the yellow solid collected via vacuum filtration. The solid was washed with ether (2×10 mL) and dried to give a yellow solid (350 mg, 93%). $^1$H NMR (400 MHz, DMSO-d$_6$) δ ppm 8.65 (s, 1H), 8.59 (d, J=8.24 Hz, 1H), 7.35 (d, J=7.33 Hz, 1H), 7.25 (t, J=7.30 Hz, 1H), 7.08 (t, J=8.20 Hz, 1H), 5.87 (m, 1H), 3.48 (dd, J=15.57, 8.70 Hz, 1H), 2.81 (d, J=15.57 Hz, 1H), 1.25 (d, J=5.95 Hz, 3H).

Intermediate 44

Tert-butyl 4-[[(7-methylsulfanylthiazolo[5,4-d]pyrimidine-2-carbonyl)amino]methyl]piperidine-1-carboxylate

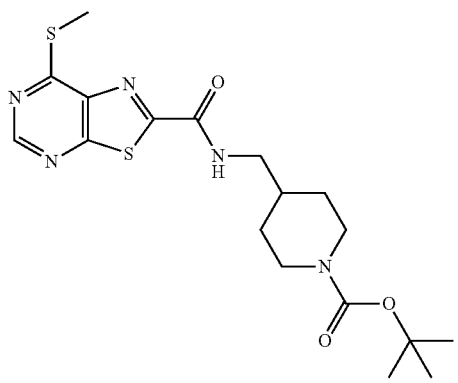 [SMILES: CSc1ncnc2sc(C(=O)NCC3CCN(C(=O)OC(C)(C)C)CC3)nc12]

Thionyl chloride (30 ml) was added to Intermediate 2 (4.45 g, 19.6 mmol) and heated at reflux for 2 hours. The mixture was cooled, concentrated and the residue taken up in DCM. To this was added triethylamine (8.48 ml, 58.8 mmol), followed by a solution of tert-butyl 4-(aminomethyl)piperidine-1-carboxylate (4.61 g, 21.6 mmol) in DCM and stirred overnight. DCM and water were added to the mixture, the organic phase was separated, dried and concentrated onto silica. Purification by column chromatography (gradient elution from 10-50% EtOAc in Pet. Ether) gave a peach solid (5.49 g, 68%); $^1$H NMR (400 MHz, CHLOROFORM-d) δ ppm 1.23-1.31 (m, 2H), 1.46 (s, 9H), 1.72-1.80 (m, 2H), 1.81-1.90 (m, 1H), 2.69-2.76 (m, 5H), 3.43 (t, J=6.64 Hz, 2H), 4.11-4.21 (m, 2H), 7.49 (br. t, J=6.00, 6.00 Hz, 1H), 8.90 (s, 1H); LC-MS (ESI): (MH$^+$—BOC) 324.0

Intermediate 45

Tert-butyl 4-[[(7-chlorothiazolo[5,4-d]pyrimidine-2-carbonyl)amino]methyl]piperidine-1-carboxylate

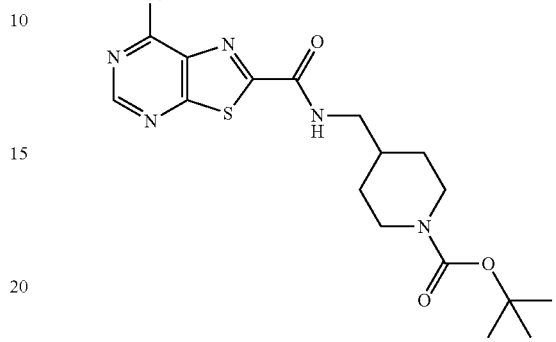

To a solution of Intermediate 44 (2.5 g, 5.9 mmol) in acetonitrile (50 ml) and DCM (20 ml), at −10° C. in an ice/salt bath, was added a solution of sulfuryl chloride (0.96 ml, 11.8 mmol) in DCM (10 ml) dropwise. The reaction was left to stir at −10° C. for 1 hour. The mixture was concentrated to give tert-butyl 4-[[7-chlorothiazolo[5,4-d]pyrimidine-2-carbonyl)amino]methyl]piperidine-1-carboxylate, a yellow solid (2.51 g, 112% mass recovery); $^1$H NMR (400 MHz, CHLOROFORM-d) δ ppm 1.21-1.31 (m, 2H), 1.46 (s, 9H), 1.75-1.81 (m, 2H), 1.85-1.91 (m, 1H), 2.65-2.76 (m, 2H), 3.45 (t, J=6.60 Hz, 2H), 4.14-4.20 (m, 2H), 7.55 (br. t, J=6.00, 8.00 Hz, 1H), 9.00 (s, 1H); LC-MS (ESI): (MH$^+$—BOC) 312.0

Intermediate 46

2-(5-Fluoro-1H-indol-3-yl)ethanol

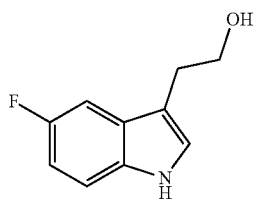

To a solution of 5-fluoroindole-3-acetic acid (1 g, 5.2 mmol) in THF (20 ml) was added a 1M solution of lithium aluminium hydride in THF (10.4 ml, 10.4 mmol) and the mixture refluxed for 1.5 hours. The mixture was cooled, 0.39 ml of water and then 0.39 ml of 15% NaOH$_{(aq)}$ added, followed by 1.2 ml of water. The precipitate was collected via vacuum filtration and the filtrate concentrated to give 2-(5-fluoro-1H-indol-3-yl)ethanol, an orange oil (0.927 g, 100%); $^1$H NMR (400 MHz, CHLOROFORM-d) δ ppm 2.98 (t, J=6.41 Hz, 2H), 3.89 (t, J=6.18 Hz, 2H), 6.95 (td, J=9.04, 2.52 Hz, 1H), 7.12 (s, 1H), 7.22-7.30 (m, 2H), 8.06 (br. s., 1H).

Intermediate 47

2-(5-Fluoroindolin-3-yl)ethanol

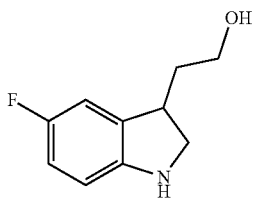

To a solution of Intermediate 46 (927 mg, 5.2 mmol) in DCM (20 ml) and TFA (5 ml) was added sodium borohydride (393 mg, 10.4 mmol) and stirred for 4 hours. The mixture was diluted with DCM and basified with sat. NaHCO$_{3(aq)}$. The organic layer was separated, dried and concentrated onto silica. The compound was purified via column chromatography (gradient elution from 20-100% EtOAc in Pet. Ether) to give a yellow oil (416 mg, 44%); $^1$H NMR (400 MHz, CHLOROFORM-d) δ ppm 1.74-1.85 (m, 1H), 2.06-2.14 (m, 1H), 3.28-3.36 (m, 1H), 3.40-3.50 (m, 1H), 3.55-3.63 (m, 1H), 3.67-3.78 (m, 2H), 6.59 (dd, J=8.47, 4.35 Hz, 1H), 6.75 (td, J=8.82, 2.52 Hz, 1H), 6.83 (dd, J=8.47, 2.52 Hz, 1H); LC-MS (ESI): (MH$^+$) 312.0

Intermediate 48

Methyl 3-methylindoline-3-carboxylate

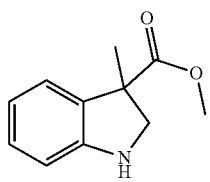

To a solution of Intermediate 27 (250 mg, 0.92 mmol) in DMF (10 ml) was added a 60% dispersion of sodium hydride in mineral oil (41 mg, 1.0 mmol), immediately followed by methyl iodide (0.17 ml, 2.8 mmol) and stirred for 2 h. The mixture was diluted with EtOAc and washed with water (×3). The organic phase was separated, dried and concentrated to an oil. The oil was taken up in DCM (5 ml), TFA (1 ml) added and stirred for 1 hour. The mixture was passed through a SCX cartridge, the product being eluted with 2M NH$_3$ in MeOH to give methyl 3-methylindoline-3-carboxylate, a brown oil (118 mg, 67%); $^1$H NMR (400 MHz, CHLOROFORM-d) δ ppm 1.59 (s, 3H), 3.38 (d, J=9.62 Hz, 1H), 3.73 (s, 3H), 4.16 (d, J=9.16 Hz, 1H), 6.70 (d, J=8.24 Hz, 1H), 6.80 (td, J=7.50, 1.10 Hz, 1H), 7.11 (td, J=7.50, 1.14 Hz, 1H), 7.27-7.31 (m, 1H); LC-MS (ESI): (MH$^+$) 192.1

Intermediate 49

(3-Methylindolin-3-yl)methanol

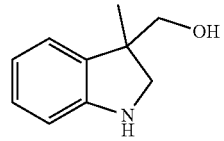

To a solution of Intermediate 48 (118 mg, 0.62 mmol) In THF (5 ml) was added a 1M solution of lithium aluminium hydride in THF (1.24 ml, 1.2 mmol) dropwise and the reaction stirred for 2 hours at room temperature. The reaction mixture was quenched by addition of water and 15% NaOH$_{(aq)}$. The solids were removed via vacuum filtration and the filtrate concentrated to give a yellow oil (100 mg, 99%); $^1$H NMR (400 MHz, CHLOROFORM-d) δ ppm 1.34 (s, 3H), 3.28 (d, J=9.16 Hz, 1H), 3.54-3.58 (m, 2H), 3.61 (d, J=8.20 Hz, 1H), 3.63-3.68 (m, 1H), 6.63-6.69 (m, 1H), 6.72-6.79 (m, 1H), 7.07 (m, J=7.30 Hz, 2H); LC-MS (ESI): (MH$^+$) 164.1

Intermediate 50

(5-Fluoro-3-methyl-indolin-3-yl)methanol

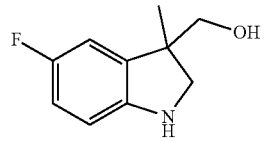

Intermediate 50 was made in an analogous manner to Intermediate starting from methyl 5-fluoro-1H-indole-3-carboxylate; $^1$H NMR (400 MHz, CHLOROFORM-d) δ ppm 1.31 (s, 3H), 3.28-3.32 (m, 1H), 3.57-3.63 (m, 3H), 6.56-6.60 (m, 1H), 6.78 (m, 2H); LC-MS (ESI): (MH$^+$) 182.1

Intermediate 51

Methyl 2-(1H-indol-3-yl)acetate

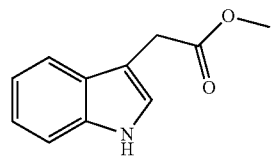

To a solution of 3-indole acetic acid (500 mg, 2.9 mmol) in MeOH (20 ml) was added conc. H$_2$SO$_4$ (1 ml) and the mixture stirred for 1 hour. The mixture was quenched with sat. NaHCO$_{3(aq)}$ and extracted with DCM. The organic phase was separated, dried and concentrated to give a yellow oil (531 mg, 99%); $^1$H NMR (400 MHz, CHLOROFORM-d) δ ppm 3.72 (s, 3H), 3.82 (s, 2H), 7.13-7.19 (m, 2H), 7.20-7.25 (m, 1H), 7.34-7.39 (m, 1H), 7.61-7.66 (m, 1H), 8.02-8.23 (m, 1H).

Intermediate 52

Methyl 2-indolin-3-ylacetate

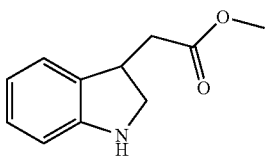

To a solution of Intermediate 51 (311 mg, 1.6 mmol) in DCM (10 ml) and TFA (2 ml) was added sodium borohydride (125 mg, 3.2 mmol) and stirred for 2 hours. The mixture was diluted with DCM and quenched with sat. NaHCO$_{3(aq)}$. The organic phase was separated, dried and concentrated to give a yellow oil (302 mg, 96%); $^1$H NMR (400 MHz, CHLOROFORM-d) δ ppm 2.60 (dd, J=16.50, 9.10 Hz, 1H), 2.80 (dd, J=16.50, 5.50 Hz, 1H), 3.31 (dd, J=8.93, 6.18 Hz, 1H), 3.43-3.60 (m, 1H), 3.71-3.78 (m, 4H), 3.79-3.86 (m, 1H), 6.72 (d, J=−7.79 Hz, 1H), 6.78 (td, J=7.33, 0.92 Hz, 1H), 7.06-7.13 (m, 2H); LC-MS (ESI): (MH$^+$) 192.1

Intermediate 53

Tert-butyl 3-(2-methoxy-2-oxo-ethyl)indoline-1-carboxylate

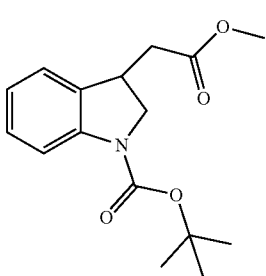 [SMILES: COC(=O)CC1CN(C(=O)OC(C)(C)C)c2ccccc21]

To a solution of Intermediate 52 (140 mg, 0.73 mmol) in triethylamine (0.21 ml, 1.4 mmol) and DCM (5 ml) was added DMAP (9 mg, 0.07 mmol), followed by BOC anhydride (168 mg, 0.77 mmol). The mixture was stirred overnight. The mixture was diluted with DCM and water, the organic layer separated, dried and concentrated onto silica. The compound was purified via column chromatography (gradient elution from 5-50% EtOAc in Pet. Ether) to give a yellow oil (148 mg, 70%); $^1$H NMR (400 MHz, CHLOROFORM-d) δ ppm 1.55 (br. s., 9H), 2.50-2.59 (m, 1H), 2.69-2.86 (m, 1H), 3.59-3.69 (m, 1H), 3.70-3.78 (m, 4H), 4.15-4.23 (m, 1H), 6.93 (td, J=7.30, 0.90 Hz, 1H), 7.11 (d, J=7.30 Hz, 1H), 7.18 (t, J=7.78 Hz, 1H), 7.34-7.93 (m, 1H); LC-MS (ESI): (MH$^+$—BOC) 192.1

Intermediate 54

Tert-butyl 3-(2-hydroxy-2-methyl-propyl)indoline-1-carboxylate

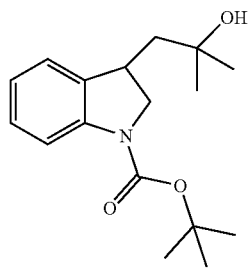 [SMILES: CC(C)(O)CC1CN(C(=O)OC(C)(C)C)c2ccccc21]

To a solution of Intermediate 53 (148 mg, 0.51 mmol) in THF (5 ml) was added a 3M solution of methyl magnesium bromide in THF (0.84 ml, 2.5 mmol) and stirred for 1 hour. The reaction was quenched with sat. NH$_4$Cl$_{(aq)}$ and extracted with DCM. The organic layer was separated, dried and concentrated to give a yellow oil (150 mg, 99%); $^1$H NMR (400 MHz, CHLOROFORM-d) δ ppm 1.32 (s, 6H), 1.58 (s, 9H), 1.76 (dd, J=14.20, 10.53 Hz, 1H), 1.97-2.09 (m, 1H), 3.41-3.54 (m, 1H), 3.73 (d, J=6.87 Hz, 1H), 4.16-4.35 (m, 1H), 6.94 (td, J=7.33, 0.92 Hz, 1H), 7.07-7.19 (m, 2H), 7.35-8.01 (m, 1H); LC-MS (ESI): (MH$^+$—BOC) 192.1

Intermediate 55

1-Indolin-3-yl-2-methyl-propan-2-ol

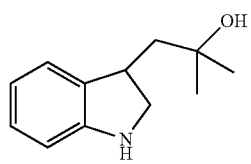

To a solution of Intermediate 54 (150 mg, 0.51 mmol) in DCM (10 ml) was added TFA (1 ml) and stirred for 3 hours. The mixture was passed through a SCX cartridge, the product being eluted with 2M NH$_3$ in MeOH to give 1-indolin-3-yl-2-methyl-propan-2-ol, a yellow oil (76 mg, 78%); $^1$H NMR (400 MHz, CHLOROFORM-d) δ ppm 1.32 (d, J=8.24 Hz, 6H), 1.78 (dd, J=14.43, 9.85 Hz, 1H), 2.12 (dd, d=14.43, 2.52 Hz, 1H), 3.33 (t, J=8.70 Hz, 1H), 3.42-3.51 (m, 1H), 3.84 (t, J=8.70 Hz, 1H), 6.70 (d, J=7.30 Hz, 1H), 6.78 (td, J=7.30, 0.90 Hz, 1H), 7.03-7.08 (m, 1H), 7.10 (d, J=7.30 Hz, 1H), LC-MS (ESI): (MH$^+$) 192.1

Intermediate 56

1-(5-Fluoroindolin-3-yl)-2-methyl-propan-2-ol

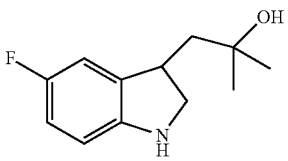

Intermediate 56 was made in an analogous manner to Intermediate 55 starting from 5-fluoro-3-indole acetic acid to give 1-(5-fluoroindolin-3-yl)-2-methyl-propan-2-ol; $^1$H NMR (400 MHz, CHLOROFORM-d) δ ppm 1.30 (d, J=9.16 Hz, 6H), 1.74-1.82 (m, 1H), 1.98-2.05 (m, 1H), 3.46-3.53 (m, 2H), 3.86-3.94 (m, 1H), 6.75-6.81 (m, 2H), 6.83-6.88 (m, 1H); LC-MS (ESI): (MH$^+$) 210.1

Intermediate 57

O1-tert-butyl O3-methyl 3-methylindoline-1,3-dicarboxylate

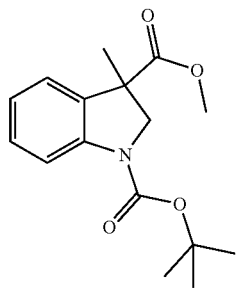 [SMILES: COC(=O)C1(C)CN(C(=O)OC(C)(C)C)c2ccccc21]

To a solution of Intermediate 27 (1 g, 3.7 mmol) in DMF (25 ml) was added a 60% dispersion of sodium hydride in mineral oil (162 mg, 4.0 mmol), immediately followed by methyl iodide (0.68 ml, 11.0 mmol) and stirred for 2 hours. The mixture was diluted with EtOAc and washed with water (×3). The organic phase was separated, dried and concentrated to give an orange oil (1.07 g, 100%); $^1$H NMR (400 MHz, CHLOROFORM-d) δ ppm 1.56-1.61 (m, 12H), 3.67-3.79 (m, 4H), 4.58 (d, J=11.40 Hz, 1H), 6.98 (td, J=7.30, 0.90 Hz, 1H), 7.20-7.26 (m, 1H), 7.31 (dd, J=7.80, 0.90 Hz, 1H), 7.38-7.94 (m, 1H); LC-MS (ESI): (MH$^+$—BOC) 192.1

Intermediate 58

1-Tert-butoxycarbonyl-3-methyl-indoline-3-carboxylic acid

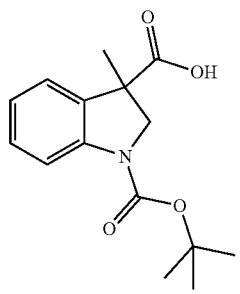 [SMILES: CC(C)(C)OC(=O)N1CC(C)(C(=O)O)c2ccccc21]

To a solution of Intermediate 57 (1.07 g, 3.7 mmol) in THF (20 ml) was added 15% NaOH$_{(aq)}$ (20 ml) and the mixture heated at 50° C. for 3 hours, then at room temperature overnight. The mixture was acidified with 1M HCl$_{(aq)}$ and extracted with ethyl acetate. The organic phase was separated, dried and concentrated to give an orange oil (1 g, 100%); $^1$H NMR (400 MHz, CHLOROFORM-d) δ ppm 1.54 (br. s, 9H), 1.61 (s, 3H), 3.66-3.77 (m, 1H), 4.57 (d, J=11.45 Hz, 1H), 6.98 (td, J=7.80, 0.90 Hz, 1H), 7.23 (t, J=7.80 Hz, 1H), 7.34 (dd, J=7.30, 0.90 Hz, 1H), 7.40-7.92 (m, 1H); LC-MS (ESI): (MH$^+$—BOC) 178.1

Intermediate 59

2-(1-Tert-butoxycarbonyl-3-methyl-indolin-3-yl)-2-oxo-ethanediazonium

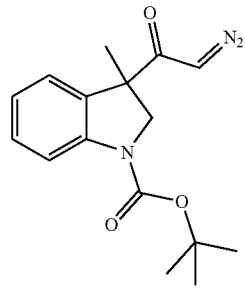

To a solution of Intermediate 58 (1 g, 3.6 mmol) and triethylamine (1.04 ml, 7.2 mmol) in DCM (20 ml) at 0° C. was added DMF (56 μL, 0.72 mmol) followed by the dropwise addition of oxalyl chloride (0.45 ml, 5.4 mmol). The reaction was stirred for 4 hours, warming to room temperature. More oxalyl chloride (0.3 ml, 3.6 mmol) was added and stirring was continued overnight. The mixture was concentrated and the residue taken up in THF (20 ml) and acetonitrile (10 ml). A 2M solution of trimethylsilane diazomethane in diethyl ether (3.6 ml, 7.2 mmol) was added and the mixture was stirred for 2 hours. The mixture was quenched with 10% Citric acid$_{(aq)}$ until effervescence ceased. DCM and water were added, the organic layer separated, dried and concentrated onto silica. The compound was purified via column chromatography (gradient elution from 2-10% EtOAc in Pet. Ether) to give a yellow oil (401 mg, 37%); $^1$H NMR (400 MHz, CHLOROFORM-d) δ ppm 1.52-1.61 (m, 12H), 3.72 (br. d, J=11.90 Hz, 1H), 4.35 (d, J=11.90 Hz, 1H), 5.12 (s, 1H), 7.01 (td, J=7.80, 0.90 Hz, 1H), 7.16 (dd, J=7.80, 0.90 Hz, 1H), 7.24-7.30 (m, 1H), 7.37-8.01 (m, 1H).

Intermediate 60

Tert-butyl 3-(2-methoxy-2-oxo-ethyl)-3-methyl-indoline-1-carboxylate

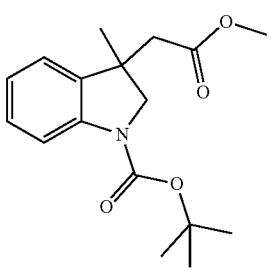 [SMILES: COC(=O)CC1(C)CN(C(=O)OC(C)(C)C)c2ccccc21]

To a solution of Intermediate 59 (401 mg, 1.3 mmol) and triethylamine (0.58 ml, 4.0 mmol) in methanol (10 ml) was added silver benzoate (152 mg, 0.66 mol). The mixture was stirred for 1.5 hours. DCM and water were added to the mixture, the organic layer separated, dried and concentrated onto silica. The compound was purified via column chromatography (gradient elution from 2-12% EtOAc in Pet. Ether) to give a colourless oil (230 mg, 57%); $^1$H NMR (400 MHz, CHLOROFORM-d) δ ppm 1.38 (s, 3H), 1.55 (br. s, 9H), 2.54-2.72 (m, 2H), 3.62 (s, 3H), 3.75 (d, J=11.40 Hz, 1H), 4.10 (d, J=11.40 Hz, 1H), 6.95 (td, J=7.30, 0.90 Hz, 1H), 7.08 (d, J=7.30 Hz, 1H), 7.18 (t, J=7.30 Hz, 1H), 7.34-8.10 (m, 1H); LC-MS (ESI): (MH$^+$—BOC) 206.1

Intermediate 61

Methyl 2-(3-methylindolin-3-yl)acetate

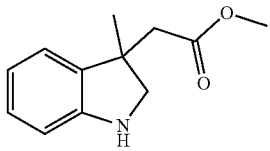

To a solution of Intermediate 60 (230 mg, 0.75 mmol) in DCM (10 ml) was added TFA (2 ml) and stirred for 15 minutes. Sat.NaHCO$_{3(aq)}$ was added to neutralise the mixture, the organic layer was separated, dried and concentrated to give methyl 2-(3-methylindolin-3-yl)acetate, an orange oil (140 mg, 90%); $^1$H NMR (400 MHz, CHLOROFORM-d) δ ppm 1.41 (s, 3H) 2.62 (d, J=1.37 Hz, 2H) 3.36 (d, J=9.16 Hz, 1H) 3.63-3.66 (m, 3H) 3.67-3.70 (m, 1H) 6.65-6.68 (m, 1H) 6.72-6.77 (m, 1H) 7.02-7.08 (m, 2H); LC-MS (ESI): (MH$^+$) 206.1

Intermediate 62

2-(3-Methy indolin-3-yl ethanol

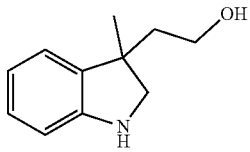

To a solution of Intermediate 61 (140 mg, 0.68 mmol) in THF (5 ml) was added a 1M solution of lithium aluminium hydride in THF (1.36 ml, 1.4 mmol) drop wise and stirred for 30 min. 52 μL of water was carefully added, followed by 52 μL 15% NaOH$_{(aq)}$ and finally 0.15 ml of water. The solids were removed via vacuum filtration and the filtrate concentrated to give a light brown oil (108 mg, 90%); $^1$H NMR (400 MHz, CHLOROFORM-d) δ ppm 1.40 (s, 3H), 1.61-1.70 (m, 1H), 1.90-2.00 (m, 1H), 3.16-3.24 (m, 1H), 3.30 (d, J=8.70 Hz, 1H), 3.49-3.54 (m, 2H), 6.72 (d, J=7.78 Hz, 1H), 6.79-6.86 (m, 1H), 7.01 (d, J=7.33 Hz, 1H), 7.07 (td, J=7.80, 0.90 Hz, 1H); LC-MS (ESI): (MH$^+$) 178.1

Intermediate 63

7-[5-Fluoro-3-(2-hydroxyethyl)indolin-1-yl]-N-tetrahydropyran-4-yl-thiazolo[5,4-d]pyrimidine-2-carboxamide

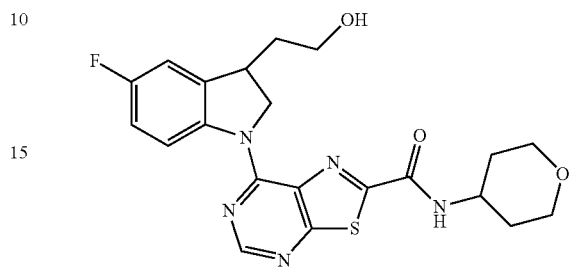

Intermediate 18 (200 mg, 0.67 mmol), Intermediate 47 and propan-2-ol were combined, sealed in a vial and heated at 50° C. for 3 hours. The mixture was cooled and concentrated to give a yellow solid (300 mg, 100%); $^1$H NMR (400 MHz, CHLOROFORM-d) δ ppm 1.67-1.76 (m, 2H), 1.90-1.96 (m, 1H), 1.98-2.04 (m, 2H), 2.13-2.21 (m, 1H), 3.50-3.57 (m, 2H), 3.68-3.76 (m, 1H), 3.83-3.91 (m, 1H), 3.92-3.98 (m, 1H), 3.99-4.04 (m, 2H), 4.14-4.26 (m, 1H), 4.79 (dd, J=12.59, 6.18 Hz, 1H), 5.23 (dd, J=12.36, 9.16 Hz, 1H), 6.98-7.06 (m, 2H), 7.31 (d, J=8.24 Hz, 1H), 8.59-8.66 (m, 2H); LC-MS (ESI): (MH$^+$) 444.0

Intermediate 64

7-[-3-(2-Hydroxyethyl)indolin-1-yl]-N-tetrahydropyran-4-yl-thiazolo[5,4-d]pyrimidine-2-carboxamide

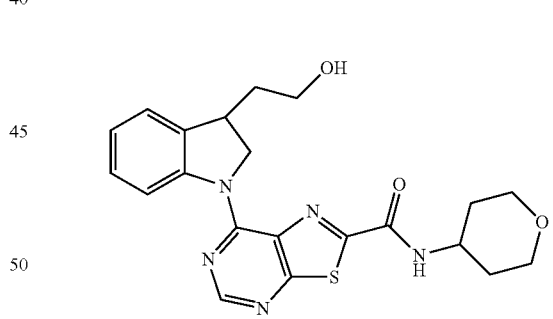

Intermediate 18 (114 mg, 0.38 mmol), Intermediate 31 (62 mg, 0.38 mmol) and propan-2-ol were combined, sealed in a vial and heated at 80° C. for 3 hours. The mixture was cooled and concentrated onto silica, and purified via column chromatography (gradient elution from 0-5% MeOH in EtOAc) to give a yellow solid (210 mg); $^1$H NMR (400 MHz, DMSO-d$_6$) δ ppm 1.71-1.91 (m, 4H) 3.35-3.46 (m, 2H) 3.59-3.72 (m, 3H) 3.92 (dd, J=11.22, 2.98 Hz, 2H) 4.00-4.13 (m, 1H) 4.70 (dd, J=12.59, 4.35 Hz, 1H) 4.96 (dd, J=12.59, 8.47 Hz, 1H) 7.10 (td, J=7.44, 1.14 Hz, 1H) 7.25-7.33 (m, 1H) 7.39-7.48 (m, 1H) 8.62 (d, J=8.24 Hz, 1H) 8.67 (s, 1H) 8.71 (d, J=8.24 Hz, 1H); LC-MS (ESI): (MH$^+$) 412.1

Intermediate 65

7-Chloro-N-methyl-thiazolo[5,4-d]pyrimidine-2-carboxamide

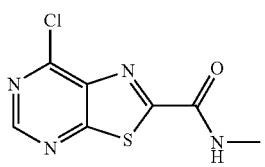

Intermediate 65 was prepared analogously to Intermediate 18. $^1$H NMR (400 MHz, CHLOROFORM-d) δ ppm 8.97 (s, 1H), 7.44 (br. s, NH), 3.12 (d, J=5.50 Hz, 3H).

Intermediate 66

Ethyl 7-chlorothiazolo[5,4-d]pyrimidine-2-carboxylate

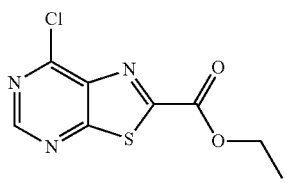

To a solution of ethyl 7-methylsulfanylthiazolo[5,4-d]pyrimidine-2-carboxylate (1 g, 3.9 mmol) in DCM (20 ml) at 0° C. was added sulfuryl chloride (0.63 ml, 7.8 mmol) dropwise. The mixture was stirred for 1 hour and then concentrated to give a yellow solid (952 mg, 100%); $^1$H NMR (400 MHz, CHLOROFORM-d) δ ppm 1.51 (t, J=7.20 Hz, 3H), 4.60 (q, J=7.17 Hz, 2H), 9.02 (s, 1H).

Intermediate 67

Ethyl 7-(3,3-dimethylindolin-1-yl)thiazolo[5,4-d]pyrimidine-2-carboxylate

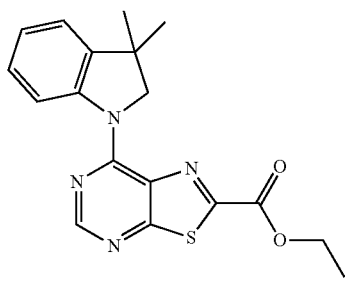 [SMILES: CCOC(=O)c1nc2c(N3CC(C)(C)c4ccccc43)ncnc2s1]

Intermediate 66 (300 mg, 1.2 mmol), 3,3-dimethylindoline (182 mg, 1.2 mmol) and propan-2-ol (3 ml) were sealed in a vial and heated at 70° C. for 4 hours. The mixture was cooled, at which point a precipitate formed. This was collected and dried via vacuum filtration to afford ethyl 7-(3,3-dimethylindolin-1-yl)thiazolo[5,4-d]pyrimidine-2-carboxylate, as a yellow solid (322 mg, 74%); $^1$H NMR (400 MHz, CHLOROFORM-d) δ ppm 1.48 (m, 9H), 4.56 (q, J=7.33 Hz, 2H), 4.80 (s, 2H), 7.31-7.41 (m, 3H), 8.65 (d, J=7.78 Hz, 1H), 8.75 (s, 1H); LC-MS (ESI): (MH$^+$)355.0

Intermediate 68

7-(3,3-Dimethylindolin-1-yl)thiazolo[5,4-d]pyrimidine-2-carboxylic acid

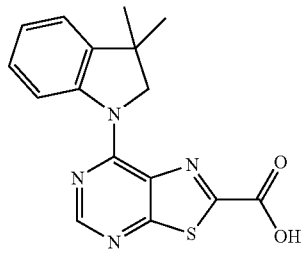 [SMILES: CC1(C)CN(c2ncnc3sc(C(=O)O)nc23)c2ccccc21]

To a solution of Intermediate 67 (322 mg, 0.9 mmol) In THF (10 ml) was added 15% NaOH$_{(aq)}$ and stirred for 1 hour. The mixture was acidified, at which point a precipitate formed. This was collected and dried by vacuum filtration to give a yellow solid (243 mg, 82%); $^1$H NMR (400 MHz, DMSO-d) δ ppm 1.42 (s, 6H), 4.60 (s, 2H), 7.10-7.18 (m, 1H), 7.25-7.32 (m, 1H), 7.38 (dd, J=7.80, 0.90 Hz, 1H), 8.61 (d, J=7.78 Hz, 1H), 8.71 (s, 1H).

Intermediate 69

(1R,2R)-2-(5-fluoro-2-nitro-phenoxy)cyclohexanol

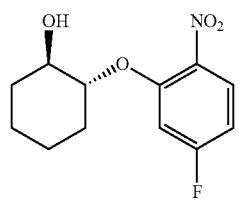 [SMILES: O=[N+]([O-])c1ccc(F)cc1O[C@@H]1CCCC[C@H]1O]

LiHMDS (8.6 ml, 8.6 mmol, 1M in THF) was added slowly to (1R,2R)-cyclohexane-1,2-diol (1 g, 8.6 mmol) in THF (10 ml) at room temperature. An additional (5 ml) of THF was added and the mixture was stirred for 5 minutes, then 2,4-difluoro-1-nitro-benzene (0.943 ml, 8.6 mmol) was added dropwise. The mixture stirred at room temperature overnight. The mixture was diluted with EtOAc and 2M HCl (aq), the organic layer separated and washed with 2M NaOH (aq), then eluted through a phase separator and concentrated. Purification by column chromatography, eluting with 0-15% EtOAc/petroleum ether gave a yellow solid (1.2 g, 55%); $^1$H NMR (400 MHz, DMSO-d$_6$) δ ppm 0.97-1.44 (m, 4H), 1.48-1.65 (m, 2H), 1.69-1.85 (m, 1H), 1.87-2.10 (m, 1H), 3.41-3.68 (m, 1H), 4.12-4.41 (m, 1H), 4.92 (br. s, 1H), 6.76-7.02 (m, 1H), 7.39 (dd, J=11.45, 2.75 Hz, 1H), 7.91 (dd, J=9.16, 6.41 Hz, 1H)

Intermediate 70

(1R,2R)-2-(2-amino-5-fluoro-phenoxy)cyclohexanol

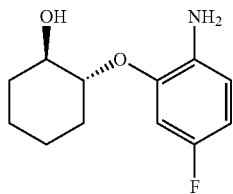

A solution of Intermediate 69 (1.2 g, 4.7 mmol) in 5:1 EtOH:EtOAc (120 ml) was passed through an H-Cube reactor (Cartridge: 10% Pd/C; flow rate: ml/min-1; temperature: room temperature; pressure: 1 bar). The solution was concentrated to give (1R,2R)-2-(2-amino-5-fluoro-phenoxy)cyclohexanol as a brown gum (1.05 mg, 99%); $^1$H NMR (400 MHz, DMSO-do) δ ppm 1.16-1.37 (m, 4H), 1.51-1.64 (m, 2H), 1.78-1.88 (m, 1H), 1.95 (s, 1H), 3.44-3.56 (m, 1H), 3.69-3.81 (m, 1H), 4.66 (br. s., 2H), 5.04 (d, J=4.58 Hz, 1H), 6.47 (m, 1H), 6.50-6.58 (m, 1H), 6.65-6.73 (m, 1H); LC-MS (ESI): (MH$^+$) 226.1

Intermediate 71

4-Fluoro-2-(1R,2R)-2-methoxycyclohexoxy-1-nitrobenzene

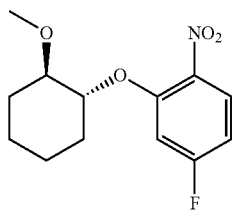 [SMILES: CO[C@@H]1CCCC[C@H]1Oc1cc(F)ccc1[N+](=O)[O-]]

Intermediate 69 (1.36 g, 5.33 mmol) and trimethyloxonium tetrafluoroborate (2.36 g, 16 mmol) were combined in DCM (30 ml) and stirred at room temperature overnight. The mixture was diluted with water, the organic layer separated, dried over MgSO$_4$ and concentrated. Purification by column chromatography, eluting with 2-5% EtOAc/petroleum ether gave a yellow oil (19 g, 70%); $^1$H NMR (400 MHz, CHLOROFORM-d) δ ppm 1.16-1.43 (m, 3H), 1.50-1.65 (m, 1H), 1.66-1.85 (m, 2H), 2.01-2.21 (m, 2H), 3.29-3.41 (m, 4H), 4.14-4.27 (m, 1H), 6.62-6.72 (m, 1H), 6.87-6.94 (m, 1H), 7.82-7.91 (m, 1H)

Intermediate 72

4-Fluoro-2-[(1R,2R)-2-methoxycyclohexoxy]aniline

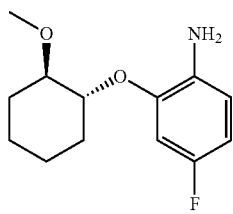

Intermediate 72 was prepared analogously to Intermediate 70 to give a golden oil (0.84 g, 95%); $^1$H NMR (400 MHz, CHLOROFORM-d) δ ppm 1.18-1.39 (m, 3H), 1.42-1.56 (m, 1H), 1.63-1.79 (m, 2H), 2.05-2.18 (m, 2H), 3.28-3.38 (m, 1H), 3.44 (s, 3H), 3.94 (m, 1H), 6.49-6.58 (m, 1H), 6.63-6.72 (m, 2H); (MH$^+$) 240.2.

Intermediate 73

(1S,2S)-2-(5-fluoro-2-nitro-phenoxy)cyclohexanol

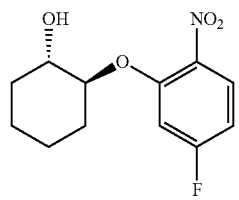 [SMILES: Nc1ccc(F)cc1O[C@H]1CCCC[C@@H]1O]

Prepared analogously to Intermediate 69 to give a yellow solid (1.9 g, 29%); $^1$H NMR (400 MHz, DMSO-d$_6$) δ ppm 1.14-1.41 (m, 4H), 1.51-1.63 (m, 2H), 1.75-1.85 (m, 1H), 1.90-2.01 (m, 1H), 3.44-3.53 (m, 1H), 4.26-4.35 (m, 1H), 4.94 (d, J=5.04 Hz, 1H), 6.84-6.92 (m, 1H), 7.39 (dd, J=11.45, 2.29 Hz, 1H), 7.91 (dd, J=9.16, 5.95 Hz, 1H)

Intermediate 74

(1S,2S)-2-(2-amino-5-fluoro-phenoxy)cyclohexanol

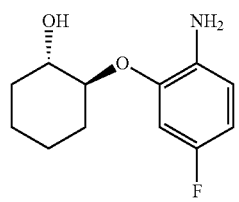

Prepared analogously to Intermediate 70 to give (1S,2S)-2-(2-amino-5-fluoro-phenoxy)cyclohexanol as a brown gum (0.95 g), which was used in the next step without further purification. $^1$H NMR (400 MHz, DMSO-d$_6$) δ ppm 1.16-1.33 (m, 4H), 1.48-1.66 (m, 2H), 1.78-1.87 (m, 1H), 1.93-2.04 (m, 1H), 3.45-3.54 (m, 1H), 3.71-3.80 (m, 1H), 4.63 (s, 2H), 5.04 (d, J=4.58 Hz, 1H), 6.42-6.49 (m, 1H), 6.50-6.57 (m, 1H), 6.65-6.72 (m, 1H); (MH$^+$) 226

Intermediate 75

4-fluoro-2-[(1S,2S)-2-methoxycyclohexoxy]-1-nitrobenzene

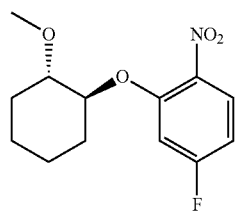 [SMILES: CO[C@H]1CCCC[C@@H]1Oc1cc(F)ccc1[N+](=O)[O-]]

Intermediate 75 was prepared analogously to Intermediate 71 to a yellow oil (0.63 g, 66%); $^1$H NMR (400 MHz, CHLOROFORM-d) δ ppm 1.22-1.41 (m, 3H), 1.55 (m, 1H), 1.66-1.81 (m, 2H), 2.02-2.18 (m, 2H), 3.29-3.41 (m, 4H), 4.13-4.25 (m, 1H), 6.62-6.72 (m, 1H), 6.91 (dd, J=10.53, 2.75 Hz, 1H), 7.82-7.91 (m, 1H)

Intermediate 76

4-fluoro-2-[(1S,2S)-2-methoxycyclohexoxy]aniline

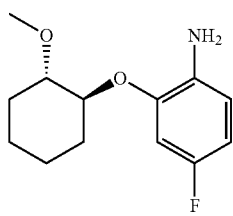

Prepared analogously to Intermediate 70 to give 4-fluoro-2-[(1S,2S)-2-methoxycyclohexoxy]aniline as a brown oil (0.54 g, 97%); $^1$H NMR (400 MHz, CHLOROFORM-d) δ ppm 1.21-1.39 (m, 3H), 1.42-1.54 (m, 1H), 1.63-1.81 (m, 2H), 2.03-2.17 (m, 2H), 3.28-3.36 (m, 1H), 3.44 (s, 3H), 3.88-3.99 (m, 1H), 6.50-6.58 (m, 1H), 6.65-6.72 (m, 2H); (MH$^+$) 240.2

Intermediate 77

Ethyl 7-(5-nitro-2,3-dihydro-1H-indol-1-yl)[1,3]thiazolo[5,4-d]pyrimidine-2-carboxylate

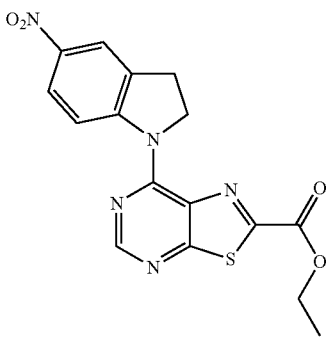 [SMILES: CCOC(=O)c1nc2c(N3CCc4cc([N+](=O)[O-])ccc43)ncnc2s1]

A mixture of Intermediate 66 (50 mg, 0.205 mmol) and 5-nitroindoline (34 mg, 0.205 mmol) in IPA (2 ml) was stirred and heated at 80° C. for 5 hours. The mixture was cooled to rt and a yellow solid was isolated by filtration (44 mg, 58%). $^1$H NMR (400 MHz, CHLOROFORM-d) δ ppm 1.50 (t, J=7.33 Hz, 3H), 3.44 (t, J=8.70 Hz, 2H), 4.56 (q, J=7.33 Hz, 2H), 5.03-5.12 (m, 2H), 8.14-8.18 (m, 1H), 8.23 (dd, J=8.93, 2.52 Hz, 1H), 8.81 (s, 1H), 8.86 (d, J=8.70 Hz, 1H).

Intermediate 78

7-(5-Nitro-2,3-dihydro-1H-indol-1-yl)[1,3]thiazolo[5,4-d]pyrimidine-2-carboxylic acid

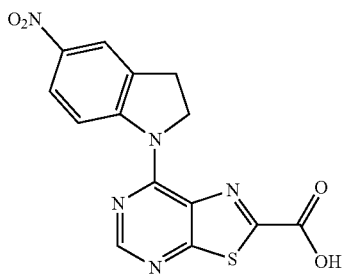 [SMILES: O=C(O)c1nc2c(N3CCc4cc([N+](=O)[O-])ccc43)ncnc2s1]

A mixture of Intermediate 77 (651 mg, 1.75 mmol) and 1 N NaOH (aq) in 1:1 EtOH:THF (30 ml) was stirred at rt for 3 hours. The reaction mixture was concentrated to a small volume and then diluted with water. 1 M HCl was added to pH=3-4. A yellow solid was isolated by filtration. The solid was diluted with MeOH and the mixture was concentrated to dryness (660 mg, 110%). $^1$H NMR (400 MHz, DMSO-d$_6$) δ ppm 3.41 (t, J=8.47 Hz, 2H), 4.92 (t, J=8.47 Hz, 2H), 8.16-8.25 (m, 2H), 8.74-8.80 (m, 1H), 8.83 (s, 1H).

Intermediate 79

7-(5-Amino-2,3-dihydro-1H-indol-1-yl)-N-(1-methylpiperidin-4-yl)[1,3]thiazolo[5,4-d]pyrimidine-2-carboxamide

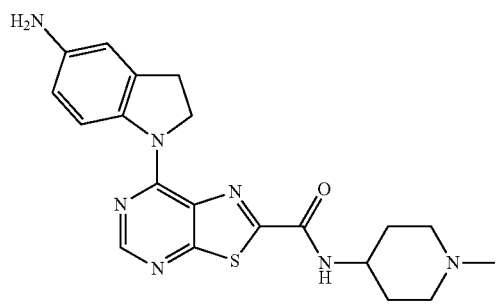

A mixture of Example 45 (210 mg, 0.478 mmol), ammonium chloride (127 mg, 2.39 mmol) and zinc powder (155 mg, 2.39 mmol) in 1:1:1 MeOH:THF:water (30 ml) was stirred and heated at 60° C. for 5 hours. The mixture was the cooled to rt and concentrated to dryness. The solid residue was pre-absorbed onto silica gel prior to purification by flash column chromatography on silica gel eluting with 10:1 DCM: 2M NH$_3$ in MeOH to provide a yellow solid (62 mg, 32%). $^1$H NMR (400 MHz, DMSO-d$_6$) δ ppm 1.71-1.85 (m, 4H), 1.89-2.03 (m, 2H), 2.18 (a, 3H), 2.82 (d, J=11.45 Hz, 2H), 3.15-3.26 (m, 2H), 3.71-3.87 (m, 1H), 4.81 (t, J=8.24 Hz, 2H), 5.07 (s, 2H), 6.46 (dd, J=8.70, 2.29 Hz, 1H), 6.58 (d, J=2.29 Hz, 1H), 8.37 (d, J=8.70 Hz, 1H), 8.53 (s, 1H), 8.66 (d, J=8.24 Hz, 1H). (ES+APCl)$^+$: 410 [M+H]$^+$

95

Intermediate 80

Tert-butyl 4-[[(7-chlorothiazolo[5,4-d]pyrimidine-2-carbonyl)amino]methyl]piperidine-1-carboxylate

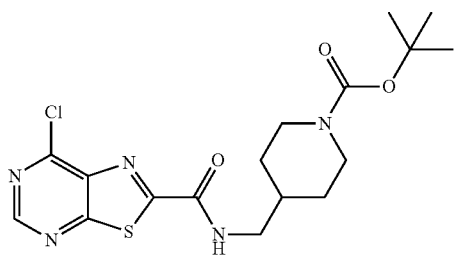 [SMILES: CC(C)(C)OC(=O)N1CCC(CNC(=O)c2nc3c(Cl)ncnc3s2)CC1]

To a stirred solution of Intermediate 3 (1.02 g, 2.4 mmol) in acetonitrile (40 ml) with ice cooling was added, dropwise, a solution of $SO_2Cl_2$ (0.39 ml, 4.8 mmol). The resulting mixture was stirred at 0° C. for 2 h and then quenched with sat. $NaHCO_3$(aq). The layers were separated, and the aqueous phase was extracted with DCM and the combined organic extracts were washed (brine), dried ($MgSO_4$) and concentrated under reduced pressure to give an off-white solid (1 g), which was used in the next step without further purification.

Example 1

7-(4-Fluoro-2-isopropoxy-anilino)thiazolo[5,4-d]pyrimidine-2-carboxylic acid

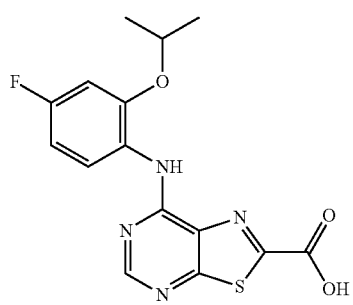 [SMILES: CC(C)Oc1cc(F)ccc1Nc1ncnc2sc(C(=O)O)nc12]

To a solution of Intermediate 1 (326 mg, 0.87 mmol) in THF (6 ml) was added 2M $NaOH_{(aq)}$ (2 ml) and the mixture was stirred for 1 hours. The reaction was acidified with 2M HCl. and concentrated to remove THF and the resulting brown precipitate collected and dried via vacuum filtration to give a dark yellow solid (285 mg, 95%); $^1$H NMR (400 MHz, DMSO-$d_6$) δ ppm 1.23 (d, J=6.00 Hz, 6H), 4.69 (spt, J=6.00 Hz, 1H), 6.82 (td, J=8.59, 2.52 Hz, 1H), 7.04-7.12 (m, 1H), 7.86-7.95 (m, 1H), 8.55 (s, 1H), 9.42 (8, 1H); LC-MS (ESI): (MH$^+$) 349.0

96

Example 2

7-{[4-Fluoro-2-(propan-2-yloxy)phenyl]amino}-N-methyl[f, 3]thiazolo[5,4-d]pyrimidine-2-carboxamide

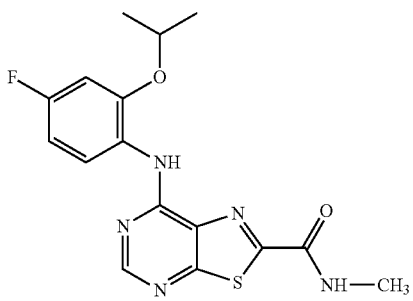 [SMILES: CNC(=O)c1nc2c(Nc3ccc(F)cc3OC(C)C)ncnc2s1]

A mixture of Example 1 (100 mg, 0.287 mmol), methylamine hydrochloride (20 mg, 0.287 mmol), EDC hydrochloride (55 mg, 0.287 mmol) and HOBt (39 mg, 0.287 mmol) in DCM (5 ml) was stirred at rt overnight. A further 47 mg of methylamine hydrochloride was added and the reaction mixture was stirred at rt overnight. The reaction mixture was diluted with DCM and was pre-absorbed onto silica gel prior to purification by flash column chromatography on silica gel, eluting with 1:1 petrol:EtOAc to provide a yellow solid (17 mg, 16%). $^1$H NMR (400 MHz, DMSO-$d_6$) δ ppm 1.30 (d, J=6.41 Hz, 6H), 2.90 (d, J=5.04 Hz, 3H), 4.73 (dt, J=12.25, 6.01 Hz, 1H), 6.85 (td, J=8.70, 2.75 Hz, 1H), 7.12 (dd, J=11.45, 2.75 Hz, 1H), 8.15 (dd, J=9.16, 6.41 Hz, 1H), 8.59 (s, 1H), 8.76-8.99 (m, 2H). m/z (ES+APCl): 362 [M+H]$^+$

Example 3

N-[3-(Dimethylamino)propyl]-7-(4-fluoro-2-isopropoxy-anilino)thiazolo[5,4-d]pyrimidine-2-carboxamide

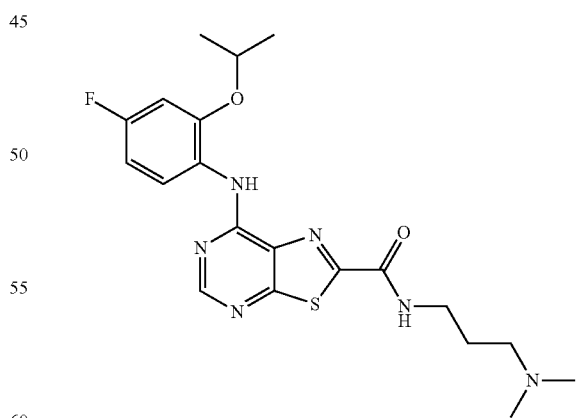

Example 1 (100 mg, 0.29 mmol), N,N-dimethylaminopropylamine (35 μL, 0.27 mmol), HATU (153 mg, 0.40 mmol), DIPEA (0.32 ml, 1.7 mmol) and DMF (5 ml) were combined and stirred overnight. The reaction was diluted with EtOAc and washed with water (×3). The organic layer was separated, dried and concentrated onto silica. The compound was purified via column chromatography (0-30% MeOH in DCM) to give the product (6 mg, 5%); $^1$H NMR (400 MHz, CHLOROFORM-d) δ ppm 1.47 (d, J=6.41 Hz, 6H), 2.15 (quin, J=6.64 Hz, 2H), 2.67 (s, 6H), 2.94 (t, J=6.87 Hz, 2H), 3.70 (q, J=6.30 Hz, 2H), 4.62 (spt, J=6.00 Hz, 1H), 6.64-6.81 (m, 2H), 8.33 (br. t, J=5.50, 5.50 Hz, 1H), 8.43 (br. s, 1H), 8.48 (dd, J=8.70, 6.41 Hz, 1H), 8.64 (s, 1H); LC-MS (ESI): (MH$^+$) 433.1

Example 4

7-(4-fluoro-2-isopropoxy-anilino)-N-(morpholin-2-ylmethyl)thiazolo[5,4-d]pyrimidine-2-carboxamide

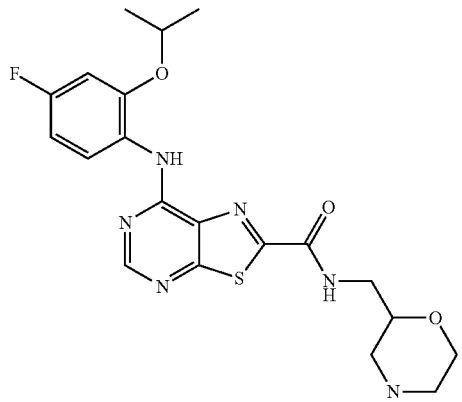 [SMILES: CC(C)Oc1cc(F)ccc1Nc1ncnc2sc(C(=O)NCC3CNCCO3)nc12]

Example 1 (75 mg, 0.22 mmol), tert-butyl 2-(aminomethyl)morpholine-4-carboxylate (46 mg, 0.22 mmol), HATU (115 mg, 0.30 mmol), DIPEA (0.2 ml, 1.1 mmol) and DMF (1 ml) were combined and stirred overnight. The mixture was diluted with EtOAc and washed with water (×3). The organic layer was separated, dried and concentrated onto silica. The compound was purified via column chromatography (gradient elution from 40-100% EtOAc in Pet. Ether). The purified BOC protected compound was taken up in DCM (1 ml), TFA (1 ml) added and stirred for 30 mins. The mixture was passed through an amino propyl cartridge, eluting with 2M NH$_3$ In MeOH to give the product (28.9 mg, 30%); $^1$H NMR (400 MHz, CHLOROFORM-d) δ ppm 1.48 (d, J=6.00 Hz, 6H), 2.68-2.78 (m, 1H), 2.90-2.97 (m, 2H), 3.05 (d, J=11.45 Hz, 1H), 3.36-3.48 (m, 1H), 3.69-3.85 (m, 3H), 3.94 (dt, J=11.00, 2.30 Hz, 1H), 4.64 (quin, J=6.18 Hz, 1H), 6.69-6.82 (m, 2H), 7.59 (br. t, J=6.90, 6.90 Hz, 1H), 8.60 (s, 1H), 8.67-8.72 (m, 2H); LC-MS (ESI): (MH$^+$) 447.1

Example 5-14

Example 5-14 In the table below were prepared analogously to Example 3 and Example 4 from 7-(4-fluoro-2-isopropoxy-anilino)thiazolo[5,4-d]pyrimidine-2-carboxylic acid and the appropriate, optionally BOC protected, amine.

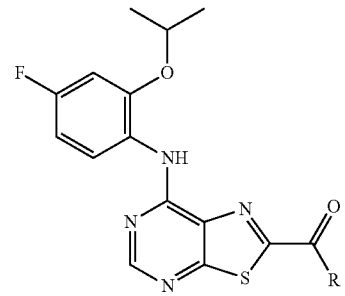

| Example | R | IUPAC Name | LC-MS (ESI): (MH$^+$) | $^1$H NMR |
|---|---|---|---|---|
| 5 | HN-[8-azabicyclo[3.2.1]octane] | N-(8-azabicyclo[3.2.1]octan-3-yl)-7-(4-fluoro-2-isopropoxy-anilino)thiazolo[5,4-d]pyrimidine-2-carboxamide | 457.2 | $^1$H NMR (400 MHz, CHLOROFORM-d) δ ppm 1.45 (d, J = 6.00 Hz, 6 H), 1.93 (d, J = 14.20 Hz, 2 H), 2.09 (s, 4 H), 2.25-2.37 (m, 2 H), 3.73 (br. s., 2 H), 4.42 (q, J = 6.87 Hz, 1 H), 4.66 (spt, J = 6.03 Hz, 1 H), 6.69-6.83 (m, 2 H), 7.69 (d, J = 7.78 Hz, 1 H), 8.47 (s, 1 H), 8.67-8.69 (m, 1 H), 8.75 (dd, J = 9.16, 6.41 Hz, 1 H) |
| 6 | HN-[8-azabicyclo[3.2.1]octane-N-CO$_2$t-Bu] | tert-butyl 3-[[7-(4-fluoro-2-isopropoxy-anilino)thiazolo[5,4-d]pyrimidine-2-carbonyl]amino]-8-azabicyclo[3.2.1]octane-8-carboxylate | 557.2 | $^1$H NMR (400 MHz, CHLOROFORM-d) δ ppm 1.44 (d, J = 6.00 Hz, 6 H), 1.49 (s, 9 H), 1.80-2.04 (m, 4 H), 2.11-2.24 (m, 2 H), 2.24-2.48 (m, 2 H), 4.23-4.45 (m, 3 H), 4.64 (spt, J = 6.00 Hz, 1 H), 6.70-6.81 (m, 2 H), 7.69 (d, J = 1.00 Hz, 1 H), 8.47 (s, 1 H), 8.66 (s, 1 H), 8.69-8.78 (m, 1 H) |

-continued

| Example | R | IUPAC Name | LC-MS (ESI): (MH⁺) | ¹H NMR |
|---|---|---|---|---|
| 7 | (2,6-diazaspiro[3.3]heptan-2-yl, N-H) | 2,6-diazaspiro[3.3]heptan-2-yl-[7-(4-fluoro-2-isopropoxy-anilino)thiazolo[5,4-d]pyrimidin-2-yl]methanone | 429.1 | ¹H NMR (400 MHz, CHLOROFORM-d) δ ppm 1.51 (d, J = 5.95 Hz, 6 H), 3.86 (dd, J = 24.30, 8.70 Hz, 4 H), 4.43 (s, 2 H), 4.69 (spt, J = 6.00 Hz, 1 H), 4.93 (s, 2 H), 6.68-6.84 (m, 2 H), 8.54-8.63 (m, 1 H), 8.68 (s, 1 H), 8.79 (dd, J = 8.93, 6.18 Hz, 1 H) |
| 8 | (NH-CH₂CH₂CH₂-OH) | 7-(4-fluoro-2-isopropoxy-anilino)-N-(3-hydroxypropyl)thiazolo[5,4-d]pyrimidine-2-carboxamide | 406.2 | ¹H NMR (400 MHz, CHLOROFORM-d) δ ppm 1.46 (d, J = 6.00 Hz, 6 H), 1.91 (quin, J = 6.00 Hz, 2 H), 3.73 (q, J = 6.41 Hz, 2 H), 3.83 (t, J = 5.50 Hz, 2 H), 4.63 (spt, J = 6.00 Hz, 1 H), 6.69-6.81 (m, 2 H), 7.64 (br. t, J = 4.60, 4.60 Hz, 1 H), 8.50 (br. s., 1 H), 8.64 (dd, J = 8.93, 6.18 Hz, 1 H), 8.67 (s, 1 H) |
| 9 | (NH-CH₂CH₂-piperazine) | 7-(4-fluoro-2-isopropoxy-anilino)-N-(2-piperazin-1-ylethyl)thiazolo[5,4-d]pyrimidine-2-carboxamide | 460.2 | ¹H NMR (400 MHz, CHLOROFORM-d) δ ppm 1.46 (d, J = 5.95 Hz, 6 H), 2.52 (br. s., 4 H), 2.65 (t, J = 5.95 Hz, 2 H), 2.95 (t, J = 4.81 Hz, 4 H), 3.65 (q, J = 6.10 Hz, 2 H), 4.63 (spt, J = 6.03 Hz, 1 H), 6.68-6.84 (m, 2 H), 7.56 (br. t, J = 5.00, 5.00 Hz, 1 H), 8.43 (br. s, 1 H), 8.62 (dd, J = 8.93, 6.18 Hz, 1 H), 8.66 (s, 1 H) |
| 10 | (NH-CH₂-4-piperidyl) | 7-(4-fluoro-2-isopropoxy-anilino)-N-(4-piperidylmethyl)thiazolo[5,4-d]pyrimidine-2-carboxamide | 445.2 | ¹H NMR (400 MHz, CHLOROFORM-d) δ ppm 1.22-1.37 (m, 2 H), 1.46 (d, J = 6.00 Hz, 6 H), 1.74-1.85 (m, 3 H), 2.65 (td, J = 12.14, 2.29 Hz, 2 H), 3.14 (dt, J = 11.90, 2.30 Hz, 2 H), 3.44 (t, J = 6.18 Hz, 2 H), 4.64 (spt, J = 6.03 Hz, 1 H), 6.69-6.84 (m, 2 H), 7.33 (br. t, J = 6.00, 6.00 Hz, 1 H), 8.53 (s, 1 H), 8.63-8.73 (m, 2 H) |

-continued

| Example | R | IUPAC Name | LC-MS (ESI): (MH+) | 1H NMR |
|---|---|---|---|---|
| 11 | (piperidin-4-yl with 2-hydroxyethyl substituent) | [7-(4-fluoro-2-isopropoxy-anilino)thiazolo[5,4-d]pyrimidin-2-yl]-(4-(2 hydroxyethyl)-1-piperidyl]methanone | 460.2 | 1H NMR (400 MHz, CHLOROFORM-d) δ ppm 1.46 (d, J = 6.00 Hz, 6 H), 2.49-2.60 (m, 1 H), 2.60-2.74 (m, 6 H), 3.70 (br. t, J = 1.00, 1.00 Hz, 2 H), 3.85-3.96 (m, 2 H), 4.50 (m, J = 4.60 Hz, 2 H), 4.64 (spt, J = 6.11 Hz, 1 H), 6.68-6.83 (m, 2 H), 8.53 (br. s, 1 H), 8.69 (s, 1 H), 8.77 (dd, J = 8.93, 6.18 Hz, 1 H) |
| 12 | (NH-CH2-CH(OH)-CH2OH) | N-(2,3-dihydroxypropyl)-7-(4-fluoro-2-isopropoxy-anilino)thiazolo[5,4-d]pyrimidine-2-carboxamide | 422.1 | 1H NMR (400 MHz, CHLOROFORM-d) δ ppm 1.47 (d, J = 5.95 Hz, 6 H), 3.57-3.71 (m, 2 H), 3.74-3.84 (m, 2 H), 3.95-4.05 (m, 1 H), 4.64 (spt, J = 6.00 Hz, 1 H), 6.68-6.82 (m, 2 H), 7.69 (br. t, J = 5.50, 5.50 Hz, 1 H), 8.54 (s, 1 H), 8.62-8.69 (m, 2 H) |
| 13 | (NH-CH2CH2CH2-pyrrolidine) | 7-(4-fluoro-2-isopropoxy-anilino)-N-(3-pyrrolidin-1-ylpropyl)thiazolo[5,4-d]pyrimidine-2-carboxamide | 459.1 | 1H NMR (400 MHz, CHLOROFORM-d) δ ppm 1.43 (d, J = 5.95 Hz, 6 H), 1.84-1.93 (m, 4 H), 1.93-2.05 (m, 2 H), 2.70-2.97 (m, 6 H), 3.65 (q, J = 6.11 Hz, 2 H), 4.61 (spt, J = 6.00 Hz, 1 H), 6.68-6.82 (m, 2 H), 8.20 (br. t, J = 4.70, 4.70 Hz, 1 H), 8.37 (br. s, 1 H), 8.48 (dd, J = 8.93, 6.18 Hz, 1 H), 8.65 (s, 1 H) |
| 14 | (NH-CH2CH2-COOH) | 3-[[7-(4-fluoro-2-isopropoxy-anilino)thiazolo[5,4-d]pyrimidine-2-carbonyl]amino]propanoic acid | 420.0 | 1H NMR (400 MHz, DMSO-d6) δ ppm 1.27 (d, J = 5.95 Hz, 6 H), 2.58 (t, J = 6.40 Hz, 2 H), 3.56 (q, J = 6.41 Hz, 2 H), 4.70 (spt, J = 6.00 Hz, 1 H), 6.84 (td, J = 8.70, 2.75 Hz, 1 H), 7.10 (dd, J = 10.99, 2.75 Hz, 1 H), 8.04 (dd, J = 8.70, 6.41 Hz, 1 H), 8.57 (s, 1 H), 8.70 (br. t, J = 6.00, 6.00 Hz, 1 H), 9.12 (br. s., 1 H) |

Example 15

N-[3-(dimethylamino)propyl]-7-[4-fluoro-2-[(1R,2R)-2-hydroxycyclohexoxy]anilino]thiazolo[5,4-d]pyrimidine-2-carboxamide

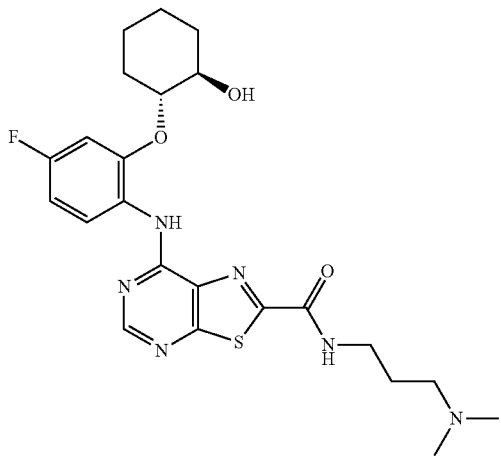 [SMILES: CN(C)CCCNC(=O)c1nc2c(Nc3ccc(F)cc3O[C@@H]3CCCC[C@H]3O)ncnc2s1]

Intermediate 70 (36 mg, 0.16 mmol), Intermediate 4 (50 mg, 0.16 mmol), TFA (50 ul) and IPA (750 ul) were combined in a sealed microwave reactor vial and heated at 170 degrees in a Biotage microwave reactor for 45 minutes. The mixture was evaporated and purified by preparative LCMS to give a yellow solid (20 mg, 26%). 1H NMR (400 MHz, DMSO-d6) δ ppm 1.12-1.42 (m, 4H), 1.51-1.60 (m, 2H), 1.63-1.73 (m, 2H), 1.77-1.86 (m, 1H), 1.98-2.07 (m, 1H), 2.12 (s, 6H), 2.27 (t, J=7.10 Hz, 2H), 3.32-3.43 (m, 2H), 3.53-3.61 (m, 1H), 3.97-4.05 (m, 1H), 5.15-5.22 (m, 1H), 6.81-6.88 (m, 1H), 7.14 (dd, J=10.53, 2.75 Hz, 1H), 8.16 (dd, J=8.70, 6.41 Hz, 1H), 8.56 (s, 1H), 8.68-8.77 (m, 1H), 9.27 (s, 1H); (MH+) 489.20

Example 16

N-[3-(dimethylamino)propyl]-7-[4-fluoro-2-[(3R)-tetrahydropyran-3-yl]oxy-anilino]thiazolo[5,4-d]pyrimidine-2-carboxamide

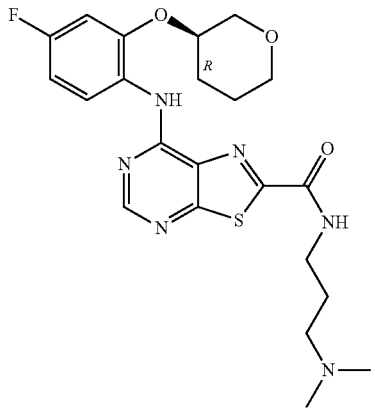

Prepared analogously to Example 15 from Intermediate 4 (75 mg, 0.241 mmol) and 4-fluoro-2-[(3R)-tetrahydropyran-3-yl]oxy-aniline (101 mg, 0.721 mmol) to give the product as a yellow solid (18 mg, 21%). 1H NMR (400 MHz, DMSO-d6) δ ppm 1.38-1.52 (m, 1H), 1.64-1.73 (m, 2H), 1.75-1.88 (m, 2H), 1.90-2.02 (m, 1H), 2.10-2.17 (m, 6H), 2.28 (t, J=6.87 Hz, 2H), 3.34-3.43 (m, 2H), 3.50-3.60 (m, 3H), 3.69 (dd, J=11.91, 2.29 Hz, 1H), 4.47-4.59 (m, 1H), 6.91 (td, J=8.70, 2.75 Hz, 1H), 7.22 (dd, J=10.53, 2.75 Hz, 1H), 8.17 (dd, J=9.16, 6.41 Hz, 1H), 8.57-8.62 (m, 1H), 8.62-8.72 (m, 1H), 9.15 (s, 1H); m/z (ES+APCl®): 475 [M+H]+

Example 17

N-[3-(dimethylamino)propyl]-7-[4-fluoro-2-[(3S)-tetrahydropyran-3-yl]oxy-anilino]thiazolo[5,4-d]pyrimidine-2-carboxamide

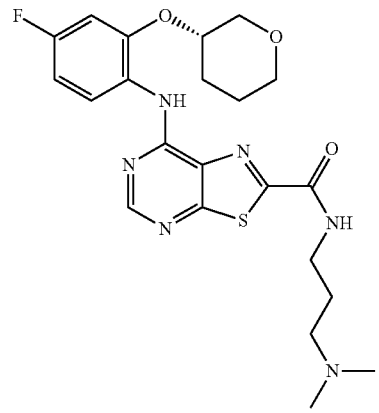 [SMILES: CN(C)CCCNC(=O)c1nc2c(Nc3ccc(F)cc3O[C@H]3CCCOC3)ncnc2s1]

Prepared analogously to Example 15 from Intermediate 4 (75 mg, 0.241 mmol) and 4-fluoro-2-[(3S)-tetrahydropyran-3-yl]oxy-aniline (101 mg, 0.721 mmol) to give the product as a yellow solid (18 mg, 21%) 1H NMR (400 MHz, DMSO-d6) δ ppm 1.39-1.52 (m, 1H), 1.64-1.74 (m, 2H), 1.74-1.89 (m, 2H), 1.91-2.01 (m, 1H), 2.10-2.17 (m, 6H), 2.28 (t, J=6.87 Hz, 2H), 3.34-3.43 (m, 2H), 3.50-3.60 (m, 3H), 3.69 (dd, J=11.91, 2.29 Hz, 1H), 4.50-4.57 (m, 1H), 6.90 (td, J=8.47, 2.75 Hz, 1H), 7.21 (dd, J=10.53, 2.75 Hz, 1H), 8.17 (dd, J=9.16, 6.41 Hz, 1H), 8.60 (s, 1H), 8.62-8.70 (m, 1H), 9.15 (s, 1H). m/z (ES+APCl)+: 475 [M+H]+

Example 18

N-[3-(dimethylamino)propyl]-7-(3-fluoro-2-isopropoxy-anilino)thiazolo[5,4-d]pyrimidine-2-carboxamide

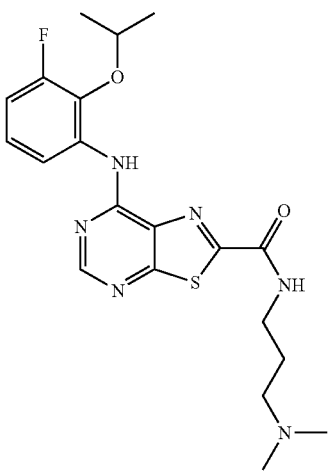 [SMILES: CC(C)Oc1c(F)cccc1Nc1ncnc2sc(C(=O)NCCCN(C)C)nc12]

Prepared analogously to Example 15 from Intermediate 4 (75 mg, 0.241 mmol) 3-fluoro-2-isopropoxy-aniline (122 mg, 0.721 mmol) to give the product as a yellow solid (18 mg, 21%) $^1$H NMR (400 MHz, DMSO-d$_6$) δ ppm 1.28 (d, J=5.95 Hz, 6H), 1.65-1.75 (m, 2H), 2.14 (s, 6H), 2.29 (t, J=6.87 Hz, 2H), 3.38 (q, J=-6.56 Hz, 2H), 4.71 (spt, J=6.11 Hz, 1H), 6.85 (td, J=8.70, 2.75 Hz, 1H), 7.12 (dd, J=10.99, 2.75 Hz, 1H), 8.10 (dd, J=8.93, 6.64 Hz, 1H), 8.56-8.59 (m, 1H), 8.89 (br. s., 1H), 8.96 (s, 1H). m/z (ES+APCl)$^+$: 433 [M+H]$^+$

Example 19

N-[3-(dimethylamino)propyl]-7-[4-fluoro-2-[(1S,2S)-2-hydroxycyclohexoxy]anilino]thiazolo[5,4-d]pyrimidine-2-carboxamide

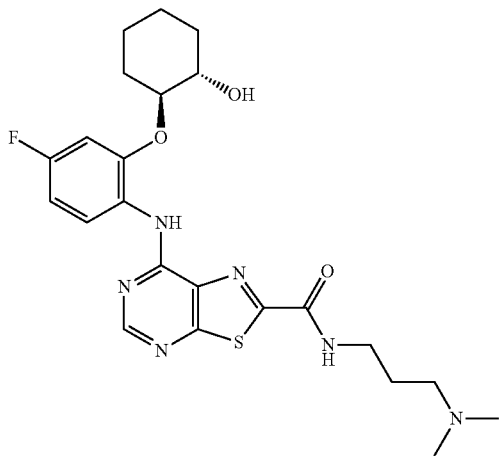 [SMILES: CN(C)CCCNC(=O)c1nc2c(Nc3ccc(F)cc3O[C@H]3CCCC[C@@H]3O)ncnc2s1]

Intermediate 74 (54 mg, 0.24 mmol), N-[3-(dimethylamino)propyl]-7-methylsulfanyl-thiazolo[5,4-d]pyrimidine-2-carboxamide (75 mg, 0.24 mmol), TFA (50 ul) and NMP (500 ul) were combined in a sealed microwave reactor vial and heated at 170 degrees in a Biotage microwave reactor for 15 minutes, then at 190 degrees for 30 minutes. The mixture was evaporated and purified by preparative LCMS to give a yellow solid (14 mg, 12%); 1H NMR (400 MHz, DMSO-d6) δ ppm 1.12-1.42 (m, 4H), 1.50-1.61 (m, 2H), 1.63-1.73 (m, 2H), 1.78-1.85 (m, 1H), 1.99-2.07 (m, 1H), 2.12 (s, 6H), 2.27 (t, J=7.10 Hz, 2H), 3.32-3.41 (m, 2H), 3.53-3.61 (m, 1H), 3.98-4.05 (m, 1H), 5.18 (d, J=4.12 Hz, 1H), 6.82-6.88 (m, 1H), 7.14 (dd, J=10.99, 2.75 Hz, 1H), 8.13-8.19 (m, 1H), 8.56 (s, 1H), 8.72 (t, J=5.72 Hz, 1H), 9.27 (s, 1H); m/z (ES+APCl)$^+$: (MH+) 489.2

Example 20

N-[3-(dimethylamino)propyl]-7-[4-fluoro-2-[(1R,2R)-2-methoxycyclohexoxy]anilino]thiazolo[5,4-d]pyrimidine-2-carboxamide

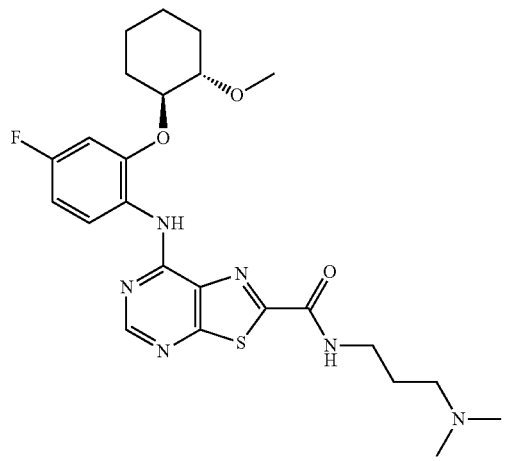 [SMILES: CO[C@H]1CCCC[C@@H]1Oc1cc(F)ccc1Nc1ncnc2sc(C(=O)NCCCN(C)C)nc12]

Intermediate 72 (115 mg, 0.48 mmol), Intermediate 4 (75 mg, 0.24 mmol), TFA (101 ul, 1.32 mmol) and IPA (700 ul) were combined in a sealed microwave reactor vial and heated at 170° C. In a Biotage microwave reactor for 30 minutes. The mixture was evaporated and purified by preparative LCMS to give a yellow solid (57 mg, 47%); 1H NMR (400 MHz, DMSO-d6) δ ppm 1.10-1.35 (m, 3H), 1.37-1.48 (m, 1H), 1.49-1.60 (m, 2H), 1.63-1.72 (m, 2H), 1.88-1.97 (m, 1H), 1.97-2.06 (m, 1H), 2.13 (s, 6H), 2.27 (t, J=6.87 Hz, 2H), 3.19 (s, 3H), 3.33-3.44 (m, 3H), 4.20-4.27 (m, 1H), 6.81-6.88 (m, 1H), 7.11-7.17 (m, 1H), 8.17-8.23 (m, 1H), 8.58 (s, 1H), 8.79-8.86 (m, 1H), 8.99 (s, 1H); m/z (ES+APCl)$^+$: (MH+) 503.3

Example 21

N-[3-(dimethylamino)propyl]-7-[2-[(1S,2S)-1-ethyl-2-methoxy-propoxy]-4-fluoro-anilino]thiazolo[5,4-d]pyrimidine-2-carboxamide

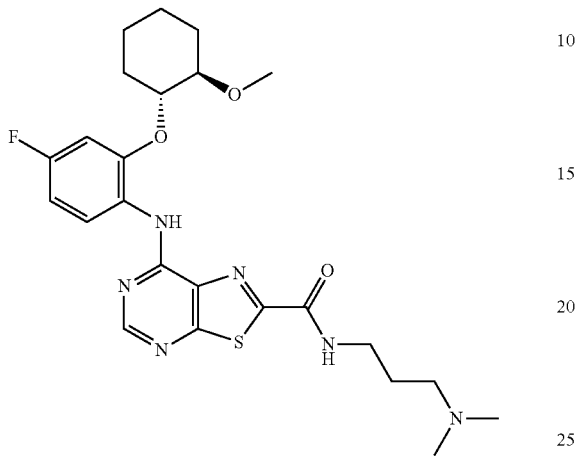

Example 21 was prepared analogously to Example 19 from Intermediate 76 and Intermediate 4 to give a gummy solid (55 mg, 45%); 1H NMR (400 MHz, DMSO-d6) δ ppm 1.11-1.36 (m, 3H), 1.36-1.48 (m, 1H), 1.49-1.61 (m, 2H), 1.63-1.71 (m, 2H), 1.88-1.97 (m, 1H), 1.97-2.06 (m, 1H), 2.12 (s, 6H), 2.24-2.31 (m, 2H), 3.19 (s, 3H), 3.33-3.45 (m, 3H), 4.19-4.29 (m, 1H), 6.80-6.88 (m, 1H), 7.10-7.17 (m, 1H), 8.17-8.24 (m, 1H), 8.58 (s, 1H), 8.79-8.86 (m, 1H), 8.99 (s, 1H); m/z (ES+APCl)$^+$: (MH+) 503.3

Example 22

7-[2-(Cyclopentoxy)-4-fluoro-anilino]-N-[3-(dimethylamino)propyl]thiazolo[5,4-d]pyrimidine-2-carboxamide

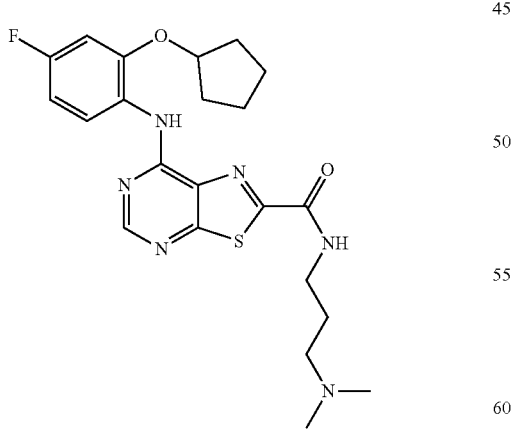

Prepared analogously to Example 19 from Intermediate 4 (68 mg, 0.22 mmol) and 2-cyclopentoxy-4-fluoro-aniline (170 mg, 0.87 mmol) to give a yellow solid (16 mg, 16%). $^1$H NMR (400 MHz, DMSO-d$_6$) δ ppm 1.45-1.60 (m, 4H), 1.63-1.78 (m, 4H), 1.79-1.95 (m, 2H), 2.11-2.19 (m, 6H), 2.24-2.35 (m, 2H), 3.34-3.43 (m, 2H), 4.74-5.04 (m, 1H), 6.84 (td, J=8.70, 2.75 Hz, 1H), 7.07 (dd, J=10.99, 2.75 Hz, 1H), 8.00 (dd, J=8.70, 6.41 Hz, 1H), 8.56 (s, 1H), 8.75 (br. s., 1H), 9.06 (s, 1H); m/z (ES+APCl)$^+$: (MH+) 459.

Example 23

N-[3-(Dimethylamino)propyl]-7-(2-isopropoxyanilino)thiazolo[5,4-d]pyrimidine-2-carboxamide

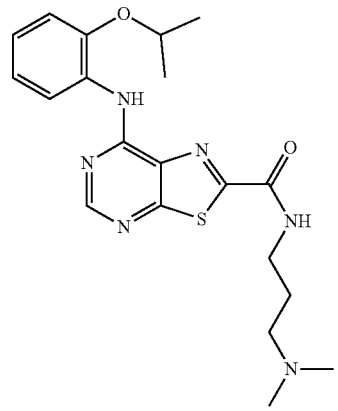 [SMILES: CC(C)Oc1ccccc1Nc1ncnc2sc(C(=O)NCCCN(C)C)nc12]

Prepared analogously to Example 19 from Intermediate 4 (68 mg, 0.22 mmol) and 2-isopropoxy-aniline (130 μl, 0.87 mmol) to give a yellow solid (12 mg, 13%). $^1$H NMR (400 MHz, DMSO-d$_6$) δ ppm 1.33 (d, J=6.41 Hz, 6H), 1.72 (quin, J=6.98 Hz, 2H), 2.16 (s, 6H), 2.31 (t, J=7.10 Hz, 2H), 3.36-3.42 (m, 2H), 4.68 (quin, J=6.07 Hz, 1H), 7.03 (td, J=7.56, 1.83 Hz, 1H), 7.10-7.21 (m, 2H), 8.35 (dd, J=7.78, 1.37 Hz, 1H), 8.64 (s, 1H), 8.95 (s, 1H), 8.99 (t, J=5.72 Hz, 1H); m/z (ES+APCl)$^+$: (MH+) 415.

Example 24

N-[3-(Dimethylamino)propyl]-7-(2-ethoxy-4-fluoroanilino)thiazolo[5,4-d]pyrimidine-2-carboxamide

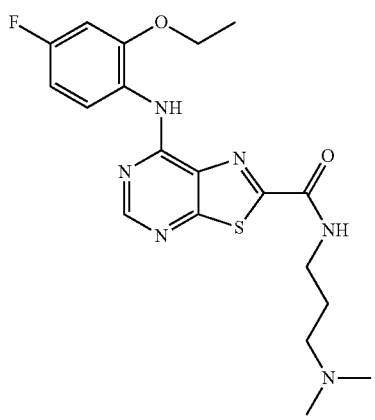 [SMILES: CCOc1cc(F)ccc1Nc1ncnc2sc(C(=O)NCCCN(C)C)nc12]

Prepared analogously to Example 19 from Intermediate 4 (68 mg, 0.22 mmol) and 2-ethoxy-4-fluoro-aniline (170 mg, 0.87 mmol) to give a yellow solid (18 mg, 20%). $^1$H NMR (400 MHz, DMSO-d$_6$) δ ppm 1.31 (t, J=6.87 Hz, 3H), 1.71

(quin, J=6.98 Hz, 2H), 2.10-2.18 (m, 6H), 2.29 (t, J=7.10 Hz, 2H), 3.38 (q, J=6.56 Hz, 2H), 4.18 (q, J=6.87 Hz, 2H), 6.86 (td, J=8.70, 2.75 Hz, 1H), 7.10 (dd, J=10.99, 2.75 Hz, 1H), 8.08 (dd, J=8.70, 6.41 Hz, 1H), 8.58 (s, 1H), 8.97 (s, 2H); m/z (ES+APCl)$^+$: (MH+) 419.

Example 25

N-[3-(Dimethylamino)propyl]-7-(3,3-dimethylindolin-1-yl)thiazolo[5,4-d]pyrimidine-2-carboxamide

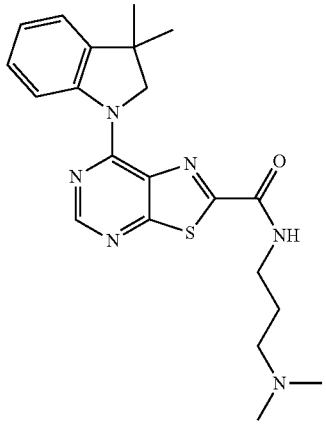 [SMILES: CN(C)CCCNC(=O)c1nc2c(N3CC(C)(C)c4ccccc43)ncnc2s1]

Prepared analogously to Example 19 from Intermediate 4 (50 mg, 0.16 mmol) and 3,3-dimethylindoline (71 mg, 0.49 mmol) to give a yellow solid (25 mg, 38%). $^1$H NMR (400 MHz, DMSO-d$_6$) δ ppm 1.41 (s, 6H), 1.74 (quin, J=6.87 Hz, 2H), 2.18 (s, 6H), 2.33 (t, J=6.87 Hz, 2H), 3.42 (q, J=6.56 Hz, 2H), 4.62 (a, 2H), 7.13 (td, J=7.33, 0.92 Hz, 1H), 7.28 (ddd, J=8.36, 7.21, 1.37 Hz, 1H), 7.37 (dd, J=7.33, 0.92 Hz, 1H), 8.59 (d, J=7.78 Hz, 1H), 8.65-8.71 (m, 1H), 9.02 (t, J=5.95 Hz, 1H); m/z (ES+APCl)$^+$: (MH+) 411.2

Example 26

7-(2,3-Dihydrobenzofuran-7-ylamino)-N-[3-(dimethylamino)propyl]thiazolo[5,4-d]pyrimidine-2-carboxamide

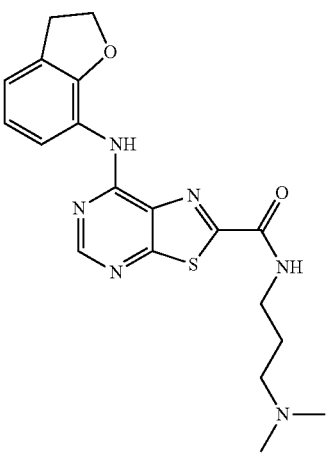 [SMILES: CN(C)CCCNC(=O)c1nc2c(Nc3cccc4c3OCC4)ncnc2s1]

Prepared analogously to Example 19 from Intermediate 4 (70 mg, 0.23 mmol) and 2,3-dihydrobenzofuran-7-amine (91 mg, 0.65 mmol) to give a yellow solid (25 mg, 27%). $^1$H NMR (400 MHz, DMSO-dc) δ ppm 1.71 (quin, J=6.98 Hz, 2H), 2.11-2.21 (m, 6H), 2.31 (t, J=8.87 Hz, 2H), 3.28 (t, J=8.93 Hz, 2H), 3.39 (q, J=6.87 Hz, 2H), 4.62 (t, J=8.70 Hz, 2H), 6.85-6.95 (m, 1H), 7.10 (dd, J=7.33, 0.92 Hz, 1H), 7.88 (d, J=8.24 Hz, 1H), 8.60 (s, 1H), 8.82 (br. s., 1H), 9.14 (t, J=5.50 Hz, 1H); m/z (ES+APCl)$^+$: (MH+) 399.

Example 27

N-[3-(Dimethylamino)propyl]-7-indolin-1-yl-thiazolo[5,4-d]pyrimidine-2-carboxamide

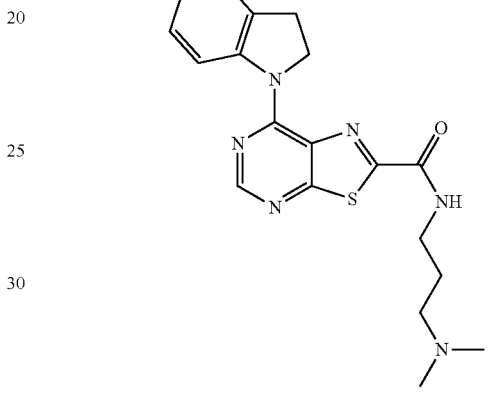

Prepared analogously to Example 19 from Intermediate 4 (60 mg, 0.19 mmol) and indoline (65 μl, 0.57 mmol) to give an off-white solid (35 mg, 48%). $^1$H NMR (400 MHz, DMSO-d$_6$) δ ppm 1.58-1.79 (m, 2H), 2.16 (s, 6H), 2.26-2.36 (m, 2H), 3.30-3.43 (m, 4H), 4.82-4.94 (m, 2H), 7.03-7.13 (m, 1H), 7.23-7.31 (m, 1H), 7.36 (d, J=7.33 Hz, 1H), 8.62-8.70 (m, 2H), 9.15 (t, J=5.95 Hz, 1H). m/z (ES+APCl)$^+$: (MH+) 383.

Example 28

N-(azetidin-3-yl)-7-{[4-fluoro-2-(propan-2-yloxy)phenyl]amino}[1,3]thiazolo[5,4-d]pyrimidine-2-carboxamide

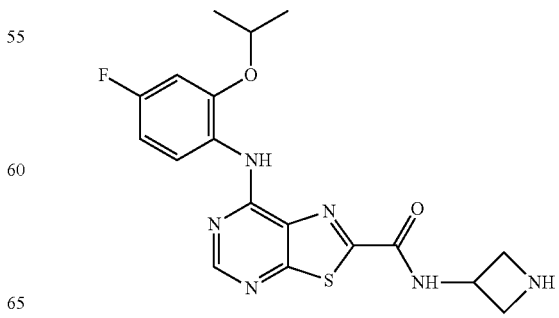

Step 1

Tert-butyl 3-{[(7-f[4-fluoro-2-(propan-2-yloxy)phenyl]amino}[1,3]thiazolo[5,4-d]pyrimidin-2-yl)carbonyl]amino)azetidine-1-carboxylate

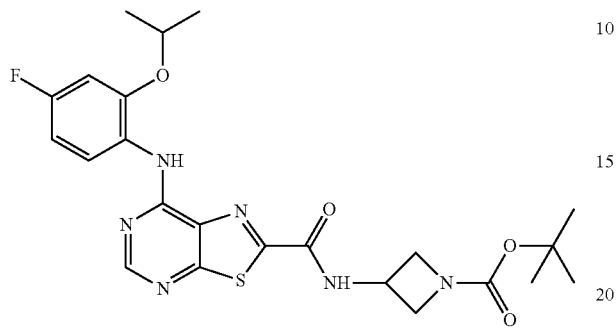

A mixture of Example 1 (400 mg, 1.15 mmol), 3-amino-1-N-Boc-azetidine (197 mg, 1.15 mmol) and DIPEA (1.0 ml, 5.75 mmol) in DMF (10 mil) was stirred at rt for 10 minutes. HATU (811 mg, 1.61 mmol) was added and the mixture was stirred at rt overnight. The reaction mixture was then diluted with EtOAc and water. The organic phase was washed with water (×3) and brine (×1), dried and concentrated. The crude product was purified by flash column chromatography on silica gel eluting with 1:1 petrol:EtOAc to give a yellow solid (280 mg, 49%). $^1$H NMR (400 MHz, DMSO-d$_6$) δ ppm 1.29 (d, J=5.95 Hz, 6H), 1.39 (s, 9H), 3.90-4.01 (m, 2H), 4.09-4.21 (m, 2H), 4.63-4.77 (m, 2H), 6.85 (td, J=8.47, 2.75 Hz, 1H), 7.12 (dd, J=10.99, 2.75 Hz, 1H), 8.10 (dd, J=8.70, 6.41 Hz, 1H), 8.59 (s, 1H), 9.01 (s, 1H), 9.54 (d, J=7.78 Hz, 1H). m/z (ES+APCl): 503 [M+H]$^+$

Step 2

Tert-butyl 3-{[(7-{[4-fluoro-2-(propan-2-yloxy)phenyl]amino}[1,3]thiazolo[5,4-d]pyrimidin-2-yl)carbon-yl]amino}azetidine-1-carboxylate (278 mg, 0.554 mmol) in 3:1 DCM:TFA (20 ml) was stirred at rt for 2 hours. The reaction was concentrated to dryness. Toluene was added to the residue and the mixture was concentrated to dryness again. The residue was dissolved in MeOH and the solution was passed through a SCX cartridge. The product was eluted with 2 M NH$_3$ in MeOH. The eluent was concentrated and the residue was purified by flash column chromatography on silica gel eluting with 20:1 DCM: 2 M NH$_3$ in MeOH to give a yellow solid (176 mg, 79%). $^1$H NMR (400 MHz, DMSO-d$_6$) δ ppm 1.28 (d, J=5.95 Hz, 6H), 3.52-3.72 (m, 4H), 4.62-4.82 (m, 2H), 6.85 (td, J=8.70, 2.75 Hz, 1H), 7.12 (dd, J=10.99, 2.75 Hz, 1H), 8.04 (dd, J=8.93, 6.64 Hz, 1H), 8.57 (s, 1H), 9.21 (br. s., 1H). m/z (ES+APCl)$^+$: 403 [M+H]$^+$

Examples 29-31

Examples 29-31 of the general formula shown below were prepared analogously to Example 28 by coupling Example 1 to the appropriate N—BOC-protected diamine followed by deprotection.

Example 29

7-{[4-Fluoro-2-(propan-2-yloxy)phenyl]amino}-N-[3-(methylamino)propyl][1,3]thiazolo[5,4-d]pyrimidine-2-carboxamide

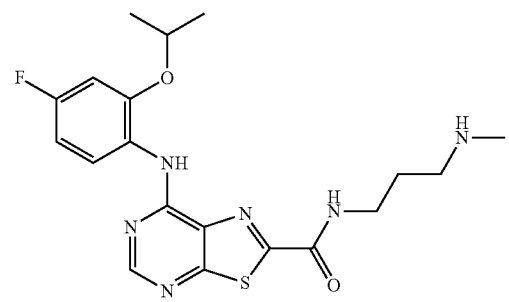 [SMILES: CNCCCNC(=O)c1nc2c(Nc3ccc(F)cc3OC(C)C)ncnc2s1]

Amine starting material used: tert-butyl N-(3-aminopropyl)-N-methyl-carbamate. $^1$H NMR (400 MHz, DMSO-d$_6$) δ ppm 1.28 (d, J=6.41 Hz, 6H), 1.71 (quin, J=6.87 Hz, 2H), 2.30 (s, 3H), 2.54-2.62 (m, 2H), 3.40 (t, J=−6.87 Hz, 3H), 4.60-4.78 (m, 1H), 6.85 (td, J=8.70, 2.75 Hz, 1H), 7.12 (dd, J=10.99, 2.75 Hz, 1H), 8.10 (dd, J=8.93, 6.64 Hz, 1H), 8.57 (s, 1H), 8.95 (br. s., 1H); m/z (ES+APCl)$^+$: 419 [M+H]$^+$.

Example 30

7-{[4-Fluoro-2-(propan-2-yloxy)phenyl]amino}-N-[2-(methylamino)ethyl][1,3]thiazolo[5,4-d]pyrimidine-2-carboxamide

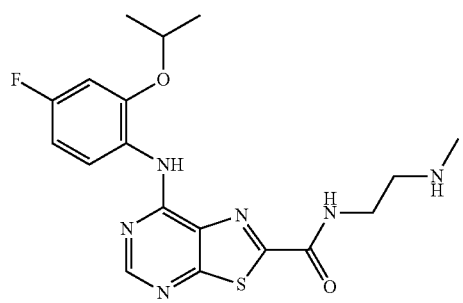

Amine starting material used: tert-butyl N-(2-aminoethyl)-N-methyl-carbamate. $^1$H NMR (400 MHz, DMSO-d$_6$) δ ppm 1.20-1.34 (m, 6H), 2.33 (s, 3H), 2.72 (t, J=6.18 Hz, 2H), 3.40-3.54 (m, 2H), 4.61-4.79 (m, 1H), 6.84 (td, J=8.70, 2.75 Hz, 1H), 7.10 (dd, J=10.99, 2.75 Hz, 1H), 8.07 (dd, J=9.16, 6.41 Hz, 1H), 8.52-8.62 (m, 2H), 9.13 (br. s., 1H); m/z (ES+APCl)$^+$: 405 [M+H]$^+$.

Example 31

7-{[4-Fluoro-2-(propan-2-yloxy)phenyl]amino}-N-(piperidin-4-yl)[1,3]thiazolo[5,4-d]pyrimidine-2-carboxamide

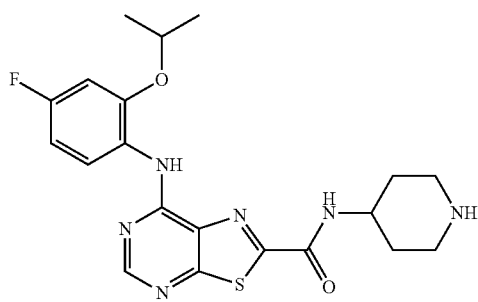 [SMILES: CC(C)Oc1cc(F)ccc1Nc1ncnc2sc(C(=O)NC3CCNCC3)nc12]

Amine starting material used: tert-butyl 4-aminopiperidine-1-carboxylate. $^1$H NMR (400 MHz, DMSO-d$_6$) δ ppm 1.18-1.32 (m, 6H), 1.38-1.55 (m, 2H), 1.80 (d, J=9.18 Hz, 2H), 2.52-2.60 (m, 2H), 2.90-3.01 (m, 2H), 3.16 (br. s., 1H), 3.76-3.93 (m, 1H), 4.70 (spt, J=6.03 Hz, 1H), 6.84 (td, J=8.70, 2.75 Hz, 1H), 7.11 (dd, J=10.99, 2.75 Hz, 1H), 7.96-8.04 (m, 1H), 8.46 (br. s., 1H), 8.56 (s, 1H), 9.19 (br. s., 1H); m/z (ES+APCl)$^+$: 431 [M+H]$^+$.

Examples 32-39

Examples 32-39 of the general formula shown below were prepared analogously to Example 3 by amide coupling of Example 1 with the appropriate amine.

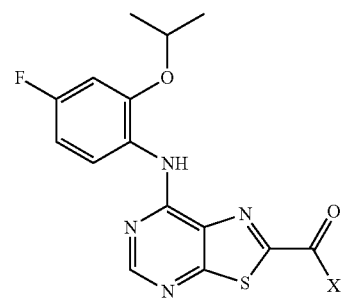

| Example | X | IUPAC name | [M + H]$^+$ | HPLC retention time (method)* |
|---|---|---|---|---|
| 32 | | 7-{[4-fluoro-2-(propan-2-yloxy)phenyl]amino}-N-(1-methylpiperidin-4-yl)[1,3]thiazolo[5,4-d]pyrimidine-2-carboxamide | 445 | 1.88 mins (A) |
| 33 | | 7-{[4-fluoro-2-(propan-2-yloxy)phenyl]amino}-N-(tetrahydro-2H-pyran-4-yl)[1,3]thiazolo[5,4-d]pyrimidine-2-carboxamide > | 432 | 1.78 mins (C) |
| 34 | ![](N-thiopyran dioxide) | N-(1,1-dioxidotetrahydro-2H-thiopyran-4-yl)-7-{[4-fluoro-2-(propan-2-yloxy)phenyl]amino}[1,3]thiazolo[5,4-d]pyrimidine-2-carboxamide | 480 | 1.64 mins (C) |
| 35 | | {4-[(dimethylamino)methyl]piperidin-1-yl}(7-{[4-fluoro-2-(propan-2-yloxy)phenyl]amino}[1,3]thiazolo[5,4-d]pyrimidin-2-yl)methanone | 473 | 2.01 mins (D) |
| 36 | | 7-{[4-fluoro-2-(propan-2-yloxy)phenyl]amino}-N-[(1-methylpiperidin-4-yl)methyl][1,3]thiazolo[5,4-d]pyrimidine-2-carboxamide | 459 | 2.33 mins (B) |
| 37 | | 7-{[4-fluoro-2-(propan-2-yloxy)phenyl]amino}-N-[2-(1-methylpiperidin-4-yl)ethyl][1,3]thiazolo[5,4-d]pyrimidine-2-carboxamide | 473 | 2.33 mins (B) |

| Example | X | IUPAC name | [M + H]⁺ | HPLC retention time (method)* |
|---|---|---|---|---|
| 38 | 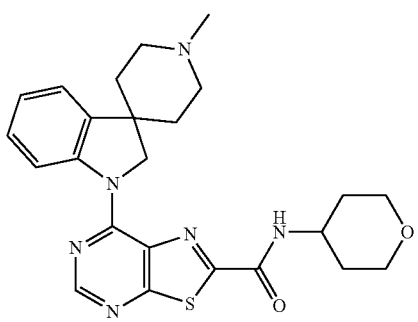 | 7-{[4-fluoro-2-(propan-2-yloxy)phenyl]amino}-N-(tetrahydro-2H-pyran-4-ylmethyl)[1,3]thiazolo[5,4-d]pyrimidine-2-carboxamide | 446 | .84 mins (D) |
| 39 | | N-[2-(dimethylamino)ethyl]-7-{[4-fluoro-2-(propan-2-yloxy)phenyl]amino}[1,3]thiazolo[5,4-d]pyrimidine-2-carboxamide | 419 | 1.78 mins (D) |

*Agilent 6120 quadrupole LC-MS with Xbridge C18 column (3.5 μm particle size and 4.6 × 30 mm) and a diode array UV detector. Flow rate 3 ml/min;
Method A pH 1; Run time: 3.2 min: Solvent A: 0.1% Trifluoro Acetic acid in water, Solvent B: Methanol; Gradient-10-100% Methanol; Gradient time: 2.35 min.
Method B pH 10; Run time: 3.2 min: Solvent A: 0.1% Ammonium Hydroxide in water, Solvent B: Methanol; Gradient-10-100% Methanol; Gradient time: 2.35 min.
Method C pH 1; Run time: 3.2 min: Solvent A: 0.1% Trifluoro Acetic acid in water, Solvent B: Acetonitrile; Gradient-10-100% Acetonitrile; Gradient time: 2.35 min.
Method D pH 10; Run time: 3.2 min: Solvent A: 0.1% Ammonium Hydroxide in water, Solvent B: Acetonitrile; Gradient-10-100% Acetonitrile; Gradient time: 2.35 mm.

Example 40

7-(1-Methylspiro[indole-3,4'-piperidin]-1(2H)-yl)-N-(tetrahydro-2H-pyran-4-yl)[1,3]thiazolo[5,4-d]pyrimidine-2-carboxamide

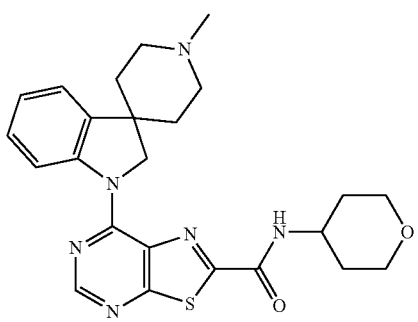 [SMILES: CN1CCC2(CC1)CN(c1ncnc3sc(C(=O)NC4CCOCC4)nc13)c1ccccc12]

A mixture of Intermediate 18 (78 mg, 0.262 mmol) and 1'-methyl-1,2-dihydrospiro-[indole-3,4'-piperidine] (53 mg, 0.262 mmol) in IPA (3 ml) was stirred and heated at 80° C. for 4 hours. The mixture was allowed to cool to rt, diluted with MeOH and the resulting solution was passed through a SCX cartridge. The product was eluted with 2 M NH₃ in MeOH and the eluent was concentrated. The residue was purified by flash column chromatography on silica gel eluting with 50:1 to 25:1 DCM: 2 M NH₃ in MeOH. Recrystallization of the chromatographed material from EtOAc gave a pale yellow solid (10 mg, 8%). ¹H NMR (400 MHz, DMSO-d) δ ppm 1.61-1.77 (m, 4H), 1.82-2.03 (m, 4H), 2.07-2.28 (m, 5H), 2.75-2.87 (m, 2H), 3.46 (td, J=1.33, 2.06 Hz, 2H), 3.85-3.95 (m, 2H), 4.00-4.15 (m, 1H), 4.79 (s, 2H), 7.09-7.17 (m, 1H), 7.27-7.35 (m, 1H), 7.38 (d, J=7.33 Hz, 1H), 8.55 (d, J=8.24 Hz, 1H), 8.62-8.74 (m, 2H). m/z (ES+APCl)⁺: 465 [M+H]⁺

Example 41

7-(Spiro[cyclopentane-1,3'-indol]-1'(2'H)-yl)-N-(tetrahydro-2H-pyran-4-yl)[1,3]thiazolo[5,4-d]pyrimidine-2-carboxamide

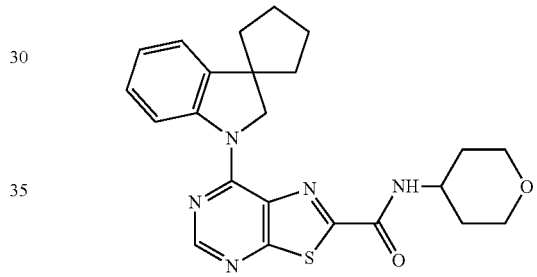

Example 41 was prepared in analogous fashion to Example 40. The product was isolated by filtration of the reaction mixture to provide a yellow solid which required no further purification (yield 70%). ¹H NMR (400 MHz, DMSO-d) δ ppm 1.59-2.07 (m, 12 H), 3.43 (td, J=11.45, 2.29 Hz, 2H), 3.84-4.12 (m, 4H), 4.70 (s, 2H), 7.13 (td, J=7.33, 0.92 Hz, 1H), 7.25-7.32 (m, 1H), 7.37 (dd, J=7.33, 0.92 Hz, 1H), 8.61 (dd, J=11.22, 8.01 Hz, 2H), 8.69 (s, 1H). m/z (ES+APCl)⁺:436 [M+H]⁺.

Example 42

7-(5-cyano-2,3-dihydro-1H-indol-1-yl)-N-(tetrahydro-2H-pyran-4-yl)[1,3]thiazolo[5,4-d]pyrimidine-2-carboxamide

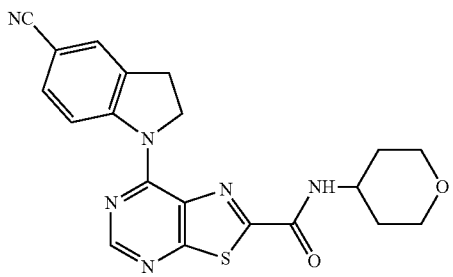 [SMILES: N#Cc1ccc2c(c1)CCN2c1ncnc2sc(C(=O)NC3CCOCC3)nc12]

Example 42 was prepared in analogous fashion to Example 40. The product was isolated by filtration of the reaction mixture to provide an off-white solid which required no further purification (yield 68%). $^1$H NMR (400 MHz, DMSO-$d_6$) δ ppm 1.69-1.88 (m, 4H), 3.31-3.46 (m, 4H), 3.87-3.97 (m, 2H), 4.01-4.18 (m, 1H), 4.95 (t, J=8.70 Hz, 2H), 7.69-7.81 (m, 2H), 8.70-8.86 (m, 3H). m/z (ES+APCl)$^+$: 407 [M+H]$^+$ Example 43

7-(2,3-Dihydro-1H-pyrrolo[3,2-c]pyridin-1-yl)-N-(tetrahydro-2H-pyran-4-yl)[1,3]thiazolo[5,4-d]pyrimidine-2-carboxamide

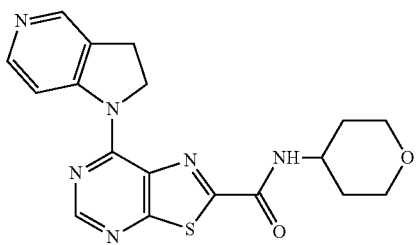 [SMILES: O=C(NC1CCOCC1)c1nc2c(N3CCc4cnccc43)ncnc2s1]

A mixture of Intermediate 18 (100 mg, 0.334 mmol), 2,3-dihydro-1H-pyrrolo[3,2-c]pyridine (52 mg, 0.435 mmol), binap (10.4 mg, 0.017 mmol), sodium t-butoxide (96 mg, 1.00 mmol) and palladium (II) acetate (3.7 mg, 0.017 mmol) in toluene (2 ml) was degassed, placed under nitrogen and stirred and heated at 100° C. overnight. The reaction was then concentrated to dryness. The residue was diluted with EtOAc and water. The organic phase was washed with water and brine. The aqueous phase was re-extracted with DCM. The organic extracts were combined, dried and concentrated.

The crude product was purified by flash column chromatography on silica gel eluting with 20:1 DCM:MeOH to give a yellow solid (34 mg, 27%). $^1$H NMR (400 MHz, DMSO-$d_6$) δ ppm 1.71-1.88 (m, 4H), 3.34-3.48 (m, 4H), 3.87-3.97 (m, 2H), 4.02-4.18 (m, 1H), 4.89-4.99 (m, 2H), 8.41 (d, J=5.50 Hz, 1H), 8.46-8.51 (m, 2H), 8.74-8.86 (m, 2H); m/z (ES+APCl)$^+$: 383 [M+H]$^+$ Example 44

7-(2,3-Dihydro-1H-pyrrolo[3,2-b]pyridin-1-yl)-N-(tetrahydro-2H-pyran-4-yl)[,3]thiazolo[5,4-d]pyrimidine-2-carboxamide

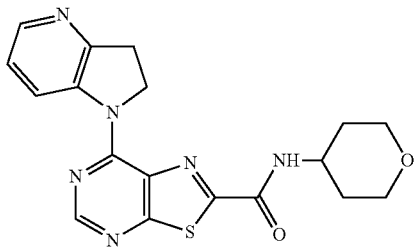 [SMILES: O=C(NC1CCOCC1)c1nc2c(N3CCc4ncccc43)ncnc2s1]

Example 44 was prepared in analogous fashion to Example 43. The crude product was dissolved in MeOH/ DCM and passed through a SCX cartridge eluting the product with 2M NH$_3$ in methanol. The eluent was concentrated to dryness and the residue was triturated with Et$_2$O to give an orange/brown coloured solid (yield 27%). $^1$H NMR (400 MHz, DMSO-$d_6$) δ ppm 1.68-1.92 (m, 4H), 3.34-3.51 (m, 4H), 3.84-3.99 (m, 2H), 4.00-4.19 (m, 1H), 4.94 (t, J=8.47 Hz, 2H), 7.27 (dd, J=8.01, 4.81 Hz, 1H), 8.19 (dd, J=4.81, 1.14 Hz, 1H), 8.71 (s, 1H), 8.76-8.90 (m, 2H); m/z (ES+APCl)$^+$: 383 [M+H]$^+$ Example 45

N-(1-methylpiperidin-4-yl)-7-(5-nitro-2,3-dihydro-1H-indol-1-yl)[1,3]thiazolo[5,4-d]pyrimidine-2-carboxamide

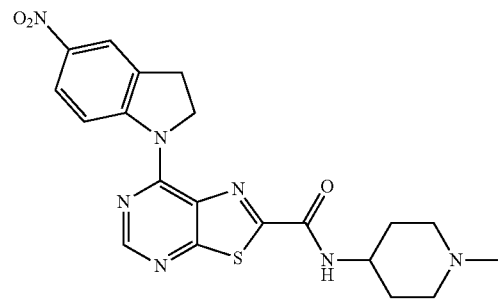 [SMILES: CN1CCC(NC(=O)c2nc3c(N4CCc5cc([N+](=O)[O-])ccc54)ncnc3s2)CC1]

Intermediate 78 (320 mg, 0.933 mmol) in thionyl chloride (4 ml) was heated under reflux for 3 hours. The reaction mixture was then concentrated to dryness. The crude acid chloride was dissolved in DCM (8 ml) and TEA (0.919 ml, 2.80 mmol) was added. A solution of 1-methylpiperidine-4-amine (160 mg, 1.40 mmol) in DCM (2 ml) was added dropwise with ice-cooling. The mixture was allowed to warm to rt and stirred overnight. The mixture was diluted with DCM and water and the organic phase was dried and concentrated. The crude product was pre-absorbed onto silica gel prior to purification by flash column chromatography on silica gel eluting with 20:1 DCM: 2 M NH$_3$ in methanol to give a yellow solid (268 mg, 65%). $^1$H NMR (400 MHz, DMSO-$d_6$) δ ppm 1.73-1.86 (m, 4H), 1.96 (br. s., 2H), 2.19 (s, 3H), 2.76-2.90 (m, 2H), 3.38-3.50 (m, 2H), 3.74-3.86 (m, 1H), 5.02 (t, J=8.70 Hz, 2H), 8.19-8.26 (m, 2H), 8.73-8.86 (m, 3H); m/z (ES+APCl)$^+$: 440 [M+H]$^+$ Example 46

7-[5-(Acetylamino)-2,3-dihydro-1H-indol-1-yl]-N-(1-methylpiperidin-4-yl)[1,3]thiazolo[5,4-d]pyrimidine-2-carboxamide

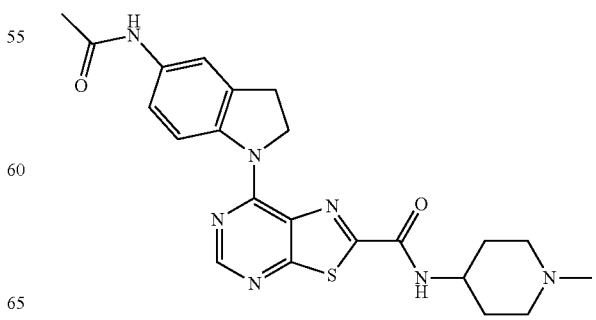

Acetyl chloride (16 μl, 0.216 mmol) was added to a mixture of Intermediate 79 (59 mg, 0.144 mmol) and TEA (40 μl, 0.289 mmol) in DCM (4 ml). The reaction mixture was stirred for 4 hours at rt and was then concentrated to dryness. The residue was pre-absorbed onto silica gel prior to purification by flash column chromatography on silica gel eluting with 10:1 DCM: 2M NH$_3$ in methanol to give a yellow solid. The chromatographed solid was further purified by trituration with EtOAc to give a yellow solid (30 mg, 46%). $^1$H NMR (400 MHz, DMSO-d$_6$) δ ppm 1.71-1.93 (m, 4H), 1.97-2.42 (m, 8H), 2.78-3.05 (m, 2H), 3.25-3.42 (m, 2H), 3.75-3.97 (m, 1H), 4.89 (t, J=8.24 Hz, 2H), 7.34 (d, J=8.70 Hz, 1H), 7.74 (s, 1H), 8.51-8.66 (m, 2H), 8.76 (d, J=8.24 Hz, 1H), 9.99 (s, 1H); m/z (ES+APCl)$^+$: 452 [M+H]$^+$ Example 47

N-[4-fluoro-2-(propan-2-yloxy)phenyl][1,3]thiazolo[5,4-d]pyrimidin-7-amine

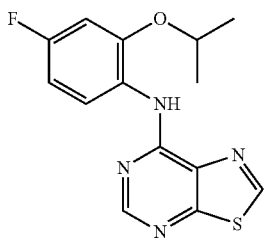 [SMILES: CC(C)Oc1cc(F)ccc1Nc1ncnc2scnc12]

A mixture of 7-chlorothiazole[5,4-d]pyrimidine (50 mg, 0.292 mmol), toluene-4-sulfonic acid (6 mg, 0.032 mmol), 4-fluoroisopropoxyaniline (49 mg, 0.290 mmol) and IPA (2 ml) were sealed in a microwave reactor vial and irradiated at 170° C. for 15 minutes in the Biotage 1-60 microwave reactor. The reaction mixture was concentrated and the residue taken up in 20% MeOH in DCM and passed through an aminopropyl cartridge. The product was recovered by washing through with 20% MeOH in DCM. The solution was concentrated and the crude product purified by flash column chromatography eluting with 10-20% EtOAc in petroleum ether to give a pale pink solid (52 mg, 58%). $^1$H NMR (400 MHz, CHLOROFORM-d) δ 1.44 (d, J=5.95 Hz, 6H), 4.56-4.64 (m, 1H), 6.69-6.77 (m, 2H), 8.58-8.62 (m, 1H), 8.64-8.65 (m, 1H), 8.67-8.72 (m, 1H), 8.88 (s, 1H); m/z (ES+APCl)$^+$:304 [M+H]$^+$ Example 48

[7-(4-Fluoro-2-isopropoxy-anilino)thiazolo[5,4-d]pyrimidin-2-yl]methanol

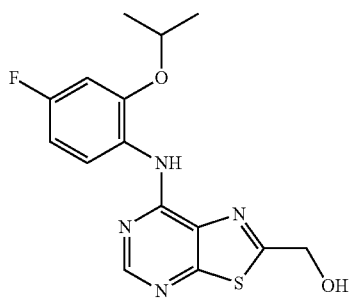 [SMILES: CC(C)Oc1cc(F)ccc1Nc1ncnc2sc(CO)nc12]

To a solution of Intermediate 1 (50 mg, 0.13 mmol) In THF (10 ml) was added a 1M solution of lithium aluminium hydride (0.26 ml, 0.26 mmol) dropwise and stirred for 2 hours. Water (10 μL) was carefully added followed by 10 μL of 15% NaOH$_{(aq)}$ and finally 0.5 ml of water. DCM was added, the organic layer separated, dried and concentrated onto silica. The compound was purified via column chromatography (gradient elution from 10-50% EtOAc in Pet. Ether) to give a light yellow solid (18 mg, 41%); $^1$H NMR (400 MHz, CHLOROFORM-d) δ ppm 1.44 (d, J=6.00 Hz, 6H), 4.61 (spt, J=6.03 Hz, 1H), 5.09 (8, 2H), 6.67-6.79 (m, 2H), 8.49 (s, 1H), 8.62 (s, 1H), 8.66 (dd, J=8.93, 6.18 Hz, 1H); LC-MS (ESI): (MH$^+$) 335.1

Example 49

N-(4-piperidylmethyl)-7-[4-[[3-(trifluoromethyl)phenyl]carbamoylamino]anilino]thiazolo[5,4-d]pyrimidine-2-carboxamide

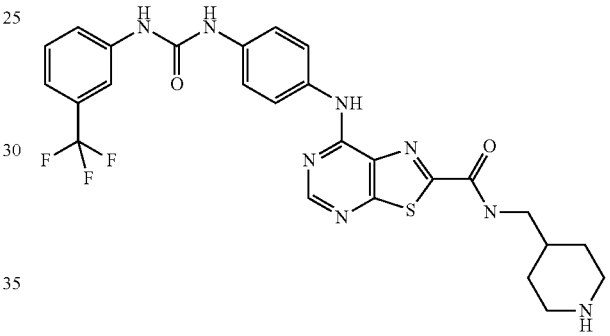

To a solution of Intermediate 3 (75 mg, 0.18 mmol) in DCM (10 ml) was added m-CPBA (79 mg, 0.36 mmol) and the mixture was stirred for 2 hours. 1-(4-aminophenyl)-3-[3-(trifluoromethyl)-phenyl]urea (52 mg, 0.18 mmol) in dioxane (5 ml) was added and heated at 60° C. overnight. The mixture was cooled, DCM and water was added, the organic layer, separated, dried and concentrated onto silica. The compound was purified via column chromatography (gradient elution from 30-100% EtOAc in Pet. Ether) to give a yellow solid. The solid was taken up in DCM (5 ml), TFA (0.75 ml) added and stirred for 15 mins. The mixture was concentrated and purified by HPLC to give a yellow solid; $^1$H NMR (400 MHz, DMSO-d$_6$) δ ppm 1.08-1.22 (m, 2H), 1.62-1.76 (m, 2H), 1.73 (s, 1H), 2.51-2.60 (m, 2H), 3.01 (d, J=11.5 Hz, 2H), 3.25 (t, J=6.2 Hz, 2H), 7.29 (d, J=7.8 Hz, 1H), 7.45-7.54 (m, 3H), 7.55-7.62 (m, 1H), 7.78 (d, J=8.7 Hz, 2H), 8.04 (s, 1H), 8.57 (s, 1H), 8.66 (br. t, 1H), 9.01 (br. s., 1H), 9.23 (br. s., 1H), 9.84 (br. s., 1H); LC-MS (ESI): (MH$^+$) 571.1

Example 50

7-(1H-indazol-5-ylamino)-N-(4-piperidylmethyl)thiazolo[5,4-d]pyrimidine-2-carboxamide

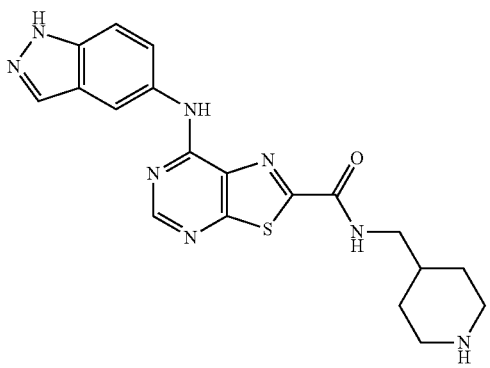 [SMILES: O=C(NCC1CCNCC1)c1nc2c(Nc3ccc4[nH]ncc4c3)ncnc2s1]

Example 50 was prepared analogously to Example 49 from Intermediate 3 and 5-aminoindazole.

$^1$H NMR (400 MHz, MeOD) δ ppm 1.25-1.39 (m, 2H) 1.79-1.93 (m, 3H) 2.68 (td, J=12.48, 2.52 Hz, 2H) 3.09-3.19 (m, 2H) 3.38 (d, J=6.41 Hz, 2H) 7.57-7.63 (m, 1H) 7.66-7.73 (m, 1H) 8.08 (d, J=0.92 Hz, 1H) 8.28 (d, J=1.83 Hz, 1H) 8.51 (s, 1H); LC-MS (ESI): (MH$^+$) 409.2

Examples 51-54

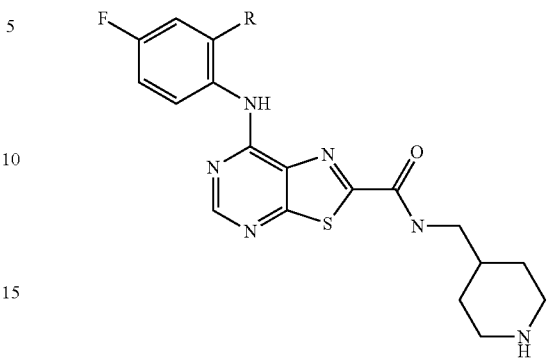

To a solution of Intermediate 3 (400 mg, 0.90 mmol) In DCM (20 ml) was added m-CPBA (317 mg, 1.8 mmol) and the resulting mixture was stirred for 2.5 hours and then concentrated under reduced pressure. The residue was dissolved in 1,4-dioxane (16 ml) divided into four equal portions heated to 90° C. in sealed tubes in the presence of the appropriate amine (0.45 mmol) overnight. The solvent was evaporated and the residue was suspended in 4M HCl in dioxane (4 ml) and stirred at room temperature for 3 h. The solvent was concentrated under reduced pressure and the residues were purified by preparative LCMS to give the desired compounds.

| Example # | R | IUPAC Name | LC-MS (ESI): (MH$^+$) | $^1$H NMR |
|---|---|---|---|---|
| 51 | cyclopentyloxy | 7-[2-(cyclopentoxy)-4-fluoro-anilino]-N-(4-piperidylmethyl)thiazolo[5,4-d]pyrimidine-2-carboxamide | 471 | $^1$H NMR (400 MHz, DMSO-d$_6$) δ ppm 0.99-1.13 (m, 2 H), 1.45-1.78 (m, 9 H), 1.80-1.92 (m, 2 H), 2.36-2.45 (m, 2 H), 2.85-3.01 (m, 2 H), 3.14-3.19 (m, 1 H), 3.22 (t, J = 6.41 Hz, 2 H), 4.10 (d, J = 4.58 Hz, 1 H), 4.84-5.07 (m, 1 H), 6.85 (td, J = 8.70, 2.75 Hz, 1 H), 7.07 (dd, J = 10.99, 2.75 Hz, 1 H), 7.96-8.17 (m, 1 H), 8.44-8.67 (m, 2 H), 9.10 (br. s., 1 H) |
| 52 | 1-(fluoromethyl)-2-fluoroethoxy | 7-[4-fluoro-2-[2-fluoro-1-(fluoromethyl)ethoxy]anilino]-N-(4-piperidylmethyl)thiazolo[5,4-d]pyrimidine-2-carboxamide | 481 | $^1$H NMR (400 MHz, DMSO-d$_6$) δ ppm 1.01-1.16 (m, 2 H), 1.63 (d, J = 12.82 Hz, 3 H), 2.44 (t, J = 11.45 Hz, 2 H), 2.94 (d, J =11.91 Hz, 2 H), 3.15-3.28 (m, 3 H), 4.58-4.81 (m, 4 H), 4.95-5.14 (m, 1 H), 6.95 (td, J = 8.70, 2.75 Hz, 1 H), 7.29 (dd, J = 10.99, 2.75 Hz, 1 H), 8.08 (dd, J = 9.16, 6.41 Hz, 1 H), 8.57 (s, 1 H), 8.63 (br. s., 1 H), 9.10 (s, 1 H) |

| Example # | R | IUPAC Name | LC-MS (ESI): (MH+) | 1H NMR |
|---|---|---|---|---|
| 53 | 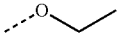 | 7-(2-ethoxy-4-fluoro-anilino)-N-(4-piperidylmethyl)thiazolo[5,4-d]pyrimidine-2-carboxamide | 431 | 1H NMR (400 MHz, DMSO-d6) δ ppm 0.99-1.14 (m, 2 H), 1.31 (t, J = 6.87 Hz, 3 H), 1.53-1.75 (m, 3 H), 2.41 (td, J = 12.02, 2.06 Hz, 2 H), 2.92 (d, J = 11.91 Hz, 2 H), 3.11-3.27 (m, 3 H), 4.15 (q, J = 7.02 Hz, 2 H), 6.86 (td, J = 8.70, 2.75 Hz, 1 H), 7.02-7.15 (m, 1 H), 8.06 (dd, J = 8.70, 6.41 Hz, 1 H), 8.57 (s, 1 H), 8.72 (br. s., 1 H), 9.06 (br. s., 1 H) |
| 54 | 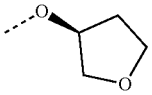 | 7-[4-fluoro-2-[(3S)-tetrahydrofuran-3-yl]oxy-anilino]-N-(4-piperidylmethyl)thiazolo[5,4-d]pyrimidine-2-carboxamide | 473 | 1H NMR (400 MHz, DMSO-d6) δ ppm 0.98-1.15 (m, 2 H), 1.54-1.72 (m, 3 H), 1.93-2.05 (m, 1 H), 2.13-2.29 (m, 1 H), 2.34-2.46 (m, 2 H), 2.93 (d, J =12.36 Hz, 2 H), 3.17 (d, J = 2.75 Hz, 1 H), 3.22 (t, J = 6.18 Hz, 2 H), 3.64-3.90 (m, 4 H), 5.11-5.20 (m, 1 H), 6.89 (td, J = 8.70, 2.75 Hz, 1 H), 7.11 (dd, J = 10.53, 2.75 Hz, 1 H), 8.06 (dd, J = 8.70, 6.41 Hz, 1 H), 8.57 (s, 1 H), 8.65 (br. s., 1 H), 9.14 (br. s., 1 H) |

Example 55

7-[(2-isopropoxy-3-pyridyl)amino]-N-(4-piperidylmethyl)thiazolo[5,4-d]pyrimidine-2-carboxamide

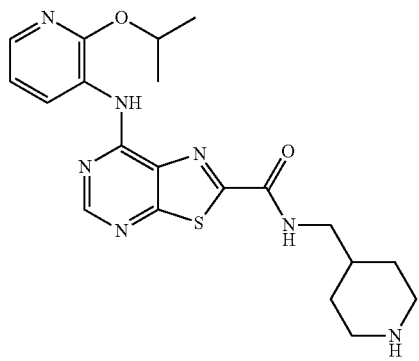 [SMILES: CC(C)Oc1ncccc1Nc1ncnc2sc(C(=O)NCC3CCNCC3)nc12]

Prepared analogously to Examples 51-54. 1H NMR (400 MHz, DMSO-d6) δ ppm 1.02-1.16 (m, 2H), 1.32 (d, J=6.41 Hz, 6H), 1.58-1.72 (m, 3H), 2.38-2.48 (m, 2H), 2.89-2.98 (m, 2H), 3.20-3.27 (m, 2H), 5.33 (quin, J=6.18 Hz, 1H), 7.02-7.10 (m, 1H), 7.94-8.00 (m, 1H), 8.50 (dd, J=7.79, 1.37 Hz, 1H), 8.65 (s, 1H), 8.71-8.81 (m, 1H); LC-MS (ESI): (MH+) 428.

Examples 56-63

Prepared Analogously to Example 51 Using the Appropriate Amine

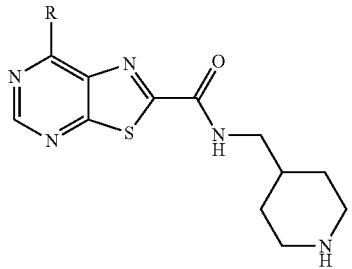

| Example # | R | IUPAC Name | LCMS retention time (Method) | LC-MS (ESI): (MH+) |
|---|---|---|---|---|
| 56 | (7-fluoro-2,3-dihydro-1,4-benzoxazin-4-yl, structure) | 7-(7-fluoro-2,3-dihydro-1,4-benzoxazin-4-yl)-N-(4-piperidylmethyl)thiazolo[5,4-d]pyrimidine-2-carboxamide | 1.61 (D) | 429 |
| 57 | (6-fluoro-4-methyl-2,3-dihydroquinoxalin-1-yl, structure) | 7-(6-fluoro-4-methyl-2,3-dihydroquinoxalin-1-yl)-N-(4-piperidylmethyl)thiazolo[5,4-d]pyrimidine-2-carboxamide | 1.88 (D) | 442 |
| 58 | (5-fluoroindolin-1-yl, structure) | 7-(5-fluoroindolin-1-yl)-N-(4-piperidylmethyl)thiazolo[5,4-d]pyrimidine-2-carboxamide | 2.2 (D) | 413 |
| 59 | (4-fluoro-2-(trifluoromethoxy)anilino, structure) | 7-[4-fluoro-2-(trifluoromethoxy)anilino]-N-(4-piperidylmethyl)thiazolo[5,4-d]pyrimidine-2-carboxamide | 1.73 (D) | 471 |
| 60 | (4-fluoro-2-[(1R,3S)-3-methoxycyclohexoxy]anilino, structure) | 7-[4-fluoro-2-[(1R,3S)-3-methoxycyclohexoxy]anilino]-N-(4-piperidylmethyl)thiazolo[5,4-d]pyrimidine-2-carboxamide | 2.06 (D) | 515 |
| 61 | (4-fluoro-2-[(1S,3R)-3-methoxycyclohexoxy]anilino, structure) | 7-[4-fluoro-2-[(1S,3R)-3-methoxycyclohexoxy]anilino]-N-(4-piperidylmethyl)thiazolo[5,4-d]pyrimidine-2-carboxamide | 2.06 (D) | 515 |
| 62 | (2-(2-furyl)anilino, structure) | 7-[2-(2-furyl)anilino]-N-(4-piperidylmethyl)thiazoio[5,4-d]pyrimidine-2-carboxamide | 1.85 (D) | 435 |
| 63 | (5-methoxyindolin-1-yl, structure) | 7-(5-methoxyindolin-1-yl)-N-(4 piperidylmethyl)thiazolo[5,4-d]pyrimidine-2-carboxamide | 2.57 (B) | 425 |

*Agilent 6120 quadrupole LC-MS with Xbridge C18 column (3.5 μm particle size and 4.6 × 30 mm) and a diode array UV detector. Flow rate 3 ml/min;
Method A pH 1; Run time: 3.2 min: Solvent A: 0.1% Trifluoro Acetic acid in water, Solvent B: Methanol; Gradient-10-100% Methanol; Gradient time: 2.35 min.
Method B pH 10; Run time: 3.2 min: Solvent A: 0.1% Ammonium Hydroxide in water, Solvent B: Methanol; Gradient-10-100% Methanol; Gradient time: 2.35 min.
Method C pH 1; Run time: 3.2 min: Solvent A: 0.1% Trifluoro Acetic acid in water, Solvent B: Acetonitrile; Gradient-10-100% Acetonitrile; Gradient time: 2.35 min.
Method D pH 10; Run time: 3.2 min: Solvent A: 0.1% Ammonium Hydroxide in water, Solvent B: Acetonitrile; Gradient-10-100% Acetonitrile; Gradient time: 2.35 min.

Example 64

N-[3-(dimethylamino)propyl]-7-(5-fluoroindolin-1-yl)thiazolo[5,4-d]pyrimidine-2-carboxamide

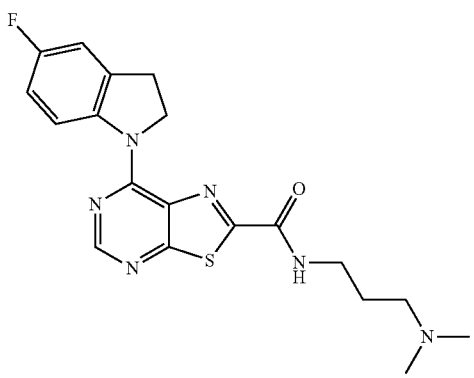 [SMILES: CN(C)CCCNC(=O)c1nc2c(N3CCc4cc(F)ccc43)ncnc2s1]

Intermediate 8 (50 mg, 0.16 mmol) and thionyl chloride (2 ml) were heated at reflux for 4 hours. The mixture was cooled and concentrated to give an orange solid, which was taken up in DCM (3 ml). Triethylamine (65 µL, 2.3 mmol) was added followed by N,N-Dimethylaminopropylamine (24 mg, 0.32 mmol) and the resulting mixture was stirred overnight. The mixture was concentrated and purified by HPLC to give the product (7.5 mg, 6%); $^1$H NMR (400 MHz, DMSO-$d_6$) δ ppm 1.68 (quin, J=7.3 Hz, 2H), 2.13 (s, 6H), 2.28 (t, J=6.9 Hz, 2H), 3.30-3.39 (m, 4H), 4.87 (t, J=8.2 Hz, 2H), 7.07 (td, J=9.7, 2.8 Hz, 1H), 7.19 (dd, J=8.2, 2.8 Hz, 1H), 8.60-8.66 (m, 2H), 9.11 (t, J=5.7 Hz, 1H); LC-MS (ESI): (MH$^+$) 401.1

Examples 65-80 In the table below were prepared analogously to Example 64 from Intermediate 8 and the appropriate, optionally BOC protected, amine.

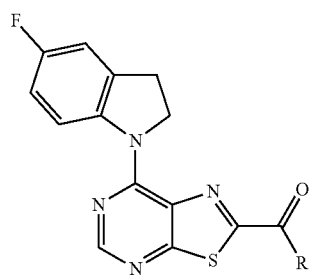

| Example # | R | IUPAC Name | LC-MS (ESI): (MH$^+$) | $^1$H NMR |
|---|---|---|---|---|
| 65 | *N-piperazinyl-N'-methyl* | [7-(5-fluoroindolin-1-yl)thiazolo[5,4-d]pyrimidin-2-yl]-(4-methylpiperazin-1-yl)methanone | 399.1 | $^1$H NMR (400 MHz, DMSO-$d_6$) δ ppm 2.20 (s, 3 H), 2.42 (br. s., 4H), 3.23-3.28 (m, 2 H), 3.67 (br. s., 2 H), 4.20(br. s., 2 H), 4.71 (t,J = 8.47 Hz, 2 H), 7.06(td, J = 9.16, 2.75 Hz, 1H), 7.19 (dd, J = 8.24,2.75 Hz, 1 H), 8.57 (dd,J = 8.93, 4.81 Hz, 1 H),8.64 (s, 1 H) |
| 66 | *NH-tetrahydropyranyl* | 7-(5-fluoroindolin-1-yl)-N-tetrahydropyran-4-yl-thiazolo[5,4-d]pyrimidine-2-carboxamide | 400.1 | $^1$H NMR (400 MHz, DMSO-$d_6$) δ ppm 1.66-1.80 (m, 4 H), 3.31-3.42 (m, 4 H), 3.78-3.91 (m, 2 H), 3.98-4.13 (m, 1 H), 4.83-4.97 (m, 2 H), 7.07 (td, J = 8.93, 2.75 Hz, 1 H), 7.20 (dd, J = 8.47, 2.98 Hz, 1 H), 8.59-8.67 (m, 2 H), 8.72 (d, J = 8.70 Hz, 1 H) |
| 67 | *NH-(1-methylpiperidin-4-yl)* | 7-(5-fluoroindolin-1-yl)-N-(1-methyl-4-piperidyl)thiazolo[5,4-d]pyrimidine-2-carboxamide | 413.1 | $^1$H NMR (400 MHz, DMSO-$d_6$) δ ppm 1.70-1.78 (m, 4 H), 1.87-1.96 (m, 2 H), 2.14 (s, 3 H), 2.77 (d, J = 11.45 Hz, 2 H), 3.31-3.34 (m, 2 H), 3.70-3.82 (m, 1 H), 4.89 (t, J = 7.80 Hz, 2 H), 7.02-7.10 (m, 1 H), 7.17-7.23 (m, 1 H), 8.59-8.64 (m, 2 H), 8.67 (d, J = 8.24 Hz, 1 H) |

| Example # | R | IUPAC Name | LC-MS (ESI): (MH+) | 1H NMR |
|---|---|---|---|---|
| 68 | | N-[3-(dimethylamino)propyl]-7-(5-fluoroindolin-1-yl)thiazolo[5,4-d]pyrimidine-2-carboxamide | 427.1 | H NMR (400 MHz, CHLOROFORM-d) δ ppm 1.72-1.82 (m, 3 H) 1.87 (quin, J = 6.53 Hz, 2 H) 2.49-2.60 (m, 4 H) 2.64 (t, J = 6.64 Hz, 2 H) 3.33 (t, J = 8.24 Hz, 2 H) 3.63 (q, J = 6.11 Hz, 2 H) 4.81-4.95 (m, 2 H) 6.90-7.04 (m, 2 H) 7.91 (t, J = 5.72 Hz, 1 H) 8.56-8.79 (m, 2 H) |
| 69 | | 7-(5-fluoroindolin-1-yl)-N-methyl-thiazolo[5,4-d]pyrimidine-2-carboxamide | 330.1 | 1H NMR (400 MHz, DMSO-d6) δ ppm 2.90 (d, J = 4.58 Hz, 3 H) 3.35 (s, 2 H) 4.89-4.96 (m, 2 H) 7.07-7.14 (m, 1 H) 7.20-7.26 (m, 1 H) 8.63-8.70 (m, 2 H) 8.94-9.00 (m, 1 H) |
| 70 | | 7-(5-fluoroindolin-1-yl)-N,N-dimethyl-thiazolo[5,4-d]pyrimidine-2-carboxamide | 344.0 | 1H NMR (400 MHz, DMSO-d6) δ ppm 8.66 (s, 1 H), 8.62 (dd, J = 9.16, 5.04 Hz, 1 H), 7.22 (dd, J = 8.70, 2.75 Hz, 1 H), 7.08 (dd, J = 9.16, 3.21 Hz, 1 H), 4.78 (m, 2 H), 3.55 (s, 3 H), 3.29 (m, 2 H), 3.11 (s, 3 H) |
| 71 | | 7-(5-fluoroindolin-1-yl)-N-[2-(methylamino)ethyl]thiazolo[5,4-d]pyrimidine-2-carboxamide | 373.1 | 1H NMR (400 MHz, DMSO-d6) δ ppm 8.91 (m, N H), 8.63 (m, 2 H), 7.19 (dd, J = 8.24, 2.75 Hz, 1 H), 7.07 (td, J = 9.20, 2.00 Hz, 1 H), 4.88 (t, J = 8.47 Hz, 2 H), 3.30 (m, 4 H), 2.66 (t, J = 6.64 Hz, 2 H), 2.28 (s, 3 H) |
| 72 | | 7-(5-fluoroindolin-1-yl)-N-[3-(methylamino)propyl]thiazolo[5,4-d]pyrimidine-2-carboxamide | 387.1 | 1H NMR (400 MHz, DMSO-d6) δ ppm 9.32 (m, NH), 8.67 (m, 2 H), 7.23 (dd, J = 8.47, 2.98 Hz, 1 H), 7.10 (td, J = 9.16, 2.75 Hz, 1 H), 4.91 (t, J = 8.47 Hz, 2 H), 3.40 (dt, J = 7.33, 1.00 Hz, 3 H), 3.34 (m, 2 H), 2.57 (t, J = 6.87 Hz, 2 H), 2.29 (s, 3 H), 1.71 (quin, J = 6.60 Hz, 2 H) |
| 73 | | N-[2-(dimethylamino)ethyl]-7-(5-fluoroindolin-1-yl)thiazolo[5,4-d]pyrimidine-2-carboxamide | 387.0 | 1H NMR (400 MHz, DMSO-d6) δ ppm 2.52-2.65 (m, 6 H) 2.84-3.06 (m, 2 H) 3.37 (m, 2 H) 3.59 (q, J = 6.11 Hz, 2 H) 4.87-4.95 (m, 2 H) 7.07-7.15 (m, 1 H) 7.20-7.27 (m, 1 H) 8.63-8.71 (m, 2H) 9.00-9.08 (m, 1 H) |

| Example # | R | IUPAC Name | LC-MS (ESI): (MH+) | 1H NMR |
|---|---|---|---|---|
| 74 | 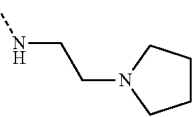 | 7-(5-fluoroindolin-1-yl)-N-(2-pyrrolidin-1-ylethyl)thiazolo[5,4-d]pyrimidine-2-carboxamide | 413.1 | 1H NMR (400 MHz, DMSO-$d_6$) δ ppm 9.04 (d, J = 6.00 Hz, NH), 8.67 (m, 2 H), 7.24 (dd, J = 8.70, 2.75 Hz, 1 H), 7.11 (td, J = 9.04, 2.98 Hz, 1 H), 4.91 (t, J = 8.47 Hz, 2 H), 3.59 (q, J = 6.11 Hz, 2 H), 3.37 (m, 2 H), 2.94 (br. s., 2 H), 2.56 (br. s, 6 H) |
| 75 | 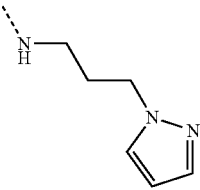 | 7-(5-fluoroindolin-1-yl)-N-(3-pyrazol-1-ylpropyl)thiazolo[5,4-d]pyrimidine-2-carboxamide | 424.0 | 1H NMR (400 MHz, DMSO-$d_6$) δ ppm 9.06 (t, J = 6.18 Hz, NH), 8.67 (m, 2 H), 7.78 (m, 1 H), 7.46 (dd, J = 1.83, 0.92 Hz, 1 H), 7.23 (dd, J = 8.24, 2.75 Hz, 1 H), 7.11 (td, J = 9.16, 2.75 Hz, 1 H), 6.24 (d, J = 2.29 Hz, 1 H), 4.92 (t, J = 8.20 Hz, 2 H), 4.20 (t, J = 6.87 Hz, 2 H), 3.36 (m, J = 3.70 Hz, 2 H), 3.33 (m, 2 H), 2.09 (quin, J = 6.98 Hz, 2 H) |
| 76 | 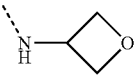 | 7-(5-fluoroindolin-1-yl)-N-(oxetan-3-yl)thiazolo[5,4-d]pyrimidine-2-carboxamide | 372.1 | 1H NMR (400 MHz, DMSO-$d_6$) δ ppm 9.56 (d, J = 6.87 Hz, NH), 8.68 (m, 2 H), 7.25 (dd, J = 8.70, 3.21 Hz, 1 H), 7.12 (td, J = 9.04, 2.98 Hz, 1 H), 5.11 (sxt, J = 7.14 Hz, 1 H), 4.96 (t, J = 8.70 Hz, 2 H), 4 81 (t, J = 6.40 Hz, 2 H), 4.77 (t, J = 6.90 Hz, 2 H), 3.37 (t, J = 8.70 Hz, 2 H) |
| 77 | 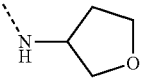 | 7-(5-fluoroindolin-1-yl)-N-tetrahydrofuran-3-yl-thiazolo[5,4-d]pyrimidine-2-carboxamide | 386.1 | 1H NMR (400 MHz, DMSO-$d_6$) δ ppm 8.95 (d, J = 7.33 Hz, NH), 8.63 (m, 2 H), 7.20 (dd, J = 8.70, 2.75 Hz, 1 H), 7.07 (td, J = 8.93, 2.75 Hz, 1 H), 4.90 (t, J = 8.70 Hz, 2H), 4.52 (m, 1 H), 3.88 (m, 2 H), 3.69 (m, 2 H), 3.32 (t, J = 8.70 Hz, 2 H), 2.19 (m, 1 H), 2.02 (m, 1 H) |
| 78 | 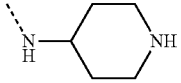 | 7-(5-fluoroindolin-1-yl)-N-(4-piperidyl)thiazolo[5,4-d]pyrimidine-2-carboxamide | 399.1 | 1H NMR (400 MHz, DMSO-$d_6$) δ ppm 8.67 (d, J = 8.24 Hz, NH), 8.62 (m, 2 H), 7.20 (dd, J = 8.70, 2.75 Hz, 1 H), 7.06 (td, J = 9.60, 2.70 Hz, 1 H), 4.88 (t, J = 8.24 Hz, 2 H), 3.85 (m, 1 H), 3.30 (m, 2 H), 2.96 (dt, J = 12.36, 3.21 Hz, 2 H), 2.51 (td, J = 13.30, 2.30 Hz, 2 H), 1.72 (m, 2 H), 1.58 (qd, J = 10.50, 6.00 Hz, 2 H) |

-continued

| Example # | R | IUPAC Name | LC-MS (ESI): (MH+) | 1H NMR |
|---|---|---|---|---|
| 79 | 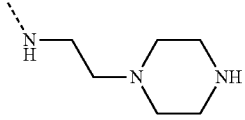 | 7-(5-fluoroindolin-1-yl)-N-(2-piperazin-1-ylethyl)thiazolo[5,4-d]pyrimidine-2-carboxamide | 428.1 | 1H NMR (400 MHz, CHLOROFORM-d) δ ppm 2.40-2.60 (m, 4 H), 2.61-2.70 (m, 2 H), 2.94 (t, J = 4.58 Hz, 4 H), 3.36 (t, J = 8.24 Hz, 2 H), 3.60 (q, J = 5.50 Hz, 2 H), 4.95 (t, J = 8.50 Hz, 2 H), 6.94-7.05 (m, 2 H), 7.97 (br. t, J = 4.60, 4.60 Hz, 1 H), 8.60-8.75 (m, 2 H) |
| 80 | 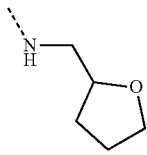 | 7-(5-fluoroindolin-1-yl)-N-((tetrahydrofuran-3-yl)methyl)thiazolo[5,4-d]pyrimidine-2-carboxamide | 400.0 | 1H NMR (400 MHz, DMSO-d6) δ ppm 9.00 (t, J = 6.18 Hz, 1 H), 8.63 (m, 2 H), 7.19 (dd, J = 8.70, 2.75 Hz, 1 H), 7.07 (td, J = 9.16, 2.75 Hz, 1 H), 4.88 (t, J = 8.47 Hz, 2 H), 4.02 (quin, J = 6.41 Hz 1 H), 3.76 (dd, J = 15.10, 7.10 Hz, 1 H), 3.61 (dd, J = 16.03, 7.03, 1 H), 3.35 (m, 2 H), 3.32 (m, 1 H), 1.77 (m, 4 H) |

Example 81

[7-(5-Fluoroindolin-1-yl)thiazolo[5,4-d]pyrimidin-2-yl]methanol

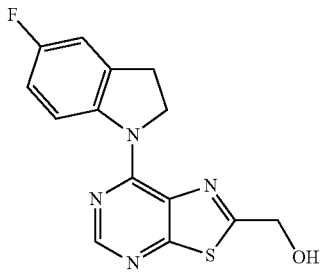 [SMILES: OCc1nc2c(N3CCc4cc(F)ccc43)ncnc2s1]

To a solution of Intermediate 7 (250 mg, 7.3 mmol) in THF (25 ml) was added a 1M solution of lithium aluminium hydride in THF (0.15 ml, 0.15 mmol) dropwise and stirred for 2.5 hours. To the mixture was carefully added 0.15 ml of water, followed by 0.15 ml of 15% NaOH₀ and finally 3 ml of water. The mixture was filtered to remove the solids. The filtrate diluted with EtOAc and water, the organic layer separated, dried and concentrated to give a yellow solid. This was triturated with minimal EtOAc to give a yellow solid (60 mg, 27%); 1H NMR (400 MHz, DMSO-d6) δ ppm 3.23 (t, J=8.47 Hz, 2H), 4.76 (t, J=8.47 Hz, 2H), 4.82 (d, J=5.95 Hz, 2H), 6.37 (t, J=6.00 Hz, 1H), 7.03 (td, J=9.20, 2.80 Hz, 1H), 7.16 (dt, J=8.20, 1.40 Hz, 1H), 8.50-8.59 (m, 2H); LC-MS (ESI): (MH+) 303.0

Example 82

2-[7-(5-Fluoroindolin-1-yl)thiazolo[5,4-d]pyrimidin-2-yl]propan-2-ol

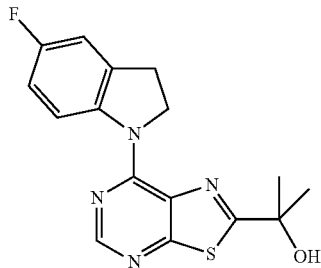 [SMILES: CC(C)(O)c1nc2c(N3CCc4cc(F)ccc43)ncnc2s1]

To a solution of Intermediate 7 (250 mg, 7.3 mmol) in THF (5 ml) was added a 3M solution of methyl magnesium chloride in THF (0.74 ml, 2.2 mmol) drop wise and stirred for 30 minutes. Saturated ammonium chloride was then added, followed by EtOAc. The organic layer was separated, dried and concentrated to give a yellow solid. This was triturated with a minimal amount of EtOAc and the solid filtered off to give 2-[7-(5-fluoroindolin-1-yl)thiazolo[5,4-d]pyrimidin-2-yl]propan-2-ol, an off white solid (138 mg, 58%); 1H NMR (400 MHz, DMSO-d6) δ ppm 1.57 (s, 6H), 3.27 (t, J=8.40 Hz, 2H), 4.80 (t, J=8.50 Hz, 2H), 6.34 (s, 1H), 7.05 (td, J=9.16, 2.75 Hz, 1H), 7.14-7.24 (m, 1H), 8.49-8.61 (m, 2H); LC-MS (ESI): (MH+) 331.0

Example 83

7-(5-Fluoroindolin-1-yl)thiazolo[5,4-d]pyrimidin-2-amine

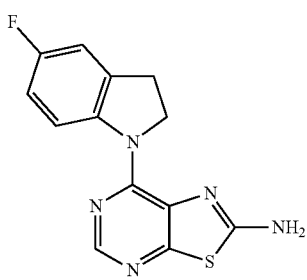 [SMILES: Nc1nc2c(N3CCc4cc(F)ccc43)ncnc2s1]

To a suspension of Intermediate 10 (100 mg, 0.20 mmol) in MeOH (20 ml) was added NaOMe (110 mg, 2.0 mmol) and the mixture refluxed overnight. The reaction mixture was cooled, a precipitate formed which was collected and dried via vacuum filtration to give 7-(5-fluoroindolin-1-yl) thiazolo[5,4-d]pyrimidin-2-amine, a light pink solid (36 mg, 46%); $^1$H NMR (400 MHz, DMSO-d$_6$) δ ppm 3.13-3.20 (m, 2H), 4.71 (t, J=8.70 Hz, 2H), 6.99 (td, J=9.04, 2.98 Hz, 1H), 7.13 (dd, J=8.47, 2.98 Hz, 1H), 7.72 (s, 2H), 8.30 (s, 1H), 8.34 (dd, J=8.70, 5.04 Hz, 1H); LC-MS (ESI): (MH$^+$) 288.0

Example 84

N-(7-(5-Fluoroindolin-1-yl)thiazolo[5,4-d]pyrimidin-2-yl)tetrahydrofuran-3-carboxamide

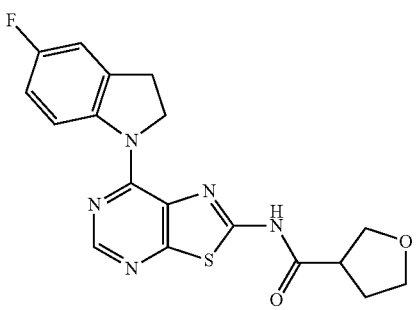 [SMILES: O=C(Nc1nc2c(N3CCc4cc(F)ccc43)ncnc2s1)C1CCOC1]

Tetrahydro-3-furoic acid (30 mg, 0.250 mmol) was added to a stirring suspension of Example 83 (75 mg, 0.248 mmol), HATU (141 mg, 0.366 mol), DIPEA (0.29 mL, 1.57 mmol) and DMF (4 mL) at room temperature. The resultant suspension was stirred at room temperature for 24 hours to give an orange suspension. The solid was filtered off and the filtrate purified by HPLC to give a yellow solid (12 mg, 13%); $^1$H NMR (400 MHz, DMSO-d$_6$) δ ppm 8.50 (s, 2H), 7.15 (dd, J=9.16, 2.75 Hz, 1H), 7.02 (dd, J=9.16, 2.75 Hz, 1H), 4.80 (t, J=9.16 Hz, 2H), 4.58 (d, J=2.75 Hz, 1H), 3.94 (m, 1H), 3.81 (m, 1H), 3.23 (t, J=8.24 Hz, 2H), 2.20 (m, 1H), 1.97 (m, 1H), 1.86 (m, 2H), 1.71 (m, 1H); LC-MS (ESI): (MH$^+$) 386.0

Example 85

N1-(7-(5-fluoroindolin-1-yl)thiazolo[5,4-d]pyrimidin-2-yl)-N3,N3-dimethylpropane-1,3-diamine

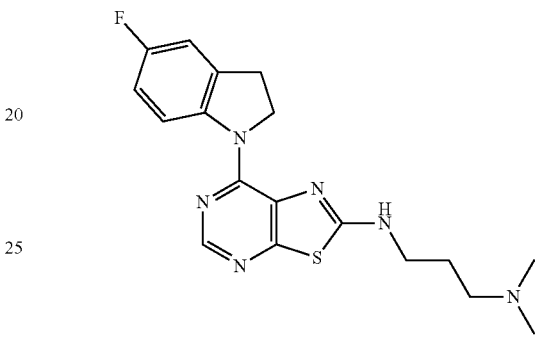

3-Dimethylamino-1-propyl chloride hydrochloride (33 mg, 0.209 mmol) was added to a stirring suspension of Intermediate 11 (50 mg, 0.174 mmol) and potassium carbonate (47 mg, 0.348 mmol) in DMF (2 mL) at room temperature. The resultant suspension was stirred for 24 hours at 80° C. to give an orange suspension. The solid was filtered off and the filtrate purified by HPLC to give a yellow solid (15 mg, 24%); $^1$H NMR (400 MHz, DMSO-d$_6$) δ ppm 8.27 (m, 3H), 7.08 (dd, J=8.70, 2.75 Hz, 1H), 6.95 (d, J=3.21 Hz, 1H), 4.70 (t, J=8.70 Hz, 2H), 3.36 (m, 2H), 3.16 (t, J=8.24 Hz, 2H), 2.28 (t, J=6.87 Hz, 2H), 2.12 (s, 6H), 1.71 (t, J=7.10 Hz, 2H); LC-MS (ESI): (MH$^+$) 373.2

Examples 86-88 in the table below were prepared analogously to Example 85 from Intermediate 11 and the appropriate amine.

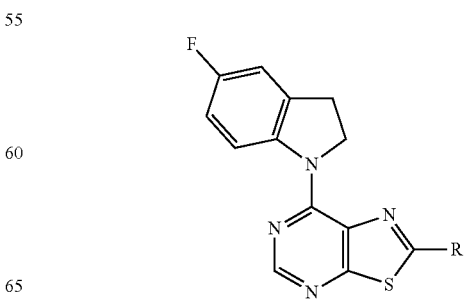

| Example # | R | IUPAC Name | LC-MS (ESI): (MH+) | 1H NMR |
|---|---|---|---|---|
| 86 | ----NH-CH2CH2-N(CH3)- | N-[7-(5-fluoroindolin-1-yl)thiazolo[5,4-d]pyrimidin-2-yl]-N',N'-dimethyl-propane-1,3-diamine | 359.2 | 1H NMR (400 MHz, DMSO-d6) δ ppm 8.43 (t, J = 5.50 Hz, NH), 8.31 (m, 2 H), 7.11 (dd, J = 8.70, 2.75 Hz, 1 H), 6.98 (td, J = 9.16, 3.21 Hz, 1 H), 4.71 (t, J = 8.70 Hz, 2 H), 3.72 (q, J = 5.95 Hz, 2 H), 3.32 (q, J = 5.50 Hz, 2 H), 3.17 (t, J = 9.20 Hz, 2 H), 2.81 (d, J = 5.04 Hz, 6 H) |
| 87 | ----N(morpholine) | 4-[7-(5-fluoroindolin-1-yl)thiazolo[5,4-d]pyrimidin-2-yl]morpholine | 358.1 | 1H NMR (400 MHz, CHLOROFORM-d) δ ppm 8.40 (m, 2 H), 6.92 (m, 2 H), 4.79 (t, J = 8.70 Hz, 2 H), 3.86 (t, J = 5.04 Hz, 4 H), 3.61 (t, 4 H), 3.22 (s, 2 H) |
| 88 | ----N(piperazine)N-CH3 | 7-(5-fluoroindolin-1-yl)-2-(4-methylpiperazin-1-yl)thiazolo[5,4-d]pyrimidine | 371.7 | 1H NMR (400 MHz, CHLOROFORM-d) δ ppm 8.40 (m, 2 H), 6.92 (m, 2 H), 4.79 (m, 2 H), 3.64 (m, 4 H), 3.21 (m, 2 H), 2.56 (s, 4 H), 2.38 (s, 3 H) |

Example 89

3-((7-(5-Fluoroindolin-1-yl)thiazolo[5,4-d]pyrimidin-2-yl)oxy)-N,N-dimethylpropan-1-amine

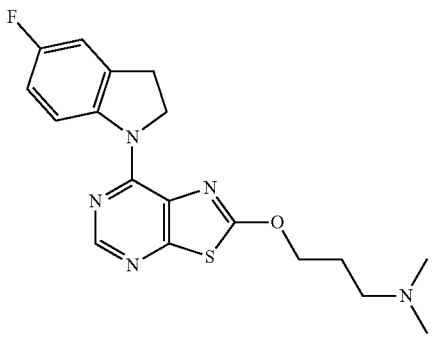 [SMILES: CN(C)CCCOc1nc2c(N3CCc4cc(F)ccc43)ncnc2s1]

A 60% dispersion of NaH in mineral oil (6 mg, 0.149 mmol) was added to a solution of 3-dimethylamino-1-propanol (16 mg, 0.157 mmol) in THF (10 mL) and left to stir at room temperature for one hour. This was then treated with Intermediate 11 (50 mg, 0.142 mmol) and stirred overnight at room temperature. A green precipitation was collected and dried via vacuum filtration, which was purified by HPLC. The product was obtained as a white solid (5 mg, 9%); 1H NMR (400 MHz, 1H NMR (400 MHz, CHLOROFORM-d) δ ppm 1.97-2.05 (m, 2H) 2.23-2.27 (m, 6H) 2.45 (t, J=7.10 Hz, 2H) 3.18-3.26 (m, 2H) 4.58 (t, J=6.41 Hz, 2H) 4.73-4.79 (m, 2H) 6.87-6.96 (m, 2H) 8.41-8.49 (m, 2H); LCMS: (MH+) 374.1

Example 90

7-(7-Fluoroindolin-1-yl)-N-tetrahydropyran-4-yl-thiazolo[5,4-d]pyridine-2-carboxamide

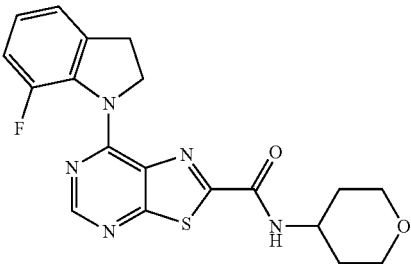 [SMILES: O=C(NC1CCOCC1)c1nc2c(N3CCc4cccc(F)c43)ncnc2s1]

Thionyl chloride (2 ml) was added to Intermediate 14 (75 mg, 0.24 mmol) and heated at 80° C. for 3 hours. The mixture was cooled and concentrated to give an orange gum. This was taken up in DCM, 4-aminotetrahydropyran (48 mg, 0.048 mmol) added and stirred overnight. The mixture was diluted with DCM and water, the organic layer separated, dried and concentrated to give a yellow solid. This was purified via HPLC purification to give a yellow solid (26 mg, 28%); 1H NMR (400 MHz, CHLOROFORM-d) δ ppm 1.55-1.67 (m, 2H), 1.96-2.09 (m, 2H), 3.30 (t, J=7.79 Hz, 2H), 3.56 (td, J=11.56, 2.06 Hz, 2H), 3.94-4.07 (m, 2H), 4.12-4.28 (m, 1H), 4.67 (t, J=7.80 Hz, 2H), 6.92-7.05 (m, 2H), 7.06-7.17 (m, 2H), 8.68 (s, 1H); LC-MS (ESI): (MH+) 400.0.

Example 91

7-(5-Chloro-7-fluoro-indolin-1-yl)-N-tetrahydropyran-4-yl-thiazolo[5,4-d]pyrimidine-2-carboxamide

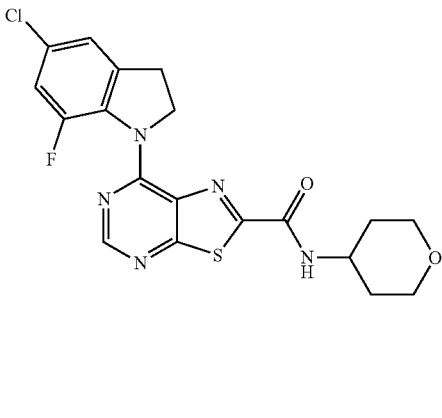 [SMILES: O=C(NC1CCOCC1)c1nc2c(N3CCc4cc(Cl)cc(F)c43)ncnc2s1]

Example 91 was isolated as by product during the formation of Example 90. (7.1 mg); $^1$H NMR (400 MHz, CHLOROFORM-d) δ ppm 1.59-1.70 (m, 2H), 2.04 (dd, J=12.59, 2.52 Hz, 2H), 3.29 (t, J=7.79 Hz, 2H), 3.57 (td, J=11.56, 2.06 Hz, 2H), 3.97-4.07 (m, 2H), 4.14-4.28 (m, 1H), 4.69 (t, J=−8.01 Hz, 2H), 6.99 (d, J=7.80 Hz, 1H), 7.05 (dd, J=10.08, 1.83 Hz, 1H), 7.13 (d, J=1.40 Hz, 1H), 8.69 (s, 1H); LC-MS (ESI): (MH$^+$) 434/436

Examples 92 and 93 in the table below were prepared analogously to Example 90 from Intermediate 14 and the appropriate amine.

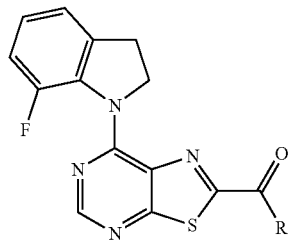

| Example # | R | IUPAC Name | LC-MS (ESI): (MH$^+$) | $^1$H NMR |
|---|---|---|---|---|
| 92 | ![R group with N-propyl-dimethylamine] | N-[3-(dimethylamino)propyl]-7-(7-fluoroindolin-1-yl)thiazolo[5,4-d]pyrimidine-2-carboxamide | 401.1 | $^1$H NMR (400 MHz, CHLOROFORM-d) δ ppm 1.80 (quin, J = 6.18 Hz, 2 H), 2.25 (s, 6 H), 2.47 (t, J = 6.18 Hz, 2 H), 3.28 (t, J = 7.80 Hz, 2 H), 3.61 (q, J = 6.40 Hz, 2 H), 4.71 (t, J = 7.80 Hz, 2 H), 6.99-7.08 (m, 1 H), 7.08-7.13 (m, 2 H), 8.62 (br. t, J = 5.00, 5.00 Hz, 1 H), 8.67 (s, 1 H) |
| 93 | ![R group with methylpiperidinyl] | 7-(7-fluoroindolin-1-yl)-N-[(1-methyl-4-piperidyl)methyl]thiazolo[5,4-d]pyrimidine-2-carboxamide | 427.1 | $^1$H NMR (400 MHz, CHLOROFORM-d) δ ppm 1.28-1.44 (m, 2 H), 1.55-1.66 (m, 1 H), 1.70-1.79 (m, 2 H), 1.93 (td, J = 11.68, 2.29 Hz, 2 H), 2.28 (s, 3 H), 2.88 (m, J = 11.90 Hz, 2 H), 3.27 (t, J = 7.80 Hz, 2 H), 3.38 (t, J = 6.64 Hz, 2 H), 4.65 (t, J = 7.80 Hz, 2 H), 6.94-7.02 (m, 1 H), 7.04-7.13 (m, 2 H), 7.22 (t, J = 6.18 Hz, 1 H), 8.67 (s, 1 H) |

Example 94

7-Indolin-1-yl-N-(4-piperidylmethyl)thiazolo[5,4-d]pyrimidine-2-carboxamide

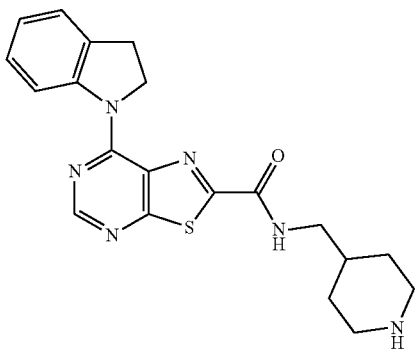 [SMILES: O=C(NCC1CCNCC1)c1nc2c(N3CCc4ccccc43)ncnc2s1]

Thionyl chloride (5 ml) was added to Intermediate 16 (50 mg, 0.17 mmol) and the suspension heated under reflux for 1 hour. The resultant solution was concentrated to give a dark orange solid. The acid chloride was taken up in DCM (2 mL), triethylamine (51 mg, 0.50 mmol) added followed by 4-(aminomethyl)-1-BOC-piperidine. The mixture was stirred room temperature for 30 minutes. TFA (1 ml) was added to the mixture and stirred for 30 minutes. The mixture was concentrated purified by HPLC to give a yellow solid (4.7 mg, 8%); $^1$H NMR (400 MHz, CHLOROFORM-d) 0 ppm 8.68 (s, 1H), 8.66 (d, J=8.70 Hz, 1H), 7.32 (d, J=7.79 Hz, 2H), 7.24 (t, J=6.41 Hz, 1H), 7.11 (td, J=7.79, 1.83 Hz, 1H), 4.84 (t, J=8.24 Hz, 2H), 3.43 (t, J=6.87 Hz, 2H), 3.37 (t, J=8.70 Hz, 2H), 3.14 (dt, J=11.90, 4.10 Hz, 2H), 2.64 (td, J=12.36, 2.75 Hz, 2H), 1.85 (m, 1H), 1.78 (m, 2H), 1.28 (qd, J=11.91, 3.66 Hz, 2H); LC-MS (ESI): (MH$^+$) 395.1

Examples 95-104

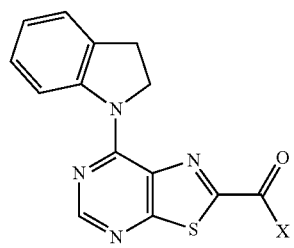

Examples 95-104 in the table below were prepared analogously to Example 94 from Intermediate 16 and the appropriate, optionally BOC protected, amine General procedure: Thionyl chloride (30 ml) was added to Intermediate 16 (650 mg, 2.18 mmol) and the suspension heated under reflux for 30 mins. The resultant solution was concentrated to give a dark orange solid. The acid chloride was taken up in DCM (32 mL) and triethylamine (0.13 mL, 0.94 mmol) added. Aliquots were added to 11 reaction vials containing a solution of the desired amine (0.24 mmol) in DCM (0.2 mL). The mixture was stirred overnight at room temperature.

Work-up for all except Examples 97 and 98: The solid was collected by vacuum filtration and purified by column chromatography or preparative LCMS.

Work-up for Examples 97 and 98: TFA (1 ml) was added to the mixture and stirred for 30 min. The mixture was concentrated purified by preparative LCMS.

| Example # | X | IUPAC Name | LC-MS (ESI): (MH$^+$) | $^1$H NMR |
|---|---|---|---|---|
| 95 | (tetrahydrofuran-3-ylmethyl)amino group | 7-(Indolin-1-yl)-N-((tetrahydrofuran-3-yl)methyl)thiazolo[5,4-d]pyrimidine-2-carboxamide | 382.1 | $^1$H NMR (400 MHz, DMSO-d6) δ ppm 9.00 (t, J = 6.40 Hz, NH), 8.63 (m, 2 H), 7.32 (d, J = 7.30 Hz, 1 H), 7.23 (t, J = 8.70 Hz, 1 H), 7.05 (t, J = 8.20 Hz, 1 H), 4.86 (t, J = 8.70 Hz, 2 H), 3.76 (m, 1 H), 3.61 (m, 1 H), 3.36 (t, J = 6.40 Hz, 2 H), 3.30 (t, J = 7.80 Hz, 2 H), 1.84 (m, 3 H), 1.59 (m, 1 H) |
| 96 | 4-methylpiperazin-1-yl | (7-indolin-1-ylthiazolo[5,4-d]pyrimidin-2-yl)-(4-methylpiperazin-1-yl)methanone | 381.1 | $^1$H NMR (400 MHz, CHLOROFORM-d) δ ppm 8.68 (s, 1 H), 8.64 (d, J = 8.70 Hz, 1 H), 7.29 (m, 2 H), 7.10 (td, J = 6.87, 0.92 Hz, 1 H), 4.74 (t, J = 8.24 Hz, 2 H), 4.37 (t, J = 4.58 Hz, 2 H), 3.88 (t, J = 5.04 Hz, 2 H), 3.33 (t, J = 8.24 Hz, 2 H), 2.55 (dt, J = 13.62, 5.09 Hz, 4 H), 2.37 (s, 3 H) |

-continued

| Example # | X | IUPAC Name | LC-MS (ESI): (MH+) | 1H NMR |
|---|---|---|---|---|
| 97 | (N-H connected to CH2CH2CH2-NH-CH3) | 7-indolin-1-yl-N-[3-(methylamino)propyl]thiazolo[5,4-d]pyrimidine-2-carboxamide | 369.1 | 1H NMR (400 MHz, DMSO-d$_6$) δ ppm 9.34 (br. s, NH), 8.68 (m, 2 H), 7.37 (d, J = 7.33 Hz, 1 H), 7.28 (t, J = 7.33 Hz, 1 H), 7.10 (td, J = 7.78, 0.92 Hz, 1 H), 4.89 (t, J = 8.70 Hz, 2 H), 3.42 (t, J = 6.41 Hz, 2 H), 3.34 (m, 2 H), 2.57 (t, J = 6.41 Hz, 2 H), 2.29 (s, 3 H), 1.72 (t, J = 6.87 Hz, 2 H) |
| 98 | (N-H connected to 4-piperidyl) | 7-indolin-1-yl-N-(4-piperidyl)thiazolo[5,4-d]pyrimidine-2-carboxamide | 381.1 | 1H NMR (400 MHz, CHLOROFORM-d) δ ppm 8.68 (s, 1 H), 8.65 (d, J = 7.78 Hz, 1 H), 7.31 (d, J = 7.78 Hz, 2 H), 7.12 (td, J = 7.33, 1.37 Hz, 1 H), 7.01 (d, J = 8.70 Hz, NH), 4.83 (t, J = 8.24 Hz, 2 H), 4.12 (m, 1 H), 3.37 (t, J = 8.70 Hz, 2 H), 3.16 (dt, J = 12.82, 3.66 Hz, 2 H), 2.79 (td, J = 11.91, 1.83 Hz, 2 H), 2.09 (m, 2 H), 1.54 (qd, J = 13.30, 4.12 Hz, 2 H) |
| 99 | (N-H connected to cyclopropyl) | N-cyclopropyl-7-indolin-1-yl-thiazolo[5,4-d]pyrimidine-2-carboxamide | 338.0 | 1H NMR (400 MHz, DMSO-d$_6$) δ ppm 9.00 (m, 1 H), 8.66 (m, 2 H), 7.35 (d, J = 6.87 Hz, 1 H), 7.26 (td, J = 7.80, 0.90 Hz, 1 H), 7.09 (td, J = 7.33, 0.92 Hz, 1 H), 4.87 (t, J = 8.24 Hz, 2 H), 3.30 (m, 2 H), 2.86 (m, 1 H), 0.74 (s, 4 H) |
| 100 | (N-H connected to oxetan-3-yl) | 7-indolin-1-yl-N-(oxetan-3-yl)thiazolo[5,4-d]pyrimidine-2-carboxamide | 354.0 | 1H NMR (400 MHz, DMSO-d$_6$) δ ppm 9.54 (d, J = 6.87 Hz, NH), 8.64 (m, 2 H), 7.34 (d, J = 7.33 Hz, 1 H), 7.24 (td, J = 7.79, 1.37 Hz, 1 H), 7.07 (td, J = 7.33, 0.92 Hz, 1 H), 5.07 (sxt, J = 7.33 Hz, 1 H), 4.90 (t, J = 8.24 Hz, 2 H), 4.76 (t, J = 7.79 Hz, 2 H), 4.73 (t, J = 6.87 Hz, 2 H), 3.34 (t, J = 8.70 Hz, 2 H) |
| 101 | (N-H connected to (1S)-1-(hydroxymethyl)-2-methyl-propyl) | N-[(1S)-1-(hydroxymethyl)-2-methyl-propyl]-7-indolin-1-yl-thiazolo[5,4-d]pyrimidine-2-carboxamide | 384.1 | 1H NMR (400 MHz, DMSO-d$_6$) δ ppm 8.68 (s, 1 H), 8.65 (d, J = 8.70 Hz, 1 H), 8.33 (d, J = 9.62 Hz, NH), 7.35 (d, J = 6.87 Hz, 1 H), 7.27 (t, J = 7.79 Hz, 1 H), 7.09 (t, J = 7.78 Hz, 1 H), 4.88 (m, 3 H), 3.79 (m, 1 H), 3.62 (t, J = 5.04 Hz, 2 H), 1.98 (m, 1 H), 0.96 (d, J = 6.87 Hz, 3H), 0.91 (d, J = 6.87 Hz, 3 H) |

| Example # | X | IUPAC Name | LC-MS (ESI): (MH+) | 1H NMR |
|---|---|---|---|---|
| 102 | (2,2-dimethylmorpholin-4-yl group) | (2,2-dimethylmorpholin-4-yl)-(7-indolin-1-ylthiazolo[5,4-d]pyrimidin-2-yl)methanone | 396.0 | 1H NMR (400 MHz, DMSO-$d_6$) δ ppm 8.69 (s, 1 H), 8.61 (d, J = 8.70 Hz, 1 H), 7.35 (d, J = 7.79 Hz, 1 H), 7.27 (t, J = 7.33 Hz, 1 H), 7.09 (t, J = 7.33 Hz, 1 H), 4.73 (q, J = 7.79 Hz, 2 H), 4.24 (dd, J = 5.95, 4.58 Hz, 1 H), 4.19 (s, 1 H), 3.76 (q, J = 4.58 Hz, 2 H), 3.56 (s, 1 H), 3.30 (m, 2 H), 1.20 (d, J = 4.58 Hz, 7 H) |
| 103 | (tetrahydropyran-4-ylmethylamino) | 7-indolin-1-yl-N-(tetrahydropyran-4-ylmethyl)thiazolo[5,4-d]pyrimidine-2-carboxamide | 396.1 | 1H NMR (400 MHz, DMSO-$d_6$) δ ppm 9.05 (t, J = 6.41 Hz, NH), 8.67 (m, 2 H), 7.36 (d, J = 7.33 Hz, 1 H), 7.27 (t, J = 8.24 Hz, 1 H), 7.08 (td, J = 7.78, 0.92 Hz, 1 H), 4.89 (t, J = 8.47 Hz, 2 H), 3.85 (dt, J = 10.10, 4.60 Hz, 2 H), 3.36 (m, 1 H), 3.26 (d, J = 6.41 Hz, 5 H), 1.88 (m, 1 H), 1.60 (m, 2 H), 1.22 (qd, J = 12.40, 10.50 Hz, 2 H) |
| 104 | (2,3-dihydroxypropylamino) | N-(2,3-dihydroxypropyl)-7-indolin-1-yl-thiazolo[5,4-d]pyrimidine-2-carboxamide | 372.1 | 1H NMR (400 MHz, DMSO-$d_6$) δ ppm 8.90 (t, J = 6.41 Hz, NH), 8.68 (m, 2 H), 7.36 (d, J = 6.87 Hz, 1 H), 7.28 (t, J = 8.24 Hz, 1 H), 7.09 (t, J = 7.79 Hz, 1 H), 4.97 (d, J = 5.04 Hz, 1 H), 4.89 (t, J = 8.24 Hz, 2 H), 4.73 (t, J = 5.95 Hz, 1 H), 3.73 (m, 1 H), 3.39 (s, 4 H), 3.29 (m, 2 H) |

Example 105

7-(5-Fluoro-3,3-dimethyl-indolin-1-yl)-N-tetrahydropyran-4-yl-thiazolo[5,4-d]pyrimidine-2-carboxamide

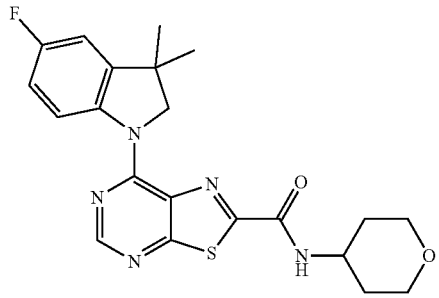 [SMILES: CC1(C)CN(c2ncnc3sc(C(=O)NC4CCOCC4)nc23)c2ccc(F)cc21]

5-Fluoro-3,3-dimethyl-indoline (28 mg, 0.17 mmol), Intermediate 18 (50 mg, 0.17 mmol) and propan-2-ol (2 ml) were combined, sealed in a microwave tube and heated at 80° C. in a heating block for 4 hours. The mixture was cooled, at which point a yellow precipitate formed. This was collected via vacuum filtration, loaded onto silica and purified via column chromatography (gradient elution from 0-5% MeOH in DCM) to give a yellow solid (24 mg, 33%); 1H NMR (400 MHz, DMSO-$d_0$) δ ppm 1.39 (s, 6H), 1.76-1.85 (m, 4H), 3.36-3.45 (m, 2H), 3.85-3.96 (m, 2H), 3.97-4.14 (m, 1H), 4.65 (s, 2H), 7.11 (td, J=9.16, 2.75 Hz, 1H), 7.29 (dd, J=8.70, 2.75 Hz, 1H), 8.57 (dd, J=8.93, 4.81 Hz, 1H), 8.62 (d, J=8.24 Hz, 1H), 8.67 (s, 1H); LC-MS (ESI): (MH+) 428.1

Example 106

7-Indolin-1-yl-N-tetrahydropyran-4-yl-thiazolo[5,4-d]pyrimidine-2-carboxamide

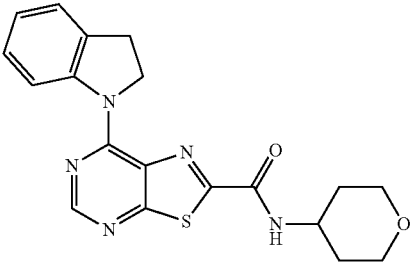 [SMILES: O=C(NC1CCOCC1)c1nc2c(N3CCc4ccccc43)ncnc2s1]

Intermediate 18 (50 mg, 0.17 mmol), indoline (20 mg, 0.17 mmol) and propan-2-ol (2 ml) were combined, sealed in a microwave tube and heated at 80° C. thermally for 1.5 hours. The mixture was cooled, at which point a yellow precipitate formed. This was collected and dried via vacuum filtration to a yellow solid (45 mg, 70%); ¹H NMR (400 MHz, DMSO-d₆) δ ppm 1.71-1.86 (m, 4H), 3.34-3.37 (m, 2H), 3.37-3.45 (m, 2H), 3.87-3.96 (m, 2H), 4.02-4.19 (m, 1H), 4.91 (t, J=8.40 Hz, 2H), 7.09 (td, J=7.33, 0.92 Hz, 1H), 7.28 (t, J=7.33 Hz, 1H), 7.37 (d, J=7.33 Hz, 1H), 8.62-8.71 (m, 2H), 8.77 (d, J=8.70 Hz, 1H); LC-MS (ESI): (MH⁺) 382.0

Examples 107-113 in the table below were prepared analogously to Example 105 from Intermediate 18 and the appropriate indoline

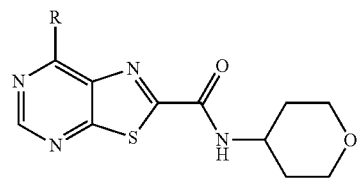

| Example # | R | IUPAC Name | LC-MS (ESI): (MH⁺) | ¹H NMR |
|---|---|---|---|---|
| 107 | ![5-fluorospiro[cyclopropane-1,3'-indoline]] | 7-(5'-fluorospiro[cyclopropane-1,3'-indoline]-1'-yl)-N-tetrahydropyran-4-yl-thiazolo[5,4-d]pyrimidine-2-carboxamide | 426.0 | ¹H NMR (400 MHz, CHLOROFORM-d) δ ppm 1.21-1.26 (m, 4 H), 1.61-1.71 (m, 2 H), 2.06 (dd, J = 12.36, 2.29 Hz, 2 H), 3.57 (td, J = 11.68, 2.29 Hz, 2 H), 4.01-4.08 (m, 2 H), 4.18-4.29 (m, 1 H), 4.79 (s, 2 H), 6.48 (dd, J = 8.24, 2.75 Hz, 1 H), 6.88 (d, J = 8.24 Hz, 1 H), 6.95 (td, J = 8.70, 2.75 Hz, 1 H), 8.64 (dd J = 8.93, 4.81 Hz, 1 H), 8.69 (s, 1 H) |
| 108 | ![spiro[indoline-3,4'-tetrahydropyran]] | 7-spiro[indoline-3,4'-tetrahydropyran]-1-yl-N-tetrahydropyran-4-yl-thiazolo[5,4-d]pyrimidine-2-carboxamide | 452.1 | ¹H NMR (400 MHz, DMSO-d₆) δ ppm 1.60 (d, J = 12.82 Hz, 2H), 1.64-1.74 (m, 2 H), 1.78-1.85 (m, 2 H), 1.95 (td, J = 12.82, 4.58 Hz, 2 H), 3.41 (td, J = 11.45, 2.29 Hz, 2 H), 3.59 (t, J = 11.45 Hz, 2 H), 3.84-3.92 (m, 4 H), 3.96-4.08 (m, 1 H), 4.85 (s, 2 H), 7.07-7.14 (m, 1 H), 7.25-7.31 (m, 1 H), 7.37-7.42 (m, 1 H), 8.61 (d, J = 7.78 Hz, 1 H), 8.64 (d, J = 8.24 Hz, 1 H), 8.67 (s, 1 H) |
| 109 | ![3-(hydroxymethyl)indoline] | 7-[3-(hydroxymethyl)indolin-1-yl]-N-tetrahydropyran-4-yl-thiazolo[5,4-d]pyrimidine-2-carboxamide | 412.0 | ¹H NMR (400 MHz, CHLOROFORM-d) δ ppm 1.69-1.78 (m, 2 H), 2.00-2.12 (m, 2 H), 3.57 (td, J = 11.79, 1.60 Hz, 2 H), 3.70-3.81 (m, 1 H), 3.88 (dd, J = 11.00, 6.90 Hz, 1 H), 3.98 (dd, J = 10.50, 5.00 Hz, 1 H), 4.01-4.09 (m, 2 H), 4.17-4.31 (m, 1 H), 4.79-4.94 (m, 2 H). 7.06 (d, J = 8.24 Hz, 1 H), 7.11-7.17 (m, 1 H), 7.33-7.40 (m, 2 H), 8.65-8.73 (m, 2 H) |

| Example # | R | IUPAC Name | LC-MS (ESI): (MH+) | 1H NMR |
|---|---|---|---|---|
| 110 | (indolin-3-yl with 2-hydroxyethyl, N-methyl) OH | 7-[3-(2-hydroxyethyl)indolin-1-yl]-N-tetrahydropyran-4-yl-thiazolo[5,4-d]pyrimidine-2-carboxamide | 426.1 | 1H NMR (400 MHz, DMSO-d6) δ ppm 1.67-1.82 (m, 5 H), 1.91-2.00 (m, 1 H), 3.34-3.43 (m, 2 H), 3.53-3.65 (m, 3 H), 3.88 (d, J = 10.99 Hz, 2H), 3.97-4.09 (m, 1 H), 4.56 (dd, J = 12.36, 5.95 Hz, 1 H), 4.62 (t, J = 5.27 Hz, 1 H), 5.03 (dd, J = 12.40, 9.20 Hz, 1 H), 7.08 (td, J = 7.44, 1.14 Hz, 1 H), 7.25 (t, J = 7.33 Hz, 1 H), 7.34 (d, J = 7.78 Hz, 1 H), 8.55 (d, J = 8.20 Hz, 1 H), 8.60 (d, J = 8.20 Hz, 1 H), 8.64 (s, 1 H) |
| 111 | (indolin-3-yl with 2-aminoethyl, N-methyl) NH2 | 7-[3-(2-aminoethyl)indolin-1-yl]-N-tetrahydropyran-4-yl-thiazolo[5,4-d]pyrimidine-2-carboxamide | 425.1 | 1H NMR (400 MHz, CHLOROFORM-d) δ ppm 1.60-1.71 (m, 2 H), 1.76-1.86 (m, 1 H), 1.99-2.10 (m, 3 H), 2.83-3.01 (m, 2 H), 3.52-3.67 (m, 3 H), 3.98-4.08 (m, 2 H), 4.16-4.30 (m, 1 H), 4.53 (dd, J = 11.91, 5.95 Hz, 1 H), 4.96 (dd, J = 11.91, 9.16 Hz, 1 H), 7.06 (d, J = 8.24 Hz, 1 H), 7.11 (td, J = 7.33, 0.92 Hz, 1 H), 7.26-7.35 (m, 2 H), 8.60 (d, J = 8.24 Hz, 1 H), 8.66 (s, 1 H) |
| 112 | (indolin-5-yl with CF3, N-methyl) | N-(tetrahydro-2H-pyran-4-yl)-7-(5-(trifluoromethyl)indolin-1-yl)thiazolo[5,4-d]pyrimidine-2-carboxamide | | 1H NMR (400 MHz, DMSO-d6) δ ppm 8.79 (d, J = 8.24 Hz, 1 H), 8.74 (s, 1 H), 7.70 (s, 1 H), 7.64 (d, J = 8.70 Hz, 1 H), 4.96 (t, J = 8.47 Hz, 2 H), 4.09 (m, 1 H), 3.93 (d, J = 10.99 Hz, 2 H), 3.41 (m, 4 H), 1.84 (m, 2 H), 1.79 (m, 2 H) |
| 113 | (3-methyl-3-(2-hydroxyethyl)indolin-1-yl, N-methyl) OH | 7-[3-(2-hydroxyethyl)-3-methyl-indolin-1-yl]-N-tetrahydropyran-4-yl-thiazolo[5,4-d]pyrimidine-2-carboxamide | 440.0 | 1H NMR (400 MHz, CHLOROFORM-d) δ ppm 1.47 (s, 3 H), 1.63-1.73 (m, 2 H), 2.02-2.07 (m, 4 H), 3.56 (m, 2 H), 3.76-3.82 (m, 2 H), 3.97-4.05 (m, 2 H), 4.15-4.28 (m, 1 H), 4.51 (d, J = 11.90 Hz, 1 H), 5.02 (d, J = 11.91 Hz, 1 H), 7.09-7.18 (m, 2 H), 7.20-7.24 (m, 1 H), 7.29-7.35 (m, 1 H), 8.59 (d, J = 8.24 Hz, 1 H), 8.65 (s, 1 H) |

| Example # | R | IUPAC Name | LC-MS (ESI): (MH+) | 1H NMR |
|---|---|---|---|---|
| 114 | HO— (5-hydroxyindolin drawing) | 7-(5-hydroxyindolin-1-yl)-N-tetrahydropyran-4-yl-thiazolo[5,4-d]pyrimidine-2-carboxamide | 398 | 1H NMR (400 MHz, DMSO-d6) δ ppm 1.72-1.85 (m, 4 H), 3.26 (t, 8.24 Hz, 2 H), 3.35-3.45 (m, 2 H), 3.86-3.95 (m, 2 H), 4.82-4.89 (m, 2 H), 6.66 (dd, J = 8.70, 2.29 Hz, 1 H), 6.77 (d, J = 2.29 Hz, 1 H), 8.48 (d, J = 8.70 Hz, 1 H), 8.57 (s, 1 H), 8.73 (d, J = 8.70 Hz, 1 H). |

Example 115

7-[3-[2-(Methylamino)ethyl]indolin-1-yl]-N-tetrahydropyran-4-yl-thiazolo[5,4-d]pyrimidine-2-carboxamide

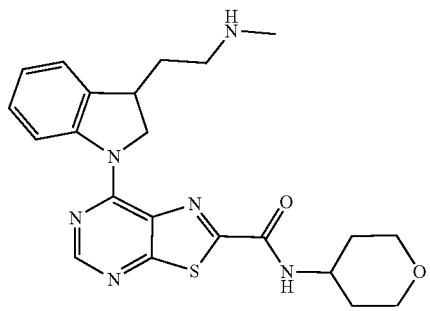 [SMILES: CNCCC1CN(c2ncnc3sc(C(=O)NC4CCOCC4)nc23)c2ccccc21]

To a solution of Example 110 (23 mg, 0.05 mmol) in DCM (1 ml) was added triethylamine (15 µL, 0.1 mmol) and mesyl chloride (6 mg, 0.05 mmol) and stirred for 45 mins. A 33% solution of methylamine in EtOH (mil) was added and stirred overnight. The mixture was concentrated and submitted for HPLC purification. To give 7-[3-[2-(methylamino)ethyl]indolin-1-yl]-N-tetrahydropyran-4-yl-thiazolo[5,4-d]pyrimidine-2-carboxamide (8.8 mg, 37%); 1H NMR (400 MHz, CHLOROFORM-d) δ ppm 1.62-1.74 (m, 2H), 1.85-1.91 (m, 1H), 2.01-2.05 (m, 2H), 2.11-2.16 (m, 1H), 2.53 (s, 3H), 2.77-2.94 (m, 2H), 3.50-3.66 (m, 3H), 3.97-4.08 (m, 2H), 4.15-4.29 (m, 1H), 4.52 (dd, J=11.91, 5.50 Hz, 1H), 4.92 (dd, J=11.91, 9.16 Hz, 1H), 7.04-7.13 (m, 1H), 7.22-7.25 (m, 1H), 7.27-7.32 (m, 2H), 8.61 (d, J=8.24 Hz, 1H), 8.67 (s, 1H); LC-MS (ESI): (MH+) 439.1

Example 116

7-(5-Isopropoxyindolin-1-yl)-N-tetrahydropyran-4-yl-thiazolo[5,4-d]pyrimidine-2-carboxamide

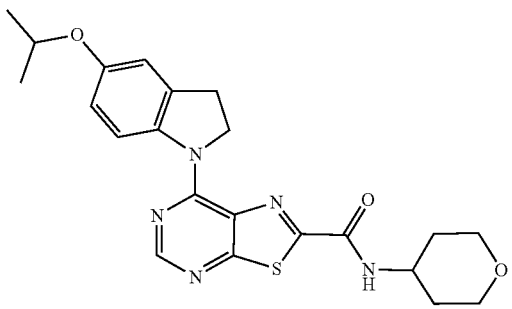 [SMILES: CC(C)Oc1ccc2c(c1)CCN2c1ncnc2sc(C(=O)NC3CCOCC3)nc12]

Example 114 (26 mg, 0.06 mmol), K2CO3 (18 mg, 0.13 mmol) and 2-bromopropane (9 µl, 0.09 mmol) were stirred in DMF (1 ml) at room temperature for 18 h. A further 2 equivalents of 2-bromopropane and 1 equivalent of K2CO3 was added and stirring was continued for a further 4 h. The mixture was quenched with water and extracted with DCM. The organic phases was washed with water and concentrated. Purification by flash chromatography gave a yellow solid (25 mg, 94%). 1H NMR (400 MHz, DMSO-d6) δ ppm 1.22-1.31 (m, 6H), 1.70-1.87 (m, 4H), 3.24-3.47 (m, 4H), 3.84-3.99 (m, 2H), 4.08 (d, J=7.78 Hz, 1H), 4.50-4.67 (m, 1H), 4.88 (t, J=8.24 Hz, 2H), 6.82 (dd, J=8.93, 2.52 Hz, 1H), 6.95 (d, J=2.29 Hz, 1H), 8.57 (d, J=9.16 Hz, 1H), 8.60 (s, 1H), 8.74 (d, J=8.70 Hz, 1H); LC-MS (ESI): (MH+) 440

Example 117

7-Indol-1-yl-N-tetrahydropyran-4-yl-thiazolo[5,4-d]pyrimidine-2-carboxamide

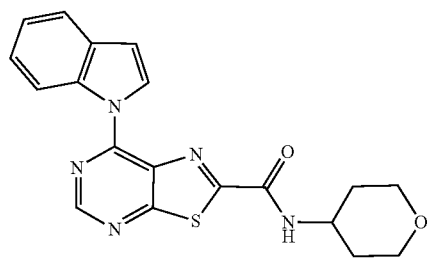 [SMILES: O=C(NC1CCOCC1)c1nc2c(-n3ccc4ccccc43)ncnc2s1]

To a solution of Intermediate 18 (50 mg, 0.17 mmol) in dioxane (3 ml) was added indole (20 mg, 0.17 mmol), Cs2CO3 (109 mg, 0.34 mmol) and Xantphos (9.7 mg, 0.017 mmol). The mixture was degassed, prior to addition of Pd(OAc)2 (7.7 mg, 0.0085 mmol). The reaction mixture was purged with nitrogen and then heated 10 90° C. for 18 h. The mixture was allowed to cool to room temperature, concentrated onto silica gel and subjected to flash chromatography (gradient elution from 0 to 50% ethyl acetate in petroleum ether) to give a brown solid, which was triturated with methanol and dried to give an off-white solid (25 mg, 39%). 1H NMR (400 MHz, CHLOROFORM-d) δ ppm 1.65-1.85 (m, 2H), 2.09 (dd, J=12.59, 2.06 Hz, 2H), 3.59 (td, J=11.91, 2.29 Hz, 2H), 4.07 (dd, J=9.85, 2.06 Hz, 2H), 4.19-4.37 (m, 1H), 6.91 (d, J=3.66 Hz, 1H), 7.14 (d, J=8.24 Hz, 1H), 7.31-7.39 (m, 1H), 7.39-7.47 (m, 1H), 7.69 (d, J=6.87 Hz, 1H), 8.90 (d, J=3.66 Hz, 1H), 8.94-9.00 (m, 1H), 9.05 (s, 1H); LC-MS (ESI): (MH+) 380.

Example 118

7-[3-Methyl-3-[2-(methylamino)ethyl]indolin-1-yl]-N-tetrahydropyran-4-yl-thiazolo[5,4-d]pyrimidine-2-carboxamide

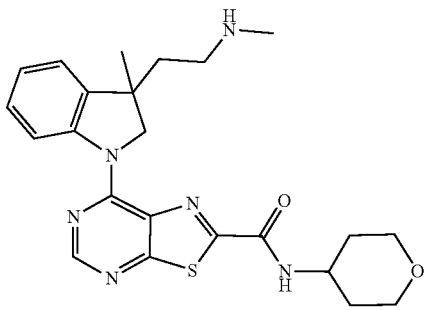 [SMILES: CNCCC1(C)CN(c2ncnc3sc(C(=O)NC4CCOCC4)nc23)c2ccccc21]

Example 118 was prepared in an analogous manner to Example 115 from Example 113. $^1$H NMR (400 MHz, CHLOROFORM-d) δ ppm 1.45 (s, 3H), 1.62-1.74 (m, 2H), 1.86-2.00 (m, 2H), 2.00-2.10 (m, 2H), 2.34 (s, 3H), 2.43-2.53 (m, 1H), 2.57-2.67 (m, 1H), 3.55 (td, J=11.68, 1.83 Hz, 2H), 4.02 (d, J=11.45 Hz, 2H), 4.16-4.30 (m, 1H), 4.42 (d, J=11.45 Hz, 1H), 4.76 (d, J=11.45 Hz, 1H), 7.05-7.16 (m, 2H), 7.18-7.23 (m, 1H), 7.27-7.33 (m, 1H), 8.55 (d, J=8.24 Hz, 1H), 8.62-8.67 (m, 1H); LC-MS (ESI): (MH+) 453.1

Example 119

7-[3-(Aminomethyl)indolin-1-yl]-N-tetrahydropyran-4-yl-thiazolo[5,4-d]pyrimidine-2-carboxamide

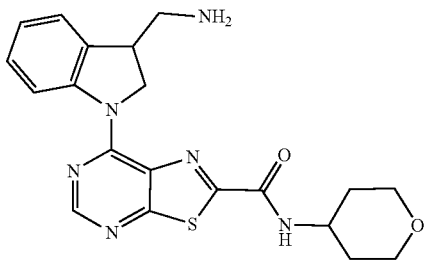 [SMILES: NCC1CN(c2ncnc3sc(C(=O)NC4CCOCC4)nc23)c2ccccc21]

To a solution of Example 109 (50 mg, 0.12 mmol) in THF (3 ml) was added triethylamine (35 μL, 2.4 mmol) and mesyl chloride (10 μL, 0.12 mmol) and stirred for 1 hour. The mixture was concentrated, taken up in DMF and potassium phthalimide (27 mg, 0.15 mmol) added and the reaction was heated at 80'C overnight. The mixture was cooled, EtOAc and water added, the organic phase separated, dried and concentrated. The residue was taken up in EtOH, 2 equivalents of hydrazine added and heated at reflux for 3 hours. The mixture was cooled, the precipitated solid removed via filtration and the filtrate concentrated. Purification by LCMS gave the desired product (2.3 mg, 5%); $^1$H NMR (400 MHz, CHLOROFORM-d) δ ppm 1.64-1.76 (m, 2H), 1.99-2.07 (m, 2H), 2.94-3.06 (m, 1H), 3.09-3.20 (m, 1H), 3.51-3.64 (m, 3H), 4.03 (m, J=10.50 Hz, 2H), 4.19-4.29 (m, 1H), 4.76 (dd, J=11.90, 4.60 Hz, 1H), 4.89 (dd, J=11.90, 9.20 Hz, 1H), 7.08-7.15 (m, 1H), 7.26 (d, J=5.04 Hz, 1H), 7.30-7.36 (m, 2H), 8.63-8.70 (m, 2H); LC-MS (ESI): (MH+) 411.1

Example 120

7-[3-(Methylaminomethyl)indolin-1-yl]-N-tetrahydropyran-4-yl-thiazolo[5,4-d]pyrimidine-2-carboxamide

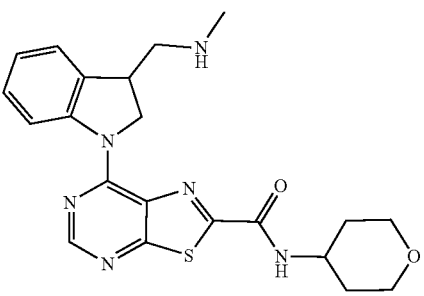 [SMILES: CNCC1CN(c2ncnc3sc(C(=O)NC4CCOCC4)nc23)c2ccccc21]

To a solution of Example 109 (50 mg, 0.12 mmol) in THF (3 ml) was added triethylamine (35 μL, 2.4 mmol) and mesyl chloride (10 μL, 0.12 mmol) and stirred for 1 hour. To the mixture was added an excess of 33% methylamine in ethanol, the vial sealed and heated at 50° C. overnight. The mixture was concentrated and submitted for HPLC purification to give 7-[3-(methylaminomethyl)indolin-1-yl]-N-tetrahydropyran-4-yl-thiazolo[5,4-d]pyrimidine-2-carboxamide (12.6 mg, 24%); $^1$H NMR (400 MHz, CHLOROFORM-d) δ ppm 1.72 (dd, J=12.82, 3.66 Hz, 2H), 1.96-2.08 (m, 2H), 2.50 (s, 3H), 2.82 (dd, J=11.91, 8.70 Hz, 1H), 3.03 (dd, J=11.68, 4.81 Hz, 1H), 3.56 (td, J=11.68, 2.29 Hz, 2H), 3.63-3.72 (m, 1H), 3.99-4.06 (m, 2H), 4.19-4.32 (m, 1H), 4.76 (dd, J=11.91, 5.50 Hz, 1H), 4.91 (dd, =−11.90, 9.20 Hz, 1H), 7.11 (td, J=7.30, 1.40 Hz, 1H), 7.28-7.35 (m, 2H), 7.47-7.54 (m, 1H), 8.63-8.70 (m, 2H); LC-MS (ESI): (MH+) 425.0

Example 121

7-[3-[(dimethylamino)methyl]indol-1-yl]-N-tetrahydropyran-4-yl-thiazolo[5,4-d]pyrimidine-2-carboxamide

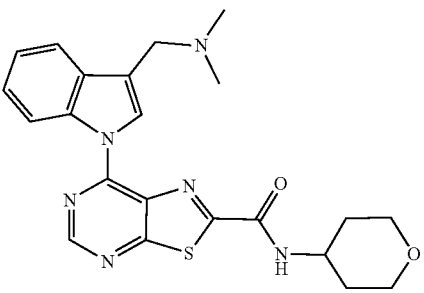 [SMILES: CN(C)Cc1cn(-c2ncnc3sc(C(=O)NC4CCOCC4)nc23)c2ccccc12]

To a solution of Example 109 (100 mg, 0.24 mmol) in THF (5 ml) was added, at 0° C., Dess-Martin Periodinane (113 mg, 0.27 mmol) and stirred overnight. The reaction mixture was concentrated and used in the next step without further purification. The residue was taken up in DCM (5 ml), dimethyl amine (40 mg, 0.48 mmol), sodium triacetoxyborohydride (78 mg, 0.37 mmol) and acetic acid (15 mg, 0.25 mmol) added and stirred overnight. Analysis indicated oxidation of the indoline to the indole. The mixture diluted with DCM and water, the organic layer separated, dried and concentrated. The residue was submitted for HPLC purification to give 7-[3-[(dimethylamino)methyl]indol-1-yl]-N-tetrahydropyran-4-yl-thiazolo[5,4-d]pyrimidine-2-carboxamide (1.7 mg, 2%); $^1$H NMR (400 MHz, CHLOROFORM-d) δ ppm 1.74-1.83 (m, 2H), 1.98-2.07 (m, 2H), 2.40 (s, 6H), 3.52-3.61 (m, 2H), 3.71 (s, 2H), 3.99-4.11 (m, 2H), 4.21-4.34 (m, 1H), 7.30-7.36 (m, 1H), 7.38-7.45 (m, 1H), 7.64-7.70 (m, 1H), 7.94-8.03 (m, 1H), 8.97 (d, J=8.70 Hz, 1H), 9.00-9.02 (m, 2H); LC-MS (ESI): (MH$^+$) 437.1

Example 122

7-(2-Methylindolin-1-yl)-N-tetrahydropyran-4-yl-thiazolo[5,4-d]pyrimidine-2-carboxamide

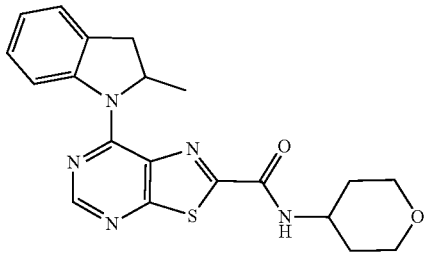 [SMILES: CC1Cc2ccccc2N1c1ncnc2sc(C(=O)NC3CCOCC3)nc12]

Thionyl chloride (5 ml) was added to Intermediate 36 (200 mg, 0.64 mmol) and the reaction heated at reflux for 1 hour. The mixture was cooled, concentrated and taken up in DCM. To the solution was added triethylamine (0.18 ml, 1.3 mmol) and 4-aminotetrahydropyran (194 mg, 1.9 mmol) and stirred for 2 hours. The mixture was diluted with DCM and water, the organic phase was separated, dried and concentrated onto silica. The compound was purified via column chromatography (gradient elution from 15-45% EtOAc in Pet. Ether) gave a light yellow solid (56 mg, 22%); $^1$H NMR (400 MHz, DMSO-d$_6$) δ ppm 1.22 (d, J=6.41 Hz, 3H), 1.68-1.84 (m, 4H), 2.85 (d, J=15.57 Hz, 1H), 3.32-3.43 (m, 2H), 3.50 (dd, J=15.80, 8.93 Hz, 1H), 3.80-3.92 (m, 2H), 4.00-4.11 (m, 1H), 6.01-6.11 (m, 1H), 7.03-7.12 (m, 1H), 7.20-7.30 (m, 1H), 7.33-7.40 (m, 1H), 8.55-8.66 (m, 3H); LC-MS (ESI): (MH$^+$) 396.1

Example 123

7-(2-Methylindolin-1-yl)-N-(1-methyl-4-piperidyl)thiazolo[5,4-d]pyrimidine-2-carboxamide

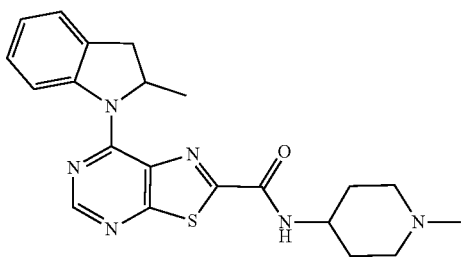 [SMILES: CC1Cc2ccccc2N1c1ncnc2sc(C(=O)NC3CCN(C)CC3)nc12]

Example 123 was prepared in an analogous manner to Example 122 from give Intermediate 36 and 1-methylpiperidin-4-amine. $^1$H NMR (400 MHz, DMSO-d$_6$) δ ppm 1.26 (d, J=6.41 Hz, 3H), 1.71-1.89 (m, 4H), 1.92-2.04 (m, 2H), 2.19 (s, 3H), 2.75-2.85 (m, 2H), 2.89 (d, J=15.57 Hz, 1H), 3.54 (dd, J=15.57, 8.70 Hz, 1H), 3.73-3.91 (m, 1H), 6.04-6.19 (m, 1H), 7.12 (td, J=7.33, 0.92 Hz, 1H), 7.30 (t, J=7.56 Hz, 1H), 7.40 (d, J=7.33 Hz, 1H), 8.59 (d, J=8.24 Hz, 1H), 8.66 (d, J=8.20 Hz, 1H), 8.68 (s, 1H); LC-MS (ESI): (MH$^+$) 409.2

Example 124

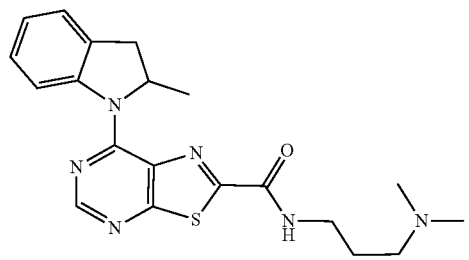 [SMILES: CC1Cc2ccccc2N1c1ncnc2sc(C(=O)NCCCN(C)C)nc12]

Example 124 was prepared in an analogous manner to Example 122 from give Intermediate 36 and N,N-dimethyl-3-propylamine. $^1$H NMR (400 MHz, CHLOROFORM-d) δ ppm 1.40 (d, J=6.41 Hz, 3H), 1.91 (br. s., 3H), 2.39 (br. s., 6H), 2.63 (br. s., 2H), 2.82-2.91 (m, 1H), 3.51-3.62 (m, 3H), 3.66-3.78 (m, 1H), 5.92-6.02 (m, 1H), 7.06-7.13 (m, 1H), 7.28-7.34 (m, 2H), 8.42 (br. s., 1H), 8.62-8.72 (m, 2H); LC-MS (ESI): (MH$^+$) 397.1

Example 125

7-(3-Methylindolin-1-yl)-N-tetrahydropyran-4-yl-thiazolo[5,4-d]pyrimidine-2-carboxamide

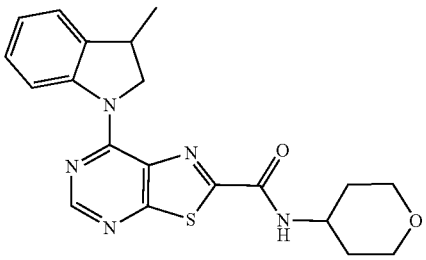 [SMILES: CC1CN(c2ncnc3sc(C(=O)NC4CCOCC4)nc23)c2ccccc21]

Example 125 was prepared in an analogous manner to Example 122 from Intermediate and 4-aminotetrahydropyran. $^1$H NMR (400 MHz, CHLOROFORM-d) δ ppm 1.47 (d, J=6.90 Hz, 2H), 1.63-1.77 (m, 2H), 2.07 (m, J=12.40, 2.30 Hz, 2H), 2.08 (s, 1H), 3.58 (td, J=11.68, 2.29 Hz, 2H), 3.61-3.71 (m, 1H), 3.99-4.11 (m, 2H), 4.20-4.28 (m, 1H), 4.31 (dd, J=11.45, 6.41 Hz, 1H), 5.01 (dd, J=11.91, 9.16 Hz, 1H), 6.99 (d, J=8.20 Hz, 1H), 7.14 (td, J=7.30, 1.00 Hz, 1H), 7.28-7.35 (m, 2H), 8.59 (d, J=7.80 Hz, 1H), 8.68 (s, 1H); LC-MS (ESI): (MH$^+$) 396.1

Example 126

7-(3-Methylindolin-1-yl)-N-(1-methyl-4-piperidyl)thiazolo[5,4-d]pyrimidine-2-carboxamide

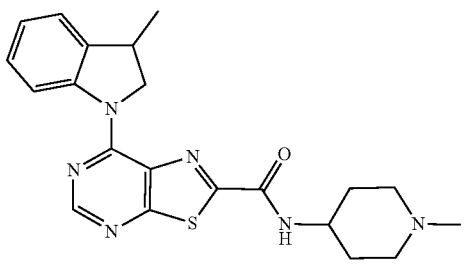 [SMILES: CC1CN(c2ncnc3sc(C(=O)NC4CCN(C)CC4)nc23)c2ccccc21]

Example 126 was prepared in an analogous manner to Example 122 from Intermediate 35 and 1-methylpiperidin-4-amine. $^1$H NMR (400 MHz, CHLOROFORM-d) δ ppm 1.45 (d, J=6.90 Hz, 3H), 1.62-1.70 (m, 2H), 2.10 (dd, J=12.82, 4.12 Hz, 2H), 2.21 (t, J=11.22 Hz, 2H), 2.34 (s, 3H), 2.77-2.92 (m, 2H), 3.59-3.70 (m, 1H), 3.98-4.11 (m, 1H), 4.30 (dd, J=11.40, 6.90 Hz, 1H), 5.01 (dd, J=11.68, 9.39 Hz, 1H), 6.95-7.07 (m, 1H), 7.13 (td, J=7.33, 0.92 Hz, 1H), 7.28-7.34 (m, 2H), 8.60 (d, J=7.78 Hz, 1H), 8.67 (s, 1H); LC-MS (ESI): (MH$^+$) 409.2

Example 127

(R)-7-(2-Methylindolin-1-yl)-N-(piperidin-4-ylmethyl)thiazolo[5,4-d]pyrimidine-2-carboxamide

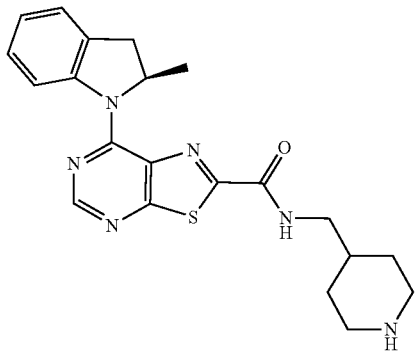 [SMILES: C[C@@H]1Cc2ccccc2N1c1ncnc2sc(C(=O)NCC3CCNCC3)nc12]

Intermediate 43 (350 mg, 1.08 mmol) and SOCl$_2$ (10 mL) were heated under reflux for 3 hours. The resultant solution was concentrated to give a dark orange gum. The acid chloride was taken up in DCM (10 mL) and a 1.4 ml aliquot of the resulting solution was added to a reaction vial containing a solution of triethylamine (0.20 mL, 1.57 mmol) and 4-aminomethyl-1-BOC-piperidine (168 mg, 7.87 mmol). The mixture was stirred overnight to give a green solution. This was treated with TFA (1 mL) and left to stir for 30 mins. To the resultant solution was added sat. NaHCO$_3$ $_{(aq)}$ (5 mL) until pH 7 was achieved. The organic layer was separated and concentrated before being sent for HPLC purification. The product, (R)-7-(2-methylindolin-1-yl)-N-(piperidin-4-ylmethyl)thiazolo[5,4-d]pyrimidine-2-carboxamide, was obtained as a yellow solid after purification (30.2 mg, 14%). $^1$H NMR (400 MHz, CHLOROFORM-d) δ ppm 8.64 (s, 1H), 8.59 (d, J=7.78 Hz, 1H), 7.31 (d, J=7.79 Hz, 1H), 7.25 (t, J=8.70 Hz, 1H), 7.11 (t, J=8.20 Hz, 1H), 5.75 (m, 1H), 3.54 (dd, J=15.11, 8.70 Hz, 1H), 3.42 (dd, J=13.74, 6.87 Hz, 2H), 3.27 (m, 2H), 2.84 (d, J=15.57 Hz, 1H), 2.75 (t, J=13.30 Hz, 2H), 1.89 (m, 3H), 1.47 (m, 2H), 1.42 (d, J=5.95 Hz, 4H); LC-MS (ESI): (MH$^+$) 409.1

Examples 128-129 were made in an analogous manner to Example 127, from Intermediate 43 and the appropriate, BOC protected, amine. Example 130 was prepared analogously to Example 122 from Intermediate 43 and 4-aminotetrahydropyran.

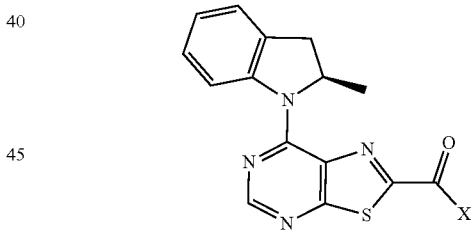

| Example # | Structure | IUPAC Name | LC-MS (ESI): (MH$^+$) | $^1$H NMR |
|---|---|---|---|---|
| 128 | ![structure] | N-[3-(methylamino)propyl]-7-[(2R)-2-methylindolin-1-yl]thiazolo[5,4-d]pyrimidine-2-carboxamide | 383.1 | $^1$H NMR (400 MHz, CHLOROFORM-d) δ ppm 8.65 (d, J = 8.70 Hz, 1 H), 8.63 (s, 1 H), 8.47 (t, J = 6.40 Hz, NH), 7.30 (m, 2 H), 7.10 (td, J = 7.33, 0.92 Hz, 1 H), 5.87 (m, 1 H), 3.64 (m, 2 H), 3.53 (dd, J = 16.03, 9.16 Hz, 1 H), 2.82 (m, 3 H), 2.47 (s, 3 H), 1.83 (quin, J = 5.95 Hz, 3 H), 1.39 (d, J = 5.95 Hz, 3 H) |

-continued

| Example # | Structure | IUPAC Name | LC-MS (ESI): (MH+) | ¹H NMR |
|---|---|---|---|---|
| 129 | 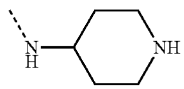 | 7-[(2R)-2-methylindolin-1-yl]-N-(4-piperidyl)thiazolo[5,4-d]pyrimidine-2-carboxamide | 395.1 | ¹H NMR (400 MHz, CHLOROFORM-d) δ ppm 8.63 (s, 1 H), 8.55 (d, J = 8.24 Hz, 1 H), 7.31 (d, J = 7.33 Hz, 2 H), 7.10 (td, J = 7.33, 0.92 Hz, 1 H), 7.01 (d, J = 8.70 Hz, NH), 5.71 (m, 1 H), 4.09 (m, 1 H), 3.54 (dd, J = 15.57, 8.70 Hz, 1 H), 3.11 (m, 2 H), 2.80 (m, 2 H), 2.07 (t, J = 13.70 Hz, 2 H), 1.52 (qd, J = 11.45, 4.12 Hz, 2 H), 1.43 (d, J = 5.95 Hz, 3 H) |
| 130 | 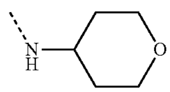 | 7-[(2R)-2-methylindolin-1-yl]-N-tetrahydropyran-4-yl-thiazolo[5,4-d]pyrimidine-2-carboxamide | 396.1 | ¹H NMR (400 MHz, CHLOROFORM-d) δ ppm 8.63 (s, 1 H), 8.55 (d, J = 8.24 Hz, 1 H), 7.31 (m, J = 7.80 Hz, 2 H), 7.11 (td, J = 7.79, 0.92 Hz, 1 H), 7.00 (d, J = 8.24 Hz, 1 H), 5.70 (m, 1 H), 4.21 (d, J = 8.24 Hz, 1 H), 4.01 (dq, J = 13.28, 3.21 Hz, 2H), 3.56 (m, 3 H), 2.83 (d, J = 15.57 Hz, 1 H), 2.05 (m, 2 H), 1.65 (s, 2 H), 1.43 (d, J = 6.41 Hz, 3 H) |

Examples 131-134 were made in an analogous manner to Example 127, from (S)-7-(2-methylindolin-1-yl)thiazolo[5,4-d]pyrimidine-2-carboxylic acid, itself made in an analogous manner to Intermediate 43, and the appropriate amine

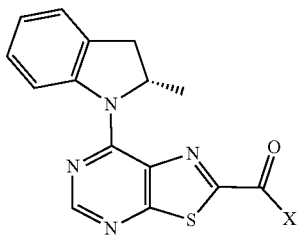

| Example # | X | IUPAC Name | LC-MS (ESI): (MH+) | ¹H NMR |
|---|---|---|---|---|
| 131 | | N-[3-(methylamino)propyl]-7-[(2S)-2-methylindolin-1-yl]thiazolo[5,4-d]pyrimidine-2-carboxamide | 383.1 | ¹H NMR (400 MHz, CHLOROFORM-d) δ ppm 8.64 (s, 2 H), 8.34 (t, J = 5.04 Hz, 1 H), 7.31 (m, 2 H), 7.10 (td, J = 7.33, 1.37 Hz, 1 H), 5.87 (m, 1 H), 3.65 (m, 2 H), 3.53 (dd, J = 16.49, 9.16 Hz, 1 H), 2.87 (m, 3 H), 2.53 (s, 3 H), 1.90 (quin, J = 6.41 Hz, 2 H), 1.40 (d, J = 6.41 Hz, 3 H) |

-continued

| Example # | X | IUPAC Name | LC-MS (ESI): (MH+) | 1H NMR |
|---|---|---|---|---|
| 132 | (4-piperidyl-amino, piperidine) | 7-[(2S)-2-methylindolin-1-yl]-N-(4-piperidyl)thiazolo[5,4-d]pyrimidine-2-carboxamide | 395.0 | 1H NMR (400 MHz, CHLOROFORM-d) δ ppm 8.64 (s, 1 H), 8.56 (d, J = 7.78 Hz, 1 H), 7.30 (s, 2 H), 7.11 (td, J = 7.79, 0.92 Hz, 1 H), 7.01 (d, J = 9.16 Hz, 1 H), 5.72 (m, 1 H), 4.11 (m, 1 H), 3.54 (dd, J = 16.03, 8.24 Hz, 1 H), 3.14 (dq, J = 12.36, 4.12 Hz, 2 H), 2.79 (m, 2 H), 2.09 (m, 2 H), 1.55 (q, J = 11.91 Hz, 2 H), 1.44 (d, J = 6.41 Hz, 3 H) |
| 133 | (tetrahydropyran-4-yl-amino) | 7-[(2S)-2-methylindolin-1-yl]-N-tetrahydropyran-4-yl-thiazolo[5,4-d]pyrimidine-2-carboxamide | 396.1 | 1H NMR (400 MHz, CHLOROFORM-d) δ ppm 8.64 (s, 1 H), 8.55 (d, J = 7.78 Hz, 1 H), 7.32 (d, J = 7.79 Hz, 2 H), 7.13 (m, 1 H), 6.99 (m, 1 H), 5.72 (m, 1 H), 4.22 (m, 1 H), 4.02 (dq, J = 11.91, 3.66 Hz, 2 H), 3.57 (m, 3 H), 2.84 (d, J = 15.11 Hz, 1 H), 2.06 (m, 2 H), 1.65 (s, 2 H), 1.44 (d, J = 6.41 Hz, 3 H) |
| 134 | (4-piperidylmethyl-amino) | 7-[(2R)-2-methylindolin-1-yl]-N-(4-piperidylmethyl)thiazolo[5,4-d]pyrimidine-2-carboxamide | 409.1 | 1H NMR (400 MHz, CHLOROFORM-d) δ ppm 8.64 (s, 1 H), 8.58 (d, J = 8.24 Hz, 1 H), 7.31 (d, J = 7.79 Hz, 2 H), 7.21 (t, J = 6.41 Hz, 1 H), 7.12 (td, J = 7.33, 0.92 Hz, 1 H), 5.75 (m, 1 H), 3.54 (dd, J = 15.57, 8.70 Hz, 1 H), 3.40 (m, 2 H), 3.19 (dt, J = 11.91, 3.21 Hz, 2 H), 2.83 (d, J = 15.11 Hz, 1 H), 2.67 (td, J = 13.28, 1.83 Hz, 2 H), 1.87 (m, 1 H), 1.80 (m, 2 H), 1.43 (d, J = 6.41 Hz, 3H), 1.34 (qd, J = 12.36, 3.66 Hz, 2 H) |

Example 135

7-[3-(Hydroxymethyl)indolin-1-yl]-N-(4-piperidyl-methyl)thiazolo[5,4-d]pyrimidine-2-carboxamide

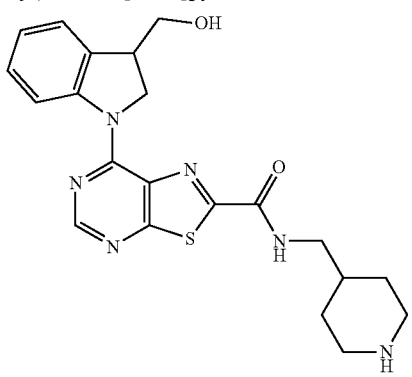

Intermediate 45 (50 mg, 0.12 mmol), Intermediate 29 (18 mg, 0.12 mmol) and propan-2-ol (2 ml) were sealed in a vial and heated at 80° C. for 3 hours. The mixture was cooled, concentrated and the BOC group removed using TFA (1 ml) in DCM (5 ml). The mixture was neutralised with sat. NaHCO$_{3(aq)}$, the organic layer separated, dried and concentrated. The residue was purified by preparative LCMS to give a yellow solid (19 mg, 36%); 1H NMR (400 MHz, CHLOROFORM-d) δ ppm 1.28-1.44 (m, 2H), 1.69-1.78 (m, 2H), 1.79-1.88 (m, 1H), 2.59-2.69 (m, 2H), 3.12 (td, J=8.01, 4.12 Hz, 2H), 3.38 (dt, J=13.51, 5.84 Hz, 1H), 3.47-3.54 (m, 1H), 3.70-3.81 (m, 2H), 3.94-4.02 (m, 1H), 4.81-4.95 (m, 2H), 7.09 (td, J=7.30, 0.90 Hz, 1H), 7.26-7.35 (m, 2H), 7.40 (br. t, J=6.00, 6.00 Hz, 1H), 8.62-8.69 (m, 2H); LC-MS (ESI): (MH+) 425.1

Examples 136-146

Examples 136-146 In the table below were prepared analogously to Example 135 from Intermediate 45 and the appropriate indoline

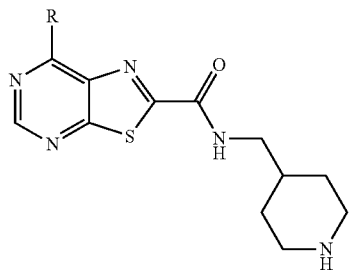

| Example # | R (IUPAC Name) | LC-MS (ES1): (MH+) | 1H NMR |
|---|---|---|---|
| 136 | (7-[3-(2-hydroxyethyl)indolin-1-yl]-N-(4-piperidylmethyl)thiazolo[5,4-d]pyrimidine-2-carboxamide) | 439.1 | 1H NMR (400 MHz, CHLOROFORM-d) δ ppm 1.56-1.71 (m, 4 H), 1.79-1.94 (m, 2 H), 2.19-2.28 (m, 1 H), 2.66-2.74 (m, 2 H), 3.13-3.23 (m, 2 H), 3.45-3.61 (m, 2 H), 3.62-3.71 (m, 1 H), 3.77-3.84 (m, 1 H), 3.89-3.96 (m, 1 H), 4.76 (dd, J = 12.80, 7.30 Hz, 1 H), 5.20 (dd, J = 12.80, 9.60 Hz, 1 H), 7.11 (td, J = 7.33, 0.92 Hz, 1 H), 7.25-7.33 (m, 3 H), 8.64 (s, 1 H), 8.73 (d, J = 8.20 Hz, 1 H) |
| 137 | (7-[(2S)-2-(hydroxymethyl)indolin-1-yl]-N-(4-piperidylmethyl)thiazolo[5,4-d]pyrimidine-2-carboxamide) | 425.0 | 1H NMR (400 MHz, CHLOROFORM-d) δ ppm 1.30-1.43 (m, 1 H), 1.47-1.60 (m, 1 H), 1.64-1.75 (m, 2 H), 1.76-1.88 (m, 1 H), 2.61 (tdd, J = 11.91, 11.91, 4.81, 2.52 Hz, 2 H), 3.02-3.15 (m, 2 H), 3.19 (d, J = 15.57 Hz, 1 H), 3.27 (dt, J = 13.74, 4.58 Hz, 1 H), 3.44-3.53 (m, 1 H), 3.56-3.67 (m, 2 H), 4.09 (dd, J = 9.16, 3.66 Hz, 1 H), 5.52-5.60 (m, 1 H), 7.06-7.13 (m, 1 H), 7.30 (t, J = 8.01 Hz, 2 H), 7.59-7.72 (m, 1 H), 8.38 (d, J = 7.79 Hz, 1 H), 8.64 (s, 1 H) |
| 138 | (7-[(2R)-2-(hydroxymethyl)indolin-1-yl]-N-(4-piperidylmethyl)thiazolo[5,4-d]pyrimidine-2-carboxamide) | 425.0 | 1H NMR (400 MHz, CHLOROFORM-d) δ ppm 1.28-1.41 (m, 1 H), 1.44-1.58 (m, 1 H), 1.70 (t, J = 12.14 Hz, 2 H), 1.75-1.87 (m, 1 H), 2.60 (tdd, J = 11.91, 11.91, 4.58, 2.75 Hz, 2 H), 3.01-3.14 (m, 2 H), 3.18 (d, J = 16.03 Hz, 1 H), 3.27 (dt, J = 13.28, 4.58 Hz, 1 H), 3.43-3.53 (m, 1 H), 3.55-3.68 (m, 2 H), 4.09 (dd, J = 9.39, 3.89 Hz, 1 H), 5.56 (td, J = 8.13, 3.89 Hz, 1 H), 7.05-7.13 (m, 1 H), 7.29 (t, J = 8.01 Hz, 2 H), 7.59-7.75 (m, 1 H), 8.38 (d, J = 8.20 Hz, 1 H), 8.63 (s, 1 H) |

| Example # | R (IUPAC Name) | LC-MS (ESI): (MH+) | ¹H NMR |
|---|---|---|---|
| 139 | (7-[5-fluoro-3-(2-hydroxyethyl)indolin-1-yl]-N-(4-piperidylmethyl)thiazolo[5,4-d]pyrimidine-2-carboxamide) | 457.1 | ¹H NMR (400 MHz, CHLOROFORM-d) δ ppm 1.59-1.73 (m, 4 H), 1.78-1.93 (m, 2 H), 2.12-2.22 (m, 1 H), 2.73 (br. s., 2 H), 2.98-3.00 (m, 1 H), 3.16-3.27 (m, 2 H), 3.49-3.60 (m, 2 H), 3.60-3.69 (m, 1 H), 3.79 (td, J = 9.27, 3.43 Hz, 1 H), 3.92 (ddd, J = 9.96, 5.61, 4.12 Hz, 1 H), 4.76 (dd, J = 12.36, 7.33 Hz, 1 H), 5.23 (dd, J = 12.59, 9.39 Hz, 1 H), 6.93-7.03 (m, 2 H), 7.26-7.33 (m, 1 H), 8.63 (s, 1 H), 8.70 (dd, J = 8.70, 4.58 Hz, 1 H) |
| 140 | (7-[3-hydroxymethyl)-3-methyl-indolin-1-yl]-N-(4-piperidylmethyl)thiazolo[5,4-d]pyrimidine-2-carboxamide) | 439.1 | ¹H NMR (400 MHz, CHLOROFORM-d) δ ppm 1.35-1.50 (m, 5 H), 1.73-1.95 (m, 3 H), 2.61-2.74 (m, 2 H), 3.13-3.25 (m, 2 H), 3.32-3.44 (m, 1 H), 3.45-3.58 (m, 1 H), 3.70 (q, J = 10.30 Hz, 2 H), 4.37 (d, J = 11.90 Hz, 1 H), 5.08 (d, J = 11.90 Hz, 1 H), 7.10-7.16 (m, 1 H), 7.19-7.24 (m, 1 H), 7.29-7.36 (m, 1 H), 7.49-7.56 (m, 1 H), 8.61-8.68 (m, 2 H) |
| 141 | (7-[5-fluoro-3-(hydroxymethyl)-3-methyl-indolin-1-yl]-N-(4-piperidylmethyl)thiazolo[5,4-d]pyrimidine-2-carboxamide) | 457.0 | ¹H NMR (400 MHz, DMSO-d₆) δ ppm 1.02-1.14 (m, 2 H), 1.40 (s, 3 H), 1.55-1.77 (m, 3 H), 2.35-2.48 (m, 2 H), 2.93 (d, J = 12.36 Hz, 2 H), 3.21-3.28 (m, 2 H), 3.48-3.57 (m, 2 H), 4.48 (d, J = 12.82 Hz, 1 H), 4.88 (d, J = 12.80 Hz, 1 H), 7.12 (td, J = 8.93, 2.75 Hz, 1 H), 7.24 (dd, J = 8.70, 2.75 Hz, 1 H), 8.59 (dd, J = 8.93, 4.81 Hz, 1 H), 8.65 (s, 1 H), 8.79-8.90 (m, 1 H) |
| 142 | (7-[3-(2-hydroxy-2-methyl-propyl)indolin-1-yl]-N-(4-piperidylmethyl)thiazolo[5,4-d]pyrimidine-2-carboxamide) | 467.1 | ¹H NMR (400 MHz, CHLOROFORM-d) δ ppm 1.31 (s, 3 H), 1.35 (s, 3 H), 1.60-1.72 (m, 4 H), 1.82-1.94 (m, 2 H), 1.95-2.02 (m, 1 H), 2.66-2.76 (m, 3 H), 3.21 (td, J = 7.33, 3.21 Hz, 2 H), 3.43-3.50 (m, 1 H), 3.51-3.59 (m, 1 H), 3.66-3.76 (m, 1 H), 4.73 (dd, J = 12.80, 7.30 Hz, 1 H), 5.19 (dd, J = 12.80, 9.20 Hz, 1 H), 7.09 (td, J = 7.30, 0.90 Hz, 1 H), 7.21 (d, J = 7.33 Hz, 1 H), 7.26-7.35 (m, 2 H), 8.62 (s, 1 H), 8.72 (d, J = 8.20 Hz, 1 H) |

-continued

| Example # | R (IUPAC Name) | LC-MS (ES1): (MH+) | 1H NMR |
|---|---|---|---|
| 143 | 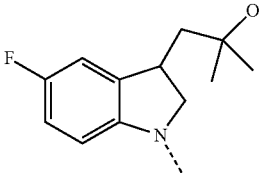<br>(7-[5-fluoro-3-(2-hydroxy-2-methyl-propyl)indolin-1-yl]-N-(4-piperidylmethyl)thiazolo[5,4-d]pyrimidine-2-carboxamide) | 485.1 | 1H NMR (400 MHz, DMSO-d6) δ ppm 1.09-1.20 (m, 2 H), 1.24 (s, 6 H), 1.59-1.78 (m, 4 H), 1.97-2.10 (m, 1 H), 2.46 (br. s., 2 H), 2.92-3.05 (m, 2 H), 3.17-3.28 (m, 2 H), 3.63-3.77 (m, 1 H), 4.59-4.65 (m, 1 H), 5.17-5.30 (m, 1 H), 7.10 (td, J = 9.10, 2.80 Hz, 1 H), 7.24 (dd, J = 9.20, 2.30 Hz, 1 H), 8.46 (t, J = 6.00 Hz, 1 H), 8.60 (dd, J = 9.20, 5.00 Hz, 1 H), 8.66 (s, 1 H) |
| 144 | 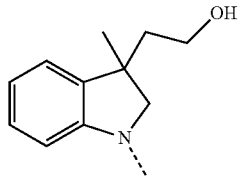<br>(7-[3-(2-hydroxyethyl)-3-methyl-indolin-1-yl]-N-(4-piperidylmethyl)thiazolo[5,4-d]pyrimidine-2-carboxamide) | 453.1 | 1H NMR (400 MHz, CHLOROFORM-d) δ ppm 1.41 (s, 3 H), 1.55-1.74 (m, 4 H), 1.82-1.96 (m, 2 H), 2.02-2.11 (m, 1 H), 2.63-2.76 (m, 2 H), 3.12-3.24 (m, 2 H), 3.36-3.45 (m, 1 H), 3.60-3.69 (m, 1 H), 3.76-3.93 (m, 2 H), 4.63 (d, J = 11.90 Hz, 1 H), 5.15 (d, J = 11.91 Hz, 1 H), 7.11 (td, J = 7.30, 0.90 Hz, 1 H), 7.19 (dd, J = 7.30, 0.90 Hz, 1 H), 7.27-7.39 (m, 2 H), 8.64 (s, 1 H), 8.70 (d, J = 7.80 Hz, 1 H) |
| 145 | 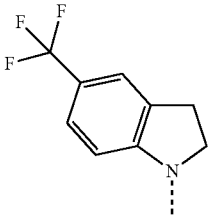<br>(N-(4-piperidylmethyl)-7-[5-(trifluoromethyl)indolin-1-yl]thiazolo[5,4-d]pyrimidine-2-carboxamide) | 463.0 | 1H NMR (400 MHz, CHLOROFORM-d) δ ppm 9.07 (t, J = 6.41 Hz, NH), 8.79 (d, J = 8.70 Hz, 1 H), 8.76 (s, 1 H), 7.70 (s, 1 H), 7.65 (d, J = 8.24 Hz, 1 H), 4.95 (t, J = 8.24 Hz, 2 H), 3.41 (t, J = 8.70 Hz, 2 H), 3.24 (t, J = 6.87 Hz, 2 H), 3.02 (m, 2 H), 2.55 (m, 2 H), 1.77 (m, 1 H), 1.66 (m, 2 H), 1.15 (qd, J = 13.70, 4.58 Hz, 2 H) |
| 146 | 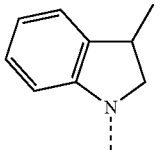<br>(7-(3-methylindolin-1-yl)-N-(piperidin-4-ylmethyl)thiazolo[5,4-d]pyrimidine-2-carboxamide) | 409.1 | 1H NMR (400 MHz, CHLOROFORM-d) δ ppm 8.65 (s, 1 H), 8.59 (d, J = 7.78 Hz, 1 H), 7.27 (m, 2 H), 7.11 (td, J = 7.33, 1.00 Hz, 1 H), 4.99 (dd, J = 9.62, 5.50 Hz, 1 H), 4.29 (dd, J = 11.45, 6.41 Hz, 1 H), 3.63 (sxt, J = 6.90 Hz, 1 H), 3.42 (m, 2 H), 3.20 (dt, J = 11.91, 2.75 Hz, 2 H), 2.67 (td, J = 12.36, 2.75 Hz, 2 H), 1.88 (m, 1 H), 1.81 (d, J = 13.28 Hz, 2 H), 1.45 (d, J = 6.87 Hz, 3 H), 1.36 (qd, J = 12.36, 3.66 Hz, 2 H) |

Examples 147-151

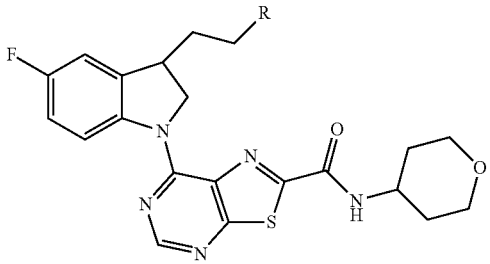

To a solution of Intermediate 63 (250 mg, 0.68 mmol) and triethylamine (0.2 ml, 1.35 mmol) in DCM (5 ml) was added mesyl chloride (55 μL, 0.074 mmol) drop wise and stirred for 2 hours. The mixture was diluted with DCM, washed with water, the organic phase separated, dried and concentrated. The residue was taken up in DMF (10 ml) and the solution dispensed into five separate vials. To each of these vials was added $K_2CO_3$ (4 mg, 0.11 mmol) and the desired amine (0.23 mmol). The vials were sealed and heated at 80° C. overnight. The mixtures were cooled, submitted to an aqueous work, the organic layer separated, dried and concentrated. Samples were purified via HPLC to give the desired products as yellow solids.

| Example # | R | IUPAC Name | LC-MS (ESI): (MH+) | 1H NMR |
|---|---|---|---|---|
| 147 | H-N— | 7-[5-fluoro-3-[2-(methylamino)ethyl]indolin-1-yl]-N-tetrahydropyran-4-yl-thiazolo[5,4-d]pyrimidine-2-carboxamide | 457.0 | 1H NMR (400 MHz, CHLOROFORM-d) δ ppm 1.63-1.77 (m, 2 H), 1.81-1.94 (m, 2 H), 1.98-2.07 (m, 2 H), 2.07-2.19 (m, 1 H), 2.53 (s, 3 H), 2.76-2.93 (m, 2 H), 3.50-3.58 (m, 2 H), 3.59-3.67 (m, 1 H), 3.96-4.06 (m, 3 H), 4.16-4.30 (m, 1 H), 4.55 (dd, J = 11.90, 6.00 Hz, 1 H), 4.97 (dd, J = 11.90, 9.60 Hz, 1 H), 6.91-7.00 (m, 2 H), 7.37 (d, J = 8.20 Hz, 1 H), 8.56-8.67 (m, 2 H) |
| 148 | \N— / | 7-[3-[2-(dimethylamino)ethyl]-5-fluoro-indolin-1-yl]-N-tetrahydropyran-4-yl-thiazolo[5,4-d]pyrimidine-2-carboxamide | 471.1 | 1H NMR (400 MHz, CHLOROFORM-d) δ ppm 1.65-1.78 (m, 2 H), 1.82-1.93 (m, 1 H), 2.01-2.09 (m, 2 H), 2.09-2.16 (m, 1 H), 2.35 (s, 6 H), 2.41-2.50 (m, 1 H), 2.51-2.61 (m, 1 H), 3.53-3.60 (m, 2 H), 3.61-3.68 (m, 1 H), 4.01-4.10 (m, 2 H), 4.18-4.32 (m, 1 H), 4.63 (dd, J = 11.91, 5.95 Hz, 1 H), 4.98 (dd, J = 11.91, 9.16 Hz, 1 H), 6.96-7.05 (m, 2 H), 7.16-7.26 (m, 1 H), 8.60-8.68 (m, 2 H) |
| 149 | pyrrolidine | 7-[5-fluoro-3-(2-pyrrolidin-1-ylethyl)indolin-1-yl]-N-tetrahydropyran-4-yl-thiazolo[5,4-d]pyrimidine-2-carboxamide | 497.1 | 1H NMR (400 MHz, CHLOROFORM-d) δ ppm 1.69 (dd, J = 12.59, 4.35 Hz, 2 H), 1.77-1.84 (m, 4 H), 1.84-1.93 (m, 1 H), 2.00-2.09 (m, 2 H), 2.10-2.18 (m, 1 H), 2.48-2.63 (m, 5 H), 2.66-2.75 (m, 1 H), 3.51-3.60 (m, 2 H), 3.61-3.68 (m, 1 H), 3.97-4.09 (m, 2 H), 4.16-4.32 (m, 1 H), 4.59 (dd, J = 11.90, 6.00 Hz, 1 H), 4.95 (dd, J = 11.90, 9.20 Hz, 1 H), 6.94-7.03 (m, 2 H), 7.13 (d, J = 7.80 Hz, 1 H), 8.56-8.67 (m, 2 H) |
| 150 | 4-methylpiperazine | 7-[5-fluoro-3-[2-(4-methylpiperazin-1-yl)ethyl]indolin-1-yl]-N-tetrahydropyran-4-yl-thiazolo[5,4-d]pyrimidine-2-carboxamide | 526.1 | 1H NMR (400 MHz, CHLOROFORM-d) δ ppm 1.61-1.76 (m, 2 H), 1.81-1.94 (m, 1 H), 2.02-2.13 (m, 3 H), 2.31 (s, 3 H), 2.39-2.70 (m, 9 H), 3.51-3.67 (m, 3H), 3.97-4.10 (m, 2 H), 4.17-4.30 (m, 1 H), 4.64 (dd, J = 11.90, 6.00 Hz, 1 H), 4.92 (dd, J = 11.90, 9.20 Hz, 1 H), 6.95-7.02 (m, 2 H), 7.04-7.12 (m, 1 H), 8.60 (dd, J = 9.39, 4.81 Hz, 1 H), 8.65 (s, 1 H) |
| 151 | morpholine | 7-[5-fluoro-3-(2-morpholinoethyl)indolin-1-yl]-N-tetrahydropyran-4-yl-thiazolo[5,4-d]pyrimidine-2-carboxamide | 513.1 | 1H NMR (400 MHz, CHLOROFORM-d) δ ppm 1.57-1.70 (m, 2 H), 1.80-1.90 (m, 1 H), 1.95-2.11 (m, 3 H), 2.37-2.60 (m, 6 H), 3.55 (td, J = 11.68, 1.83 Hz, 3 H), 3.69 (t, J = 4.58 Hz, 4 H), 3.96-4.05 (m, 2 H), 4.15-4.28 (m, 1 H), 4.56 (dd, J = 11.90, 5.50 Hz, 1 H), 4.90 (dd, J = 11.90, 9.20 Hz, 1 H), 6.92-7.05 (m, 3 H), 8.51-8.60 (m, 1 H), 8.62 (s, 1 H) |

Examples 152-155

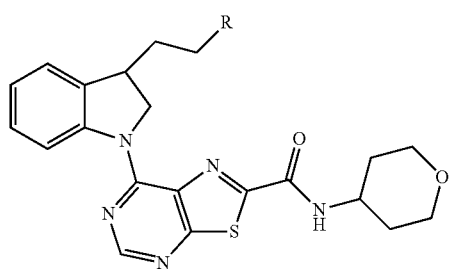

To a solution of Intermediate 64 (210 mg, 0.49 mmol) in DCM (5 mL) was added triethylamine (0.14 mL, 0.99 mmol) and mesyl chloride (0.04 mL, 0.49 mmol). The mixture was stirred for 1 hour. The mixture was diluted with DCM (5 mL) and partitioned with water (10 mL). The organic phase was washed with water (2×10 mL). The combined organic layers were dried and concentrated to give an orange solid. This was taken up in DMF (9 mL) and an aliquot added to a vial containing the desired amine (0.14 mmol) and $K_2CO_3$ (19 mg, 0.14 mmol). The resultant mixture was heated at 80° C. for four hours. Once cooled EtOAc (5 mL) and water (5 mL) were added and the organic phase separated. The organic phase was washed with water (2×10 mL), dried and concentrated. Samples were purified via HPLC to give the desired products as yellow solids.

| Example # | R | IUPAC Name | LC-MS (ESI): (MH+) | 1H NMR |
|---|---|---|---|---|
| 152 | 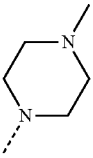 | 7-[3-[2-(dimethylamino)ethyl]-indolin-1-yl]-N-tetrahydropyran-4-yl-thiazolo[5,4-d]pyrimidine-2-carboxamide | 453.1 | 1H NMR (400 MHz, CHLOROFORM-d) δ ppm 8.66 (s, 1 H), 8.63 (d, J = 8.24 Hz, 1 H), 7.31 (t, J = 7.33 Hz, 1 H), 7.27 (d, J = 7.33 Hz, 1 H), 7.12 (td, J = 7.33, 0.92 Hz, 1 H), 4.91 (dd, J = 11.91, 9.16 Hz, 1 H), 4.60 (m, 1 H), 4.24 (m, 1 H), 4.03 (dq, J = 11.45, 1.83 Hz, 2 H), 3.63 (m, 1 H), 3.54 (td, J = 12.36, 2.29 Hz, 2 H), 2.64 (m, 2 H), 2.41 (br.s, 6H), 2.17 (m, 1 H), 2.03 (m, 2 H), 1.88 (m, 1 H), 1.73 (qd, J = 12.40, 5.00 Hz, 2 H) |
| 153 |  | 7-[3-(2-pyrrolidin-1-ylethyl)indolin-1-yl]-N-tetrahydropyran-4-yl-thiazolo[5,4-d]pyrimidine-2-carboxamide | 479.1 | 1H NMR (400 MHz, CHLOROFORM-d) δ ppm 8.66 (m, 2 H), 7.31 (t, J = 8.20 Hz, 2 H), 7.25 (d, J = 6.41 Hz, 1 H), 7.10 (td, J = 7.79, 0.92 Hz, 1 H), 4.88 (dd, J = 8.70, 5.95 Hz, 1 H), 4.64 (dd, J = 11.45, 5.50 Hz, 1 H), 4.23 (m, 1 H), 4.02 (dq, J = 10.53, 1.83 Hz, 2 H), 3.63 (m, 1 H), 3.55 (td, J = 11.91, 2.29 Hz, 2 H), 2.90 (m, 6 H), 2.21 (m, 2 H), 2.01 (m, 2 H), 1.93 (m, 4 H), 1.74 (m, 2 H) |
| 154 | 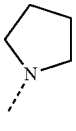 | 7-[3-(2-morpholinoethyl)indolin-1-yl]-N-tetrahydropyran-4-yl-thiazolo[5,4-d]pyrimidine-2-carboxamide | 495.1 | 1H NMR (400 MHz, CHLOROFORM-d) δ ppm 1.59-1.77 (m, 4 H) 1.80-2.27 (m, 4 H) 2.49 (m, 4 H) 3.45-3.50 (m, 1 H) 3.55 (t, J = 11.68 Hz, 2 H) 3.59-3.89 (m, 4 H) 4.02 (d, J = 11.45 Hz, 2 H) 4.17-4.29 (m, 1 H) 4.43-4.74 (m, 1 H) 4.82-4.90 (m, 1 H) 7.08-7.13 (m, 1 H) 7.25-7.28 (m, 1 H) 7.29-7.34 (m, 1 H) 8.51-8.71 (m, 2 H) |
| 155 | 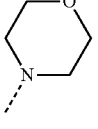 | 7-[3-[2-(4-methylpiperazin-1-yl)ethyl]indolin-1-yl]-N-tetrahydropyran-4-yl-thiazolo[5,4-d]pyrimidine-2-carboxamide | 508.1 | 1H NMR (400 MHz, CHLOROFORM-d) δ ppm 8.66 (s, 1 H), 8.59 (d, J = 8.24 Hz, 1 H), 7.31 (t, J = 8.24 Hz, 1 H), 7.27 (m, 1 H), 7.11 (td, J = 7.33, 0.92 Hz, 1 H), 4.86 (dd, J = 9.16, 5.95 Hz, 1 H), 4.57 (m, 1 H), 4.22 (m, 1 H), 4.01 (m, 2 H), 3.56 (td, J = 12.82, 2.29 Hz, 2 H), 2.55 (m, 6 H), 2.33 (br. s, 3 H), 2.13 (m, 1 H), 2.03 (m, 2 H), 1.86 (m, 1 H), 1.69 (m, 2 H), 1.59 (br. s, 4 H) |

Example 156

N-methyl-7-(3-methylindolin-1-yl)thiazolo[5,4-d]pyrimidine-2-carboxamide

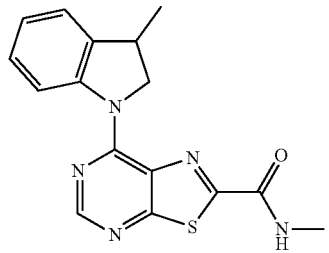 [SMILES: CNC(=O)c1nc2c(N3CC(C)c4ccccc43)ncnc2s1]

To a solution 3-methylindoline (54 mg, 0.41 mmol) in IPA (2 mL) was added Intermediate 65 (93 mg, 0.41 mmol) and the mixture stirred at 70° C. for 16 hours. The mixture was concentrated and by preparative LCMS to give the desired product (23 mg, 17%); 1H NMR (400 MHz, CHLOROFORM-d) δ ppm 8.67 (s, 1H), 8.62 (d, J=7.79 Hz, 1H), 7.32 (m, 2H), 7.16 (td, J=8.24, 0.92 Hz, 1H), 7.11 (br.s, NH), 5.07 (dd, J=9.16, 6.41 Hz, 1H), 4.35 (t, J=6.41 Hz, 1H), 3.65 (sxt, J=7.33 Hz, 1H), 3.12 (d, J=5.04 Hz, 3H), 1.47 (d, J=6.87 Hz, 3H); LC-MS (ESI): (MH+)326.0

Examples 157-158

Examples 157-158 in the table below were prepared analogously to Example 156 from Intermediate 65 and the appropriate indoline

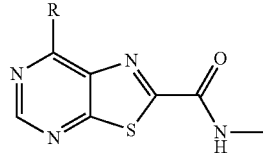

| Example # | R (IUPAC Name) | LC-MS (ESI): (MH+) | 1H NMR |
|---|---|---|---|
| 157 | OH, (7-[3-(2-hydroxyethyl)indolin-1-yl]-N-methyl-thiazolo[5,4-d]pyrimidine-2-carboxamide) | 356.0 | 1H NMR (400 MHz, CHLOROFORM-d) δ ppm 2.05-2.14 (m, 1 H), 2.39-2.47 (m, 1 H), 3.06 (d, J = 5.00 Hz, 3 H), 3.73-3.78 (m, 1 H), 4.46 (m, 1 H), 4.54-4.62 (m, 2 H), 5.23 (dd, J = 12.36, 9.16 Hz, 1 H), 7.12 (td, J = 7.33, 0.92 Hz, 1 H), 7.25-7.28 (m, 1 H), 7.31-7.36 (m, 1 H), 7.59 (m, 1 H), 8.67 (s, 1 H), 8.73 (d, J = 8.24 Hz, 1 H) |
| 158 | (N-methyl-7-[5-(trifluoromethyl)indolin-1-yl]thiazolo[5,4-d]pyrimidine-2-carboxamide) | — | 1H NMR (400 MHz, CHLOROFORM-d) δ ppm 8.75 (d, J = 8.70 Hz, 1 H), 8.70 (s, 1 H), 7.53 (d, J = 8.00 Hz, 1 H), 7.51 (s, 1 H), 7.15 (m, NH), 4.89 (t, J = 8.70 Hz, 2 H), 3.38 (t, J = 8.70 Hz, 2 H), 3.10 (d, J = 5.50 Hz, 3 H) |

*LC-MS (pH10, MeCN) retention time 1.90 mins

Examples 159-163

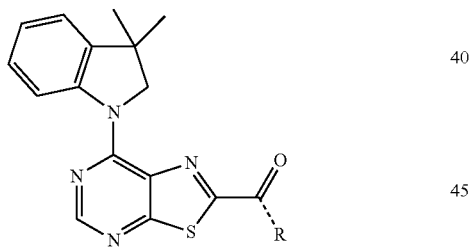

Examples 159, 161 and 162 were prepared analogously to Example 127 from Intermediate 68 and the appropriate BOC-protected amine. Examples 160 and 163 were prepared analogously to Example 122 from Intermediate 68 and the appropriate amine.

| Example # | R (IUPAC Name) | LC-MS (ESI): (MH+) | 1H NMR |
|---|---|---|---|
| 159 | (7-(3,3-dimethylindolin-1-yl)-N-[3-(methylamiono)propyl]thiazolo[5,4-d]pyrimidine-2-carboxamide) | 397.1 | 1H NMR (400 MHz, CHLOROFORM-d) δ ppm 1.46 (s, 6 H), 1.85 (quin, J = 6.00 Hz, 2 H), 2.48 (s, 3 H), 2.83 (t, J = 6.00 Hz, 2 H), 3.65 (q, J = 6.00 Hz, 2 H), 4.55 (s, 2 H), 7.12 (td, J = 7.30, 0.90 Hz, 1 H), 7.24 (dd, J = 7.30, 0.90 Hz, 1 H), 7.26-7.32 (m, 1 H), 8.50 (br. t, J = 5.20, 5.20 Hz, 1 H), 8.56 (d, J = 7.80 Hz, 1 H), 8.65 (s, 1 H) |

| Example # | R (IUPAC Name) | LC-MS (ESI): (MH+) | 1H NMR |
|---|---|---|---|
| 160 | (7-(3,3-dimethylindolin-1-yl)-N-(3-pyrrolidin-1-ylpropyl)thiazolo[5,4-d]pyrimidine-2-carboxamide) | 437.1 | 1H NMR (400 MHz, CHLOROFORM-d) δ ppm 1.45 (s, 6 H), 1.80-1.86 (m, 4 H), 1.93 (quin, J = 6.40 Hz, 2 H), 2.54-2.79 (m, 6 H), 3.64 (q, J = 6.41 Hz, 2 H), 4.55 (s, 2 H), 7.12 (td, J = 7.80, 0.90 Hz, 1 H), 7.24 (dd, J = 7.80, 0.90 Hz, 1 H), 7.26-7.31 (m, 1 H), 7.86 (br. s., 1 H), 8.55 (d, J = 8.24 Hz, 1 H), 8.62-8.67 (m, 1 H) |
| 161 | (7-(3,3-dimethylindolin-1-yl)-N-(4-piperidylmethyl)thiazolo[5,4-d]pyrimidine-2-carboxamide) | 423.1 | 1H NMR (400 MHz, CHLOROFORM-d) δ ppm 1.22-1.35 (m, 2 H), 1.44 (s, 6 H), 1.77 (br. m., 3 H), 2.59-2.69 (m, 2 H), 3.10-3.19 (m, 2 H), 3.42 (t, J = 6.40 Hz, 2 H), 4.51 (s, 2 H), 7.12 (td, J = 7.30, 0.90 Hz, 1 H), 7.18-7.25 (m, 2 H), 7.26-7.32 (m, 1 H), 8.53 (d, J = 8.24 Hz, 1 H), 8.66 (s, 1 H) |
| 162 | (7-(3,3-dimethylindolin-1-yl)-N-(4-piperidyl)thiazolo[5,4-d]pyrimidine-2-carboxamide) | 409.1 | 1H NMR (400 MHz, CHLOROFORM-d) δ ppm 1.45 (s, 6 H), 1.58-1.69 (m, 2 H), 2.09-2.18 (m, 2 H), 2.78-2.89 (m, 2 H), 3.18-3.28 (m, 2 H), 4.08-4.21 (m, 1 H), 4.53 (s, 2 H), 7.01 (d, J = 8.70 Hz, 1 H), 7.13 (td, J = 7.30, 0.90 Hz, 1 H), 7.22-7.25 (m, 1 H), 7.27-7.32 (m, 1 H), 8.54 (d, J = 8.24 Hz, 1 H), 8.66 (s, 1 H) |
| 163 | (7-(3,3-dimethylindolin-1-yl)-N-(3-hydroxypropyl)thiazolo[5,4-d]pyrimidine-2-carboxamide) | 384.1 | 1H NMR (400 MHz, CHLOROFORM-d) δ ppm 1.45 (s, 6 H), 1.91 (quin, J = 5.90 Hz, 3 H), 3.71 (q, J = 6.00 Hz, 2 H), 3.83 (t, J = 5.50 Hz, 2 H), 4.54 (s, 2 H), 7.13 (td, J = 7.30, 0.90 Hz, 1 H), 7.24 (dd, J = 7.30, 0.90 Hz, 1 H), 7.27-7.32 (m, 1 H), 7.74 (br. t, J = 5.90, 5.90 Hz, 1 H), 8.58 (d, J = 8.24 Hz, 1 H), 8.66 (s, 1 H) |

Examples 164-167

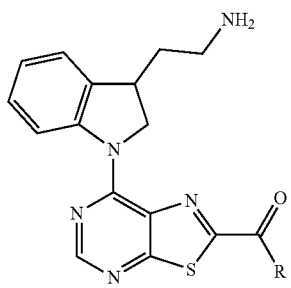

General Procedure (part of an Array)

Step 1

Intermediate 2 (640 mg, 2.80 mmol) was refluxed in SOCl$_2$ (10 mL) at 85° C. for 3 hours giving a yellow solution. Once cooled the solution was concentrated to give a yellow solid. The acid chloride was taken up in DCM (12 mL) and triethylamine (0.77 mL, 5.60 mmol) added. A 2 ml aliquot was added to a vial containing the appropriate amine (0.47 mmol) under N$_2$. The reaction mixture was stirred at room temperature for 4 hours after which it was diluted with DCM and partitioned with water. The organic phase was washed with water (2×10 mL), dried and concentrated onto silica. The compound was purified by column chromatography and used in Step 2.

Step 2

To a solution of Step 1 (0.10 mmol) in IPA (2 mL) was added Intermediate 32 (27 mg, 0.10 mmol) and the mixture heated at 80° C. for 7 hours. Once cooled the solution was concentrated in vacuo, and taken up in DCM (2 mL), TFA (1 mL) added and the solution stirred for 1 hour at room temperature. The solution was then concentrated in vacuo and the resultant residue was purified by preparative LCMS

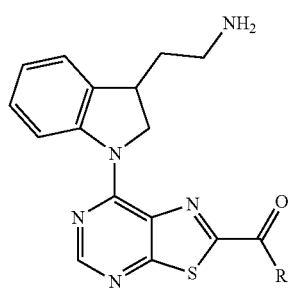

| Example # | R | IUPAC Name | LC-MS (ESI): (MH+) | 1H NMR |
|---|---|---|---|---|
| 164 | cyclopropyl-NH- | 7-(3-(2-Aminoethyl)indolin-1-yl)-N-cyclopropylthiazolo[5,4-d]pyrimidine-2-carboxamide | 381.1 | 1H NMR (400 MHz, DMSO-d6) δ ppm 8.97 (d, J = 4.12 Hz, 1 H), 8.64 (s, 1 H), 8.59 (d, J = 7.79 Hz, 1 H), 7.32 (d, J = 7.33 Hz, 1 H), 7.26 (t, J = 7.79 Hz, 1 H), 7.08 (td, J = 6.87, 1.37 Hz, 1 H), 4.99 (dd, J = 13.74, 8.70 Hz, 1 H), 4.51 (dd, J = 13.28, 5.50 Hz, 1 H), 3.57 (m, 1 H), 2.81 (m, 3 H), 1.95 (m, 1 H), 1.75 (m, 1 H), 0.77 (m, 2 H), 0.69 (m, 2 H) |
| 165 | isopentyl-NH- | 7-[3-(2-aminoethyl)indolin-1-yl]-N-isopentyl-thiazolo[5,4-d]pyrimidine-2-carboxamide | 411.1 | 1H NMR (400 MHz, DMSO-d6) δ ppm 8.90 (t, J = 6.41 Hz, NH), 8.62 (s, 1 H), 8.56 (d, J = 7.79 Hz, 1 H), 7.31 (d, J = 7.33 Hz, 1 H), 7.24 (td, J = 7.79, 0.92 Hz, 1 H), 7.06 (td, J = 7.44, 1.15 Hz, 1 H), 4.95 (dd, J = 12.36, 9.62 Hz, 1 H), 4.53 (dd, 12.82, 5.50 Hz, 1 H), 3.56 (m, 1 H), 3.33 (q, J = 8.20 Hz, 2 H), 2.69 (t, J = 6.87 Hz, 2 H), 1.82 (m, 1 H), 1.67 (m, 1 H), 1.59 (m, 1 H), 1.46 (q, J = 7.79 Hz, 2 H), 0.90 (d, J = 5.95 Hz, 6 H) |
| 166 | 3-methoxypropyl-NH- | 7-[3-(2-aminoethyl)indolin-1-yl]-N-(3-methoxypropyl)thiazolo[5,4-d]pyrimidine-2-carboxamide | 413.1 | 1H NMR (400 MHz, DMSO-d6) δ ppm 8.91 (t, J = 5.95 Hz, NH), 8.63 (s, 1 H), 8.57 (d, J = 8.24 Hz, 1 H), 7.32 (d, J = 7.79 Hz, 1 H), 7.24 (t, J = 7.33 Hz, 1 H), 7.07 (td, J = 7.33, 1.37 Hz, 1 H), 4.95 (dd, J = 13.28, 10.53 Hz, 1 H), 4.53 (dd, J = 12.36, 5.50 Hz, 1 H), 3.56 (m, 1 H), 3.38 (m, 4 H), 3.23 (s, 3 H), 2.69 (t, J = 6.87 Hz, 2 H), 1.82 (m, 4 H), 1.66 (m, 1 H) |
| 167 | 3,3,3-trifluoropropyl-NH- | 7-[3-(2-aminoethyl)indolin-1-yl]-N-(3,3,3-trifluoropropyl)thiazolo[5,4-d]pyrimidine-2-carboxamide | 437.0 | 1H NMR (400 MHz, DMSO-d6) δ ppm 9.14 (m, 1 H), 8.65 (s, 1 H), 8.58 (d, J = 8.70 Hz, 1 H), 7.33 (d, J = 7.79 Hz, 1 H), 7.27 (td, J = 8.24, 1.83 Hz, 1 H), 7.09 (td, J = 6.87, 0.92 Hz, 1 H), 4.95 (dd, J = 8.70, 6.41 Hz, 1 H), 4.55 (dd, J = 5.95, 4.58 Hz, 1 H), 3.59 (m, 3 H), 2.80 (m, 2 H), 2.62 (m, 2 H), 1.92 (m, 1 H), 1.75 (m, 1 H) |

Example 168

7-(5-Chloroindolin-1-yl-N-(4-piperidylmethyl)thiazolo[5,4-d]pyrimidine-2-carboxamide

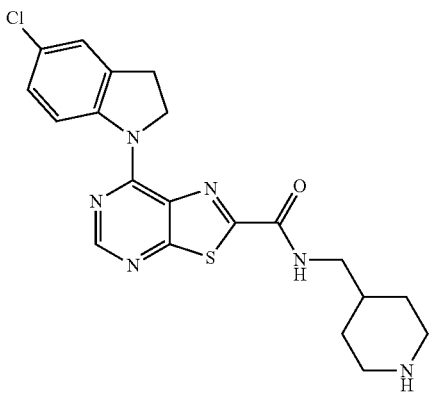 [SMILES: O=C(NCC1CCNCC1)c1nc2c(N3CCc4cc(Cl)ccc43)ncnc2s1]

Intermediate 80 (29 mg, 0.07 mmol) and 5-chloroindoline (11 mg, 0.07 mmol) were combined in isopropanol (2 ml) and stirred at room temperature for 21 h. The mixture was dissolved in DCM and concentrated onto $SiO_2$ and subjected to flash chromatography to give the N—BOC intermediate as a yellow solid. The solid was dissolved in DCM (5 ml) and treated with 4M HCl in dioxane (0.5 ml) for 2 h at room temperature. The solvents were removed under reduced pressure and the residue was taken up in 1:1 DCM-MeOH and loaded onto an SCX cartridge and eluted with DCM-MeOH 1:1 followed by 2M ammonia in methanol. The ammoniacal solution was concentrated and the residue was triturated with MeOH to give the product as a pale yellow solid (15 mg, 50%). 1H NMR (400 MHz, DMSO-d6) δ ppm 0.98-1.15 (m, 2H), 1.60 (d, J=10.99 Hz, 2H), 1.70 (br. s., 1H), 2.35-2.47 (m, 2H), 2.93 (d, J=11.45 Hz, 2H), 3.13-3.26 (m, 3H), 4.91 (t, J=8.47 Hz, 2H), 7.32 (dd, J=8.70, 2.29 Hz, 1H), 7.42 (d, J=1.83 Hz, 1H), 8.65 (d, J=8.70 Hz, 1H), 8.68 (s, 1H), 9.03 (t, J=6.18 Hz, 1H); LC-MS (ESI): (MH⁺) 429/431.

Example 169

7-(5-Bromoindolin-1-yl)-N-(4-piperidylmethyl)thiazolo[5,4-d]pyrimidine-2-carboxamide

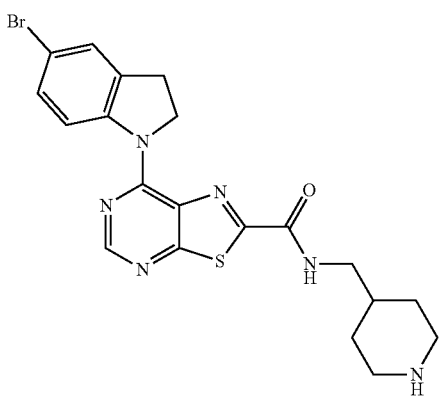 [SMILES: O=C(NCC1CCNCC1)c1nc2c(N3CCc4cc(Br)ccc43)ncnc2s1]

Prepared analogously to Example 168 from Intermediate 80 (100 mg, 0.24 mmol) and 5-bromoindoline (48 mg, 0.24 mmol) to give the product as a yellow solid (20 mg, 17%). 1H NMR (400 MHz, DMSO-d6) δ ppm 0.96-1.11 (m, 2H), 1.57 (d, J=12.36 Hz, 2H), 1.67 (br. s., 1H), 2.34-2.43 (m, 2H), 2.49-2.65 (m, 1H), 2.90 (d, J=12.36 Hz, 2H), 3.18 (t, J=6.64 Hz, 2H), 4.87 (t, J=8.47 Hz, 2H), 7.42 (dd, J=8.70, 2.29 Hz, 1H), 7.51 (d, J=2.29 Hz, 1H), 8.56 (d, J=8.70 Hz, 1H), 8.65 (s, 1H), 8.99 (t, J=5.95 Hz, 1H). LC-MS (ESI): (MH+) 473/475.

Example 170

7-(5-Methylindolin-1-yl)-N-(4-piperidylmethyl)thiazolo[5,4-d]pyrimidine-2-carboxamide

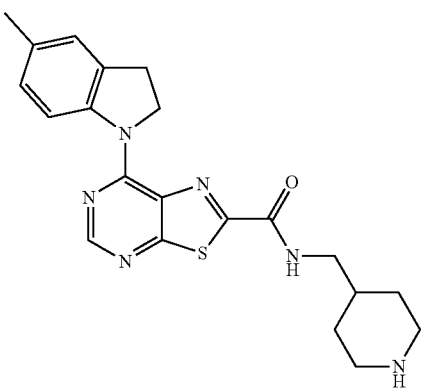 [SMILES: Cc1ccc2c(c1)CCN2c1ncnc2sc(C(=O)NCC3CCNCC3)nc12]

Prepared analogously to Example 168 from Intermediate 80 (100 mg, 0.24 mmol) and 5-methylindoline (32 mg, 0.24 mmol) to give the product as a yellow solid (50 mg, 50%). 1H NMR (400 MHz, DMSO-d6) δ ppm 1.11-1.27 (m, 3H), 1.68 (d, J=11.91 Hz, 2H), 1.78 (br. s., 1H), 2.31 (s, 3H), 2.52-2.60 (m, 2H), 2.98-3.07 (m, 2H), 3.22-3.33 (m, 4H), 4.83-4.91 (m, 2H), 7.06 (d, J=8.70 Hz, 1H), 7.16 (s, 1H), 8.52 (d, J=8.24 Hz, 1H), 8.62 (s, 1H), 8.76-8.84 (m, 1H). LC-MS (ESI): (MH+) 409.

Example 171

7-(5-Fluoroindolin-1-yl)thiazolo[5,4-d]pyrimidine

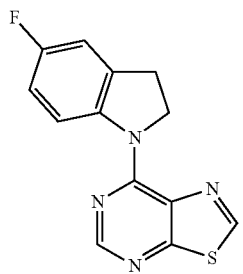 [SMILES: Fc1ccc2c(c1)CCN2c1ncnc2scnc12]

7-Chlorothiazolo[5,4-d]pyrimidine (50 mg, 0.29 mmol), 5-fluoroindoline (42 mg, 0.31 mmol), 4M HCl in dioxane (0.075 ml) In IPA (0.7 ml) were irradiated in the microwave at 100° C. for 30 min. The precipitate was filtered and washed with methanol. The residue was purified by filtration through an aminopropyl cartridge eluting with DCM:MeOH (10:1) to give a green solid (23 mg, 27%). $^1$H NMR (400 MHz, DMSO-$d_6$) δ ppm 3.29 (t, J=8.47 Hz, 2H), 4.74-4.92 (m, 2H), 7.08 (td, J=9.16, 2.75 Hz, 1H), 7.15-7.26 (m, 1H), 8.61 (dd, J=8.93, 4.81 Hz, 1H), 8.64 (s, 1H), 9.34 (s, 1H).

MNK1 and 2 Biochemical IC50 Assays

The effects of compounds on MNK1 and MNK2 activity was determined in a biochemical assay by monitoring the phosphorylation of Serine/Thereonine Kinase peptide 5FAM-RRRLSSLRA-NH2. The phosphorylated peptide product and unphosphorylated peptide substrate were detected using a Caliper Mobility Shift Assay using the Caliper LabChip EZ Reader II.

The Caliper Mobility Shift Assay technology is based on the utilisation of a microfludic chip to measure the conversion of a fluorescent non-phosphorylated peptide substrate to phosphorylated product by electrophoresis separation of substrate and product and detection via Laser-induced fluorescence. The LabChip EZ Reader software calculates the relative heights of substrate and product peaks and reports the peak ratio (Product peak(P) divided by the sum of Product peak(P) and Substrate peak(S)). The percent-conversion is calculated as 100×[(P/(P+S)]. All assays were set up to run in the linear phase with a maximum of 10 percent substrate conversion.

Reagents

The enzymes, MNK1 and MNK2 used for all screening activities were sourced from Cama Biosciences (Product codes 02-145 and 02-146 respectively). These were N-terminal GST fusion proteins expressed in baculovirus expression system and purified by glutathione sepharose affinity chromatography. Specifically these constructs comprised of Full-length human MNK1 [1-424(end) amino acids and T344D of accession number BAA19885.1] and Full-length human MNK2 [1-465(end) amino acids and T379D of accession number NP_951009.1]. A FAM-labelled generic ser/thr kinase peptide substrate was purchased from Anaspec—5-FAM-RRRLSSLRA-NH$_2$. Detection reagents for use on the Caliper-Labchip EZ reader 12-sipper (catNo. 760404), separating buffer and coating reagent-8 (CR-8)—were purchased from Perkin Elmer. All other assay reagents were sourced from Sigma.

MNK1 Assay

Compounds were serially diluted in DMSO to generate a 10-point half log dilution curve with a final top concentration of 100 uM in the assay. Reactions were set up in a total volume of 30 uL in polypropylene-384-well U-bottomed plates (Thermo Scientific 4340). Compounds were pre-incubated with enzyme and peptide in reaction buffer for 30 mins prior to addition of ATP to initiate the reaction. Final assay concentrations were 3 nM MNK1, 2 uM peptide substrate, 50 uM ATP, 50 mM Hepes pH7.0, 0.01% BSA, 10 mM MgCl$_2$, 1 mM dithiothrietol. Plates were incubated at room temperature and the reaction was stopped by the addition of 2 volumes (60 ul) of 50 mM EDTA at a point where approximately 10% substrate conversion had been achieved.

The assay incubation times were adjusted depending on the concentration of ATP used. Assays were performed at low (50 uM) and high (1 mM) ATP. The low ATP values were selected to run at Km conditions for the standard assay to allow relative potencies to be compared across other kinases. The high ATP concentration was selected as representative of cellular ATP concentrations, and for an indication of ATP competition, where a significant shift (greater than half log) in apparent potency would be expected compared to Km conditions. All IC50 values reported are the average of at least two independent experiments.

MNK2 Assay

Reactions were performed as above using 10 nM MNK2 in the assay. Standard assays contained 50 uM ATP and high concentration ATP assays contained 1 mM ATP. Time to achieve 10% conversion varied. All other conditions were the same.

MNK Cellular Activity Phospho-eIF4E Detection Assay

MNK activity in cells was measured by monitoring the phosphorylation of eIF4E at ser209, the known endogenous substrate of MNK1/2, in cell lysates. An amplified luminescent proximity homogeneous assay (Alphascreen Surefire p-eIF4E kit, Perkin Elmer) was used to enable dose-dependent responses to be quantified in a 384 format cell based assay. The assay detection is based on the formation of sandwich antibody complexes coupled to donor and acceptor beads. Excitation at 680 nm causes the transfer of a singlet oxygen species between donor and acceptor beads when they are in close proximity by binding to the analyte (p-eIF4a-ser209), which results in the emission of light at 520-620 nm.

A number of cancer cell lines were investigated, and the MV4.11 cell line (ATCC, CRL-9591), a biphenotypic B myelomonocytic leukemia cell line was selected for routine profiling of compounds. Compound dilutions were prepared in IMDM-10% FBS medium to generate a 10 point half log serial dilution starting at a final top concentration in the assay of 30 uM. Frozen cells were suspended in IMDM-10% FBS medium at a concentration of 1.2×10$^6$/ml. 4 ul (4,800 cells per well) was dispensed into each well of a 384-tissue culture Proxiplate plates (Perkin Elmer 6008238) and 4 ul of compound media dilution was added to the cells and incubated for 1.5 hr at 37 C, 5% CO$_2$. Cells were then lysed and the Aphascreen Surefire protocol followed according to manufacturer's recommendations. 8 ul Acceptor beads (1:50 dilution in kit activation buffer) was added to lysate, shaken 150 rpm for 2 min and incubated for 1.5 hr at room temperature. 3 ul Donor beads (1:20 dilution in kit dilution buffer) were then added, shaken 150 rpm for 2 min and incubated for a further 1.5 hr at room temperature after which the plates were read on Pherastar FS using Alphascreen optic module.

Data were normalised relative to untreated DMSO only controls and curves repeated in duplicate within experiments. Data reported are averages of at least 2 independent experiments.

Kinase Selectivity Screen

Kinase screening was carried out using commercially available reagents and protocols, by way of a third party kinase profiling service, such as Eurofins KinaseProfiler™ (see www.eurofins.com/pharmadiscovery) or similar such service provider.

The results of a kinase selectivity screen for Examples 10, 58 and 64 are shown in Table 2. Data are expressed as % inhibition of each specific kinase in the presence of 11 μM compound.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

Buxade, M., et al. (2008). "The Mnks: MAP kinase-interacting kinases (MAP kinase signal-integrating kinases)." *Front Biosci* 13: 5359-5373.

Buxade, M., et al. (2005). "The Mnks are novel components in the control of TNF alpha biosynthesis and phosphorylate and regulate hnRNP A1." *Immunity* 23(2): 177-189.

Cherla, R. P., et al. (2006). "Shiga toxin 1-induced cytokine production is mediated by MAP kinase pathways and translation initiation factor eIF4E in the macrophage-like THP-1 cell line." *J Leukoc Biol* 79(2): 397-407.

Chrestensen, C. A., et al. (2007). "Loss of MNK function sensitizes fibroblasts to serum-withdrawal induced apoptosis." *Genes Cells* 12(10): 1133-1140.

Jauch, R., et al. (2006). "Mitogen-activated protein kinases interacting kinases are autoinhibited by a reprogrammed activation segment." *EMBO J* 25(17): 4020-4032.

Kjellerup, R. B., at al. (2008). "Pro-inflammatory cytokine release in keratinocytes is mediated through the MAPK signal-integrating kinases." *Exp Dermatol* 17(6): 498-504.

Konicek, B. W., et al. (2008). "Targeting the eIF4F translation initiation complex for cancer therapy." *Cell Cycle* 7(16): 2466-2471.

Konicek, B. W., et al. (2011). "Therapeutic inhibition of MAP kinase interacting kinase blocks eukaryotic initiation factor 4E phosphorylation and suppresses outgrowth of experimental lung metastases." *Cancer Res* 71(5): 1849-1857.

Nikolcheva, T., et al. (2002). "A translational rheostat for RFLAT-1 regulates RANTES expression in T lymphocytes." *J Clin Invest* 110(1): 119-126.

Noubade, R., et al. (2011). "Activation of p38 MAPK in CD4 T cells controls IL-17 production and autoimmune encephalomyelitis." *Blood* 118(12): 3290-3300.

Rowlett, R. M., et al. (2008). "MNK kinases regulate multiple TLR pathways and innate proinflammatory cytokines in macrophages." *Am J Physiol Gastrointest Liver Physiol* 294(2): G452-459.

Teo, T., et al. (2015). "Pharmacologic Inhibition of MNKs in Acute Myeloid Leukemia." *Mol Pharmacol* 88(2): 380-389.

Teo, T., et al. (2015). "Pharmacologic co-inhibition of Mnks and mTORC1 synergistically suppresses proliferation and perturbs cell cycle progression in blast crisis-chronic myeloid leukemia cells." *Cancer Lett* 357(2): 612-623.

Ueda, T., et al. (2010). "Combined deficiency for MAP kinase-interacting kinase 1 and 2 (Mnk1 and Mnk2) delays tumor development." *Proc Natl Acad Sci USA* 107(32): 13984-13990.

Wendel, H. G., et al. (2007). "Dissecting eIF4E action in tumorigenesis." *Genes Dev* 21(24): 3232-3237.

TABLE 1

Selected compounds according to the invention

| STRUCTURE | Example # | P(IC50) eIF4E | MNK1 | MNK2 |
|---|---|---|---|---|
| 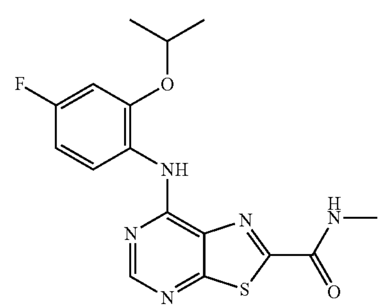 [SMILES: CNC(=O)c1nc2c(Nc3ccc(F)cc3OC(C)C)ncnc2s1] | 1 | 7.6 | 7.3 | 7.5 |
| 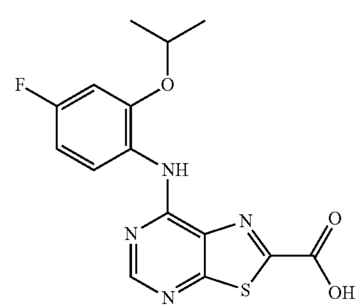 [SMILES: CC(C)Oc1cc(F)ccc1Nc1ncnc2sc(C(=O)O)nc12] | 2 | 6.4 | 6.3 | 6.6 |

TABLE 1-continued

Selected compounds according to the invention

| STRUCTURE | Example # | P(IC50) elF4E | MNK1 | MNK2 |
|---|---|---|---|---|
| | 3 | 7.3 | 7.2 | 7.3 |
| | 4 | 7.0 | 7.3 | 7.4 |
| | 5 | 7.0 | 6.8 | 7.1 |
| | 6 | 6.6 | 6.1 | 6.4 |

TABLE 1-continued
Selected compounds according to the invention
| STRUCTURE | Example # | P(IC50) | | |
|---|---|---|---|---|
| | | eIF4E | MNK1 | MNK2 |
| 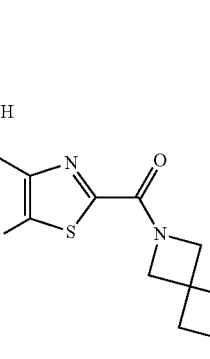 | 7 | 6.5 | 6.6 | 6.6 |
| 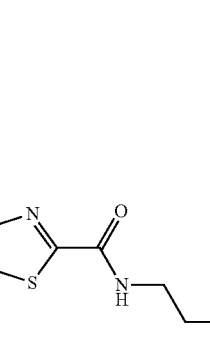 | 8 | 7.2 | 7.3 | 7.3 |
| 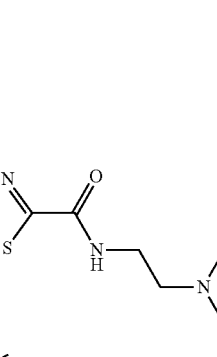 | 9 | 7.4 | 7.3 | 7.5 |
| 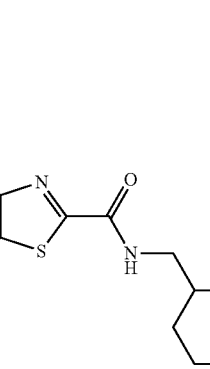 | 10 | 7.1 | 7.3 | 7.3 |

TABLE 1-continued

Selected compounds according to the invention

| STRUCTURE | Example # | P(IC50) eIF4E | MNK1 | MNK2 |
|---|---|---|---|---|
| | 11 | 6.5 | 6.4 | 6.5 |
| | 12 | 7.3 | 6.9 | 7.2 |
| | 13 | 7.4 | 7.3 | 7.4 |

TABLE 1-continued

Selected compounds according to the invention

| STRUCTURE | Example # | P(IC50) | | |
|---|---|---|---|---|
| | | eIF4E | MNK1 | MNK2 |
| (structure) | 14 | 6.4 | 6.8 | 7.1 |
| (structure) | 15 | 6.6 | 6.1 | 6.2 |
| (structure) | 16 | 6.8 | 7.0 | 7.0 |

TABLE 1-continued

Selected compounds according to the invention

| STRUCTURE | Example # | P(IC50) eIF4E | MNK1 | MNK2 |
|---|---|---|---|---|
| | 17 | 7.0 | 6.9 | 7.0 |
| | 18 | 7.4 | 7.3 | 7.3 |
| | 19 | 6.6 | 6.1 | 6.1 |

TABLE 1-continued
Selected compounds according to the invention
| STRUCTURE | Example # | P(IC50) elF4E | MNK1 | MNK2 |
|---|---|---|---|---|
| 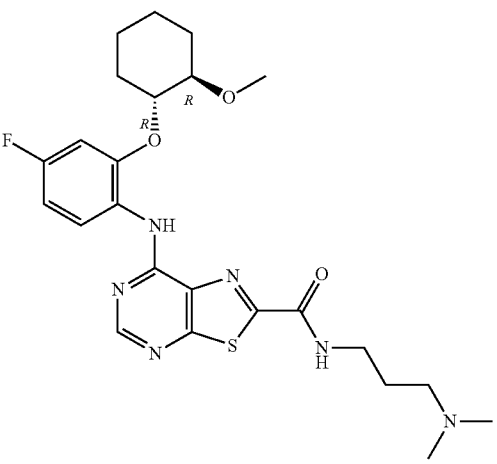 | 20 | 6.5 | 6.1 | 6.4 |
| 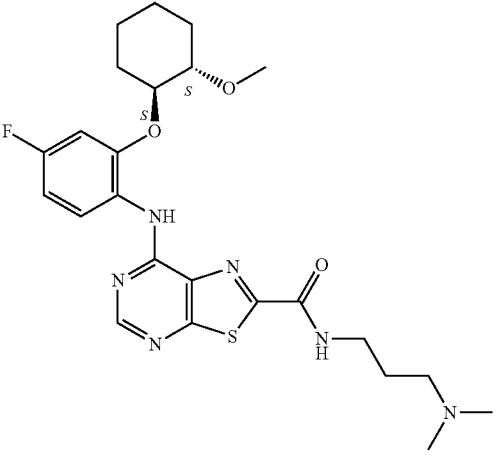 | 21 | 6.5 | 5.7 | 5.9 |
| 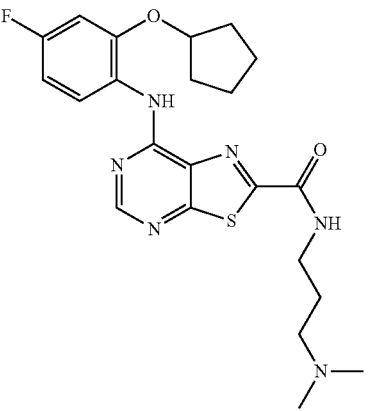 [SMILES: CN(C)CCCNC(=O)c1nc2c(Nc3ccc(F)cc3OC3CCCC3)ncnc2s1] | 22 | 7.2 | 7.0 | 7.2 |

TABLE 1-continued

Selected compounds according to the invention

| STRUCTURE | Example # | P(IC50) elF4E | MNK1 | MNK2 |
|---|---|---|---|---|
| | 23 | 7.2 | 7.0 | 7.2 |
| | 24 | 7.1 | 7.0 | 7.0 |
| | 25 | 7.8 | 8.2 | 8.4 |

TABLE 1-continued

Selected compounds according to the invention

| STRUCTURE | Example # | P(IC50) elF4E | MNK1 | MNK2 |
|---|---|---|---|---|
| | 26 | 6.0 | 5.8 | 5.8 |
| | 27 | 7.5 | 8.0 | 8.1 |
| | 28 | 7.1 | 6.9 | 7.1 |
| | 29 | 7.4 | 7.2 | 7.3 |

TABLE 1-continued
Selected compounds according to the invention
| STRUCTURE | Example # | P(IC50) eIF4E | MNK1 | MNK2 |
|---|---|---|---|---|
| 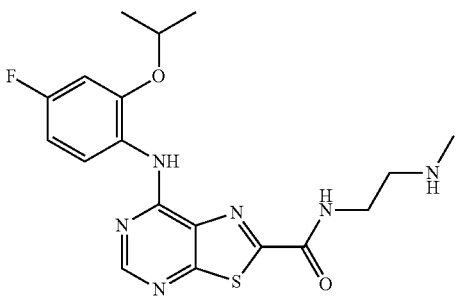 [SMILES: CNCCNC(=O)c1nc2c(Nc3ccc(F)cc3OC(C)C)ncnc2s1] | 30 | 7.0 | 6.7 | 6.9 |
| 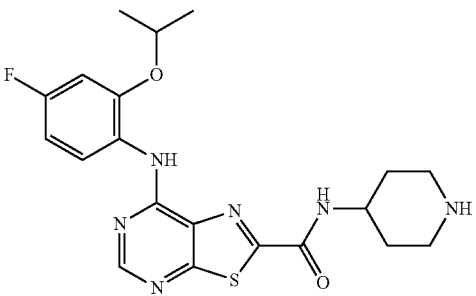 [SMILES: CC(C)Oc1cc(F)ccc1Nc1ncnc2sc(C(=O)NC3CCNCC3)nc12] | 31 | 7.3 | 7.2 | 7.3 |
| 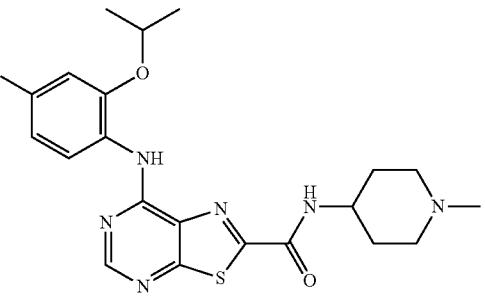 | 32 | 7.4 | 7.3 | 7.4 |
| 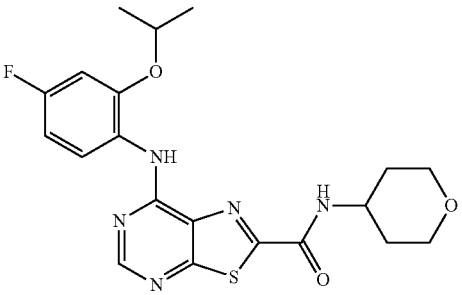 [SMILES: CC(C)Oc1cc(F)ccc1Nc1ncnc2sc(C(=O)NC3CCOCC3)nc12] | 33 | 7.1 | 7.0 | 7.1 |
| 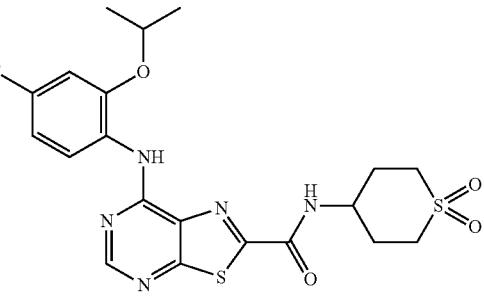 | 34 | 7.1 | 6.7 | 6.8 |

TABLE 1-continued

Selected compounds according to the invention

| STRUCTURE | Example # | P(IC50) eIF4E | MNK1 | MNK2 |
|---|---|---|---|---|
| (structure 35) | 35 | 6.5 | 6.8 | 6.7 |
| (structure 36) | 36 | 7.3 | 7.3 | 7.3 |
| (structure 37) | 37 | 7.6 | 7.4 | 7.4 |
| (structure 38) | 38 | 7.1 | 7.0 | 7.2 |
| (structure 39) | 39 | 7.2 | 6.8 | 6.9 |

TABLE 1-continued
Selected compounds according to the invention
| STRUCTURE | Example # | P(IC50) eIF4E | MNK1 | MNK2 |
|---|---|---|---|---|
| 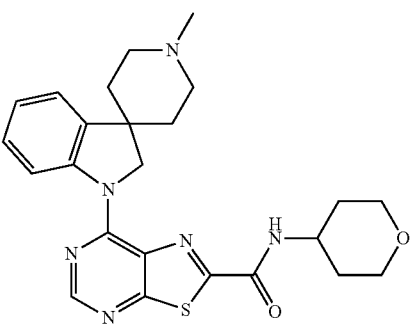 [SMILES: CN1CCC2(CC1)CN(c1ncnc3sc(C(=O)NC4CCOCC4)nc13)c1ccccc12] | 40 | 7.3 | 7.9 | 7.7 |
| 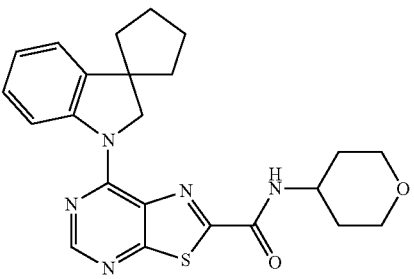 [SMILES: O=C(NC1CCOCC1)c1nc2c(N3CC4(CCCC4)c4ccccc43)ncnc2s1] | 41 | 7.7 | 7.6 | 7.9 |
| 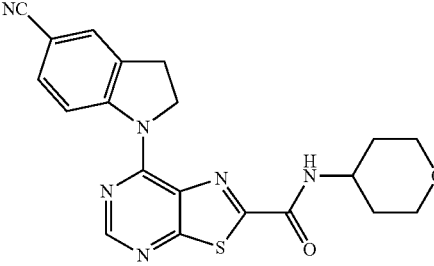 | 42 | 7.5 | 7.5 | 7.7 |
| 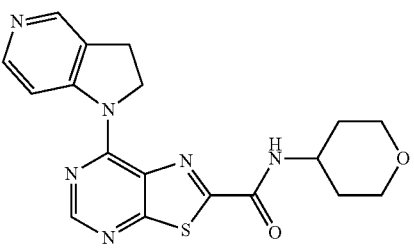 [SMILES: O=C(NC1CCOCC1)c1nc2c(N3CCc4cnccc43)ncnc2s1] | 43 | 7.6 | 7.4 | 7.5 |
| 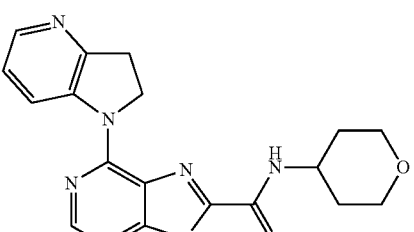 | 44 | 7.0 | 6.8 | 7.0 |

TABLE 1-continued

Selected compounds according to the invention

| STRUCTURE | Example # | P(IC50) | | |
|---|---|---|---|---|
| | | elF4E | MNK1 | MNK2 |
| (structure) | 45 | 7.5 | 7.8 | 7.7 |
| (structure) | 46 | 7.0 | 6.3 | 6.7 |
| (structure) | 47 | 6.9 | 6.6 | 6.7 |
| (structure) | 48 | 7.7 | 7.2 | 7.4 |

TABLE 1-continued

Selected compounds according to the invention

| STRUCTURE | Example # | P(IC50) eIF4E | MNK1 | MNK2 |
|---|---|---|---|---|
| | 49 | 7.1 | 6.8 | 7.2 |
| | 50 | 6.1 | 7.7 | 7.5 |
| | 51 | 6.9 | 6.9 | 7.0 |
| | 52 | 7.0 | 7.2 | 7.2 |

TABLE 1-continued
Selected compounds according to the invention
| STRUCTURE | Example # | P(IC50) | | |
|---|---|---|---|---|
| | | eIF4E | MNK1 | MNK2 |
| 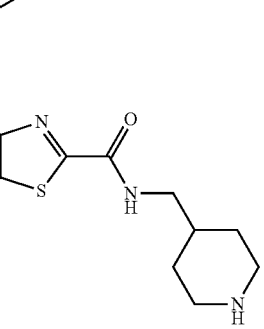 | 53 | 6.9 | 7.0 | 6.9 |
| 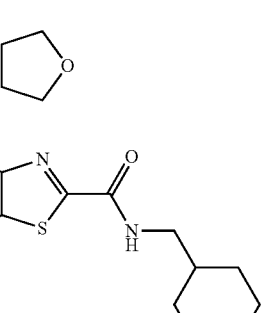 | 54 | 6.7 | 7.1 | 7.0 |
| 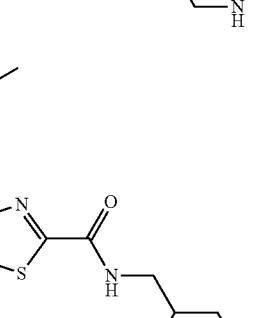 | 55 | 6.5 | 6.5 | 6.6 |
| 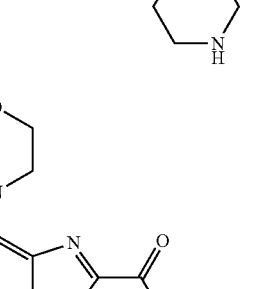 | 56 | 6.1 | 6.0 | 6.1 |

TABLE 1-continued

Selected compounds according to the invention

| STRUCTURE | Example # | P(IC50) | | |
|---|---|---|---|---|
| | | elF4E | MNK1 | MNK2 |
| | 57 | 6.6 | 6.6 | 6.6 |
| | 58 | 8.1 | 8.3 | 8.4 |
| | 59 | 6.2 | 5.7 | 5.8 |

TABLE 1-continued
Selected compounds according to the invention
| STRUCTURE | Example # | P(IC50) | | |
|---|---|---|---|---|
| | | eIF4E | MNK1 | MNK2 |
| 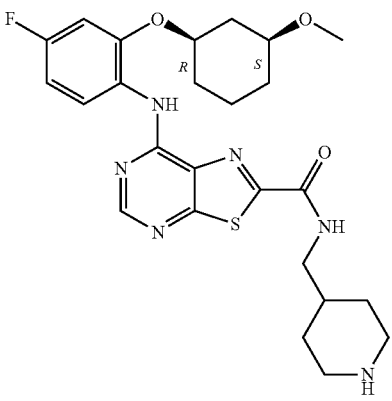 | 60 | 6.2 | 6.1 | 6.0 |
| 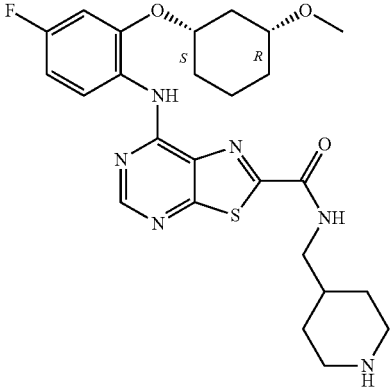 | 61 | 7.1 | 7.0 | 6.9 |
| 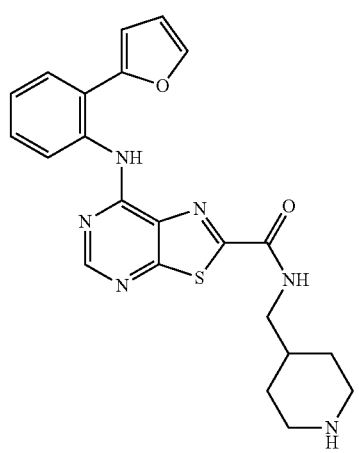 [SMILES: O=C(NCC1CCNCC1)c1nc2c(Nc3ccccc3-c3ccco3)ncnc2s1] | 62 | 6.5 | 6.2 | 6.5 |

TABLE 1-continued
Selected compounds according to the invention
| STRUCTURE | Example # | P(IC50) eIF4E | MNK1 | MNK2 |
|---|---|---|---|---|
| 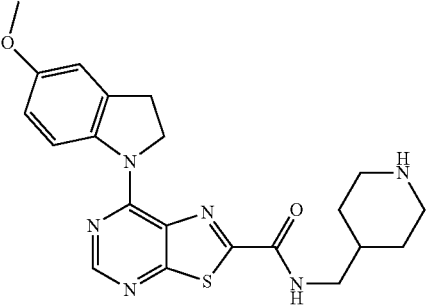 [SMILES: COc1ccc2c(c1)CCN2c1ncnc2sc(C(=O)NCC3CCNCC3)nc12] | 63 | 7.4 | 7.1 | 7.2 |
| 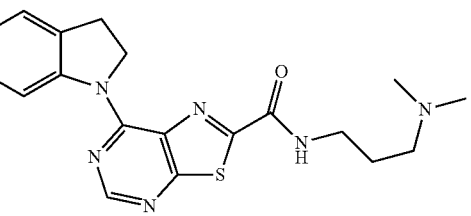 | 64 | 8.1 | 8.6 | 8.7 |
| 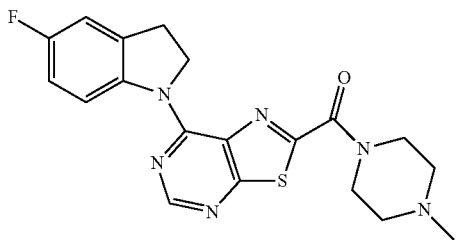 [SMILES: CN1CCN(C(=O)c2nc3c(N4CCc5cc(F)ccc54)ncnc3s2)CC1] | 65 | 6.6 | 7.1 | 7.1 |
| 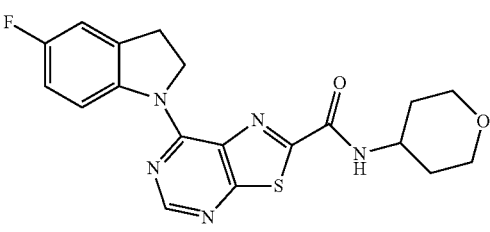 [SMILES: O=C(NC1CCOCC1)c1nc2c(N3CCc4cc(F)ccc43)ncnc2s1] | 66 | 8.0 | 8.3 | 8.4 |
| 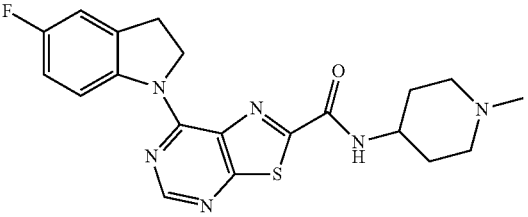 [SMILES: CN1CCC(NC(=O)c2nc3c(N4CCc5cc(F)ccc54)ncnc3s2)CC1] | 67 | 8.4 | 8.4 | 8.5 |
| 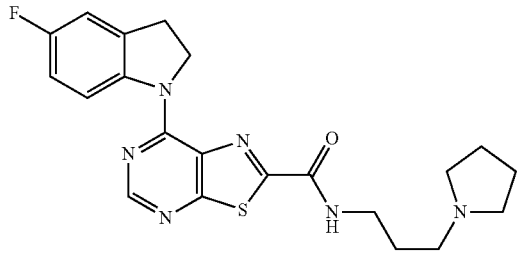 [SMILES: O=C(NCCCN1CCCC1)c1nc2c(N3CCc4cc(F)ccc43)ncnc2s1] | 68 | 8.2 | 8.7 | 8.7 |

TABLE 1-continued

Selected compounds according to the invention

| STRUCTURE | Example # | P(IC50) eIF4E | MNK1 | MNK2 |
|---|---|---|---|---|
| (5-fluoro-2,3-dihydroindol-1-yl thiazolopyrimidine, N-methyl carboxamide) | 69 | 8.2 | 8.2 | 8.3 |
| (5-fluoro-2,3-dihydroindol-1-yl thiazolopyrimidine, N,N-dimethyl carboxamide) | 70 | 7.2 | 7.3 | 7.7 |
| (5-fluoro-2,3-dihydroindol-1-yl thiazolopyrimidine, N-(2-methylaminoethyl) carboxamide) | 71 | 7.8 | 8.0 | 8.2 |
| (5-fluoro-2,3-dihydroindol-1-yl thiazolopyrimidine, N-(3-methylaminopropyl) carboxamide) | 72 | 8.3 | 8.3 | 8.3 |

TABLE 1-continued

Selected compounds according to the invention

| STRUCTURE | Example # | P(IC50) | | |
|---|---|---|---|---|
| | | eIF4E | MNK1 | MNK2 |
| (structure 73) | 73 | 7.8 | 8.3 | 8.3 |
| (structure 74) | 74 | 7.7 | 8.2 | 8.3 |
| (structure 75) | 75 | 7.8 | 8.5 | 8.5 |
| (structure 76) | 76 | 8.1 | 8.2 | 8.5 |

TABLE 1-continued
Selected compounds according to the invention
| STRUCTURE | Example # | P(IC50) eIF4E | MNK1 | MNK2 |
|---|---|---|---|---|
| 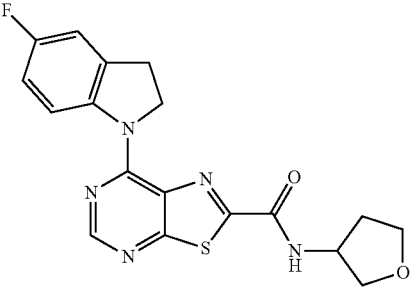 [SMILES: O=C(NC1CCOC1)c1nc2c(N3CCc4cc(F)ccc43)ncnc2s1] | 77 | 8.4 | 8.7 | 8.7 |
| 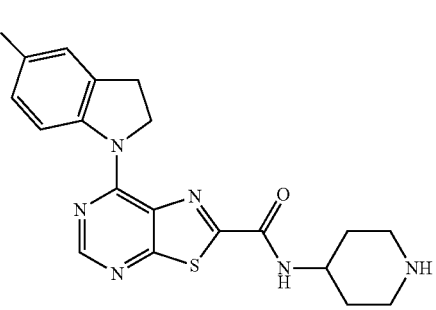 | 78 | 8.5 | 8.7 | 8.7 |
| 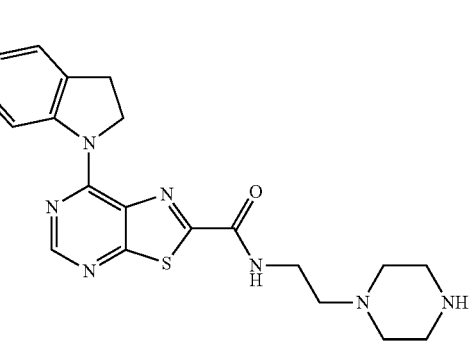 | 79 | 8.0 | 8.5 | 8.5 |
| 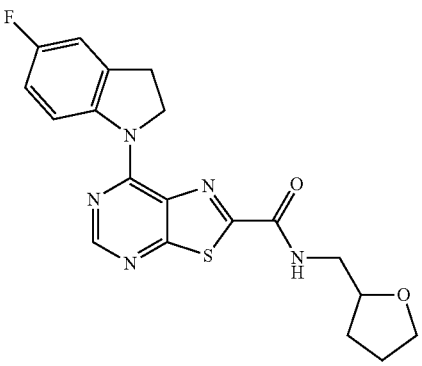 [SMILES: O=C(NCC1CCCO1)c1nc2c(N3CCc4cc(F)ccc43)ncnc2s1] | 80 | 7.7 | 8.1 | 8.3 |
| 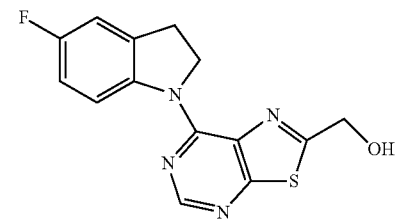 [SMILES: OCc1nc2c(N3CCc4cc(F)ccc43)ncnc2s1] | 81 | 7.0 | 7.4 | 7.7 |

TABLE 1-continued

Selected compounds according to the invention

| STRUCTURE | Example # | P(IC50) | | |
|---|---|---|---|---|
| | | eIF4E | MNK1 | MNK2 |
| (structure 82) | 82 | 6.8 | 7.5 | 7.5 |
| (structure 83) | 83 | 6.9 | 7.5 | 7.4 |
| (structure 84) | 84 | 7.3 | 8.4 | 8.3 |
| (structure 85) | 85 | 7.0 | 8.0 | 7.7 |
| (structure 86) | 86 | 6.6 | 7.2 | 7.1 |

TABLE 1-continued
Selected compounds according to the invention
| STRUCTURE | Example # | P(IC50) | | |
|---|---|---|---|---|
| | | eIF4E | MNK1 | MNK2 |
| 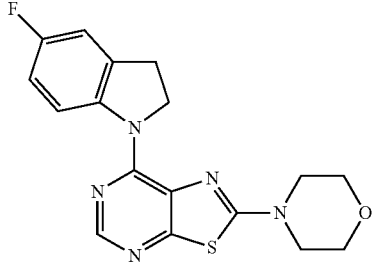 [SMILES: Fc1ccc2c(c1)CCN2c1ncnc2sc(N3CCOCC3)nc12] | 87 | 6.7 | 6.9 | 7.1 |
| 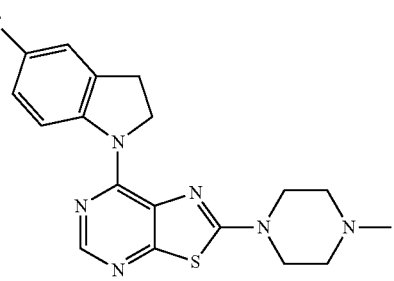 | 88 | 6.6 | 7.1 | 7.3 |
| 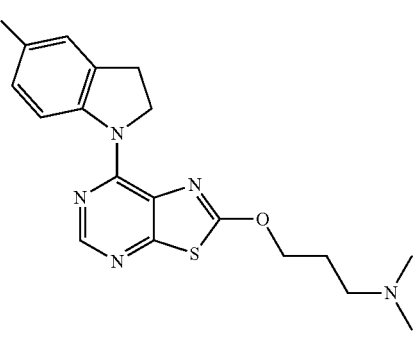 | 89 | 6.7 | 7.4 | 7.2 |
| 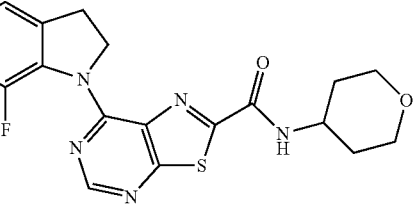 | 90 | 6.8 | 6.9 | 6.9 |
| 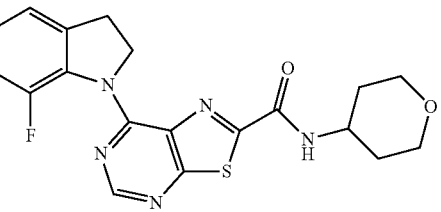 | 91 | 7.0 | 7.2 | 7.3 |

TABLE 1-continued

Selected compounds according to the invention

| STRUCTURE | Example # | P(IC50) | | |
|---|---|---|---|---|
| | | eIF4E | MNK1 | MNK2 |
| | 92 | 6.6 | 6.8 | 6.9 |
| | 93 | 6.6 | 6.7 | 6.8 |
| | 94 | 8.1 | 8.2 | 8.4 |
| | 95 | 7.0 | 7.4 | 7.6 |

TABLE 1-continued

Selected compounds according to the invention

| STRUCTURE | Example # | P(IC50) | | |
|---|---|---|---|---|
| | | eIF4E | MNK1 | MNK2 |
| | 96 | 6.3 | 6.4 | 6.6 |
| | 97 | 7.8 | 8.1 | 8.1 |
| | 98 | 8.4 | 8.5 | 8.4 |
| | 99 | 7.8 | 7.9 | 8.3 |
| | 100 | 7.8 | 7.6 | 7.7 |

TABLE 1-continued
Selected compounds according to the invention
| STRUCTURE | Example # | P(IC50) eIF4E | MNK1 | MNK2 |
|---|---|---|---|---|
| 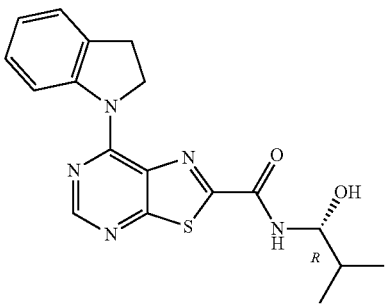 | 101 | 7.5 | 8.0 | 7.9 |
| 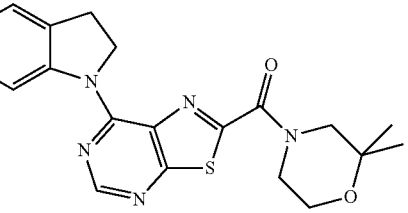 | 102 | 6.2 | 6.8 | 6.7 |
| 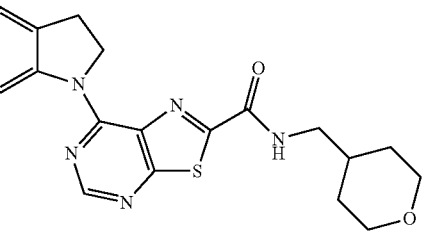 | 103 | 7.2 | 8.0 | 8.0 |
| 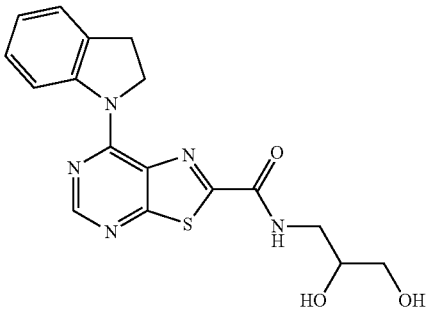 [SMILES: O=C(NCC(O)CO)c1nc2c(N3CCc4ccccc43)ncnc2s1] | 104 | 8.0 | 7.7 | 7.9 |
| 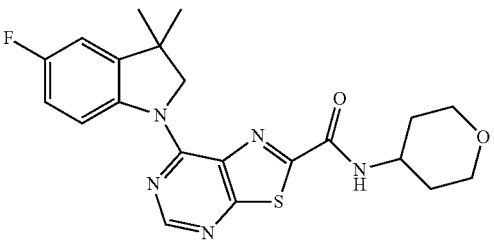 [SMILES: CC1(C)CN(c2ncnc3sc(C(=O)NC4CCOCC4)nc23)c2ccc(F)cc21] | 105 | 8.6 | 8.7 | 8.5 |

TABLE 1-continued
Selected compounds according to the invention
| STRUCTURE | Example # | P(IC50) | | |
|---|---|---|---|---|
| | | eIF4E | MNK1 | MNK2 |
| 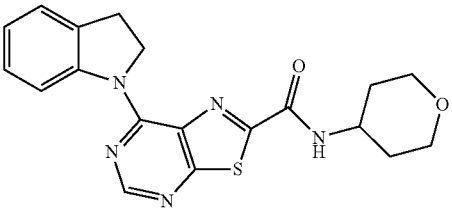 [SMILES: O=C(NC1CCOCC1)c1nc2c(N3CCc4ccccc43)ncnc2s1] | 106 | 7.7 | 7.9 | 8.1 |
| 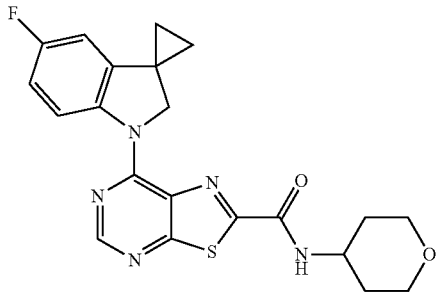 | 107 | 8.7 | 8.8 | 8.5 |
| 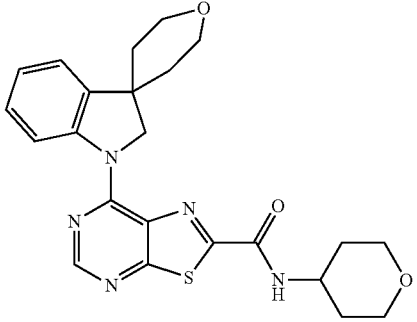 [SMILES: O=C(NC1CCOCC1)c1nc2c(N3CC4(CCOCC4)c4ccccc43)ncnc2s1] | 108 | 7.5 | 7.2 | 7.4 |
| 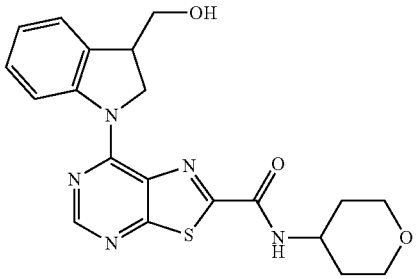 [SMILES: O=C(NC1CCOCC1)c1nc2c(N3CC(CO)c4ccccc43)ncnc2s1] | 109 | 7.9 | 7.9 | 8.1 |
| 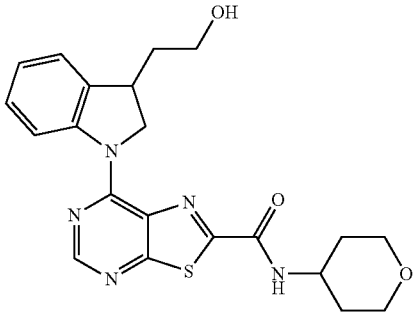 | 110 | 8.0 | 8.0 | 8.0 |

TABLE 1-continued
Selected compounds according to the invention
| STRUCTURE | Example # | P(IC50) eIF4E | MNK1 | MNK2 |
|---|---|---|---|---|
| 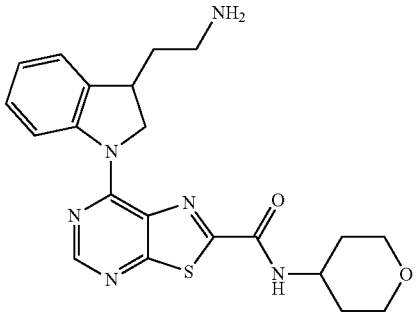 [SMILES: NCCC1CN(c2ncnc3sc(C(=O)NC4CCOCC4)nc23)c2ccccc21] | 111 | 7.2 | 8.3 | 8.2 |
| 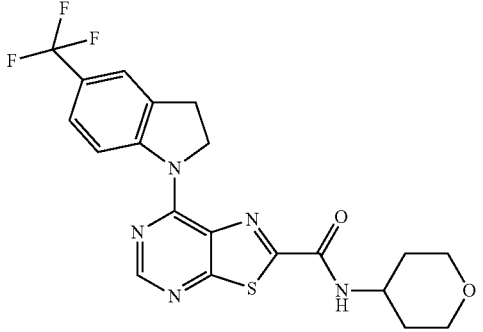 [SMILES: O=C(NC1CCOCC1)c1nc2c(N3CCc4cc(C(F)(F)F)ccc43)ncnc2s1] | 112 | 6.5 | 6.7 | 6.9 |
| 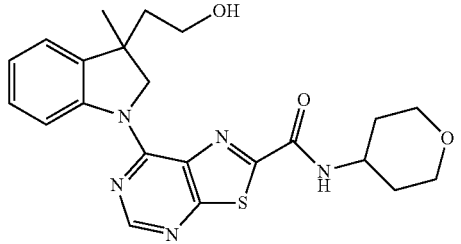 [SMILES: CC1(CCO)CN(c2ncnc3sc(C(=O)NC4CCOCC4)nc23)c2ccccc21] | 113 | 7.4 | 7.4 | 7.4 |
| 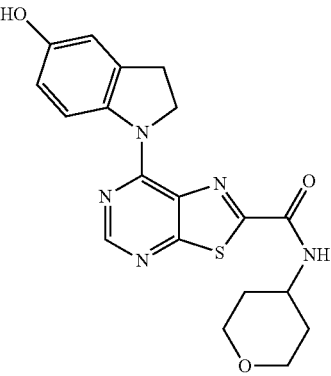 | 114 | 8.8 | 8.6 | 8.6 |

TABLE 1-continued
Selected compounds according to the invention
| STRUCTURE | Example # | P(IC50) elF4E | MNK1 | MNK2 |
|---|---|---|---|---|
| 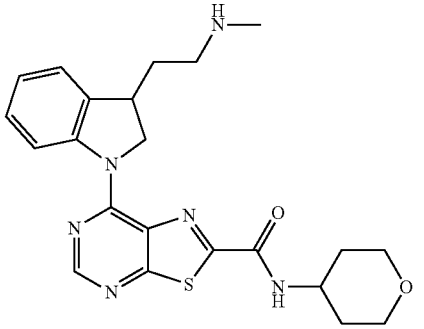 [SMILES: CNCCC1CN(c2ncnc3sc(C(=O)NC4CCOCC4)nc23)c2ccccc21] | 115 | 6.9 | 7.5 | 7.8 |
| 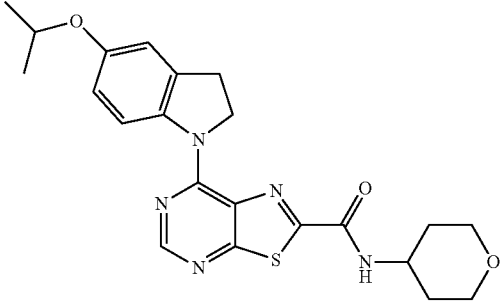 [SMILES: CC(C)Oc1ccc2c(c1)CCN2c1ncnc2sc(C(=O)NC3CCOCC3)nc12] | 116 | 6.3 | 5.7 | 6.2 |
| 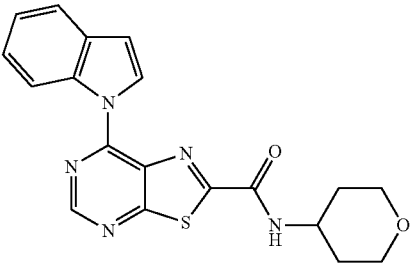 [SMILES: O=C(NC1CCOCC1)c1nc2c(-n3ccc4ccccc43)ncnc2s1] | 117 | 7.3 | 7.3 | 7.5 |
| 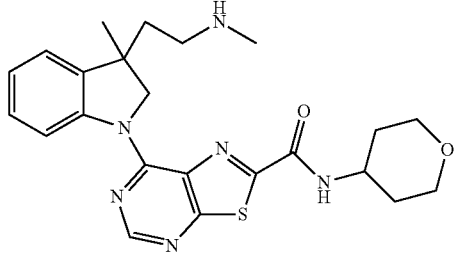 [SMILES: CNCCC1(C)CN(c2ncnc3sc(C(=O)NC4CCOCC4)nc23)c2ccccc21] | 118 | 6.6 | 6.9 | 6.8 |
| 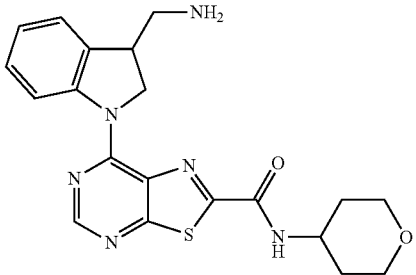 | 119 | 7.7 | 7.9 | 7.8 |

TABLE 1-continued

Selected compounds according to the invention

| STRUCTURE | Example # | P(IC50) | | |
|---|---|---|---|---|
| | | eIF4E | MNK1 | MNK2 |
| *(structure)* | 120 | 6.9 | 7.3 | 7.5 |
| *(structure)* | 121 | 7.1 | 7.4 | 7.1 |
| *(structure)* | 122 | 7.3 | 7.4 | 7.5 |
| *(structure)* | 123 | 7.7 | 7.6 | 7.8 |
| *(structure)* | 125 | 8.4 | 8.5 | 8.4 |

TABLE 1-continued
Selected compounds according to the invention
| STRUCTURE | Example # | P(IC50) eIF4E | MNK1 | MNK2 |
|---|---|---|---|---|
| 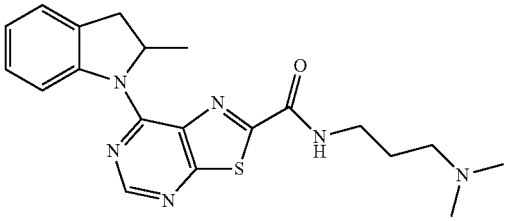 [SMILES: CC1Cc2ccccc2N1c1ncnc2sc(C(=O)NCCCN(C)C)nc12] | 124 | 7.5 | 7.5 | 7.7 |
| 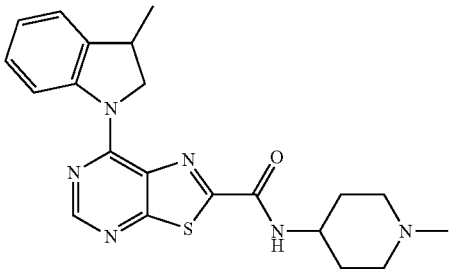 [SMILES: CC1CN(c2ncnc3sc(C(=O)NC4CCN(C)CC4)nc23)c2ccccc21] | 126 | 8.4 | 8.4 | 8.2 |
| 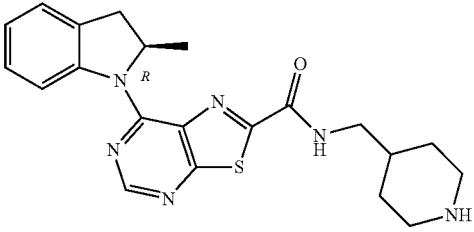 | 127 | 7.8 | 7.9 | 7.8 |
| 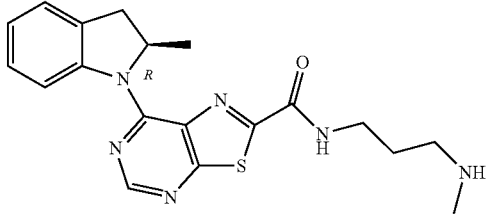 | 128 | 7.1 | 7.7 | 7.9 |
| 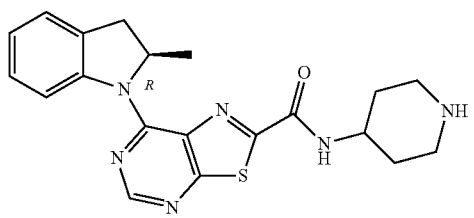 | 129 | 7.1 | 7.8 | 7.8 |
| 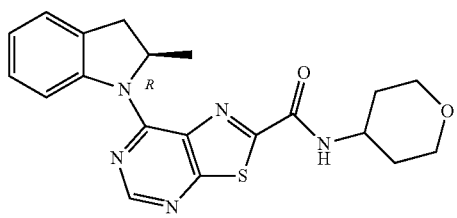 | 130 | 7.3 | 7.3 | 7.4 |

TABLE 1-continued
Selected compounds according to the invention
| STRUCTURE | Example # | P(IC50) eIF4E | MNK1 | MNK2 |
|---|---|---|---|---|
| 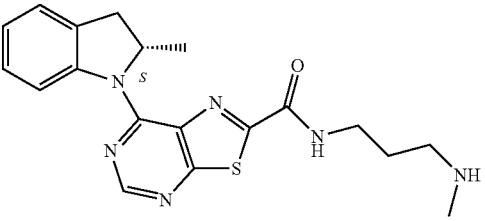 | 131 | 7.4 | 7.0 | 7.5 |
| 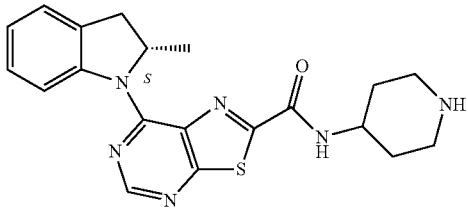 | 132 | 7.6 | 7.7 | 7.8 |
| 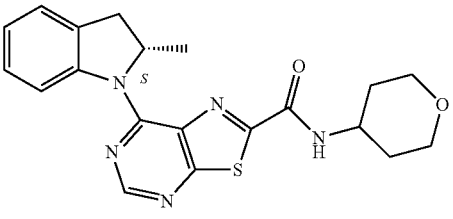 | 133 | 7.3 | 7.1 | 7.4 |
| 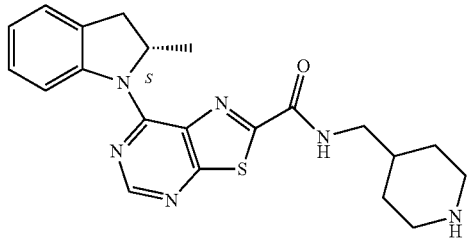 | 134 | 7.4 | 7.5 | 7.6 |
| 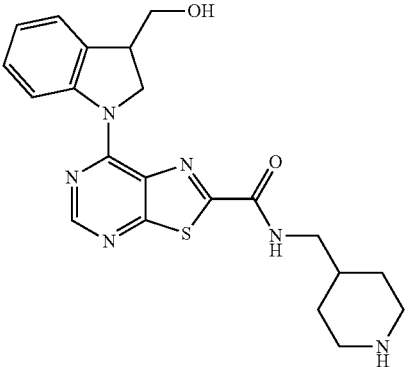 [SMILES: O=C(NCC1CCNCC1)c1nc2c(N3CC(CO)c4ccccc43)ncnc2s1] | 135 | 7.5 | 8.0 | 8.1 |

TABLE 1-continued

Selected compounds according to the invention

| STRUCTURE | Example # | P(IC50) eIF4E | MNK1 | MNK2 |
|---|---|---|---|---|
| 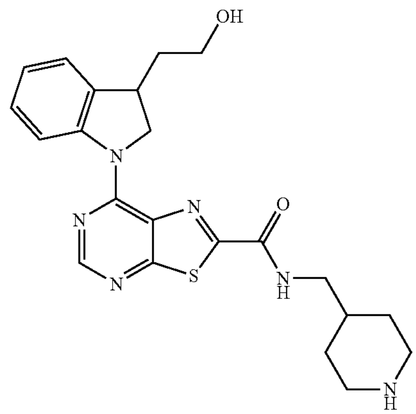 [SMILES: O=C(NCC1CCNCC1)c1nc2c(N3CC(CCO)c4ccccc43)ncnc2s1] | 136 | 8.2 | 8.1 | 8.3 |
| 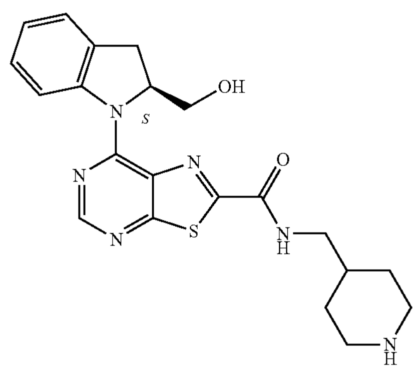 | 137 | 6.8 | 6.7 | 6.9 |
| 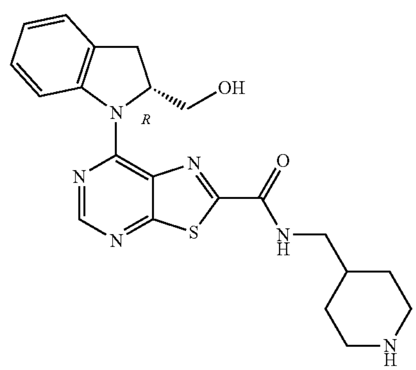 | 138 | 6.7 | 6.4 | 6.5 |
| 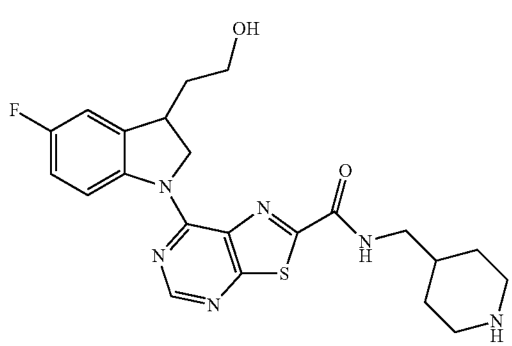 [SMILES: O=C(NCC1CCNCC1)c1nc2c(N3CC(CCO)c4cc(F)ccc43)ncnc2s1] | 139 | 7.5 | 8.6 | 8.5 |

TABLE 1-continued

Selected compounds according to the invention

| STRUCTURE | Example # | P(IC50) | | |
|---|---|---|---|---|
| | | eIF4E | MNK1 | MNK2 |
| (structure) | 140 | 7.4 | 8.2 | 8.2 |
| (structure) | 141 | 7.7 | 8.5 | 8.3 |
| (structure) | 142 | 8.0 | 7.8 | 7.8 |
| (structure) | 143 | 8.3 | 8.1 | 8.2 |

TABLE 1-continued
Selected compounds according to the invention
| STRUCTURE | Example # | P(IC50) | | |
|---|---|---|---|---|
| | | eIF4E | MNK1 | MNK2 |
| 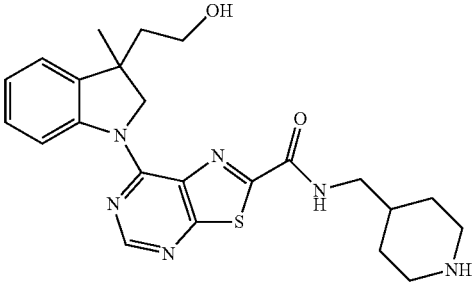 [SMILES: CC1(CCO)CN(c2ncnc3sc(C(=O)NCC4CCNCC4)nc23)c2ccccc21] | 144 | 7.7 | 7.9 | 7.8 |
| 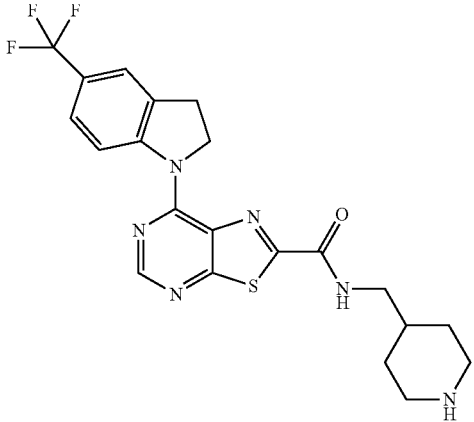 [SMILES: O=C(NCC1CCNCC1)c1nc2c(N3CCc4cc(C(F)(F)F)ccc43)ncnc2s1] | 145 | 6.3 | 6.9 | 7.0 |
| 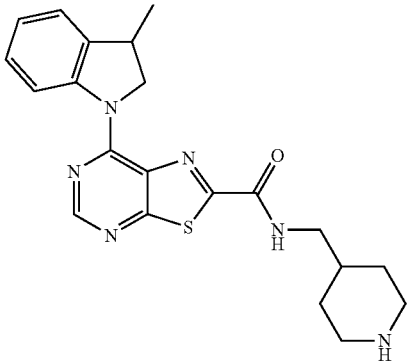 [SMILES: CC1CN(c2ncnc3sc(C(=O)NCC4CCNCC4)nc23)c2ccccc21] | 146 | 8.3 | 8.2 | 8.1 |
| 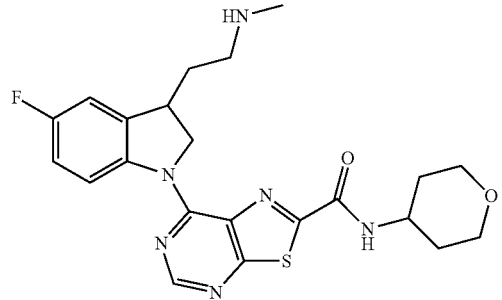 [SMILES: CNCCC1CN(c2ncnc3sc(C(=O)NC4CCOCC4)nc23)c2ccc(F)cc21] | 147 | 7.8 | 8.1 | 8.0 |

TABLE 1-continued
Selected compounds according to the invention
| STRUCTURE | Example # | P(IC50) eIF4E | MNK1 | MNK2 |
|---|---|---|---|---|
| 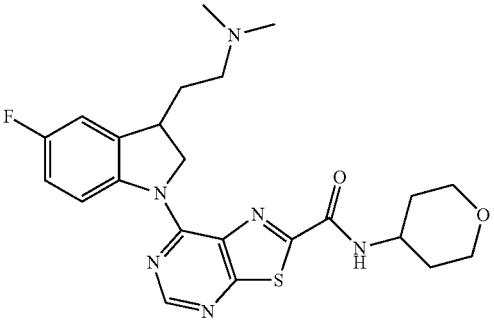 [SMILES: CN(C)CCC1CN(c2ncnc3sc(C(=O)NC4CCOCC4)nc23)c2ccc(F)cc21] | 148 | 7.2 | 7.3 | 7.2 |
| 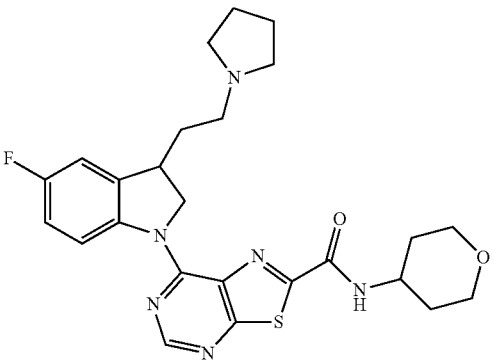 [SMILES: O=C(NC1CCOCC1)c1nc2c(N3CC(CCN4CCCC4)c4cc(F)ccc43)ncnc2s1] | 149 | 7.2 | 7.5 | 7.3 |
| 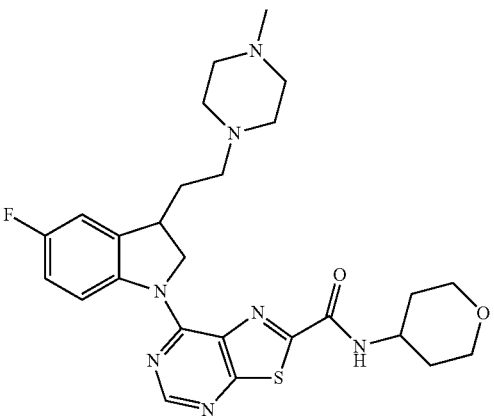 [SMILES: CN1CCN(CCC2CN(c3ncnc4sc(C(=O)NC5CCOCC5)nc34)c3ccc(F)cc32)CC1] | 150 | 7.6 | 7.2 | 7.2 |
| 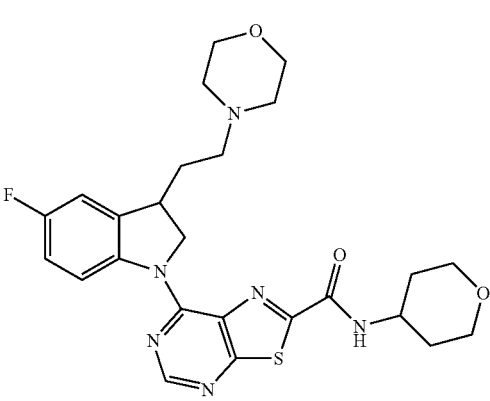 [SMILES: O=C(NC1CCOCC1)c1nc2c(N3CC(CCN4CCOCC4)c4cc(F)ccc43)ncnc2s1] | 151 | 7.5 | 7.0 | 7.0 |

TABLE 1-continued
Selected compounds according to the invention
| STRUCTURE | Example # | P(IC50) | | |
|---|---|---|---|---|
| | | eIF4E | MNK1 | MNK2 |
| 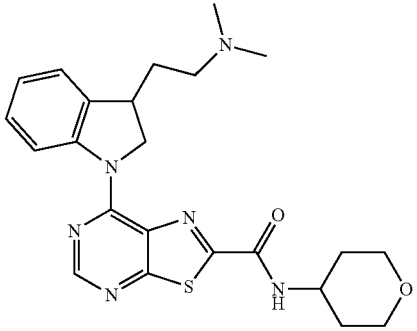 [SMILES: CN(C)CCC1CN(c2ncnc3sc(C(=O)NC4CCOCC4)nc23)c2ccccc21] | 152 | 7.3 | 7.0 | 7.1 |
| 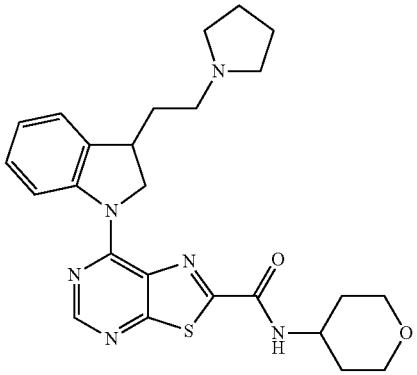 [SMILES: O=C(NC1CCOCC1)c1nc2c(N3CC(CCN4CCCC4)c4ccccc43)ncnc2s1] | 153 | 7.0 | 7.3 | 7.3 |
| 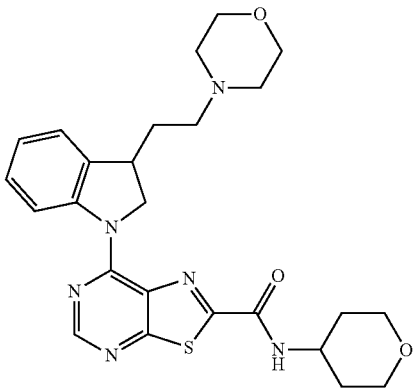 [SMILES: O=C(NC1CCOCC1)c1nc2c(N3CC(CCN4CCOCC4)c4ccccc43)ncnc2s1] | 154 | 7.0 | 7.1 | 7.1 |
| 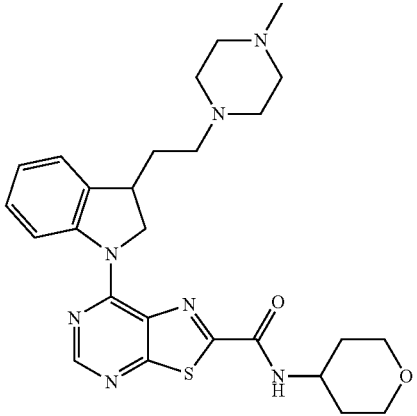 [SMILES: CN1CCN(CCC2CN(c3ncnc4sc(C(=O)NC5CCOCC5)nc34)c3ccccc32)CC1] | 155 | 7.3 | 6.9 | 7.1 |

TABLE 1-continued
Selected compounds according to the invention
| STRUCTURE | Example # | P(IC50) elF4E | MNK1 | MNK2 |
|---|---|---|---|---|
| 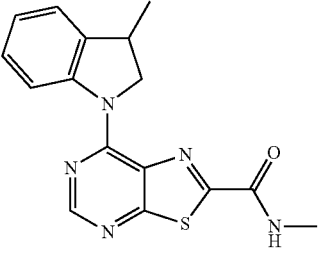 [SMILES: CNC(=O)c1nc2c(N3CC(C)c4ccccc43)ncnc2s1] | 156 | 8.3 | 8.0 | 8.1 |
| 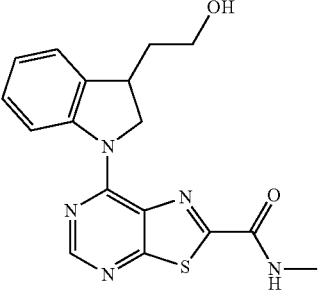 [SMILES: CNC(=O)c1nc2c(N3CC(CCO)c4ccccc43)ncnc2s1] | 157 | 8.0 | 7.5 | 7.7 |
| 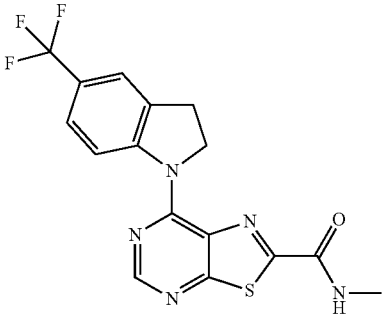 [SMILES: CNC(=O)c1nc2c(N3CCc4cc(C(F)(F)F)ccc43)ncnc2s1] | 158 | 6.3 | 6.5 | 6.9 |
| 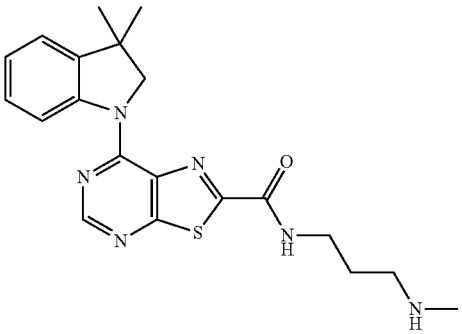 [SMILES: CNCCCNC(=O)c1nc2c(N3CC(C)(C)c4ccccc43)ncnc2s1] | 159 | 8.3 | 8.3 | 8.5 |

TABLE 1-continued
Selected compounds according to the invention
| STRUCTURE | Example # | P(IC50) eIF4E | MNK1 | MNK2 |
|---|---|---|---|---|
| 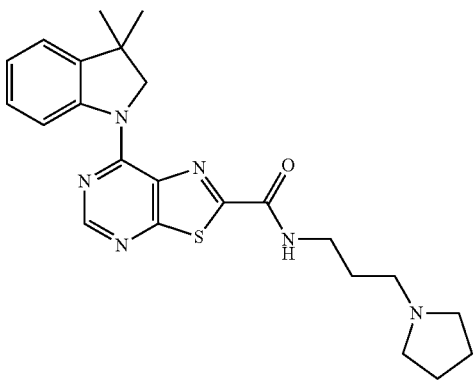 [SMILES: CC1(C)CN(c2ncnc3sc(C(=O)NCCCN4CCCC4)nc23)c2ccccc21] | 160 | 8.1 | 8.2 | 8.2 |
| 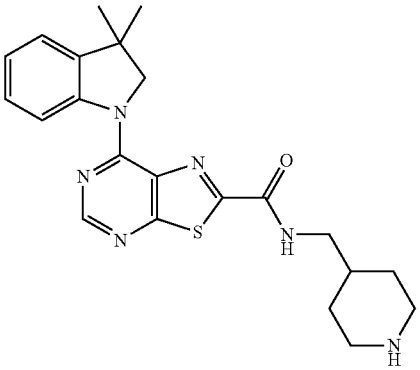 [SMILES: CC1(C)CN(c2ncnc3sc(C(=O)NCC4CCNCC4)nc23)c2ccccc21] | 161 | 8.5 | 8.5 | 8.6 |
| 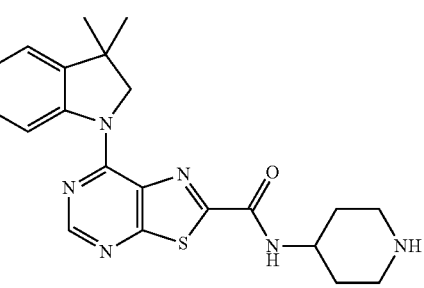 | 162 | 8.1 | 8.2 | 8.3 |
| 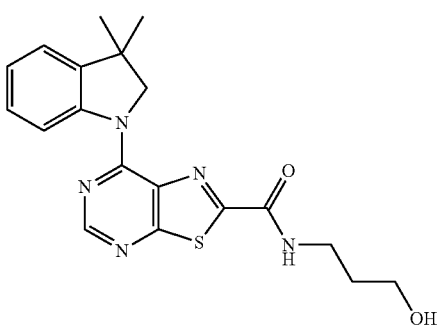 [SMILES: CC1(C)CN(c2ncnc3sc(C(=O)NCCCO)nc23)c2ccccc21] | 163 | 8.3 | 8.0 | 8.4 |

TABLE 1-continued
Selected compounds according to the invention
| STRUCTURE | Example # | P(IC50) elF4E | MNK1 | MNK2 |
|---|---|---|---|---|
| 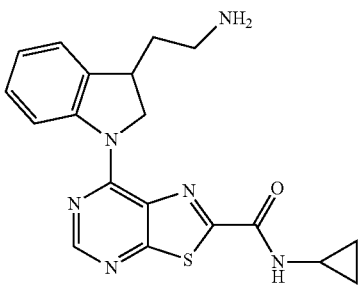 [SMILES: NCCC1CN(c2ncnc3sc(C(=O)NC4CC4)nc23)c2ccccc21] | 164 | 8.3 | 8.3 | 8.3 |
| 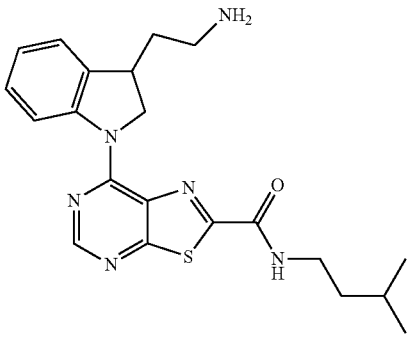 [SMILES: CC(C)CCNC(=O)c1nc2c(N3CC(CCN)c4ccccc43)ncnc2s1] | 165 | 7.8 | 8.0 | 8.0 |
| 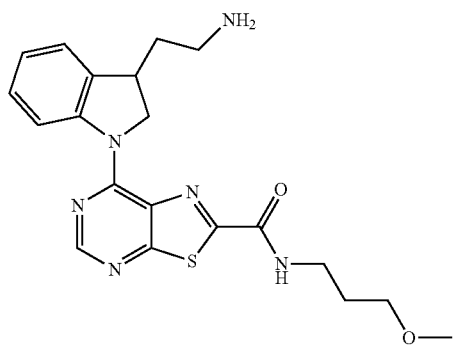 [SMILES: COCCCNC(=O)c1nc2c(N3CC(CCN)c4ccccc43)ncnc2s1] | 166 | 8.4 | 8.3 | 8.3 |
| 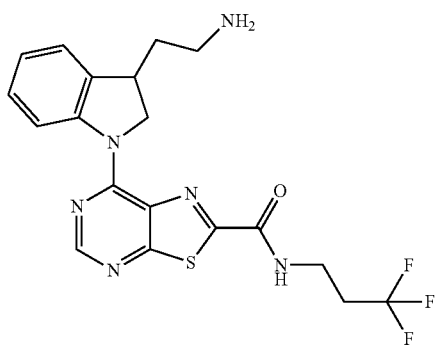 [SMILES: NCCC1CN(c2ncnc3sc(C(=O)NCCC(F)(F)F)nc23)c2ccccc21] | 167 | 7.8 | 8.1 | 8.3 |

TABLE 1-continued
Selected compounds according to the invention
| STRUCTURE | Example # | P(IC50) eIF4E | MNK1 | MNK2 |
|---|---|---|---|---|
| 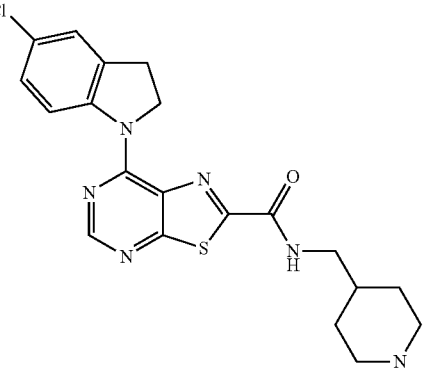 | 168 | 7.5 | 8.5 | 8.5 |
| 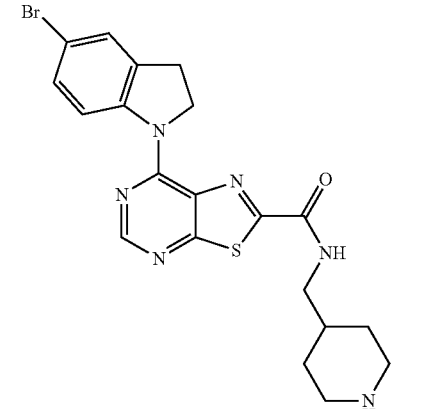 | 169 | 7.5 | 8.1 | 8.1 |
| 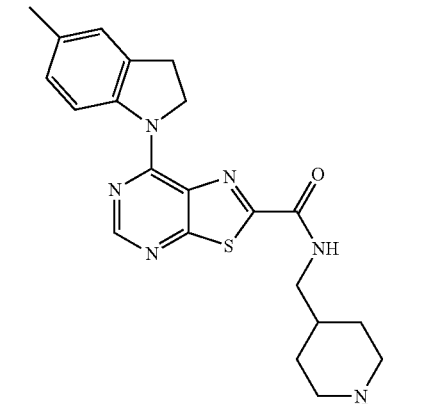 | 170 | 7.1 | 7.2 | 7.6 |
| 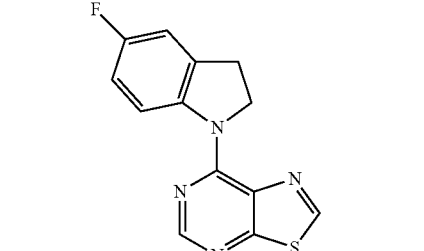 | 171 | 6.6 | 7.1 | 7.2 |

TABLE 2

Kinase selectivity data for Examples 10, 58 and 64

| Kinase | Example 10 | Example 58 | Example 64 |
|---|---|---|---|
| MKNK2 | 81 | 93 | 96 |
| STK10 | 28 | 71 | 81 |
| STK17A | 2 | 41 | 70 |
| RPS6KA1 | 30 | 36 | 49 |
| NUAK1 | 15 | 33 | 43 |
| MAP3K9 | 11 | 24 | 1 |
| SGK1 | 14 | 24 | 41 |
| DYRK2 | 7 | 21 | 44 |
| ULK2 | 0 | 21 | 81 |
| INSR | 8 | 20 | 0 |
| TYRO3 | 0 | 20 | 0 |
| CAMK2B | 2 | 17 | 57 |
| TBK1 | 14 | 17 | 7 |
| FES | 13 | 16 | 1 |
| MYLK | 10 | 15 | 15 |
| MAP3K7 | 20 | 14 | 0 |
| YES1 | 4 | 14 | 4 |
| INSRR | 10 | 13 | 0 |
| PIM2 | 7 | 13 | 42 |
| CDK9/CCNT1 | 2 | 11 | 4 |
| CaMK1 | 11 | 11 | 18 |
| IGF1R | 12 | 11 | 0 |
| FGFR4 | 0 | 10 | 0 |
| BTK | 6 | 9 | 0 |
| PAK1 | 0 | 9 | 0 |
| ROCK2 | 1 | 8 | 18 |
| ALK | 10 | 7 | 3 |
| KIT | 0 | 7 | 0 |
| MAP2K1 | 0 | 7 | 5 |
| PIP4K2A | 12 | 7 | 0 |
| STK11 | 21 | 7 | 10 |
| ABL1 | 4 | 6 | 4 |
| CHEK1 | 0 | 6 | 35 |
| FLT1 | 12 | 6 | 27 |
| PIP5K1C | 6 | 6 | 3 |
| AURKC | 14 | 5 | 15 |
| MAPK8 | 5 | 1 | 0 |
| PIP5K1A | 2 | 1 | 0 |
| PLK1 | 0 | 1 | 0 |
| PRKAA2 | 1 | 1 | 45 |
| RAF1 | 0 | 1 | 0 |
| AKT1 | 0 | 0 | 0 |
| EPHA5 | 11 | 0 | 0 |
| ACVR1B | 6 | 0 | 15 |
| BLK | 18 | 0 | 1 |
| FER | 4 | 0 | 0 |
| PAK7 | 1 | 0 | 0 |
| PIK3CG | 6 | 0 | 3 |
| BMX | 0 | 0 | 6 |
| FGFR3 | 0 | 0 | 3 |
| CDK1/CCNB1 | 8 | 0 | 4 |
| CDK6/CCND3 | 3 | 0 | 9 |
| PTK2 | 16 | 0 | 0 |
| PTK6 | 0 | 0 | 4 |
| RPS6KA5 | 0 | 0 | 24 |
| EEF2K | 4 | 0 | 0 |
| EGFR | 0 | 0 | 5 |
| FGFR1 | 1 | 0 | 2 |
| RET | 0 | 0 | 0 |
| SRC | 5 | 0 | 0 |
| ABL2 | 0 | 0 | 0 |
| DMPK | 0 | 0 | 0 |
| PRKCA | 8 | 0 | 0 |
| ROCK1 | 0 | 0 | 4 |
| RPS6KB1 | 0 | 0 | 0 |
| EPHB4 | 4 | 0 | 8 |
| PAK4 | 15 | 0 | 4 |
| PRKCE | 4 | 0 | 0 |
| LCK | 12 | 0 | 0 |
| MTOR | 4 | 0 | 3 |
| NTRK1 | 10 | 0 | 5 |
| PRAK | 0 | 0 | 0 |

The invention claimed is:

1. A compound of formula (II), or a pharmaceutically acceptable salt or ester thereof, $$(II)$$

wherein:
- $R_b$ is selected from alkyl, cycloalkyl and heterocycloalkyl, each of which may be optionally substituted by one or more groups selected from halo and alkoxy;
- $R_{1a}$ is alkyl optionally substituted by one or more groups selected from $NR_{10}R_{11}$ and a heterocycloalkyl group selected from piperidinyl, morpholinyl, piperazinyl, pyrrolidinyl, tetrahydropyranyl, wherein said heterocycloalkyl group is optionally substituted by one or more $R_{10}$ groups;
- $Z_1$, $Z_2$, $Z_3$ and $Z_4$ are all C;
- $R_6$, $R_8$ and $R_9$ are each independently selected from H, CN, $NO_2$, OH, alkoxy, NHCO-alkyl, halo and haloalkyl;
- $R_7$ is halo; or
- $Z_2$, $Z_3$ and $Z_4$ are all C, $Z_1$ is N, $R_6$ is absent and $R_7$, $R_8$ and $R_9$ are as defined above; and
- each $R_{10}$ and $R_{11}$ is independently alkyl.

2. A compound according to claim 1 wherein $Z_1$, $Z_2$, $Z_3$ and $Z_4$ are all C; and $R_6$, $R_8$ and $R_9$ are all H and $R_7$ is halo.

3. A compound according to claim 1 wherein $Z_1$, $Z_2$, $Z_3$ and $Z_4$ are all C, $R_6$, $R_8$ and $R_9$ are all H, and $R_7$ is fluoro.

4. A compound according to claim 1 wherein $R_b$ is alkyl.

5. A pharmaceutical composition comprising a compound according to claim 1 and a pharmaceutically acceptable carrier, diluent or excipient.

6. A method of treating a proliferative disorder selected from a haematological tumour, a solid tumour and/or metastases thereof comprising administering to a subject in need thereof a compound of claim 1.

7. A method of treating a disease of uncontrolled cell growth, proliferation and/or survival, an inappropriate cellular immune response, or an inappropriate cellular inflammatory response, or a neurodegenerative disorder in a mammal, said method comprises administering to a mammal a therapeutically effective amount of a compound according to claim 1.

8. A method of treating a mammal having a disease state alleviated by the inhibition of MNK, wherein the method comprises administering to a mammal a therapeutically effective amount of a compound according to claim 1.

9. A combination comprising a compound according to claim 1 and a further therapeutic agent.

10. A compound according to claim 1, wherein Rh is isopropyl.

11. A compound of formula (II), or a pharmaceutically acceptable salt thereof,

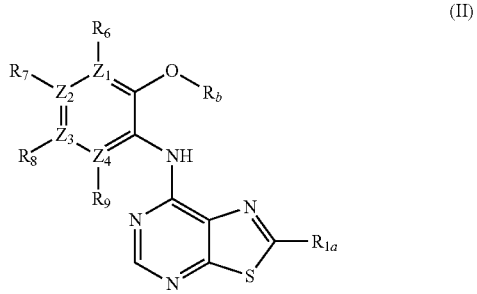

(II)

wherein:

$R_b$ is selected from alkyl, cycloalkyl and heterocycloalkyl, each of which may be optionally substituted by one or more groups selected from halo and alkoxy;

$R_{1a}$ is alkyl optionally substituted by one or more groups selected from $NR_{10}R_{11}$ and a heterocycloalkyl group selected from piperidinyl, morpholinyl, piperazinyl, pyrrolidinyl, tetrahydropyranyl, wherein said heterocycloalkyl group is optionally substituted by one or more $R_{10}$ groups:

wherein $Z_2$, $Z_3$ and $Z_4$ are all C, $Z_1$ is N and $R_6$ is absent;

$R_7$, $R_8$ and $R_9$ are each independently selected from H, CN, $NO_2$, OH, alkoxy, NHCO-alkyl, halo and haloalkyl; and each $R_{10}$ and $R_{11}$ is independently alkyl.

12. A pharmaceutical composition comprising a compound according to claim 11 and a pharmaceutically acceptable carrier, diluent or excipient.

13. A method of treating a proliferative disorder selected from a haematological tumour, a solid tumour and/or metastases thereof, comprising administering to a subject in need thereof a compound of claim 11.

14. A method of treating a disease of uncontrolled cell growth, proliferation and/or survival, an inappropriate cellular immune response, or an inappropriate cellular inflammatory response, or a neurodegenerative disorder in a mammal, said method comprises administering to a mammal a therapeutically effective amount of a compound according to claim 11.

15. A method of treating a mammal having a disease state alleviated by the inhibition of MNK, wherein the method comprises administering to a mammal a therapeutically effective amount of a compound according to claim 11.

16. A combination comprising a compound according to claim 11 and a further therapeutic agent.

* * * * *